United States Patent
Cook et al.

(10) Patent No.: US 8,785,445 B2
(45) Date of Patent: Jul. 22, 2014

(54) 7-PHENOXYCHROMAN CARBOXYLIC ACID DERIVATIVES

(75) Inventors: Adam Cook, Boulder, CO (US); Kevin W. Hunt, Boulder, CO (US); Robert Kirk Delisle, Boulder, CO (US); Todd Romoff, Bradenton, FL (US); Christopher T. Clark, Boulder, CO (US); Ganghyeok Kim, Boulder, CO (US); Christopher P. Corrette, Boulder, CO (US); George A. Doherty, Boulder, CO (US); Laurence E. Burgess, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 57 days.

(21) Appl. No.: 13/141,675

(22) PCT Filed: Dec. 18, 2009

(86) PCT No.: PCT/US2009/068672
§ 371 (c)(1),
(2), (4) Date: Jun. 22, 2011

(87) PCT Pub. No.: WO2010/075200
PCT Pub. Date: Jul. 1, 2010

(65) Prior Publication Data
US 2012/0101103 A1    Apr. 26, 2012

Related U.S. Application Data

(60) Provisional application No. 61/139,981, filed on Dec. 22, 2008.

(51) Int. Cl.
| | | |
|---|---|---|
| *C07D 405/12* | (2006.01) | |
| *A61K 31/4433* | (2006.01) | |
| *C07D 241/20* | (2006.01) | |
| *A61K 31/497* | (2006.01) | |
| *A61K 31/501* | (2006.01) | |
| *A61P 11/06* | (2006.01) | |
| *A61P 27/14* | (2006.01) | |
| *A61P 17/00* | (2006.01) | |
| *A61P 29/00* | (2006.01) | |

(52) U.S. Cl.
USPC .............. 514/252.01; 514/337; 514/255.06; 544/336; 544/238; 546/282.7

(58) Field of Classification Search
USPC ............. 546/282.7; 514/337, 255.06, 252.01; 544/336, 238
See application file for complete search history.

(56) References Cited

U.S. PATENT DOCUMENTS

2010/0273850 A1    10/2010    Doherty

FOREIGN PATENT DOCUMENTS

| WO | 2004/058164 A2 | 7/2004 |
|---|---|---|
| WO | 2007/144625 A1 | 12/2007 |
| WO | 2008/024746 A1 | 2/2008 |
| WO | 2008/054675 A2 | 5/2008 |
| WO | 2009/158426 A1 | 12/2009 |

OTHER PUBLICATIONS

Eisenberg, Journal of Autoimmunity, vol. 32, Issues 3-4, May-Jun. 2009, 223-230.*
Norman, Expert Opin. Investig. Drugs (2010)19 (8), 947-961.*
Bain, et al., J. Clin. Pharmacol. 2012; 52: 148201493.*
Stebbins, et al., Europ. J. Pharmacol., vol. 638, Issues 1-3, Jul. 25, 2010, 142-149.*
Wechsler, et al., J. Allergy Clin. Immunol. Sep. 2012; 130 (3), 563-571.*
Norman, Peter, "Indole-Based CRTH2 Antagonists", Expert Opinion, Ther. Patents (2005), 15 (12):1817-1823.
Pettipher, Roy et al., "Antagonism of the Prostaglandin D2 Receptors DP1 and CRTH2 as an Approach to Treat Allergic Diseases", Nature Reviews, Drug Discovery, vol. 6, Apr. 2007, pp. 313-325.
PCT—International Search Report published with Corresponding PCT Application No. PCT/US2009/068672 on Jul. 1, 2010.

* cited by examiner

*Primary Examiner* — Emily Bernhardt
*Assistant Examiner* — Cecilia M Jaisle
(74) *Attorney, Agent, or Firm* — Viksnins Harris & Padys PLLP; Sarah S. Mastous

(57) ABSTRACT

Compounds of Formula I: (I) in which A, $A^1$, $R^1$, $R^{7a}$, $R^{7b}$, $R^8$ and $R^{10}$ have the meanings given in the specification, are DP2 receptor inhibitors useful in the treatment of useful in the treatment and prevention of immunologic diseases, allergic diseases such as asthma, allergic rhinitis and atopic dermatitis, and other inflammatory diseases mediated by prostaglandin $D_2$ ($PGD_2$). The compounds of Formula I may also be useful in treating diseases or medical conditions involving the Th2 T cell via production of IL-4, IL-5 and/or IL-13.

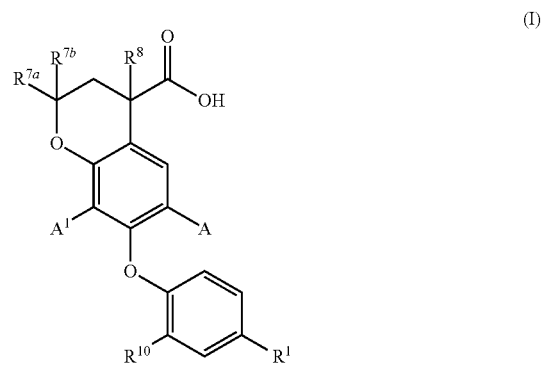

(I)

14 Claims, No Drawings

7-PHENOXYCHROMAN CARBOXYLIC ACID DERIVATIVES

RELATED APPLICATIONS

This application claims priority to U.S. Provisional Application No. 61/139,981 that was filed on Dec. 22, 2008.

The present invention relates to novel compounds, to pharmaceutical compositions comprising the compounds, to a process for making the compounds and to the use of the compounds in therapy. More particularly, it relates to certain 7-phenoxychroman carboxylic acid derivatives useful in the treatment and prevention of immunologic diseases and allergic diseases such as asthma, allergic rhinitis and atopic dermatitis, and other inflammatory diseases mediated by prostaglandin $D_2$ ($PGD_2$). The compounds of formula I may also be useful in treating diseases or medical conditions involving the Th2 T cell via production of IL-4, IL-5 and/or IL-13.

DP2 is a G-protein coupled receptor that is selectively expressed on cell types that mediate allergic inflammation including mast cells, basophils, eosinophils and Th2 cells and there is growing evidence that it plays a critical role in the pathophysiology of allergy (Hirai et. al., Journal of Experimental Medicine (2001) 193:255-261). The endogenous ligands for DP2 (PGD2 and its active metabolites) are made by activated mast cells and by Th2 cells, and can be readily detected at sites of allergic disease. Agonism of DP2 promotes the migration and or activation of basophils, eosinophils and Th2 cells in vitro and in vivo (Kostenis and Ulven, Trends in Molecular Medicine (2006) 12:1471-148-158), suggesting that this receptor may drive disease processes in vivo. In support of this mice made deficient in DP2 by gene inactivation through homologous recombination show evidence of reduced allergic responses in pre-clinical models of asthma and atopic dermatitis. Similar results have been reported using selective small molecule inhibitors of DP2 (reviewed in Pettipher, et. al., Nature Reviews Drug Discovery (2007) 6:313-325).

Clinical validation for DP2 as a target for allergic disease is also provided by Ramatroban (BAY u34505). Ramatroban was originally developed as a Thromboxane A2 (TP) receptor antagonist but showed unexpected clinical activity in allergy, which could not be readily explained by its activity against TP. It has recently been shown that Ramatroban is also an inhibitor of DP2 and its activity in pre-clinical models of allergy can be recapitulated using selective inhibitors of DP2 but not of TP (Sugimoto et. al., Journal of Pharmacology and Experimental Therapeutics (2003) 305:347-352; Takeshiti et al., International Immunology (2004) 16:947-959). These findings support the view that the clinical efficacy seen with Ramatroban in allergic disease is due to its activity against DP2. Ramatroban is currently approved in Japan for the treatment of seasonal allergic rhinitis. Based on the validation of DP2 as a drug target in allergy many companies have sought to develop inhibitors of DP2 for the treatment of allergic disease, and the first of these has now entered clinical development.

International patent application, publication number WO 2004/058164 discloses inter alia, certain 2-substituted phenoxyphenylacetic acid derivatives that modulate the $PGD_2$-selective receptor CRTH2 (chemoattractant receptor-homologous molecule expressed on Th2 cells), now more commonly referred to as DP2. The compounds are said to be useful in the treatment of immunologic diseases such as asthma and allergic inflammation.

International application publication No. WO 2008/024746, published Feb. 28, 2008, discloses 4-substituted phenoxyphenylacetic acid derivatives useful in the treatment and prevention of allergic diseases such as asthma, allergic rhinitis and atopic dermatitis and other inflammatory diseases mediated by prostaglandin D2 (PGD2).

It has now been found that certain 7-phenoxychroman carboxylic acid derivatives having a heteroaryl substituent linked to the 4-position of the phenoxy moiety are DP2 receptor antagonists.

In one embodiment, the present invention provides a compound of general Formula I:

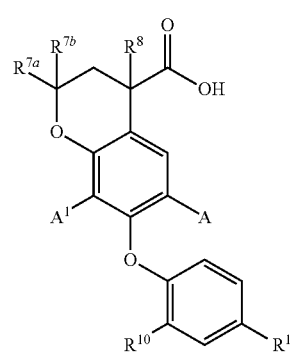

or a pharmaceutically acceptable salt thereof, wherein:
A is H, CN, Cl, F, cyclopropyl, (1-4 C)alkyl or OMe;
$A^1$ is H, Cl, Br, F, cyclopropyl, (1-4 C)alkyl or OMe;
$R^1$ is —W-$L^1$-hetAr$^1$;
W is —CONR$^{3a}$— or —NR$^{3b}$CO—;
$R^{3a}$ and $R^{3b}$ are each H or methyl;
$L^1$ is a —(CR$^a$R$^b$)$_n$— or

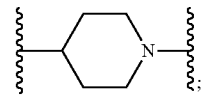 [SMILES: *C1CCN(*)CC1]

n is 0 or 2;
$R^a$ and $R^b$ are independently H, F, methyl, or cyclopropyl, or
$R^a$ and $R^b$ together with the carbon to which they are attached form a cyclopropyl ring;
hetAr$^1$ is heteroaryl ring selected from the structures:

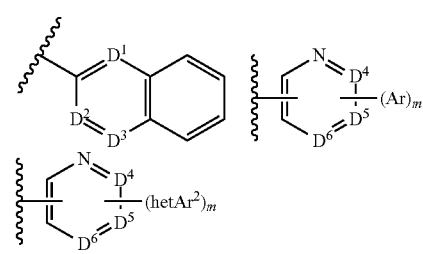

wherein m is 0 or 1 and each of said heteroaryl rings is optionally substituted with one or more R$^c$ substituents,
or hetAr$^1$ is a 5-membered heteroaryl ring having 1-3 ring heteroatoms independently selected from N, O and S, wherein at least one of said heteroatoms is N, wherein the ring is optionally substituted with one or more substituents independently selected from (1-4C)alkyl and phenyl which is optionally substituted with one or more substituents independently selected from halogen, —O(1-6Calkyl), (1-6C)alkyl and $CF_3$;

or $hetAr^1$ is a 5,6-bicyclic heteroaryl having two ring heteroatoms independently selected from N, O and S, wherein at least one of said heteroatoms is N, wherein said ring is optionally substituted with one or more substituents independently selected from —O(1-6Calkyl), (1-6C)alkyl, halogen and $CF_3$;

or $hetAr^1$ is 2-oxopyridin-1(2H)-yl optionally substituted with halogen;

one or two of $D^1$, $D^2$ and $D^3$ is N, the remainder being CH;

zero or one of $D^4$, $D^5$ and $D^6$ is N, the remainder being CH;

each $R^c$ is independently selected from halogen, $CF_3$, (1-6C)alkyl, —O(1-6C alkyl), cyclopropyl, —O—($CH_2CH_2$)OMe, —S(1-6C alkyl), di(1-6C alkyl)amino, and a 5-6 membered azacycle;

Ar is phenyl optionally substituted with one or more $R^d$ substituents;

each $R^d$ is independently selected from (1-6C)alkyl, —O(1-6C)alkyl, halogen, —S(1-6C alkyl), and $CF_3$, or two adjacent $R^d$ substituents together with the atoms to which they are attached form a 5-6 membered oxacyclic ring;

$hetAr^2$ is pyridyl optionally substituted with one or more substituents independently selected from $CF_3$ and —O(1-6C alkyl);

$R^{7a}$, $R^{7b}$ and $R^8$ are independently H or methyl; and $R^{10}$ is H, Me or $NH_2$.

In one embodiment, the present invention provides a compound of Formula I

I or a pharmaceutically acceptable salt thereof, wherein:

A is H, CN, Cl, F, cyclopropyl, (1-4 C)alkyl or OMe;

$A^1$ is H, Cl, Br, F, cyclopropyl, (1-4 C)alkyl, or OMe;

$R^1$ is —W-$L^1$-$hetAr^1$;

W is —$CONR^{3a}$— or —$NR^{3b}CO$—;

$R^{3a}$ and $R^{3b}$ are each H or methyl;

$L^1$ is —$(CR^aR^b)_n$—;

n is 0 or 2;

$R^a$ and $R^b$ are independently H, F, methyl, or cyclopropyl, or $R^a$ and $R^b$ together with the carbon to which they are attached form a cyclopropyl ring;

$hetAr^1$ is heteroaryl ring selected from the structures:

wherein m is 0 or 1 and each of said heteroaryl rings is optionally substituted with one or more $R^c$ substituents, or $hetAr^1$ is a C-linked 5-membered heteroaryl ring having 2-3 ring heteroatoms independently selected from N, O and S, wherein at least one of said heteroatoms is N, wherein the ring is optionally substituted by 1-2 substituents independently selected from (1-4C)alkyl and phenyl which is optionally substituted with one or more substituents independently selected from halogen and OMe;

one or two of $D^1$, $D^2$ and $D^3$ is N, the remainder being CH;

zero or one of $D^4$, $D^5$ and $D^6$ is N, the remainder being CH;

each $R^c$ is independently selected from halogen, $CF_3$, (1-6C)alkyl, —O(1-6C alkyl), cyclopropyl, —O—($CH_2CH_2$)OMe, —S(1-6C alkyl) and di(1-6C alkyl)amino;

Ar is phenyl optionally substituted with one or more $R^d$ substituents;

each $R^d$ is independently selected from (1-6C)alkyl, —O(1-6C)alkyl, halogen, —S(1-6C alkyl), and $CF_3$, or two adjacent $R^d$ substituents together with the atoms to which they are attached form a 5-6 membered oxacyclic ring;

$hetAr^2$ is pyridyl optionally substituted with one or more substituents independently selected from $CF_3$ and —O(1-6C alkyl);

$R^{7a}$, $R^{7b}$ and $R^8$ are independently H or methyl; and $R^{10}$ is H, Me or $NH_2$.

Compounds according to the present invention have been found to be DP2 antagonists and are useful in the treatment of immunologic diseases such as asthma and allergic inflammation. The term "allergic inflammation" includes asthma, atopic dermatitis, and allergic rhinitis, among other inflammatory diseases and disorders.

It will be appreciated that certain compounds according to the invention may contain one or more centers of asymmetry and may therefore be prepared and isolated in a mixture of isomers such as a racemic mixture, or in an enantiomerically pure form.

Accordingly, in one embodiment the compound of Formula I is a racemic mixture. In another embodiment, the compound of Formula I is an isolated enantiomer.

The compounds of Formula I include pharmaceutically acceptable salts thereof. Examples of salts of Formula I include alkali metal salts, such as lithium, sodium or potassium salts, or alkaline earth metal salts, such as calcium salts. A particular example is a sodium salt of a compound of Formula I.

In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

It will further be appreciated that the compounds of Formula I or their salts may be isolated in the form of solvates, and accordingly any such solvate is included within the scope of the present invention.

Also provided herein are prodrugs of the compound of Formula I.

A "prodrug" is a compound that may be converted under physiological conditions or by solvolysis to the specified compound or to a salt of such compound.

The compounds of Formula I also include compounds that differ only in the presence of one or more isotopically enriched atoms. For example, compounds of the invention include compounds wherein one or more hydrogen atoms are replaced deuterium or tritium, or one or more carbon atoms are replaced by a $^{13}$C- or $^{14}$C-enriched carbon are within the scope of this invention.

The terms "(1-6C)alkyl" and "(1-4C)alkyl" as used herein refer to a saturated linear or branched-chain monovalent hydrocarbon radical of one to six carbon atoms or one to four carbon atoms, respectively. Examples of alkyl groups include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

The term "O(1-6Calkyl)" as used herein refer to a saturated linear or branched-chain monovalent hydrocarbon alkoxy radical of one to six carbon atoms, respectively, wherein the radical is on the oxygen atom. Examples include, but are not limited to, methoxy, ethoxy, propoxy, isopropoxy, butoxy, and the like.

The term "halogen" as used herein includes F, Cl, Br and I.

In one embodiment, W is —CONR$^{3a}$—. An example of a particular value for R$^{3a}$ is hydrogen. In one embodiment, W is —NR$^{3b}$CO—. In one embodiment, R$^{3b}$ is hydrogen. In another embodiment, R$^{3b}$ is methyl. Examples of particular values for W are CONH, NHCO and N(CH$_3$)CO.

In one embodiment, L$^1$ is —(CR$^a$R$^b$)$_n$— where n is 0, that is, L$^1$ is a bond.

In one embodiment, L$^1$ is —(CR$^a$R$^b$)$_n$— where n is 2. In one embodiment, R$^a$ and R$^b$ are hydrogen. In one embodiment, R$^a$ and R$^b$ together with the carbon atom to which are attached form a cyclopropylidine ring. In one embodiment, R$^a$ and R$^b$ are attached to the same carbon. In other embodiments, R$^a$ and R$^b$ are attached to different carbon atoms.

In one embodiment, L$^1$ is a group having the formula:

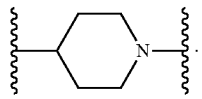

In certain embodiment, L$^1$ is selected from a bond, —CH$_2$CH$_2$—, -cyclopropylideneCH$_2$— and group having the formula:

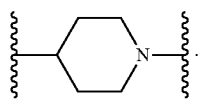 [SMILES: *C1CCN(*)CC1 ; "."]

In certain embodiment, L$^1$ is selected from a bond, —CH$_2$CH$_2$—, and -cyclopropylideneCH$_2$—

Particular values for L$^1$ are —CH$_2$CH$_2$— and -cyclopropylideneCH$_2$—.

Examples of values for -L$^1$-W— are —CONH—, —CH$_2$CH$_2$CONH—, —NHCO—, —CH$_2$CH$_2$NHCO—, -cyclopropylideneCH$_2$NHCO—, -cyclopropylidineN-HCO— and a group having the formula

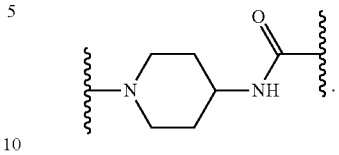

Examples of particular values for -L$^1$-W— are —CONH—, —CH$_2$CH$_2$CONH—, —NHCO—, —CH$_2$CH$_2$NHCO—, -cyclopropylideneCH$_2$NHCO—, and -cyclopropylidineNHCO—.

In certain embodiments, -L$^1$-W— is —NHCO— or —CH$_2$CH$_2$NHCO—. Particular mention is made of compounds wherein -L$^1$-W— is —NHCO—.

In one embodiment, hetAr$^1$ is a heteroaryl ring having the structure:

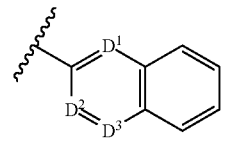

where D$^1$, D$^2$ and D$^3$ are as defined herein. Examples of values for hetAr$^1$ include optionally substituted quinolinyl, isoquinolinyl, quinoxalinyl, and quinazolinyl rings. In one embodiment, hetAr$^1$ is optionally substituted with one or more R$^c$ substituents independently selected from halogen, CF$_3$, (1-6C)alkyl and —O(1-6C alkyl). Particular examples of R$^c$ substituents include Cl, CF$_3$, Me, and OMe. In one embodiment, hetAr$^1$ is optionally substituted with one or two R$^c$ substituents.

Particular values for hetAr$^1$ include the structures:

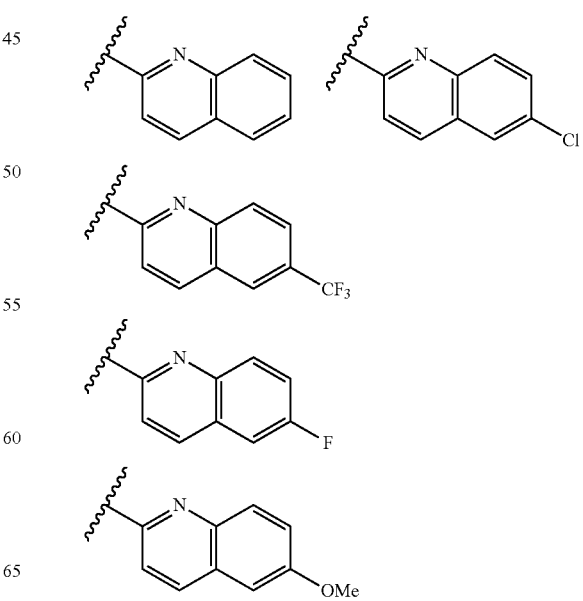

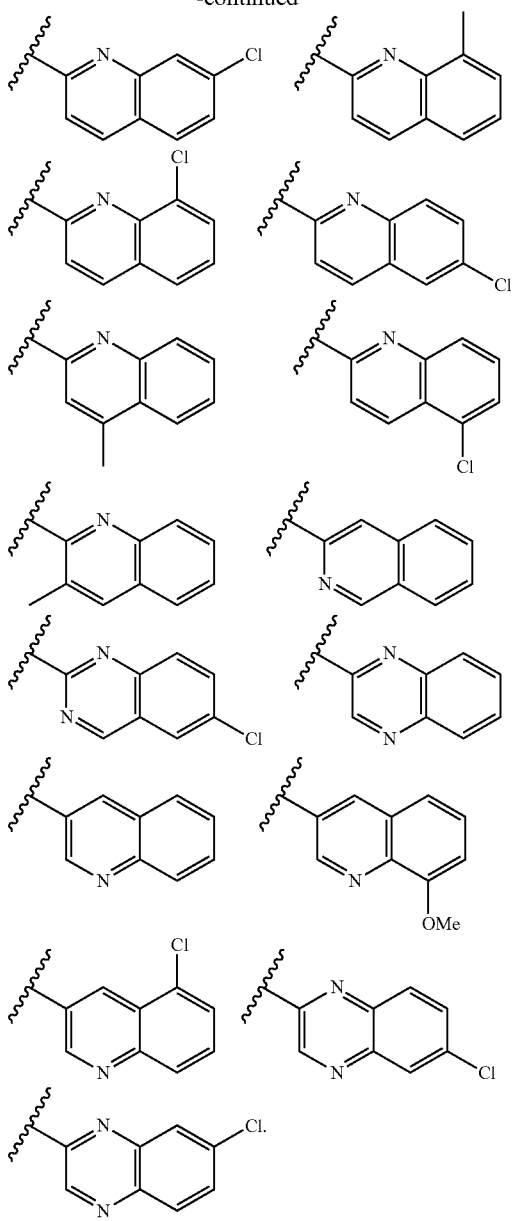

In one embodiment, hetAr¹ is a heteroaryl ring having the structure:

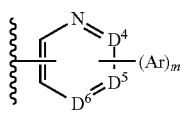

in which zero or one of $D^4$, $D^5$ and $D^6$ is N, the remainder being CH, and m is zero. Examples of hetAr¹ include pyridyl, pyridazinyl, pyrimidyl and pyrazinyl rings. In one embodiment, the hetAr¹ ring is optionally substituted with one or more $R^c$ substituents.

Examples of $R^c$ substituents include Cl, $CF_3$, tert-butyl, isobutyl, cyclopropyl, —OMe, —OEt, —OiPr, —SC(CH$_3$)$_3$, —NMe$_2$, —OCH$_2$CH$_2$OMe, and piperidinyl.

In certain embodiments, $R^c$ is selected from Cl, $CF_3$, tert-butyl, isobutyl, cyclopropyl, —OMe, —OEt, —SC(CH$_3$)$_3$, —NMe$_2$ and —OCH$_2$CH$_2$OMe.

In one embodiment, hetAr¹ is optionally substituted with one or two $R^c$ substituents.

Examples of hetAr¹ when m is zero include the structures:

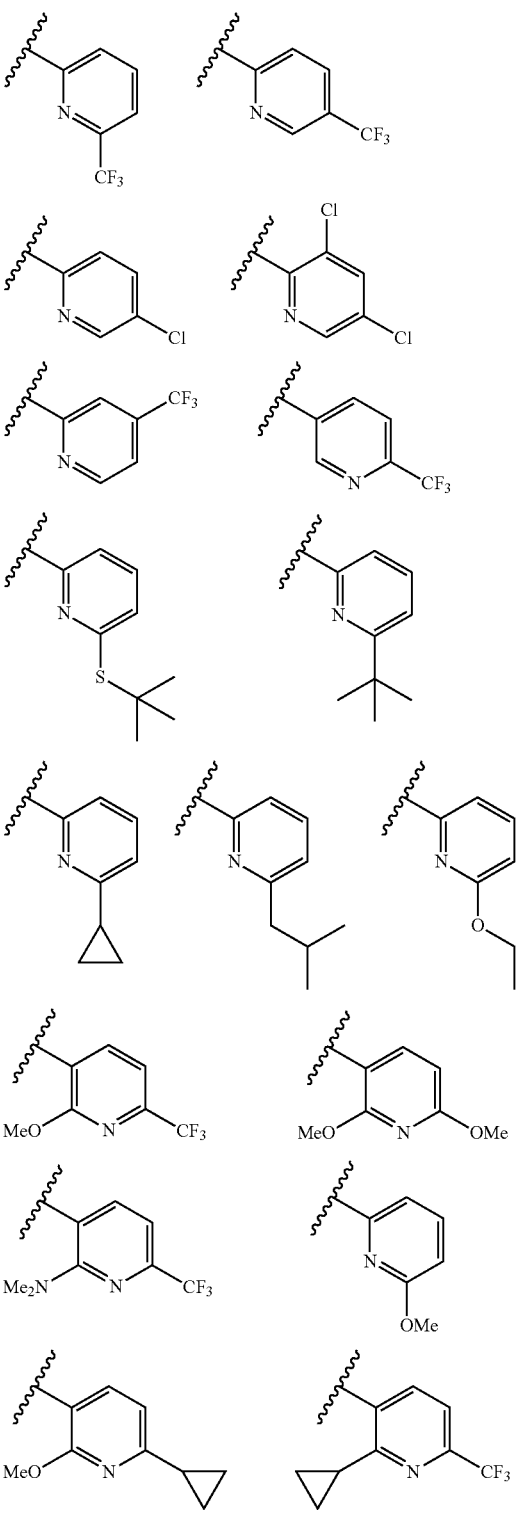

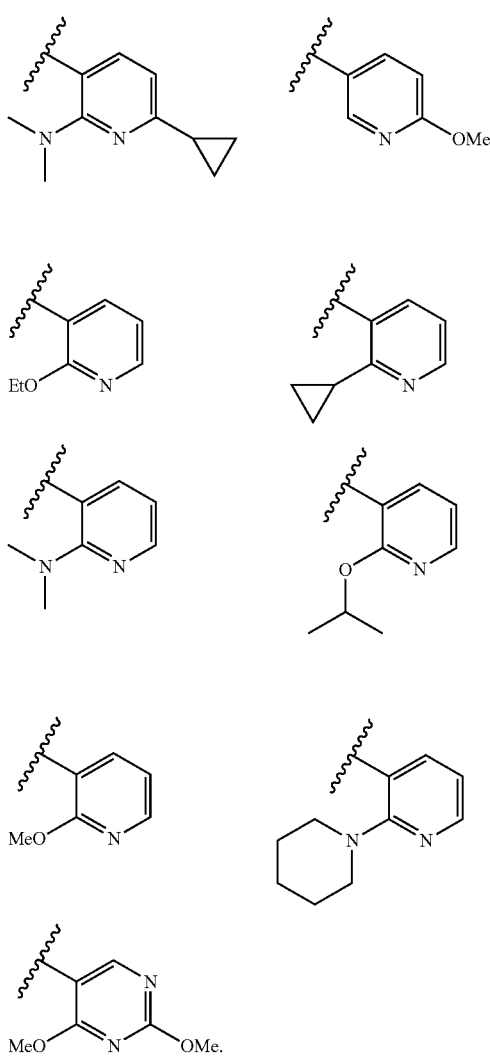

Particular values for hetAr¹ when m is zero include the structures:

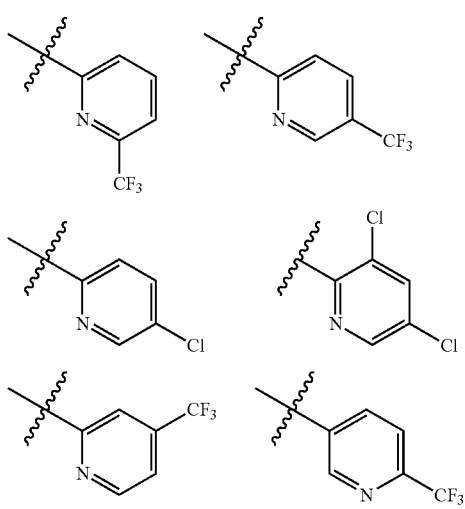

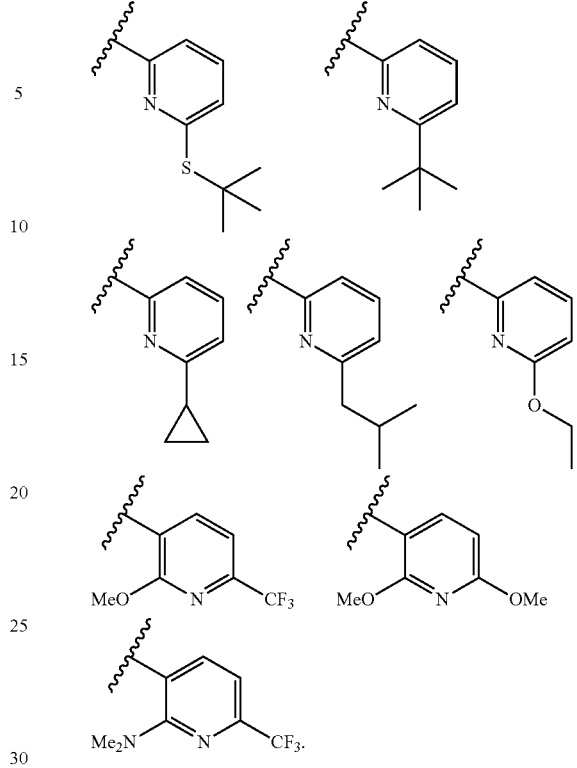

In one embodiment, hetAr¹ is a heteroaryl ring having the structure:

in which zero or one of $D^4$, $D^5$ and $D^6$ is N, the remainder being CH, and m is 1. Examples of hetAr¹ include pyridyl, pyridazinyl, pyrimidyl and pyrazinyl rings. In one embodiment, hetAr¹ is optionally substituted with one or more $R^c$ substituents. Examples of $R^c$ substituents include halogen and (1-6C alkyl). Particular values of $R^c$ substituents include F and methyl.

In one embodiment, Ar is an unsubstituted phenyl. In one embodiment, Ar is phenyl substituted with one or more $R^d$ substituents independently selected from (1-6C)alkyl, halogen, —O(1-6C alkyl), —S(1-6C alkyl), and $CF_3$. Particular values include F, Cl, $CF_3$, OMe, Me, t-Bu and SMe. In certain embodiments, Ar is phenyl optionally substituted with 1-3 $R^d$ substituents.

Examples of Ar include phenyl, trifluoromethylphenyl, fluorophenyl, methylphenyl, chlorophenyl, methoxyphenyl, chlorotrifluoromethylphenyl, fluorotrifluoromethylphenyl, dichlorophenyl, chloromethoxyphenyl, difluorophenyl, fluoromethylphenyl, tert-butylphenyl, chlorofluorophenyl, dimethylphenyl, methylsulfonylphenyl and methylthiophenyl.

Particular examples of Ar include phenyl, 3-trifluoromethylphenyl, 4-trifluoromethylphenyl, 4-fluorophenyl, 3-methylphenyl, 4-methylphenyl, 2-chlorophenyl, 3-chlorophenyl, 4-chlorophenyl, 4-methyoxyphenyl, 3-trifluoromethyl-4-chlorophenyl, 2,4-dichlorophenyl, 3,4-dichlorophenyl, 2-methoxy-4-chlorophenyl, 3,4-difluorophenyl, 2,4-difluorophenyl, 2,3-difluorophenyl, 3,5-difluorophenyl, 3-methyl-4-fluorophenyl, 4-tert-butylphenyl, 3-fluoro-4-chlorophenyl, 2-fluoro-4-chlorophenyl, 3-fluoro-4-methylphenyl, 2,3-dimethylphenyl, 3,4-dimethylphenyl, 4-methylthiophenyl, 2-chloro-4-trifluoromethylphenyl, 3-chloro-4-trifluoromethylphenyl and 2-fluoro-4-trifluoromethylphenyl.

In one embodiment, two adjacent $R^d$ substituents on the Ar group together with the atoms to which they are attached form a 5-6 membered oxacyclic ring. In one embodiment, Ar is a 2,3-dihydrobenzofuranyl group.

Particular values of hetAr$^1$ when m is 1 include the structures:

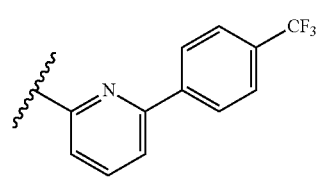
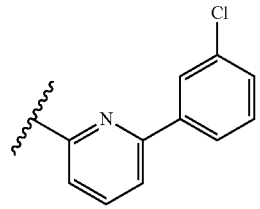
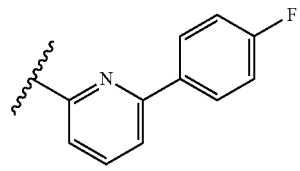
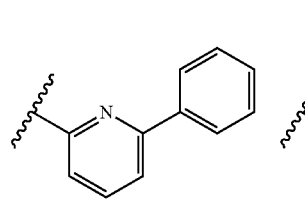
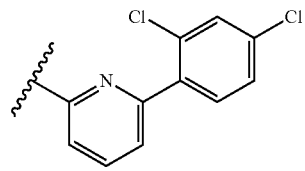
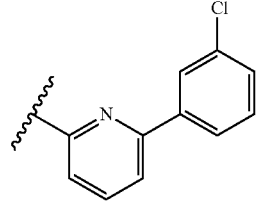
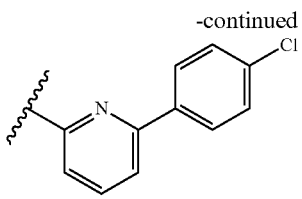
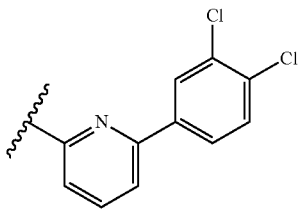
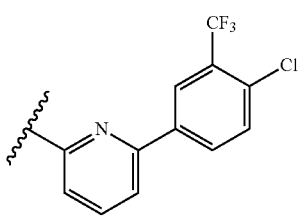
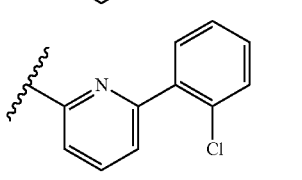
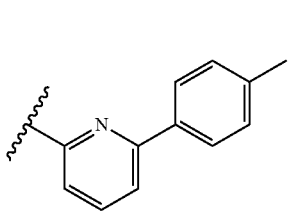
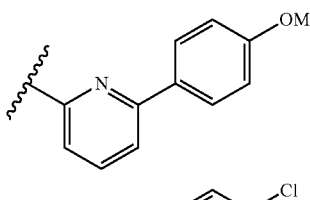
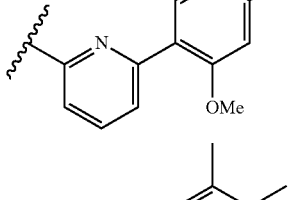
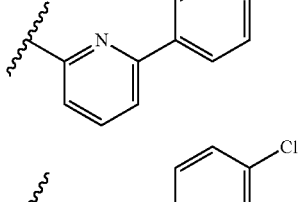
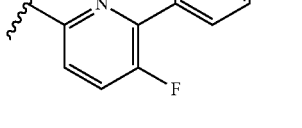

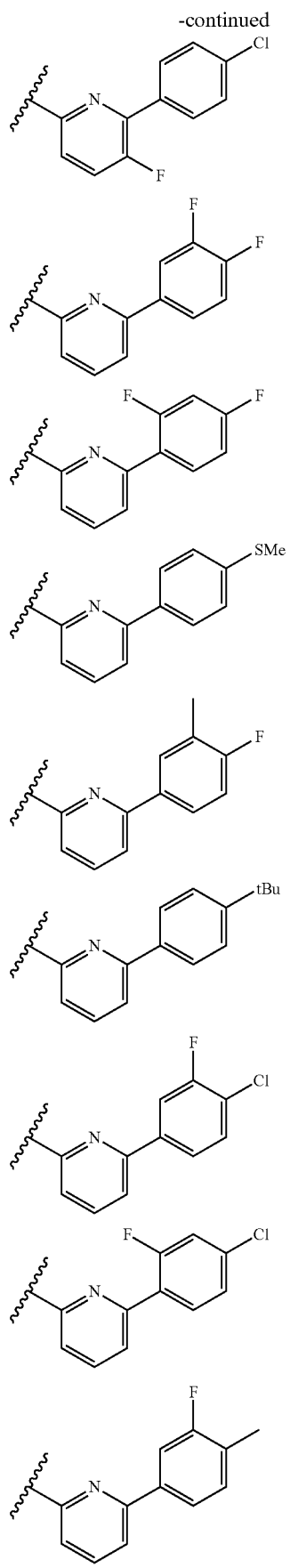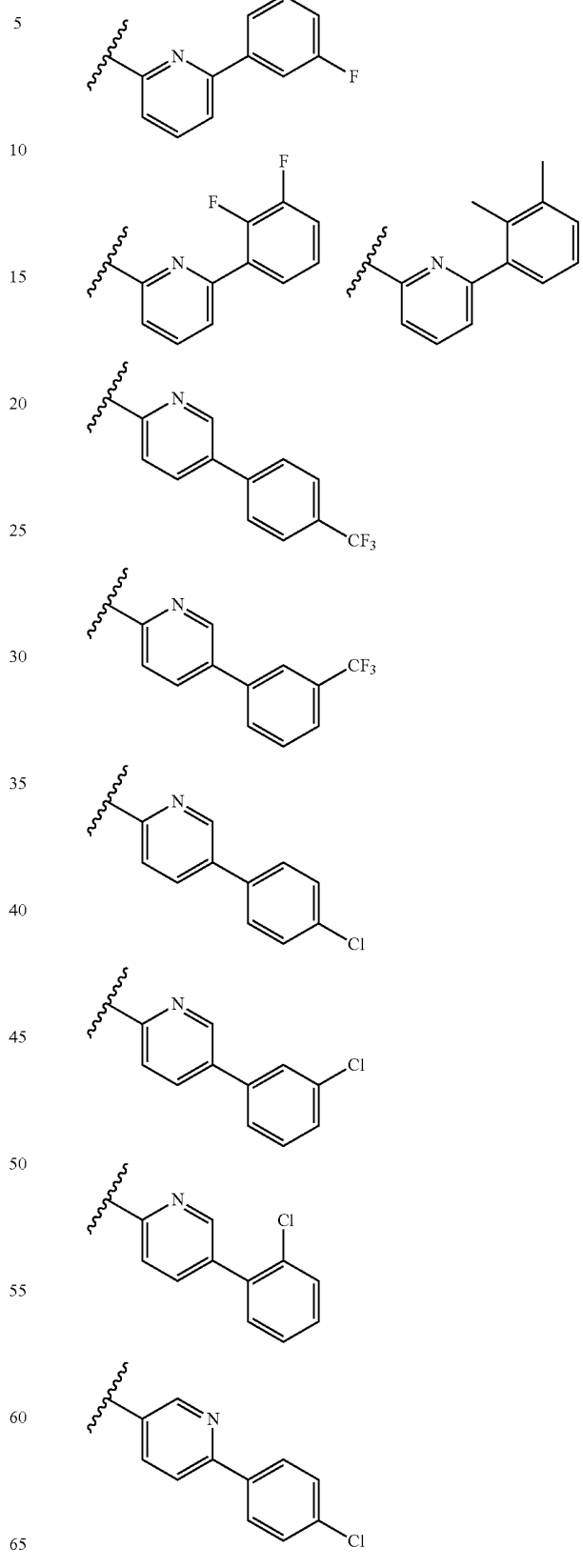

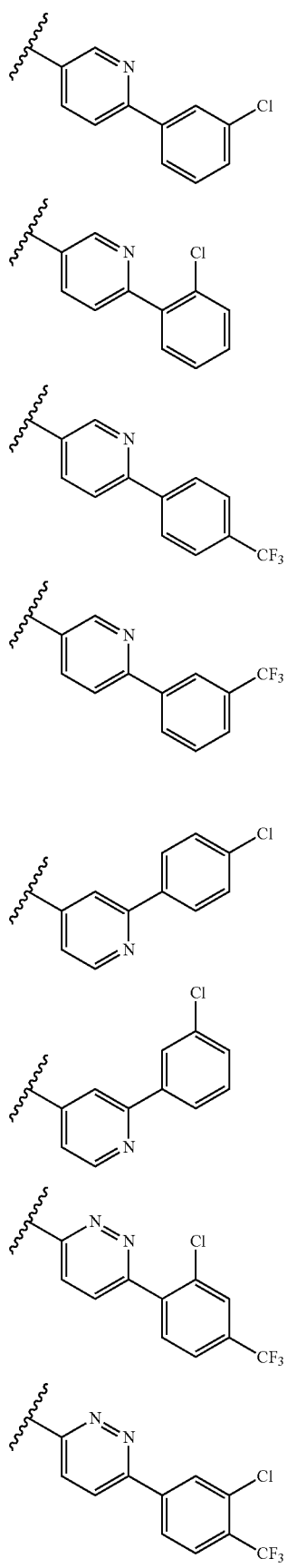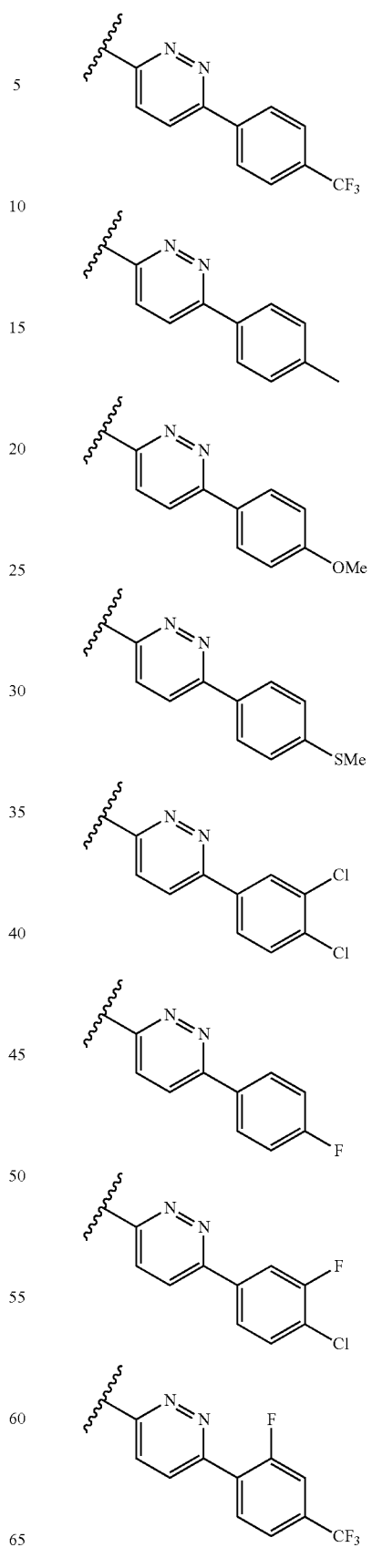

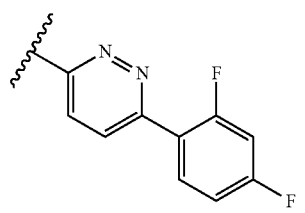
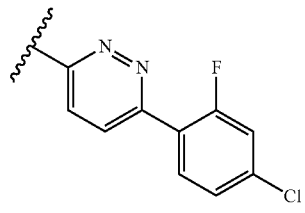
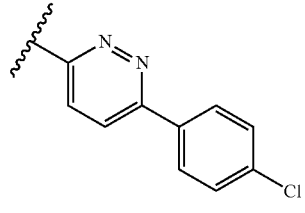
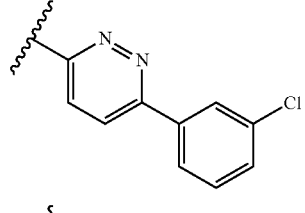
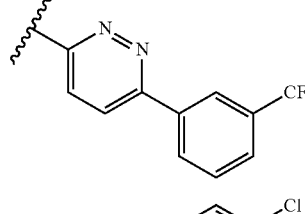
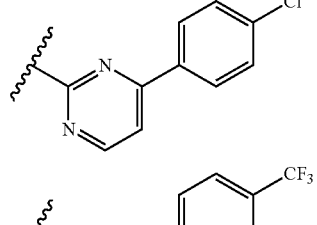
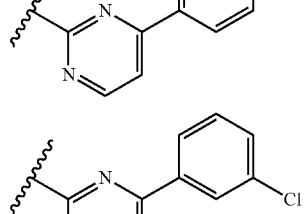
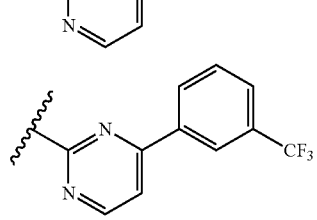
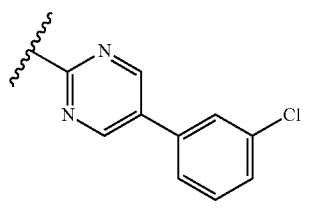
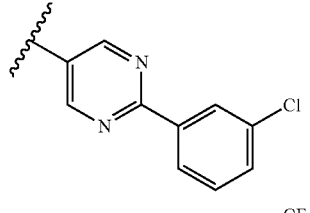
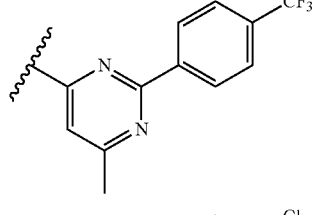
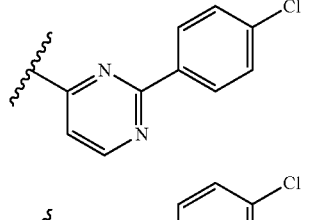
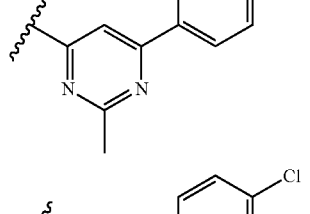
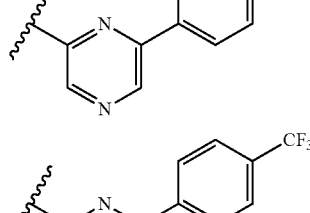
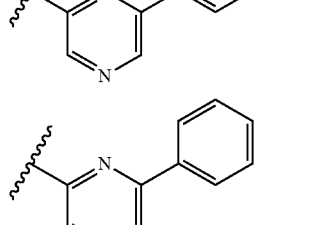
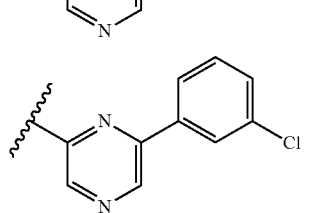

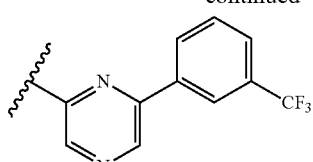
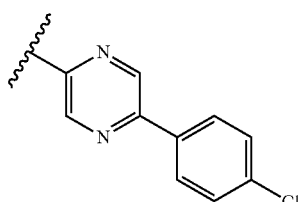
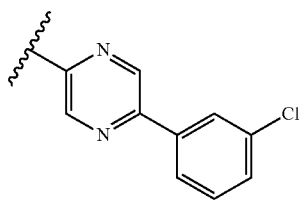
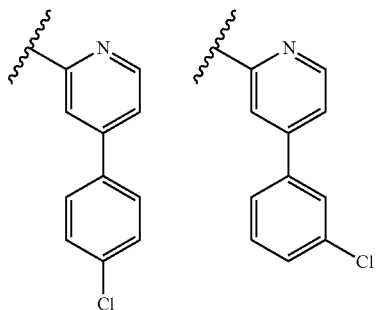
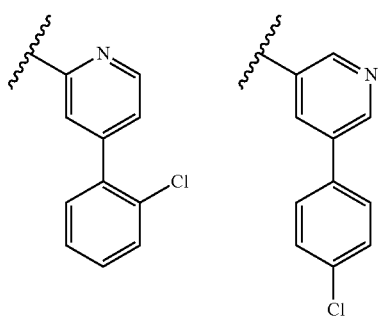
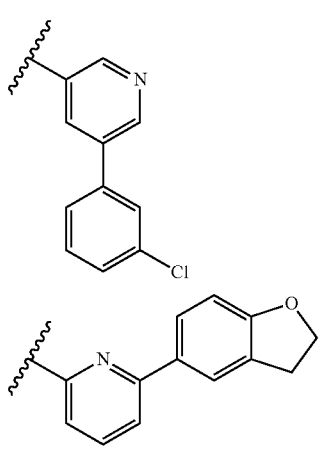

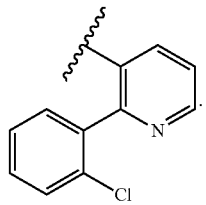 [SMILES: *c1cccnc1-c1ccccc1Cl ; "."]

In certain embodiments, values of hetAr¹ when m is 1 include any of the aforementioned structures with the exception of the following structure:

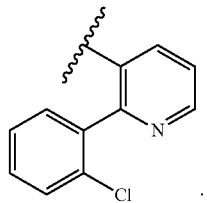

In one embodiment, hetAr¹ is a heteroaryl ring having the structure:

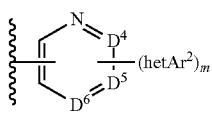

where the heteroaryl ring is optionally substituted with one or more $R^c$ substituents. In one embodiment, m is 0. In one embodiment, m is 1. In certain embodiments, the hetAr¹ ring is optionally substituted with one to two $R^c$ substituents independently selected from halogen and $CF_3$, for example Cl and $CF_3$.

Examples of hetAr² include pyridyl optionally substituted with one or more substituents independently selected from $CF_3$, OMe and OEt. Examples of hetAr² include pyridyl, methoxypyridyl, dimethoxypyridyl, and trifluoromethylpyridyl. Particular examples of hetAr² include pyridyl, 2-trifluoromethylpyrid-4-yl, 2-methoxypyrid-5-yl, and 2,6-dimethoxypyrid-4-yl.

Particular values of hetAr¹ when m is 1 include the structures:

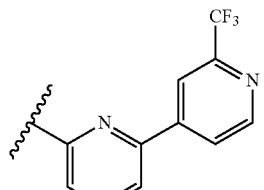

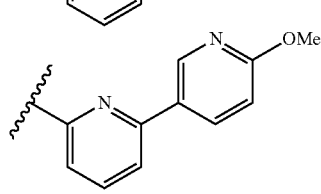

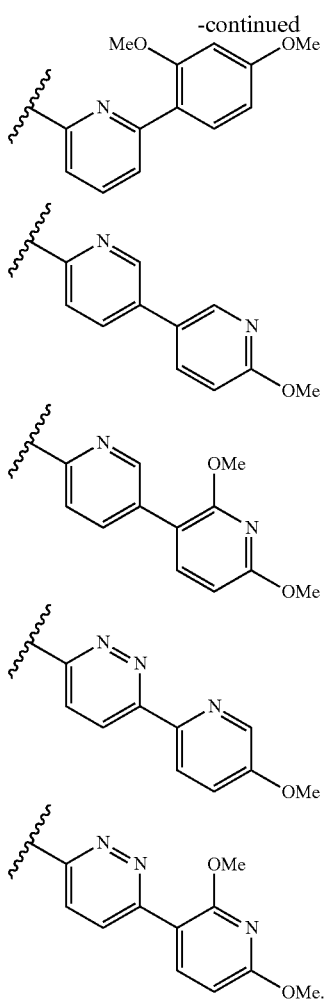

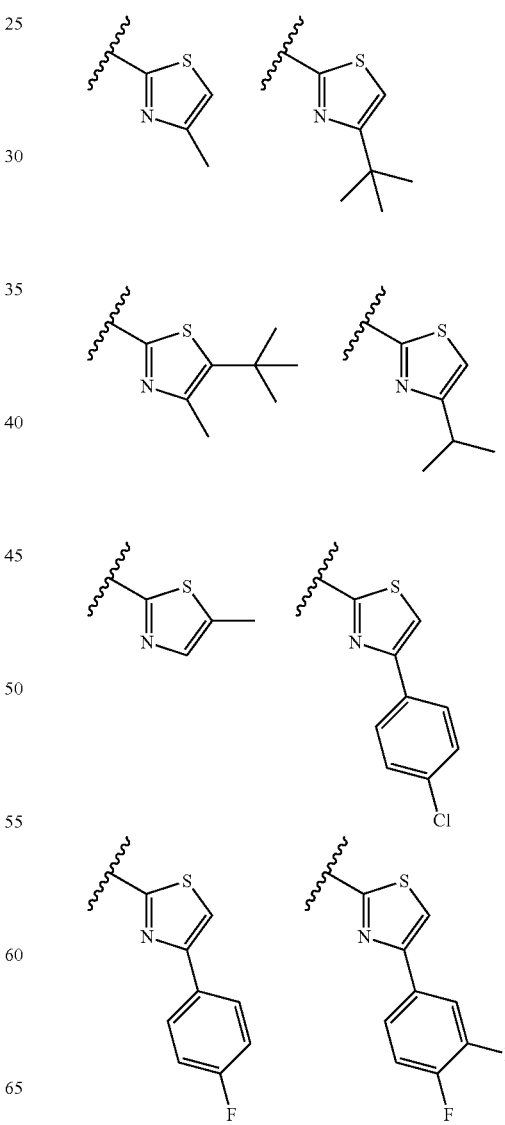

In certain embodiments the 5-membered heteroaryl ring is a thiadiazolyl, thiazolyl, isoxazolyl, oxazolyl, or a pyrazolyl ring.

In certain embodiments, the 5 membered heteroaryl ring is optionally substituted with one or two substituents independently selected from methyl, ethyl, isopropyl, t-butyl, phenyl, chlorophenyl, fluorophenyl, difluorophenyl, fluorochlorophenyl, dichlorophenyl, methoxyphenyl, methylphenyl and trifluoromethylphenyl.

In certain embodiments, the 5 membered heteroaryl ring is optionally substituted with 1-2 substituents independently selected from methyl, ethyl, isopropyl, t-butyl, phenyl, chlorophenyl, fluorophenyl, difluorophenyl, fluorochlorophenyl, dichlorophenyl, and methoxyphenyl.

In certain embodiment wherein the 5-membered ring is disubstituted, only one of said substituents is a phenyl or substituted phenyl, the other substituent being a (1-4C)alkyl substituent.

Particular values for hetAr$^1$ when represented by a 5-membered heteroaryl ring include the structures:

In certain embodiments, hetAr$^1$ is a 5-membered heteroaryl ring having 1-3 ring heteroatoms independently selected from N, O and S, wherein at least one of said heteroatoms is N, wherein the ring is optionally substituted with one or more substituents independently selected from (1-4C) alkyl and phenyl, wherein the phenyl group is optionally substituted with one or more substituents independently selected from halogen, —O(1-6Calkyl), (1-6C)alkyl and CF$_3$.

In certain embodiments, hetAr$^1$ is a C-linked 5-membered heteroaryl ring having 2-3 ring heteroatoms independently selected from N, O and S, wherein at least one of said heteroatoms is N, wherein the ring is optionally substituted by 1-2 substituents independently selected from (1-4C)alkyl and phenyl which is optionally substituted with one or more substituents independently selected from halogen and OMe.

In certain embodiments, hetAr$^1$ is a nitrogen-linked 5-membered heteroaryl ring having 2-3 ring heteroatoms independently selected from N, O and S, wherein at least one of said heteroatoms is N, wherein the ring is optionally substituted by one or more substituents independently selected from (1-4C)alkyl and phenyl which is optionally substituted with one or more substituents independently selected from halogen and OMe.

Examples of 5-membered heteroaryl rings include pyrrolyl, thiadiazolyl, thiazolyl, isoxazolyl, oxazolyl, and pyrazolyl rings.

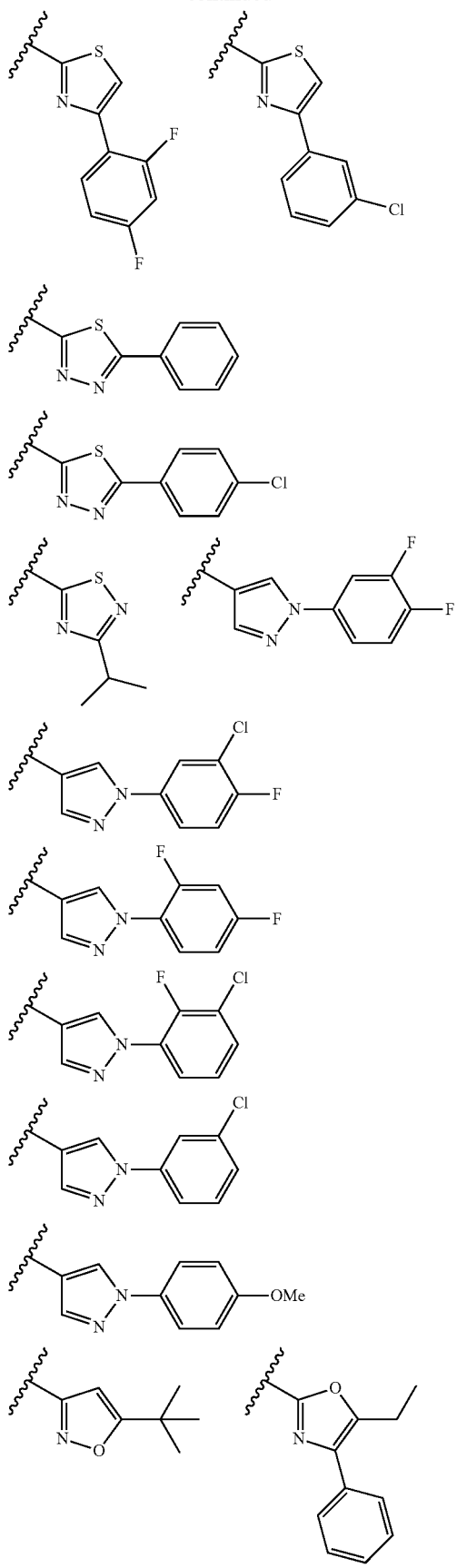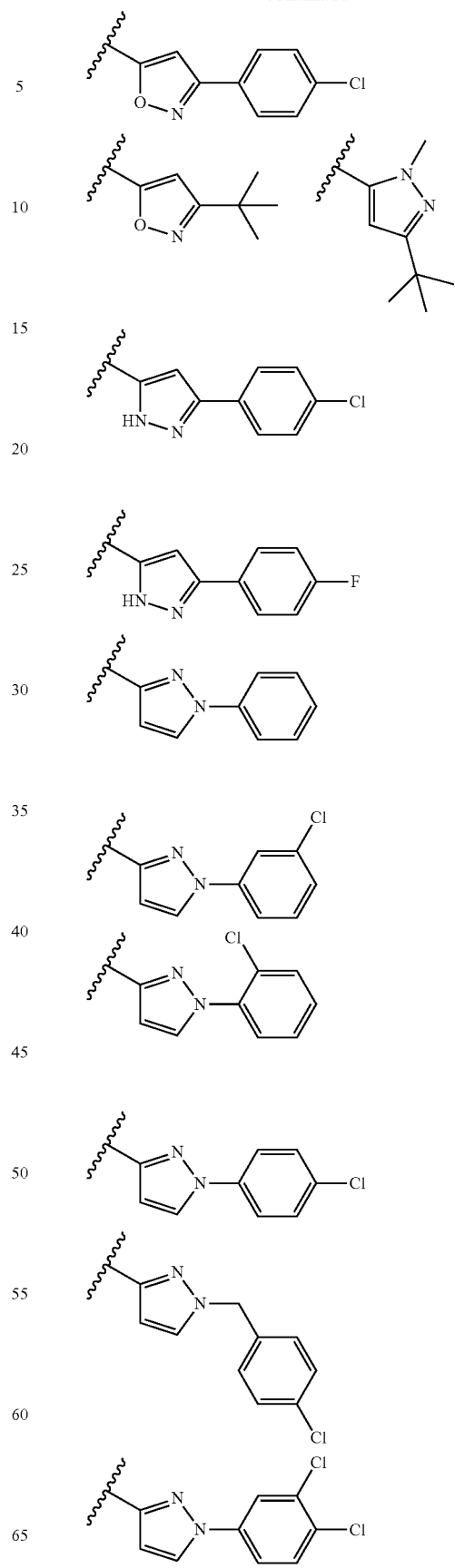

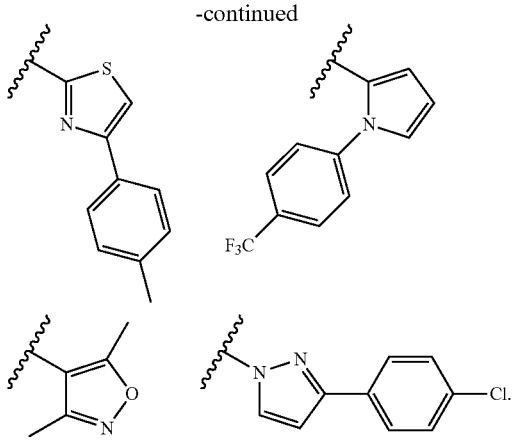

In certain embodiments, hetAr¹ is represented by any of the aforementioned 5-membered heteroaryl rings with the exception of the following structures:

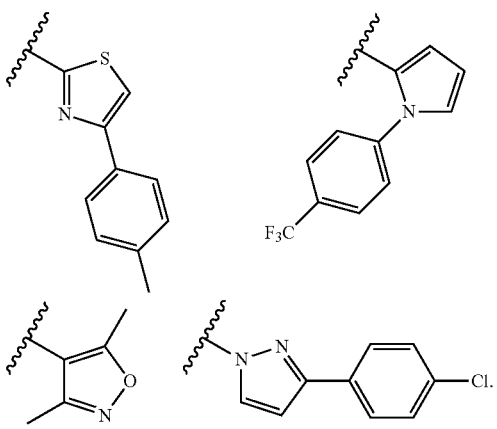

In certain embodiments, hetAr¹ is a 5,6-bicyclic heteroaryl having two ring heteroatoms independently selected from N, O and S, wherein at least one of said heteroatoms is N, wherein said ring is optionally substituted with one or more substituents independently selected from —O(1-6Calkyl), (1-6C)alkyl, halogen and $CF_3$. In certain embodiments, the 5,6-bicyclic heteroaryl is a 5-membered heteroaryl ring fused to a benzo ring, wherein the 5-membered heteroaryl ring has two ring heteroatoms independently selected from N, O and S, wherein at least one of said heteroatoms is N, wherein the bicyclic ring is optionally substituted. In certain embodiments, the bicyclic ring is optionally substituted with one or more substituents independently selected from methyl, $CF_3$, F, Cl and methoxy.

Examples of hetAr¹ when represented by a 5,6-bicyclic heteroaryl include the structures:

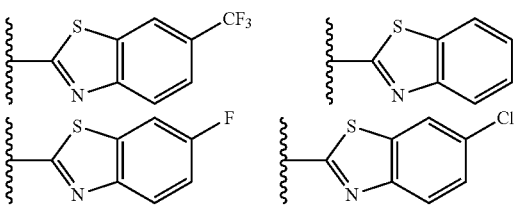

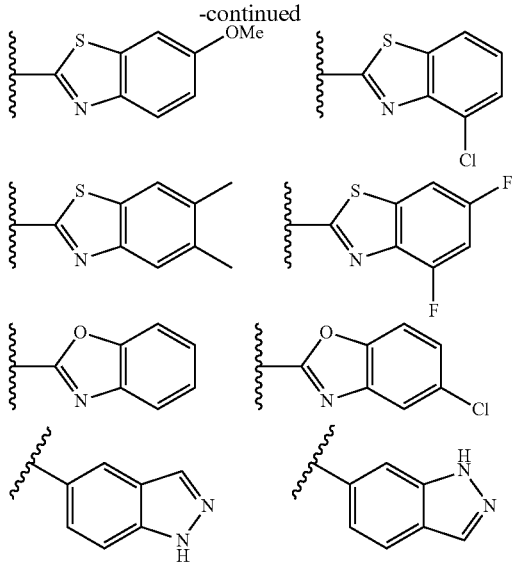

In certain embodiments, hetAr¹ is 2-oxopyridin-1(2H)-yl optionally substituted with halogen, for example chloro. A particular example of hetAr¹ is the structure:

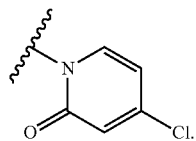 [SMILES: *n1ccc(Cl)cc1=O]

In one embodiment, A is hydrogen.
In one embodiment, A is Cl.
In one embodiment, A is CN.
In one embodiment, A is cyclopropyl.
In one embodiment, A is F.
In one embodiment, A is (1-3C)alkyl. A particular example is methyl
In one embodiment, A is OMe.
In one embodiment, A is CN, Cl, or cyclopropyl.
In one embodiment, A¹ is hydrogen.
In one embodiment, A¹ is Cl.
In one embodiment, A¹ is Br.
In one embodiment, A¹ is cyclopropyl.
In one embodiment, A¹ is F.
In one embodiment, A¹ is OMe.
In one embodiment, A¹ is H, cyclopropyl, Br, or Cl.
In one embodiment, A is CN, Cl, or cyclopropyl and A¹ is H, cyclopropyl, Br, or Cl.
In one embodiment, $R^{7a}$ and $R^{7b}$ are each hydrogen.
In one embodiment, $R^8$ is hydrogen.
In one embodiment, $R^{10}$ is hydrogen.
In one embodiment, $R^{10}$ is hydrogen.

In one embodiment, $R^{10}$ is Me.

In one embodiment, $R^{10}$ is $NH_2$.

According to another aspect, the present invention provides a process for the preparation a compound of Formula I or a pharmaceutically acceptable salt thereof, which comprises:

(a) for a compound of Formula I in which A is CN and $A^1$ is hydrogen, reacting a corresponding compound having the formula (II):

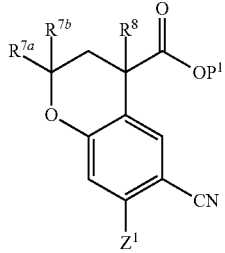

(II)

in which $P^1$ represents a hydrogen atom or a carboxyl protecting group and $Z^1$ represents a leaving atom or group, with a corresponding compound having the formula (III)

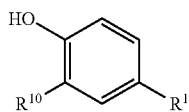

(III)

in the presence of a base; or (b) for a compound of Formula I in which A is H, Cl, (1-4C alkyl), OMe or cyclopropyl and $A^1$ is H, Cl, (1-4C alkyl), OMe or cyclopropyl, coupling a corresponding compound having the formula (IV)

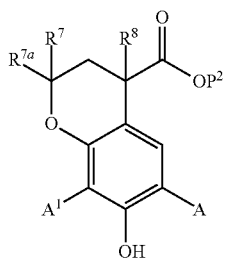

(IV)

in which $P^2$ is as defined for $P^1$, with a corresponding compound having the formula (V)

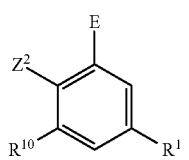

(V)

wherein E is an electron withdrawing group and $Z^2$ is a leaving atom, in the presence of a base, and if desired removing said electron withdrawing group; or (c) for a compound of Formula I in which A is H, Cl, (1-4C alkyl) or cyclopropyl and $A^1$ is (1-4C alkyl), Cl, Br or cyclopropyl, coupling a corresponding compound having the formula (VI)

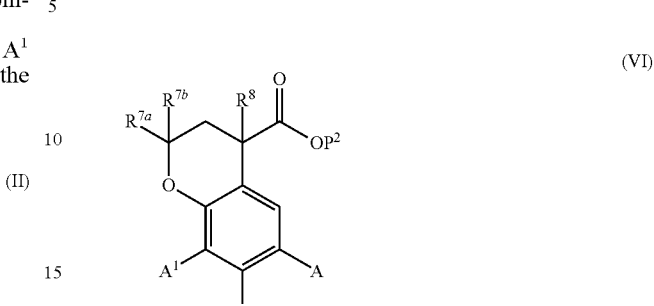

(VI)

in which $P^2$ is as defined for $P^1$, with a corresponding compound having the formula (VII)

(VII)

in the presence of a copper salt or a palladium catalyst in the presence of a ligand and a base; or (d) for a compound of Formula I in which $hetAr^1$ is a heteroaryl ring having the structure

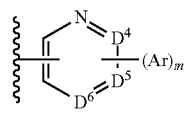

where m is 1, reacting a corresponding compound having the formula (VIIIa)

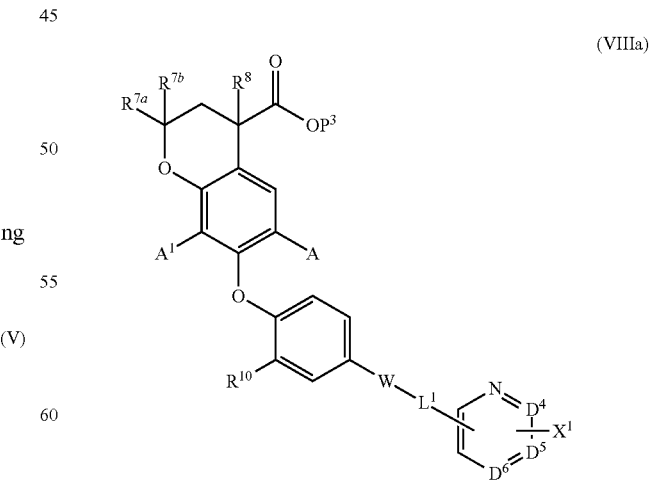

(VIIIa)

where $P^3$ is as defined for $P^1$, and $X^1$ is leaving atom or group, with a compound having the formula $ArB(OH)_2$ or ArZnBr in the presence of a palladium catalyst and a base; or (e) coupling a corresponding compound of formula (IX)

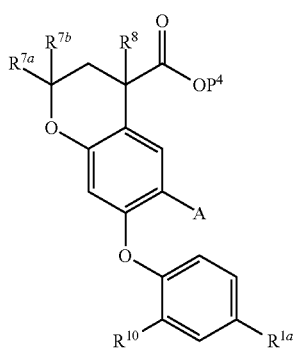

in which $P^4$ is as defined for $P^1$, and $R^{1a}$ represents $H$—$X^a H$ in which $X^a$ is HN or OC(=O), or a reactive derivative thereof; with a compound of formula (X)

$$R^1\text{-}L^1\text{-}X^b\text{—H} \qquad (X)$$

in which $X^b$ represents C(=O)O or NH, or a reactive derivative thereof;

(f) for a compound of Formula I where $L^1$ is a bond, reacting a corresponding compound having the formula (XI)

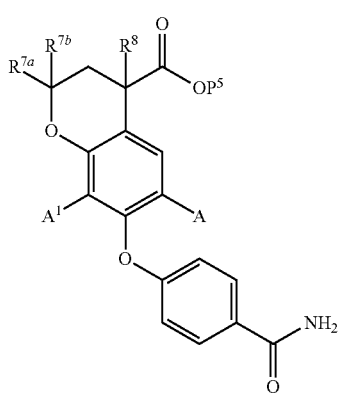

in which $P^5$ is as defined for $P^1$, with a compound having the formula $X^2$—$R^1$, where $X^2$ is a leaving group or atom, in the presence of a palladium catalyst and a ligand;

(g) for a compound of Formula I where A is cyclopropyl, $A^1$ is cyclopropyl, and W is C(=O)NH, reacting a corresponding compound having the formula (XII)

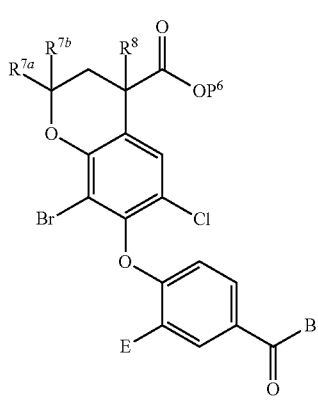

wherein $P^6$ is as defined for $P^1$, E is an electron withdrawing group, and B is —O-tert-butyl, —$NH_2$ or —NH-$L^1$-$R^1$, with about 4 equivalents of cyclopropylboronic acid in the presence of a suitable base, a metal catalyst and a ligand at temperatures between about 100° C. and 150° C., followed by removal of the electron withdrawing group, if desired, and coupling with a compound having the formula $H_2$N-$L^1$-$R^1$ when B is O-tBu or coupling with a compound having the formula $X^3$-$L^1$-$R^1$ when B is $NH_2$, where $X^3$ is a leaving group or atom; or (h) for a compound of Formula I where A is cyclopropyl, $A^1$ is hydrogen, and W is C(=O)NH, reacting a corresponding compound having the formula (XIII)

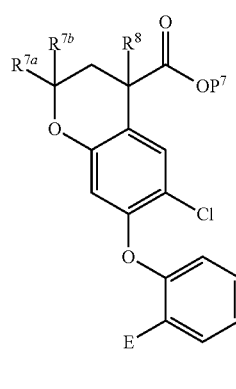

wherein $P^7$ is as defined for $P^1$, E is an electron withdrawing group, and B is O-tertbutyl, $NH_2$ or NH-$L^1$-$R^1$, with about 3 equivalents of cyclopropylboronic acid in the presence of a suitable base, a metal catalyst and a ligand at temperatures between about 90° C. and 150° C., for example 120° C., followed by removal of the electron withdrawing group, if desired, and coupling with a compound having the formula $H_2$N-$L^1$-$R^1$ when B is O-tBu or coupling with a compound having the formula $X^3$-$L^1$-$R^1$ when B is $NH_2$, where $X^3$ is a leaving group or atom; and removing any protecting group or groups and, if desired, forming a salt.

Referring to process (a), the leaving atom or group represented by $Z^1$ may be, for example, a halogen atom such as a fluorine atom. The carboxyl protecting group may be any convenient carboxyl protecting group, for example as described in Greene & Wuts, eds., "Protecting Groups in Organic Synthesis", John Wiley & Sons, Inc. Examples of carboxyl protecting groups include (1-6C)alkyl groups, such as methyl, ethyl and t-butyl. The base may be, for example, an alkali metal hydride or carbonate, such as sodium hydride, sodium carbonate or potassium carbonate, or a tertiary amine, such as triethylamine or N,N-diisopropylethylamine. Convenient solvents include amides, sulfoxides and nitriles, such as DMF, DMSO or acetonitrile. The reaction can be performed at an elevated temperature, such as in the range of from 50 to 150° C.

Compounds of formula (II) are known or can be prepared by treating the corresponding bromo derivative having formula (IIa)

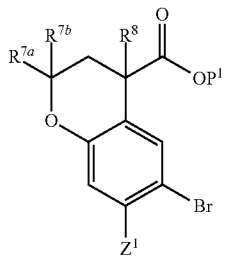

(IIa)

with Cu(I)CN in an appropriate solvent, such as N-methylpyrrolidone. The reaction is conveniently performed at elevated temperatures, for example between 100 and 200° C., such as at 160° C.

Compounds of formula (IIa) can be prepared by treating the corresponding derivative having formula (IIb)

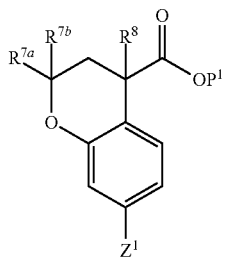

(IIb)

with N-bromosuccinimide in an appropriate solvent, such as DMF. The reaction is conveniently performed at temperatures between ambient temperature and 100° C., for example at 50° C.

Compounds of formula (IIb) wherein $R^8$ is Me can be prepared by reacting a corresponding compound of formula (IIb) wherein $R^8$ is H with methyl iodide in the presence of a suitable base, such as an alkali metal carbonate (e.g., sodium carbonate, potassium carbonate or cesium carbonate) or an alkali metal hydride (e.g., sodium hydride).

Compounds of formula (IIb) can be prepared by homologating a corresponding compound having formula (IIc)

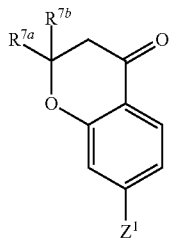

(IIc)

using methodologies known in the art, such as via enol ethers, epoxides, cyanohydrins, α,β-unsaturated sulfones, ketene thioacetals, glycidic esters, nitriles and α-acetoxyacrylonitriles, to add the one carbon unit. For example, in one embodiment, the compound of formula (IIc) can be treated with tetramethylsilylnitrile and a catalyst such as zinc iodide in a suitable solvent, for example DMF. The reaction is conveniently performed at ambient temperature.

Compound of formula (IIb) wherein $R^{7a}$ and $R^{7b}$ are each Me can be prepared by cyclizing a compound having the formula

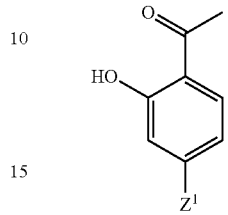

with 2-propanone in the presence of a suitable base, for example an amine base such as pyrrolidine. The reaction is conveniently preformed at elevated temperatures, such as between 50-100° C., for example 80° C.

Referring to process (b), examples of leaving atoms include F, Cl, Br and I. Examples of electron withdrawing groups include $NO_2$. In embodiments wherein the electron withdrawing group is $NO_2$, this group can be removed, if desired, by reducing the nitro group to an amino group using any convenient reducing conditions (for example, Zn and $NH_4Cl$) followed by cleavage of the amino group (for example, by treating the amino compound with isobutyl nitrite).

Compounds of the formula (IV) wherein $R^{7a}$, $R^{7b}$ and $R^8$ are H can be prepared by reacting a corresponding compound of formula (IVa)

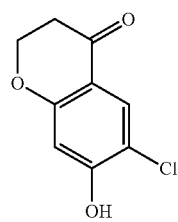

(IVa)

with trimethylsilanecarbonitrile in the presence of zinc (II) chloride, followed by treating the resulting intermediate with tin (II) chloride in the presence of an acid, for example acetic acid.

Compounds of the formula (IVa) can be prepared by cyclizing a compound having the formula (IVb)

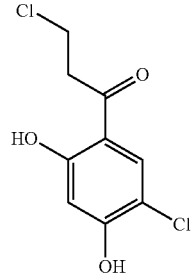

(IVb)

in the presence of a base, for example an alkali metal hydroxide such as sodium hydroxide.

Referring to process (c), suitable copper salts include copper (I) or copper (II) halides, for example copper (I) chloride. The copper salt can be used in catalytic, stoichiometric, or greater than stoichiometric amounts. In one embodiment, the reaction is performed using 2 equivalents of the copper salt. Suitable palladium catalysts include Pc(0) catalysts, for example Pd(PPh$_3$)$_4$. Suitable ligands include 2,2,6,6-tetramethyl-3,5-heptanedione, pyridine-type ligands, or phosphine-type ligands. The ligand is suitably used in catalytic amounts. The base may be, for example, an alkali metal carbonate, such as cesium carbonate, sodium carbonate, or potassium carbonate. Appropriate solvents include aprotic solvents such as N-methylpyrrolidinone, dimethylformamide, dimethylacetamide or dimethyl sulfoxide. The reaction is conveniently performed at elevated temperatures, for example between 50 and 200° C., for example 100° C.

Referring to process (d), the leaving atom can be, for example, a halogen, for example, bromide. An example of a leaving group is a triflate. Suitable palladium catalysts include Pd(PPh$_3$)$_4$, or a palladium (II) catalyst in the presence of a ligand, for example Pd$_2$dba$_3$, Pd(OAc)$_2$, or PdCl$_2$ in the presence of a ligand, for example a phosphine-type ligand. Suitable bases include alkali metal carbonates such as sodium carbonate, potassium carbonate or cesium carbonate. Suitable solvents include toluene or ethers (for example, THF or dioxane). The reaction is conveniently performed at temperatures ranging from ambient temperature to about 150° C., for example from ambient temperature to 110° C., for example 50-100° C.

Referring to process (e), the coupling of the compound of formula (VIII) with a compound of formula (IX) may be performed using conventional amide bond formation conditions, for example by reacting an amine with a reactive derivative of a carboxylic acid, for example an acid halide, such as an acid chloride. An example of A$^1$ when it represents a protected form of A is a group of formula —CH$_2$NR$^4$P$^8$ in which P$^8$ represents an amine protecting group. The amine protecting group may be any convenient amine protecting group, for example as described in Greene & Wuts, eds., "Protecting Groups in Organic Synthesis", John Wiley & Sons, Inc. Examples of amine protecting groups include acyl and alkoxycarbonyl groups, such as t-butoxycarbonyl (BOC).

Referring to process (f), the leaving atom can be, for example, a halogen, for example, bromide. An example of a leaving group is a triflate. Suitable palladium catalysts include Pd(PPh$_3$)$_4$, or a palladium (II) catalyst in the presence of a ligand, for example Pd$_2$dba$_3$, Pd(OAc)$_2$, or PdCl$_2$ in the presence of a ligand, for example a phosphine-type ligand such as XPHOS (dicyclohexyl(2',4',6'-triisopropylbiphenyl-2-yl)phosphine) or triphenylphosphine. Suitable solvents include toluene or ethers (for example, THF or dioxane).

Referring to processes (g) and (h), suitable bases include inorganic bases, for example alkali metal phosphates, such as potassium phosphate. Suitable catalysts include palladium catalysts, such as Pd(II) catalysts, for example Pd(OAc)$_2$ in the presence of a suitable ligand. The ligand can be a phosphine ligand, such as tricyclohexylphosphine. Examples of electron withdrawing groups include NO$_2$. In embodiments wherein the electron withdrawing group is NO$_2$, this group can be removed, if desired, by reducing the nitro group to an amino group using any convenient reducing conditions (for example, Zn and NH$_4$Cl) followed by cleavage of the amino group (for example, by treating the amino compound with isobutyl nitrite). Suitable solvents include xylene and toluene. The reaction is conveniently performed at the reflux temperature of the solvent.

Also provided herein is a compound of general Formula Ie:

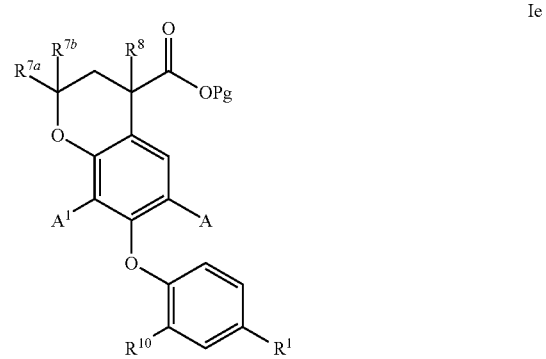

or a salt thereof, wherein:
Pg is a carboxyl protecting group;
A is H, CN, Cl, F, cyclopropyl, (1-4 C)alkyl or OMe;
A$^1$ is H, Cl, Br, F, cyclopropyl, (1-4 C)alkyl or OMe;
R$^1$ is —W-L$^1$-hetAr$^1$;
W is —CONR$^{3a}$— or —NR$^{3b}$CO—;
R$^{3a}$ and R$^{3b}$ are each H or methyl;
L$^1$ is a —(CR$^a$R$^b$)$_n$— or

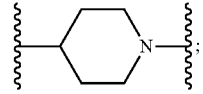

n is 0 or 2;
R$^a$ and R$^b$ are independently H, F, methyl, or cyclopropyl, or
R$^a$ and R$^b$ together with the carbon to which they are attached form a cyclopropyl ring;
hetAr$^1$ is heteroaryl ring selected from the structures:

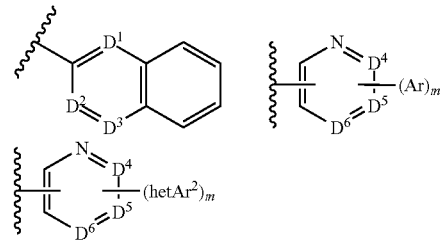

wherein m is 0 or 1 and each of said heteroaryl rings is optionally substituted with one or more R$^c$ substituents,
or hetAr$^1$ is a 5-membered heteroaryl ring having 1-3 ring heteroatoms independently selected from N, O and S, wherein at least one of said heteroatoms is N, wherein the ring is optionally substituted with one or more substituents independently selected from (1-4C)alkyl and phenyl which is optionally substituted with one or more substituents independently selected from halogen, —O(1-6Calkyl), (1-6C)alkyl and CF$_3$;
or hetAr$^1$ is a 5,6-bicyclic heteroaryl having two ring heteroatoms independently selected from N, O and S, wherein at least one of said heteroatoms is N, wherein said ring is optionally substituted with one or more substituents independently selected from —O(1-6Calkyl), (1-6C)alkyl, halogen and $CF_3$;

or hetAr$^1$ is 2-oxopyridin-1(2H)-yl optionally substituted with halogen;

one or two of D$^1$, D$^2$ and D$^3$ is N, the remainder being CH;
zero or one of D$^4$, D$^5$ and D$^6$ is N, the remainder being CH;
each R$^c$ is independently selected from halogen, $CF_3$, (1-6C)alkyl, —O(1-6C alkyl), cyclopropyl, —O—(CH$_2$CH$_2$)OMe, —S(1-6C alkyl), di(1-6C alkyl)amino, and a 5-6 membered azacycle;

Ar is phenyl optionally substituted with one or more R$^d$ substituents;

each R$^d$ is independently selected from (1-6C)alkyl, —O(1-6C)alkyl, halogen, —S(1-6C alkyl), and $CF_3$, or two adjacent R$^d$ substituents together with the atoms to which they are attached form a 5-6 membered oxacyclic ring;

hetAr$^2$ is pyridyl optionally substituted with one or more substituents independently selected from $CF_3$ and —O(1-6C alkyl);

R$^{7a}$, R$^{7b}$ and R$^8$ are independently H or methyl; and
R$^{10}$ is H, Me or NH$_2$.

The ability of test compounds to act as DP2 receptor inhibitors may be demonstrated by the assays described in Example A.

Compounds which are inhibitors of DP2 are useful in the treatment of diseases or disorders mediated by PGD$_2$, for example, diseases or disorders associated with overproduction or dysregulation of PGD$_2$.

Further, the compounds which are inhibitors of DP2 are useful in the treatment of diseases and disorders mediated by metabolites of PGD2 and other prostaglandins (and their corresponding metabolites) that may be acting via the DP2 receptor.

As used herein, the term treatment includes prophylaxis as well as treatment of an existing condition.

Examples of disorders or diseases that may be treated with compounds according to the invention include immunologic diseases. In addition, compounds of the invention may be useful for treating inflammatory diseases and disorders. Compounds of the invention may also be useful for treating itching/pruritis.

Examples of immunologic diseases include allergic inflammatory disease such as asthma, dermatitis, allergic rhinitis, urticaria, anaphylaxis, angioedema, allergies, contact hypersensitivity (e.g., nickel sensitivity), drug hypersensitivity, and allergic conjunctivitis in addition to inflammatory autoimmune diseases such as hyper-eosinophilic syndromes, psoriasis, systemic mast cell disorders, chronic obstructive pulmonary disease, inflammatory bowel disease, and arthritis.

Particular examples of immunologic diseases include allergic inflammatory diseases, such as asthma, atopic dermatitis, allergic rhinitis, seasonal allergies, food allergies, contact hypersensitivity (e.g., nickel sensitivity), hyper-eosinophilic syndromes, and allergic conjunctivitis.

Further examples of allergic inflammatory diseases include asthma (including mild-to-moderate asthma, severe asthma, refractory asthma, steroid-resistant asthma, teroid-insensitive asthma, and exercise-induced asthma), allergies such as severe allergy/anaphylaxis, food allergies, plant allergies, drug allergies, latex allergy, allergic reactions to venomous stings, seasonal allergic rhinitis, and perennial allergic rhinitis, chronic rhinosinusitis, cystic fibrosis, eosinophilic diseases and disorders (including eosinophilic gastroenteritis, eosinophilic esophagitis, acute eosinophilic pneumonia, chronic eosinophilic pneumonia, pulmonary eosinophilia (Loeffler's Disease), eosinophilia-myalgia syndrome, Chrug-Strauss syndrome, eosinophilic fasciitis, familial eosinophilic cellulitis, cutaneous eosinophilia, nonallergic rhinitis with eosinophilia syndrome, familial eosinophilia, and drug reaction with eosinophilia and systemic symptoms), hyper IgE syndrome, allergic diseases of the gastrointestinal tract, celiac sprue, gluten enteropathy, gluten intolerance, acute hypersensitivy reaction, and delayed hypersensitivity reaction.

Further examples of allergic inflammatory diseases include severe allergy/anaphylaxis, eosinophilic gastroenteritis, eosinophilic esophagitis, severe asthma, refractory asthma, steroid-resistance asthma, allergic diseases of the gastrointestinal tract, celiac sprue, gluten enteropathy, gluten intolerance, acute hypersensitivy reaction, and delayed hypersensitivity reaction.

Additional diseases or disorders which may be treated with the compounds of this invention include inflammatory bowel diseases such as Crohn's disease, ulcerative colitis, ileitis and enteritis, vasculitis, Behcet's syndrome, psoriasis and inflammatory dermatoses such as dermatitis, eczema, urticaria, viral cutaneous pathologies such as those derived from human papillomavirus, HIV or RLV infection, bacterial, fungal and other parasital cutaneous pathologies, and cutaneous lupus erythematosus, respiratory allergic diseases such as persensitivity lung diseases, chronic obstructive pulmonary disease and the like, autoimmune diseases, such as arthritis (including rheumatoid and psoriatic), systemic lupus erythematosus, type I diabetes, myasthenia gravis, multiple sclerosis, Graves' disease, glomerulonephritis and the like, graft rejection (including allograft rejection and graft-v-host disease), e.g., skin graft rejection, solid organ transplant rejection, bone marrow transplant rejection, fever, cardiovascular disorders such as acute heart failure, hypotension, hypertension, angina pectoris, myocardial infarction, cardiomyopathy, congestive heart failure, atherosclerosis, coronary artery disease, restenosis, thrombosis and vascular stenosis, cerebrovascular disorders such as traumatic brain injury, stroke, ischemic reperfusion injury and aneurysm, cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system, fibrosis, connective tissue disease and sarcoidosis, genital and reproductive conditions such as erectile dysfunction, gastrointestinal disorders such as gastritis, ulcers, nausea, pancreatitis and vomiting; neurological disorders, such as Alzheimer's disease, sleep disorders such as insomnia, narcolepsy, sleep apnea syndrome and Pickwick Syndrome, pain, renal disorders, ocular disorders such as glaucoma, infectious diseases, viral infections such as HIV, and bacterial infections such as sepsis, inflammation, flushing, nasal congestion, and otitis media.

Additional diseases or disorders which may be treated with compounds of this invention include inflammatory bowel diseases such as IgA deficiency, inflammatory dermatoses such as chronic urticaria, acute urticaria, seborrheic dermatitis, contact dermatitis, pemphigus, and exfoliative dermatitis (etythroderma), dermatitis herpetiformis, trichinosis, visceral larva migraines, trichuriasis, ascariasis, strongyloidiasis, hookworm infection, clonorchiasis, pragonimiasis, fascioliasis, cysticerosis, echinococcosis, filariasis, schistocomiasis, brucellosis, cat scratch fever, infectious lymphocytosis, acute coccidiodomycosis, infectious mononucleosis, mycobacterial disease, scarlet fever, tuberculosis, and cutaneous lupus erythematosus, respiratory allergic diseases such as hypersensitivity lung diseases, allergic broncopulmonary aspergillosis, tropical pulmonary eosinophilia, and the like, autoimmune diseases such as mastocytosis, leukocytoclastic vasculitis, urticarial vasculitis, basophilic leukocytosis, adrenal hypofunction and the like, cardiovascular disorders such as Coombs'-positive hemolytic anemias, Hashimoto's thyroiditis, Goodpasture's syndrome, serum sickness, polyarteritis nodosa, Dressler's syndrome, Wiskott-Aldrich syndrome, scleroderma, cirrhosis, and sarcoidosis, and ocular disorders such as vernal keratoconjunctivitis, atopic keartoconjunctivitis, giant papullary conjunctvitis.

Accordingly, another aspect of this invention provides a method of treating diseases or medical conditions in a mammal mediated by PGD2, comprising administering to said mammal one or more compounds of Formula I or a pharmaceutically acceptable salt or prodrug thereof in an amount effective to treat or prevent said disorder.

Another aspect of this invention provides a method of treating diseases or medical conditions in a mammal mediated by the DP2 receptor comprising administering to said mammal one or more compounds of Formula I or a pharmaceutically acceptable salt or prodrug thereof in an amount effective to treat or prevent said disorder.

Another aspect of this invention provides a method of treating diseases or medical conditions in a mammal involving the Th2 T cell via production of IL-4, IL-5 and/or IL-13 comprising administering to said mammal one or more compounds of Formula I or a pharmaceutically acceptable salt or prodrug thereof in an amount effective to treat or prevent said disorder.

Another aspect of this invention provides a method of treating diseases or medical conditions in a mammal involving the activation and trafficking of granulocytes (mast cell, eosinophil, neutrophil, basophil, etc.) comprising administering to said mammal one or more compounds of Formula I or a pharmaceutically acceptable salt or prodrug thereof in an amount effective to treat or prevent said disorder.

The phrase "effective amount" means an amount of compound that, when administered to a mammal in need of such treatment, is sufficient to (i) treat or prevent a particular disease, condition, or disorder mediated by PGD2, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional drugs that work by the same or a different mechanism of action. Examples include anti-inflammatory compounds, steroids (e.g., dexamethasone, cortisone and fluticasone), NSAIDs (e.g., ibuprofen, indomethacin, and ketoprofen), anti-histamines, and anti-leukotrienes (e.g., Singulair®).

The compounds of the invention may be administered by any convenient route, e.g., by dermal application (i.e., topical application to the skin), transdermally, or into the gastrointestinal tract (e.g. rectally or orally), nose, lungs (e.g., via inhalation), musculature or vasculature. In particular embodiments, a compound of Formula I is administered topically to the skin or by inhalation.

The compounds may be administered in any convenient administrative form, e.g., creams, tablets, powders, capsules, solutions, dispersions, suspensions, syrups, sprays, suppositories, gels, emulsions, and drug delivery devices such as patches, etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

According to another aspect, the present invention provides a compound of Formula I or a pharmaceutically acceptable salt thereof, for use in therapy, for example, in the treatment of a $PGD_2$-mediated condition, for example an immunologic disorder, as defined hereinabove.

According to a further aspect, the present invention provides the use of a compound of Formula I or a pharmaceutically acceptable salt thereof, in the manufacture of a medicament to treat a $PGD_2$-mediated condition, for example an immunologic disorder, as defined hereinabove.

Particular compounds of the invention include:
7-(4-((5-(Trifluoromethyl)pyridin-2-yl)carbamoyl)phenoxy)-6-cyanochroman-4-carboxylic acid;
7-(4-(5-Chloropyridin-2-ylcarbamoyl)phenoxy)-6-cyanochroman-4-carboxylic acid;
6-Cyano-7-(4-(quinolin-2-ylcarbamoyl)phenoxy)chroman-4-carboxylic acid;
6-Cyano-7-(4-(quinoxalin-2-ylcarbamoyl)phenoxy)chroman-4-carboxylic acid;
7-(4-(6-Chloroquinolin-2-ylcarbamoyl)phenoxy)-6-cyanochroman-4-carboxylic acid;
7-(4-((6-(Trifluoromethyl)pyridin-3-yl)carbamoyl)phenoxy)-6-cyanochroman-4-carboxylic acid;
6-Cyano-7-(4-(8-methoxyquinolin-3-ylcarbamoyl)phenoxy)chroman-4-carboxylic acid;
7-(4-(6-Chloroquinazolin-2-ylcarbamoyl)phenoxy)-6-cyanochroman-4-carboxylic acid;
6-Cyano-7-(4-(isoquinolin-3-ylcarbamoyl)phenoxy)chroman-4-carboxylic acid
6-Cyano-7-(4-(quinolin-3-ylcarbamoyl)phenoxy)chroman-4-carboxylic acid;
6-Cyano-7-(4-(quinolin-3-ylcarbamoyl)phenoxy)chroman-4-carboxylic acid;
6-Cyano-7-(4-(2-(6-(trifluoromethyl)pyridin-3-yl)ethylcarbamoyl)phenoxy)chroman-4-carboxylic acid;
6-Cyano-7-(4-(6-(3,4-dimethylphenyl)pyridin-2-ylcarbamoyl)phenoxy)chroman-4-carboxylic acid;
6-Cyano-7-(2-methyl-4-(6-(trifluoromethyl)pyridin-3-ylcarbamoyl)phenoxy)chroman-4-carboxylic acid;
6-Chloro-7-(4-(6-chloroquinoxalin-2-ylcarbamoyl)phenoxy)chroman-4-carboxylic acid;
6-Chloro-7-(4-(6-(trifluoromethyl)quinolin-2-ylcarbamoyl)phenoxy)chroman-4-carboxylic acid;
6-Chloro-7-(4-(7-chloroquinolin-2-ylcarbamoyl)phenoxy)chroman-4-carboxylic acid;

6-Chloro-7-(4-(6-fluoroquinolin-2-ylcarbamoyl)phenoxy)chroman-4-carboxylic acid;
6-Chloro-7-(4-(5-chloroquinolin-2-ylcarbamoyl)phenoxy)chroman-4-carboxylic acid;
6-Chloro-7-(4-(7-chloroquinoxalin-2-ylcarbamoyl)phenoxy)chroman-4-carboxylic acid;
6-Chloro-7-(4-(4-methylquinolin-2-ylcarbamoyl)phenoxy)chroman-4-carboxylic acid;
6-Chloro-7-(4-(6-methoxyquinolin-2-ylcarbamoyl)phenoxy)chroman-4-carboxylic acid;
6-Chloro-7-(4-(quinolin-2-ylcarbamoyl)phenoxy)chroman-4-carboxylic acid;
6-Chloro-7-(4-(8-methylquinolin-2-ylcarbamoyl)phenoxy)chroman-4-carboxylic acid;
6-Chloro-7-(4-(8-chloroquinolin-2-ylcarbamoyl)phenoxy)chroman-4-carboxylic acid;
6-Chloro-7-(4-(3-methylquinolin-2-ylcarbamoyl)phenoxy)chroman-4-carboxylic acid;
6-chloro-7-(4-(6-phenylpyridin-2-ylcarbamoyl)phenoxy)chroman-4-carboxylic acid;
6-Chloro-7-(4-(6-(trifluoromethyl)pyridin-2-ylcarbamoyl)phenoxy)chroman-4-carboxylic acid;
6-Chloro-7-(4-(6-(trifluoromethyl)pyridin-3-ylcarbamoyl)phenoxy)chroman-4-carboxylic acid;
6-Chloro-7-(4-(6-chloroquinolin-2-ylcarbamoyl)phenoxy)chroman-4-carboxylic acid;
6-Chloro-7-(4-(4-(trifluoromethyl)pyridin-2-ylcarbamoyl)phenoxy)chroman-4-carboxylic acid;
6-Chloro-7-(4-(6-phenylpyrazin-2-ylcarbamoyl)phenoxy)chroman-4-carboxylic acid;
6-Chloro-7-(4-(6-(4-chlorophenyl)pyridin-2-ylcarbamoyl)phenoxy)chroman-4-carboxylic acid;
6-Chloro-7-(4-(6-(3-chlorophenyl)pyridin-2-ylcarbamoyl)phenoxy)chroman-4-carboxylic acid;
6-chloro-7-(4-(6-chloroquinolin-2-ylcarbamoyl)phenoxy)chroman-4-carboxylic acid;
6-Chloro-7-(4-(6-chloroquinolin-2-ylcarbamoyl)phenoxy)chroman-4-carboxylic acid, Enantiomer 1;
6-Chloro-7-(4-(6-chloroquinolin-2-ylcarbamoyl)phenoxy)chroman-4-carboxylic acid, Enantiomer 2;
6-Cyano-7-(4-(2-(5-(trifluoromethyl)pyridin-2-yl)ethylcarbamoyl)phenoxy)chroman-4-carboxylic acid;
6-Cyano-7-(4-(6-(3,4-dimethylphenyl)pyridin-2-ylcarbamoyl)phenoxy)chroman-4-carboxylic acid;
6-Cyano-7-(4-(6-(2,3-dimethylphenyl)pyridin-2-ylcarbamoyl)-phenoxy)-chroman-4-carboxylic acid;
6-Cyano-7-(4-(6-(3-(trifluoromethyl)phenyl)pyridin-2-ylcarbamoyl)-phenoxy)-chroman-4-carboxylic acid;
6-Cyano-7-(4-(6-(4-(trifluoromethyl)phenyl)pyridin-2-ylcarbamoyl)-phenoxy)-chroman-4-carboxylic acid;
6-Cyano-7-(4-(6-(2,3-dihydrobenzofuran-5-yl)pyridin-2-ylcarbamoyl)-phenoxy)-chroman-4-carboxylic acid;
6-Chloro-7-(4-(6-(4-chlorophenyl)-5-fluoropyridin-2-ylcarbamoyl)phenoxy)chroman-4-carboxylic acid;
6-Chloro-7-(4-(8-methylquinolin-2-ylcarbamoyl)phenoxy)chroman-4-carboxylic acid;
6-Chloro-7-(4-(4-methylquinolin-2-ylcarbamoyl)phenoxy)chroman-4-carboxylic acid;
6-Chloro-7-(4-(5-chloroquinolin-2-ylcarbamoyl)phenoxy)chroman-4-carboxylic acid;
6-Cyano-7-(4-(6-(2,4-dichlorophenyl)pyridin-2-ylcarbamoyl)phenoxy)chroman-4-carboxylic acid;
7-(4-(6-(3-Chlorophenyl)pyridin-2-ylcarbamoyl)phenoxy)-6-cyanochroman-4-carboxylic acid;
7-(4-(6-(4-Chlorophenyl)pyridin-2-ylcarbamoyl)phenoxy)-6-cyanochroman-4-carboxylic acid;
6-Chloro-7-(4-(6-(3,4-dichlorophenyl)pyridin-2-ylcarbamoyl)phenoxy)chroman-4-carboxylic acid;
6-Chloro-7-(4-(6-(4-chloro-3-(trifluoromethyl)phenyl)pyridin-2-ylcarbamoyl)phenoxy)chroman-4-carboxylic acid;
6-chloro-7-(4-(6'-methoxy-2,3'-bipyridin-6-ylcarbamoyl)phenoxy)chroman-4-carboxylic acid;
6-chloro-7-(4-(2',6'-dimethoxy-2,3'-bipyridin-6-ylcarbamoyl)phenoxy)chroman-4-carboxylic acid;
6-Chloro-7-(4-(6-(2-chlorophenyl)pyridin-2-ylcarbamoyl)phenoxy)chroman-4-carboxylic acid;
6-Chloro-7-(4-(6-p-tolylpyridin-2-ylcarbamoyl)phenoxy)chroman-4-carboxylic acid;
6-Chloro-7-(4-(6-(4-methoxyphenyl)pyridin-2-ylcarbamoyl)phenoxy)chroman-4-carboxylic acid;
6-chloro-7-(4-(6-(2-chloro-4-(trifluoromethyl)phenyl)pyridazin-3-ylcarbamoyl)phenoxy)chroman-4-carboxylic acid;
6-chloro-7-(4-(6-(3-chloro-4-(trifluoromethyl)phenyl)pyridazin-3-ylcarbamoyl)phenoxy)chroman-4-carboxylic acid;
6-chloro-7-(4-(5-(4-(trifluoromethyl)phenyl)pyrazin-2-ylcarbamoyl)phenoxy)chroman-4-carboxylic acid;
6-chloro-7-(4-(6-p-tolylpyridazin-3-ylcarbamoyl)phenoxy)chroman-4-carboxylic acid;
6-chloro-7-(4-(6-(4-methoxyphenyl)pyridazin-3-ylcarbamoyl)phenoxy)chroman-4-carboxylic acid;
6-chloro-7-(4-(6-(4-(methylthio)phenyl)pyridazin-3-ylcarbamoyl)phenoxy)chroman-4-carboxylic acid;
6-chloro-7-(4-(6-(3,4-dichlorophenyl)pyridazin-3-ylcarbamoyl)phenoxy)chroman-4-carboxylic acid;
6-chloro-7-(4-(6-(4-fluorophenyl)pyridazin-3-ylcarbamoyl)phenoxy)chroman-4-carboxylic acid;
6-chloro-7-(4-(6-(4-chloro-3-fluorophenyl)pyridazin-3-ylcarbamoyl)phenoxy)chroman-4-carboxylic acid;
6-chloro-7-(4-(6-(6-methoxypyridin-3-yl)pyridazin-3-ylcarbamoyl)phenoxy)chroman-4-carboxylic acid;
6-chloro-7-(4-(6-(2,6-dimethoxypyridin-3-yl)pyridazin-3-ylcarbamoyl)phenoxy)chroman-4-carboxylic acid;
6-chloro-7-(4-(6-(2-fluoro-4-(trifluoromethyl)phenyl)pyridazin-3-ylcarbamoyl)phenoxy)chroman-4-carboxylic acid;
6-chloro-7-(4-(6-(2,4-difluorophenyl)pyridazin-3-ylcarbamoyl)phenoxy)chroman-4-carboxylic acid;
6-chloro-7-(4-(6-(4-chloro-2-fluorophenyl)pyridazin-3-ylcarbamoyl)phenoxy)chroman-4-carboxylic acid;
6-Chloro-7-(4-(6'-methoxy-3,3'-bipyridin-6-ylcarbamoyl)phenoxy)chroman-4-carboxylic acid;
6-Chloro-7-(4-(2',6'-dimethoxy-3,3'-bipyridin-6-ylcarbamoyl)phenoxy)chroman-4-carboxylic acid;
6-Chloro-7-(4-(6-(3-(trifluoromethyl)phenyl)pyridin-3-ylcarbamoyl)phenoxy)chroman-4-carboxylic acid;
6-Chloro-7-(4-(6-(4-(trifluoromethyl)phenyl)pyridin-3-ylcarbamoyl)phenoxy)chroman-4-carboxylic acid;
6-Chloro-7-(4-(6-phenylpyrazin-2-ylcarbamoyl)phenoxy)chroman-4-carboxylic acid;
6-Chloro-7-(4-(6-ethoxypyridin-2-ylcarbamoyl)phenoxy)chroman-4-carboxylic acid;
6-chloro-7-(4-(6-(4-chlorophenyl)pyrazin-2-ylcarbamoyl)phenoxy)chroman-4-carboxylic acid;
6-chloro-7-(4-(2-(2-methoxy-6-(trifluoromethyl)pyridin-3-yl)ethylcarbamoyl)phenoxy)chroman-4-carboxylic acid;
6-Chloro-7-(4-(6-(3,4-difluorophenyl)pyridin-2-ylcarbamoyl)phenoxy)chroman-4-carboxylic acid;
6-Chloro-7-(4-(6-(2,4-difluorophenyl)pyridin-2-ylcarbamoyl)phenoxy)chroman-4-carboxylic acid;
6-Chloro-7-(4-(6-(4-(methylthio)phenyl)pyridin-2-ylcarbamoyl)phenoxy)chroman-4-carboxylic acid;

6-Chloro-7-(4-(6-(4-fluoro-3-methylphenyl)pyridin-2-yl-carbamoyl)phenoxy)chroman-4-carboxylic acid;
7-(4-(6-(4-tert-Butylphenyl)pyridin-2-ylcarbamoyl)phenoxy)-6-chlorochroman-4-carboxylic acid;
6-Chloro-7-(4-(6-(4-chloro-3-fluorophenyl)pyridin-2-ylcarbamoyl)phenoxy)chroman-4-carboxylic acid;
6-chloro-7-(4-(6-(4-chloro-2-fluorophenyl)pyridin-2-ylcarbamoyl)phenoxy)chroman-4-carboxylic acid;
6-Chloro-7-(4-(6-(3-fluoro-4-methylphenyl)pyridin-2-yl-carbamoyl)phenoxy)chroman-4-carboxylic acid;
6-chloro-7-(4-(6-(3,5-difluorophenyl)pyridin-2-ylcarbamoyl)phenoxy)chroman-4-carboxylic acid;
6-chloro-7-(4-(6-(2,3-difluorophenyl)pyridin-2-ylcarbamoyl)phenoxy)chroman-4-carboxylic acid;
7-(4-(6-(tert-Butylthio)pyridin-2-ylcarbamoyl)phenoxy)-6-chlorochroman-4-carboxylic acid;
6-Chloro-7-(4-(6-(3-chlorophenyl)pyrazin-2-ylcarbamoyl)phenoxy)chroman-4-carboxylic acid;
6-Chloro-7-(4-(6-(4-(trifluoromethyl)phenyl)pyrazin-2-yl-carbamoyl)phenoxy)chroman-4-carboxylic acid;
6-chloro-7-(4-(6-(3-(trifluoromethyl)phenyl)pyrazin-2-yl-carbamoyl)phenoxy)chroman-4-carboxylic acid;
6-chloro-7-(4-(5-(4-chlorophenyl)pyrazin-2-ylcarbamoyl)phenoxy)chroman-4-carboxylic acid;
6-Chloro-7-(4-(5-(3-chlorophenyl)pyrazin-2-ylcarbamoyl)phenoxy)chroman-4-carboxylic acid;
6-Chloro-7-(4-(6-(3-chlorophenyl)pyridazin-3-ylcarbamoyl)phenoxy)chroman-4-carboxylic acid;
6-chloro-7-(4-(6-(4-(trifluoromethyl)phenyl)pyridazin-3-yl-carbamoyl)phenoxy)chroman-4-carboxylic acid;
6-chloro-7-(4-(6-(3-(trifluoromethyl)phenyl)pyridazin-3-yl-carbamoyl)phenoxy)chroman-4-carboxylic acid;
6-chloro-7-(4-(2-(4-chlorophenyl)pyrimidin-4-ylcarbamoyl)phenoxy)chroman-4-carboxylic acid;
6-chloro-7-(4-(6-(4-chlorophenyl)-2-methylpyrimidin-4-yl-carbamoyl)phenoxy)chroman-4-carboxylic acid;
6-chloro-7-(4-(6-methyl-2-(4-(trifluoromethyl)phenyl)pyrimidin-4-ylcarbamoyl)phenoxy)chroman-4-carboxylic acid;
6-chloro-7-(4-(6-(2,4-dichlorophenyl)pyridin-2-ylcarbamoyl)phenoxy)chroman-4-carboxylic acid;
6-chloro-7-(4-(6-(4-chloro-2-methoxyphenyl)pyridin-2-yl-carbamoyl)phenoxy)chroman-4-carboxylic acid;
6-Chloro-7-(4-(6-isobutylpyridin-2-ylcarbamoyl)phenoxy)chroman-4-carboxylic acid;
8-bromo-6-chloro-7-(4-(6-(4-chlorophenyl)pyridin-2-ylcarbamoyl)phenoxy)chroman-4-carboxylic acid;
7-(4-(6-(4-chlorophenyl)pyridin-2-ylcarbamoyl)phenoxy)-6,8-dicyclopropylchroman-4-carboxylic acid;
6-chloro-7-(4-(6-(4-chlorophenyl)pyridin-2-ylcarbamoyl)phenoxy)-8-cyclopropylchroman-4-carboxylic acid;
6-Chloro-7-(4-(6-(4-fluorophenyl)pyridin-2-ylcarbamoyl)phenoxy)chroman-4-carboxylic acid;
6-Chloro-7-(4-(6-(4-(trifluoromethyl)phenyl)pyridin-2-yl-carbamoyl)phenoxy)chroman-4-carboxylic acid;
6-Chloro-7-(4-(6-cyclopropylpyridin-2-ylcarbamoyl)phenoxy)chroman-4-carboxylic acid;
6-Chloro-7-(4-(6-(3-(trifluoromethyl)phenyl)pyridin-2-yl-carbamoyl)phenoxy)chroman-4-carboxylic acid;
6-Chloro-7-(4-(2'-(trifluoromethyl)-2,4'-bipyridin-6-ylcarbamoyl)phenoxy)chroman-4-carboxylic acid;
7-(4-(6-tert-Butylpyridin-2-ylcarbamoyl)phenoxy)-6-chlorochroman-4-carboxylic acid;
6-Chloro-7-(4-(5-(4-chlorophenyl)pyridin-2-ylcarbamoyl)phenoxy)chroman-4-carboxylic acid;
6-Chloro-7-(4-(5-(3-chlorophenyl)pyridin-2-ylcarbamoyl)phenoxy)chroman-4-carboxylic acid;
6-Chloro-7-(4-(5-(2-chlorophenyl)pyridin-2-ylcarbamoyl)phenoxy)chroman-4-carboxylic acid;
6-Chloro-7-(4-(5-(4-(trifluoromethyl)phenyl)pyridin-2-yl-carbamoyl)phenoxy)chroman-4-carboxylic acid;
6-Chloro-7-(4-(5-(3-(trifluoromethyl)phenyl)pyridin-2-yl-carbamoyl)phenoxy)chroman-4-carboxylic acid;
6-Chloro-7-(4-(4-(4-chlorophenyl)pyridin-2-ylcarbamoyl)phenoxy)chroman-4-carboxylic acid;
6-Chloro-7-(4-(4-(3-chlorophenyl)pyridin-2-ylcarbamoyl)phenoxy)chroman-4-carboxylic acid;
6-Chloro-7-(4-(4-(2-chlorophenyl)pyridin-2-ylcarbamoyl)phenoxy)chroman-4-carboxylic acid;
6-Chloro-7-(4-(6-(4-chlorophenyl)pyridin-3-ylcarbamoyl)phenoxy)chroman-4-carboxylic acid;
6-Chloro-7-(4-(6-(3-chlorophenyl)pyridin-3-ylcarbamoyl)phenoxy)chroman-4-carboxylic acid;
6-Chloro-7-(4-(6-(2-chlorophenyl)pyridin-3-ylcarbamoyl)phenoxy)chroman-4-carboxylic acid;
6-Chloro-7-(4-(5-(4-chlorophenyl)pyridin-3-ylcarbamoyl)phenoxy)chroman-4-carboxylic acid;
6-Chloro-7-(4-(5-(3-chlorophenyl)pyridin-3-ylcarbamoyl)phenoxy)chroman-4-carboxylic acid;
6-Chloro-7-(4-(2-(4-chlorophenyl)pyridin-4-ylcarbamoyl)phenoxy)chroman-4-carboxylic acid;
6-Chloro-7-(4-(2-(3-chlorophenyl)pyridin-4-ylcarbamoyl)phenoxy)chroman-4-carboxylic acid;
6-Chloro-7-(4-(4-(4-(trifluoromethyl)phenyl)pyrimidin-2-ylcarbamoyl)phenoxy)chroman-4-carboxylic acid;
6-Chloro-7-(4-(4-(3-(trifluoromethyl)phenyl)pyrimidin-2-ylcarbamoyl)phenoxy)chroman-4-carboxylic acid;
6-Chloro-7-(4-(4-(4-chlorophenyl)pyrimidin-2-ylcarbamoyl)phenoxy)chroman-4-carboxylic acid;
6-Chloro-7-(4-(4-(3-chlorophenyl)pyrimidin-2-ylcarbamoyl)phenoxy)chroman-4-carboxylic acid;
6-Chloro-7-(4-(5-(3-chlorophenyl)pyrimidin-2-ylcarbamoyl)phenoxy)chroman-4-carboxylic acid;
6-Chloro-7-(4-(2-(3-chlorophenyl)pyrimidin-5-ylcarbamoyl)phenoxy)chroman-4-carboxylic acid;
6,8-Dichloro-7-(4-(6-(4-chlorophenyl)pyrazin-2-ylcarbamoyl)phenoxy)chroman-4-carboxylic acid;
6,8-Dichloro-7-(4-(2-(4-chlorophenyl)pyrimidin-4-ylcarbamoyl)phenoxy)chroman-4-carboxylic acid;
6-chloro-7-(4-(2-(3,5-dichloropyridin-2-yl)ethylcarbamoyl)phenoxy)chroman-4-carboxylic acid;
6-chloro-7-(4-(2-(2-(dimethylamino)-6-(trifluoromethyl)pyridin-3-yl)ethylcarbamoyl)phenoxy)chroman-4-carboxylic acid;
6-chloro-7-(4-(2-(2,6-dimethoxypyridin-3-yl)ethylcarbamoyl)phenoxy)chroman-4-carboxylic acid;
6-Chloro-7-(4-(6-(4-chlorophenyl)pyridin-2-ylcarbamoyl)phenoxy)chroman-4-carboxylic acid, Enantiomer 1;
6-Chloro-7-(4-(6-(4-chlorophenyl)pyridin-2-ylcarbamoyl)phenoxy)chroman-4-carboxylic acid, Enantiomer 2;
6,8-dichloro-7-(4-(6-(4-chlorophenyl)pyridin-2-ylcarbamoyl)phenoxy)-chroman-4-carboxylic acid;
6,8-dichloro-7-(4-(6-chloroquinolin-2-ylcarbamoyl)phenoxy)chroman-4-carboxylic acid;
6,8-dichloro-7-(4-(6-(3-chlorophenyl)pyridin-3-ylcarbamoyl)phenoxy)-chroman-4-carboxylic acid;
6-Cyano-7-(4-(5-phenyl-1,3,4-thiadiazol-2-ylcarbamoyl)phenoxy)chroman-4-carboxylic acid;
7-(4-(5-(4-chlorophenyl)-1,3,4-thiadiazol-2-ylcarbamoyl)phenoxy)-6-cyanochroman-4-carboxylic acid;
6-chloro-7-(4-(5-phenyl-1,3,4-thiadiazol-2-ylcarbamoyl)phenoxy)chroman-4-carboxylic acid;
6-chloro-7-(4-(5-(4-chlorophenyl)-1,3,4-thiadiazol-2-ylcarbamoyl)phenoxy)chroman-4-carboxylic acid;

7-(4-(4-tert-butylthiazol-2-ylcarbamoyl)phenoxy)-6-chloro-chroman-4-carboxylic acid;
7-(4-(5-tert-butyl-4-methylthiazol-2-ylcarbamoyl)phenoxy)-6-chlorochroman-4-carboxylic acid;
6-chloro-7-(4-(4-(4-chlorophenyl)thiazol-2-ylcarbamoyl)phenoxy)chroman-4-carboxylic acid;
6-chloro-7-(4-(4-(4-fluorophenyl)thiazol-2-ylcarbamoyl)phenoxy)chroman-4-carboxylic acid;
6-chloro-7-(4-(4-(3,4-difluorophenyl)thiazol-2-ylcarbamoyl)phenoxy)chroman-4-carboxylic acid;
6-chloro-7-(4-(4-(2,4-difluorophenyl)thiazol-2-ylcarbamoyl)phenoxy)chroman-4-carboxylic acid;
6-chloro-7-(4-(4-isopropylthiazol-2-ylcarbamoyl)phenoxy)chroman-4-carboxylic acid;
6-chloro-7-(4-(4-(3-chlorophenyl)thiazol-2-ylcarbamoyl)phenoxy)chroman-4-carboxylic acid;
7-(4-(5-tert-butylisoxazol-3-ylcarbamoyl)phenoxy)-6-chlorochroman-4-carboxylic acid;
6-chloro-7-(4-(5-ethyl-4-phenyloxazol-2-ylcarbamoyl)phenoxy)chroman-4-carboxylic acid;
6-chloro-7-(4-(3-isopropyl-1,2,4-thiadiazol-5-ylcarbamoyl)phenoxy)chroman-4-carboxylic acid;
6-chloro-7-(4-(3-(4-chlorophenyl)isoxazol-5-ylcarbamoyl)phenoxy)chroman-4-carboxylic acid;
7-(4-(3-tert-butylisoxazol-5-ylcarbamoyl)phenoxy)-6-chlorochroman-4-carboxylic acid;
6-chloro-7-(4-(3-phenyl-1,2,4-thiadiazol-5-ylcarbamoyl)phenoxy)chroman-4-carboxylic acid;
6-chloro-7-(4-(1-(3-chlorophenyl)-1H-pyrazol-4-ylcarbamoyl)phenoxy)chroman-4-carboxylic acid;
6,8-dichloro-7-(4-(1-(3-chlorophenyl)-1H-pyrazol-4-ylcarbamoyl)phenoxy)chroman-4-carboxylic acid;
6-chloro-7-(4-(1-(3,4-difluorophenyl)-1H-pyrazol-3-ylcarbamoyl)phenoxy)chroman-4-carboxylic acid;
6-chloro-7-(4-(1-(3-chloro-4-fluorophenyl)-1H-pyrazol-3-ylcarbamoyl)phenoxy)chroman-4-carboxylic acid;
6-chloro-7-(4-(1-(2,4-difluorophenyl)-1H-pyrazol-3-ylcarbamoyl)phenoxy)chroman-4-carboxylic acid;
6-chloro-7-(4-(1-(3-chloro-2-fluorophenyl)-1H-pyrazol-3-ylcarbamoyl)phenoxy)chroman-4-carboxylic acid;
6-chloro-7-(4-(1-(4-methoxyphenyl)-1H-pyrazol-3-ylcarbamoyl)phenoxy)chroman-4-carboxylic acid;
6-chloro-7-(4-(1-phenyl-1H-pyrazol-3-ylcarbamoyl)phenoxy)chroman-4-carboxylic acid;
6-chloro-7-(4-(1-(3-chlorophenyl)-1H-pyrazol-3-ylcarbamoyl)phenoxy)chroman-4-carboxylic acid;
6-chloro-7-(4-(1-(3,4-dichlorophenyl)-1H-pyrazol-3-ylcarbamoyl)phenoxy)chroman-4-carboxylic acid;
6-chloro-7-(4-(1-(2-chlorophenyl)-1H-pyrazol-3-ylcarbamoyl)phenoxy)chroman-4-carboxylic acid;
6-chloro-7-(4-(1-(4-chlorophenyl)-1H-pyrazol-3-ylcarbamoyl)phenoxy)chroman-4-carboxylic acid;
6-cyano-7-(4-(5-methylthiazol-2-ylcarbamoyl)phenoxy)chroman-4-carboxylic acid;
6-cyano-7-(4-(4-methylthiazol-2-ylcarbamoyl)phenoxy)chroman-4-carboxylic acid;
7-(4-(3-tert-butyl-1-methyl-1H-pyrazol-5-ylcarbamoyl)phenoxy)-6-chlorochroman-4-carboxylic acid;
6-chloro-7-(4-(1-(4-chlorobenzyl)-1H-pyrazol-3-ylcarbamoyl)phenoxy)chroman-4-carboxylic acid;
6-Chloro-7-(4-(3-(4-chlorophenyl)-1H-pyrazol-5-ylcarbamoyl)phenoxy)chroman-4-carboxylic acid;
6-Chloro-7-(4-(3-(4-fluorophenyl)-1H-pyrazol-5-ylcarbamoyl)phenoxy)chroman-4-carboxylic acid;
Enantiomer 2 of 6-Chloro-7-(4-(6-(4-chlorophenyl)pyridin-2-ylcarbamoyl)phenoxy)chroman-4-carboxylic acid;
6-Chloro-7-(4-(6-(trifluoromethyl)benzo[d]thiazol-2-ylcarbamoyl)phenoxy)chroman-4-carboxylic acid;
6-Chloro-7-(4-(2-(6-cyclopropyl-2-methoxypyridin-3-yl)ethylcarbamoyl)phenoxy)chroman-4-carboxylic acid;
Enantiomer 2 of 6-Chloro-7-(4-(6-(4-(trifluoromethyl)phenyl)pyridazin-3-ylcarbamoyl)phenoxy)chroman-4-carboxylic acid;
6-Chloro-7-(4-(2-(2-cyclopropyl-6-(trifluoromethyl)pyridin-3-yl)ethylcarbamoyl)phenoxy)chroman-4-carboxylic acid;
6-chloro-7-(4-(2-(6-cyclopropyl-2-(dimethylamino)pyridin-3-yl)ethylcarbamoyl)phenoxy)chroman-4-carboxylic acid;
7-(4-(benzo[d]oxazol-6-ylcarbamoyl)phenoxy)-6-cyanochroman-4-carboxylic acid;
6-cyano-7-(4-(2-methylbenzo[d]thiazol-6-ylcarbamoyl)phenoxy)chroman-4-carboxylic acid;
6-cyano-7-(4-(3-methylbenzo[d]isothiazol-5-ylcarbamoyl)phenoxy)chroman-4-carboxylic acid;
6-cyano-7-(4-(2-(trifluoromethyl)-1H-benzo[d]imidazol-6-ylcarbamoyl)phenoxy)chroman-4-carboxylic acid;
7-(4-(1H-indazol-5-ylcarbamoyl)phenoxy)-6-cyanochroman-4-carboxylic acid;
7-(4-(1H-indazol-6-ylcarbamoyl)phenoxy)-6-cyanochroman-4-carboxylic acid;
7-(4-(benzo[d]thiazol-2-ylcarbamoyl)phenoxy)-6-cyanochroman-4-carboxylic acid;
6-cyano-7-(4-(6-fluorobenzo[d]thiazol-2-ylcarbamoyl)phenoxy)chroman-4-carboxylic acid;
7-(4-(6-chlorobenzo[d]thiazol-2-ylcarbamoyl)phenoxy)-6-cyanochroman-4-carboxylic acid;
6-cyano-7-(4-(6-methoxybenzo[d]thiazol-2-ylcarbamoyl)phenoxy)chroman-4-carboxylic acid;
6-cyano-7-(4-(2-(3,5-dimethylisoxazol-4-yl)ethylcarbamoyl)phenoxy)chroman-4-carboxylic acid;
7-(4-(4-chlorobenzo[d]thiazol-2-ylcarbamoyl)phenoxy)-6-cyanochroman-4-carboxylic acid;
6-cyano-7-(4-(5,6-dimethylbenzo[d]thiazol-2-ylcarbamoyl)phenoxy)chroman-4-carboxylic acid;
6-cyano-7-(4-(6-(trifluoromethyl)benzo[d]thiazol-2-ylcarbamoyl)phenoxy)chroman-4-carboxylic acid;
6-cyano-7-(4-(4,6-difluorobenzo[d]thiazol-2-ylcarbamoyl)phenoxy)chroman-4-carboxylic acid;
7-(4-(benzo[d]oxazol-2-ylcarbamoyl)phenoxy)-6-cyanochroman-4-carboxylic acid;
7-(4-(5-(4-chlorophenyl)-1,3,4-thiadiazol-2-ylcarbamoyl)phenoxy)-6-cyanochroman-4-carboxylic acid;
6-cyano-7-(4-(4-p-tolylthiazol-2-ylcarbamoyl)phenoxy)chroman-4-carboxylic acid;
(R)-6-chloro-7-(4-(6-(4-chlorophenyl)pyridin-2-ylcarbamoyl)phenoxy)chroman-4-carboxylic acid;
6-chloro-7-(4-(6-chlorobenzo[d]thiazol-2-ylcarbamoyl)phenoxy)chroman-4-carboxylic acid;
6-chloro-7-(4-(5-chlorobenzo[d]oxazol-2-ylcarbamoyl)phenoxy)chroman-4-carboxylic acid;
7-(4-(6-(tert-butylthio)pyridin-2-ylcarbamoyl)phenoxy)-6-chlorochroman-4-carboxylic acid;
6-chloro-7-(4-(6-(4-chlorophenyl)pyridazin-3-ylcarbamoyl)phenoxy)chroman-4-carboxylic acid;
(S)-6,8-dichloro-7-(4-(1-(3-chlorophenyl)-1H-pyrazol-3-ylcarbamoyl)phenoxy)chroman-4-carboxylic acid;
6-chloro-7-(4-(1-(6-(trifluoromethyl)pyridin-2-yl)piperidin-4-ylcarbamoyl)phenoxy)chroman-4-carboxylic acid;
6-chloro-7-(4-(2-(1-(4-(trifluoromethyl)phenyl)-1H-pyrrol-2-yl)ethylcarbamoyl)phenoxy)chroman-4-carboxylic acid;

6-chloro-7-(4-(2-(2-ethoxypyridin-3-yl)ethylcarbamoyl)
phenoxy)chroman-4-carboxylic acid;
6-chloro-7-(4-(2-(6-(4-methoxyphenyl)pyridin-2-yl)ethyl-
carbamoyl)phenoxy)chroman-4-carboxylic acid;
6-chloro-7-(4-(2-(6'-methoxy-2,3'-bipyridin-6-yl)ethylcar-
bamoyl)phenoxy)chroman-4-carboxylic acid;
6-chloro-7-(4-(2-(4-chloro-2-oxopyridin-1(2H)-yl)ethylcar-
bamoyl)phenoxy)chroman-4-carboxylic acid;
6-chloro-7-(4-(2-(6-methoxypyridin-3-yl)ethylcarbamoyl)
phenoxy)chroman-4-carboxylic acid;
6-chloro-7-(4-(2-(6-methoxypyridin-2-yl)ethylcarbamoyl)
phenoxy)chroman-4-carboxylic acid;
6-chloro-7-(4-(2-(3-(4-chlorophenyl)-1H-pyrazol-1-yl)eth-
ylcarbamoyl)phenoxy)chroman-4-carboxylic acid;
6-chloro-7-(4-(2-(2,4-dimethoxypyrimidin-5-yl)ethylcar-
bamoyl)phenoxy)chroman-4-carboxylic acid;
6-chloro-7-(4-(2-(6-(2-chlorophenyl)pyridin-2-yl)ethylcar-
bamoyl)phenoxy)chroman-4-carboxylic acid;
7-(4-(2-(4-tert-butylthiazol-2-yl)ethylcarbamoyl)phenoxy)-
6-chlorochroman-4-carboxylic acid;
6-chloro-7-(4-(2-(2-cyclopropylpyridin-3-yl)ethylcarbam-
oyl)phenoxy)chroman-4-carboxylic acid;
6-chloro-7-(4-(2-(2-(2-chlorophenyl)pyridin-3-yl)ethylcar-
bamoyl)phenoxy)chroman-4-carboxylic acid;
6-chloro-7-(4-(2-(2-(dimethylamino)pyridin-3-yl)ethylcar-
bamoyl)phenoxy)chroman-4-carboxylic acid;
6-chloro-7-(4-(2-(2-(piperidin-1-yl)pyridin-3-yl)ethylcar-
bamoyl)phenoxy)chroman-4-carboxylic acid;
6-chloro-7-(4-(2-(2-methoxypyridin-3-yl)ethylcarbamoyl)
phenoxy)chroman-4-carboxylic acid;
6-chloro-7-(4-(2-(2-isopropoxypyridin-3-yl)ethylcarbam-
oyl)phenoxy)chroman-4-carboxylic acid;
and salts thereof. Particular mention is made of the sodium salt of the aforementioned compounds.

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane ($CH_2Cl_2$, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$H NMR spectra were obtained as $CDCl_3$, D6 DMSO or $CD_3OD$ solutions (reported in ppm), using tetramethylsilane (0.00 ppm) or residual solvent ($CDCl_3$: 7.25 ppm; $CD_3OD$: 3.31 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

EXAMPLE A

DP-2 Binding Inhibition Assays

The coding sequence of human DP2 was introduced into the human Leukemic cell line K562 by electroporation and stable clones expressing DP2 were obtained by limiting dilution followed by cell surface staining with a rat monoclonal antibody specific for human DP2. Membranes were prepared from one of these DP2 expressing clones and used to determine the ability of the compounds of the present invention to inhibit binding of prostaglandin D2 (PGD2) to its receptor DP2 in the presence of one or more of the following serum protein concentrations, 0.1% BSA, 1% HSA or 4% HSA, by the following procedure. Membranes (1.25 μg/well for 0.1% BSA and 6 μg/well for 1% or 4% HSA) were mixed with $^3$H-labeled $PGD_2$ and various concentrations of test compounds in 150 μL of binding buffer (50 mM Tris-HCl, pH 7.4, 40 mM $MgCl_2$, 0.1% bovine serum albumin, 0.1% $NaN_3$) in 96-well U-bottom polypropylene plates. After incubation for 60 minutes at room temperature, the assay was transferred to a filtration plate (#MAFB; Millipore Corporation, Bedford, Mass.), and washed three times with binding buffer. Radioactivity was measured by a scintillation counter (TopCount; PerkinElmer Life Sciences, Boston, Mass.). Nonspecific binding was determined by incubations in the presence of 1 μM unlabeled $PGD_2$ or 5 μM of a known DP2 antagonist. $IC_{50}$ values for inhibition of binding were determined for each compound tested from the inflexion point of a standard 4-parameter logistical curve fitted to the values obtained. Compounds of the invention had $IC_{50}$ values less than 5 micromolar in one or more of the binding assays. Certain compounds of the invention had $IC_{50}$ values less than 1 micromolar in one or more of the binding assays. Certain compounds of the invention had $IC_{50}$ values less than 0.5 micromolar in one or more of the binding assays. Certain compounds of the invention had $IC_{50}$ values less than 0.25 micromolar in one or more of the binding assays.

When certain compounds of the invention prepared as racemic mixtures were separated to isolate each enantiomer, it was found that one enantiomer was more potent than the other enantiomer when tested in a DP2 binding inhibition assay as described above.

$EC_{50}$ values for compounds of the invention when tested in a DP2 binding inhibition assay as described above are provided in Table A.

TABLE A

| Ex. | $EC_{50}$ (nM) 4% HSA | $EC_{50}$ (nM) 1% HSA | $EC_{50}$ (nM) 0.1% BSA |
|---|---|---|---|
| 1 | | | 19.3 |
| 2 | | | 26.7 |
| 3 | | 481.9 | 12.8 |
| 4 | | 369.8 | 27.7 |
| 5 | 357.3 | 136.8 | 5.9 |
| 6 | | 523.6 | 16.9 |
| 7 | 2065.4 | | |
| 8 | 695 | | |
| 9 | 774.5 | | |
| 10 | | | 37.8 |
| 11 | | 183.2 | 47.6 |
| 12 | 666.8 | | |
| 13 | 45.1 | | |
| 14 | | | 55.8 |
| 15 | 409 | 206.5 | 17.9 |
| 16 | 141.9 | | |
| 17 | 177.8 | | |
| 18 | 185.4 | | |
| 19 | 210.4 | | |
| 20 | 254.7 | | |
| 21 | 265.5 | | |
| 22 | 465.6 | | |
| 23 | 586.1 | | |
| 24 | 763.8 | | |
| 25 | 5984.1 | | |
| 26 | 1909.9 | | |
| 27 | 173.4 | | |
| 28 | 187 | | |
| 29 | 49.5 | 660.7 | 34.7 |

TABLE A-continued

| Ex. | $EC_{50}$ (nM) 4% HSA | $EC_{50}$ (nM) 1% HSA | $EC_{50}$ (nM) 0.1% BSA |
|---|---|---|---|
| 30 | 134 | 119.7 | 13.0 |
| 31 | 1733.8 | | |
| 32 | 400.9 | | |
| 33 | 30 | | |
| 34 | 241 | | |
| 35 | 134 | 119.7 | 13.0 |
| 36 enantiomer 1 | 84 | | |
| 37 enantiomer 2 | 4000 | | |
| 38 | | 183.2 | 47.6 |
| 39 | 45.1 | | |
| 40 | 119.7 | | |
| 41 | 50.8 | | |
| 42 | 36.1 | | |
| 43 | 291.1 | | |
| 44 | 5000 | | |
| 45 | 763.8 | | |
| 46 | 265.5 | | |
| 47 | 210.4 | | |
| 48 | 173.4 | | |
| 49 | 87.3 | | |
| 50 | 134.9 | | |
| 51 | 51.3 | | |
| 52 | 50.8 | | |
| 53 | 40.9 | | |
| 54 | 336.5 | | |
| 55 | 258.2 | | |
| 56 | 582.1 | | |
| 57 | 39.4 | | |
| 58 | 67 | | |
| 59 | 282.5 | | |
| 60 | 63 | | |
| 61 | 539.5 | | |
| 62 | 327.3 | | |
| 63 | 1455.5 | | |
| 64 | 343.6 | | |
| 65 | 96.2 | | |
| 66 | 306 | | |
| 67 | 203 | | |
| 68 | 869 | | |
| 69 | 1778.3 | | |
| 70 | 437.5 | | |
| 71 | 1506.6 | | |
| 72 | 1109.2 | | |
| 73 | 959.4 | | |
| 74 | 794.3 | | |
| 75 | 149 | | |
| 76 | 100.7 | | |
| 77 | 400.9 | | |
| 78 | 739.6 | | |
| 79 | 105 | | |
| 80 | 25.1 | | |
| 81 | 97.9 | | |
| 82 | 119.9 | | |
| 83 | 71.3 | | |
| 84 | 144.5 | | |
| 85 | 22.5 | | |
| 86 | 49.5 | | |
| 87 | 41.4 | | |
| 88 | 55.5 | | |
| 89 | 250.6 | | |
| 90 | 166 | | |
| 91 | 897.4 | | |
| 92 | 415 | | |
| 93 | 80.5 | | |
| 94 | 208.4 | | |
| 95 | 364.8 | | |
| 96 | 274.2 | | |
| 97 | 202.8 | | |
| 98 | 112 | | 17.9 |
| 99 | 235 | | |
| 100 | 46 | | |
| 101 | 997.7 | | |
| 102 | 21.2 | | |
| 103 | 57.1 | | |
| 104 | 116.4 | | |
| 105 | 133 | | |
| 106 | 87.7 | | |
| 107 | 52.2 | | |
| 108 | 144 | | 8 |
| 109 | 128.8 | | |
| 110 | 25.2 | | |
| 111 | 1462.2 | | |
| 112 | 46 | | |
| 113 | 451.9 | | |
| 114 | 276.1 | | |
| 115 | 342 | | |
| 116 | 82.8 | | |
| 117 | 264.2 | | |
| 118 | 100 | | |
| 119 | 421.7 | | |
| 120 | 2729 | | |
| 121 | 1892.3 | | |
| 122 | 2576.3 | | |
| 123 | 294.4 | | |
| 124 | 133 | | |
| 125 | 626.6 | | |
| 126 | 468.8 | | |
| 127 | 690.2 | | |
| 128 | 595.7 | | |
| 129 | 437.5 | | |
| 130 | 138.7 | | |
| 131 | 128.5 | | |
| 132 | 128.2 | | |
| 133 | 260.6 | | |
| 134 | 425.6 | | |
| 135 | 313.3 | | |
| 136 | 441.6 | | |
| 137 | 80.9 | | |
| 138 | 687.1 | | |
| 139 | 40 | | |
| 140 | 106.9 | | |
| 141 | 3917.4 | | |
| 142 | 21.7 | | |
| 143 | 83.4 | | |
| 144 | 299.2 | | |
| 145 | 160 | | |
| 146 | 727.8 | | |
| 147 | 3443 | | |
| 148 | 5457.6 | | |
| 149 | 1663.4 | | |
| 150 | 32.7 | | |
| 151 | 473.2 | | |
| 152 | 45.3 | | |
| 153 | 67.5 | | |
| 154 | 59 | | |
| 155 | 68.9 | | |
| 156 | 157 | | |
| 157 | 16.6 | | |
| 158 | 154.9 | | |
| 159 | 437.5 | | |
| 160 | 849.2 | | |
| 161 | 74.6 | | |
| 162 | 1600 | | |
| 163 | 563.6 | | |
| 164 | 143.2 | | |
| 165 | 187.5 | | |
| 166 | 85.1 | | |
| 167 | 46.8 | | |
| 168 | 111.7 | | |
| 169 | 76 | | |
| 170 | 292.4 | | |
| 171 | 97.5 | | |
| 172 | 55 | | |
| 173 | 22.9 | | |
| 174 | 47.1 | | |
| 175 | 80.7 | | |
| 176 | | | 62.7 |
| 177 | | | 68.2 |
| 178 | 950.6 | | |
| 179 | 247.2 | | |
| 180 | 406.4 | | |
| 181 | 312.6 | | |

TABLE A-continued

| Ex. | EC$_{50}$ (nM) 4% HSA | EC$_{50}$ (nM) 1% HSA | EC$_{50}$ (nM) 0.1% BSA |
|---|---|---|---|
| 182 | 22 | | |
| 183 | 45.8 | | |
| 184 | 42.1 | | |
| 185 | 60 | | 1.2 |
| 186 | 32.6 | | |
| 187 | 45.2 | | |
| 188 | | | 301.3 |
| 189 | | | 43.3 |
| 190 | | | 49.3 |
| 191 | | 137.4 | 41.5 |
| 192 | | | 492 |
| 193 | | | 36.7 |
| 194 | | 1238.8 | 10.7 |
| 195 | | 194.1 | 12.9 |
| 196 | | 352.4 | 11 |
| 197 | | 145.9 | 9.3 |
| 198 | | | 1238.8 |
| 199 | | | 10.8 |
| 200 | | | 7.6 |
| 201 | 355 | | 5.1 |
| 202 | | | 24.5 |
| 203 | | | 69 |
| 204 | 3443.5 | | |
| 205 | 96.2 | | |
| 206 | 5000 | | |
| 207 | 105 | | |
| 208 | 736.2 | | |
| 209 | 207 | | |
| 210 | 160.7 | | |
| 211 | 420.7 | | |
| 212 | 3006.1 | | |
| 213 | 188.4 | | |
| 214 | 1352.1 | | |
| 215 | 1603.2 | | |
| 216 | 2228.4 | | |
| 217 | 1367.7 | | |
| 218 | 403.6 | | |
| 219 | 1374 | | |
| 220 | 379.3 | | |
| 221 | 961.6 | | |
| 222 | 1071.5 | | |
| 223 | 209.9 | | |
| 224 | 997.7 | | |
| 225 | 663.7 | | |
| 226 | 1923.1 | | |
| 227 | 857 | | |
| 228 | 195 | | |

Preparation A

Preparation of 4-(6,8-dichloro-4-(ethoxycarbonyl)chroman-7-yloxy)benzoic acid

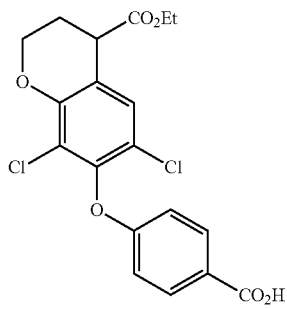 [SMILES: CCOC(=O)C1CCOc2c1cc(Cl)c(Oc1ccc(C(=O)O)cc1)c2Cl]

Step A: Preparation of ethyl 6,8-dichloro-7-hydroxychroman-4-carboxylate

To a solution of ethyl 6-chloro-7-hydroxychroman-4-carboxylate (5.04 g, 19.6 mmol) in 50 mL of DMF was added of n-chlorosuccinimide (2.74 g, 20.5 mmol). The resulting mixture was heated at 60° C. for 40 minutes and poured into water. The reaction was extracted with ethyl acetate and the combined organics were washed with brine, dried over sodium sulfate, filtered and concentrated. The crude product was dissolved in dichloromethane, concentrated onto silica gel and purified by flash column chromatography, eluting with 25% ethyl acetate in hexanes to give ethyl 6,8-dichloro-7-hydroxychroman-4-carboxylate (3.5 g, 61.2% yield) as a an oil which was used without further characterization.

Step B: Preparation of ethyl 7-(4-(tert-butoxycarbonyl)-2-nitrophenoxy)-6,8-dichlorochroman-4-carboxylate A mixture of ethyl 6,8-dichloro-7-hydroxychroman-4-carboxylate (2.50 g, 8.59 mmol), tert-butyl 4-fluoro-3-nitrobenzoate (2.20 g, 9.12 mmol) and potassium carbonate (1.8 g, 13 mmol) in 50 mL of NMP was degassed with argon for 10 minutes and was heated at 80° C. overnight. After stirring overnight the reaction mixture was cooled to ambient temperature and diluted with 600 mL of water. The pH was adjusted to 1-2 with 1 N HCl and the resulting solids were collected by filtration. The solids were dissolved in ethyl acetate and the solution was washed with brine, dried over sodium sulfate, filtered and concentrated. The crude product was purified by flash column chromatography, eluting with 20% ethyl acetate in hexanes to give ethyl 7-(4-(tert-butoxycarbonyl)-2-nitrophenoxy)-6,8-dichlorochroman-4-carboxylate (2.74 g, 62.3% yield) as an oil.

Step C: Preparation of ethyl 7-(2-amino-4-(tert-butoxycarbonyl)phenoxy)-6,8-dichlorochroman-4-carboxylate To a mixture of ethyl 7-(4-(tert-butoxycarbonyl)-2-nitrophenoxy)-6,8-dichlorochroman-4-carboxylate (2.70 g, 5.27 mmol) in 25 mL of THF and 25 mL of saturated ammonium chloride was added zinc dust (3.45 g, 52.7 mmol) under argon. After 1 hour at ambient temperature, the reaction was diluted with ethyl acetate and filtered. The biphasic filtrate was separated and the organic layer was washed with brine. The organic layer was dried over sodium sulfate, filtered and concentrated. The crude product was dissolved in dichloromethane, concentrated onto silica gel and purified by flash column chromatography, eluting with 20% ethyl acetate in hexanes to give ethyl 7-(2-amino-4-(tert-butoxycarbonyl)phenoxy)-6,8-dichlorochroman-4-carboxylate (2.20 g, 86.5% yield) as a white foam. MS (ESI) m/z=482 (M+H).

Step D: Preparation of ethyl 7-(4-(tert-butoxycarbonyl)phenoxy)-6,8-dichlorochroman-4-carboxylate To a solution of ethyl 7-(2-amino-4-(tert-butoxycarbonyl)phenoxy)-6,8-dichlorochroman-4-carboxylate (2.1 g, 4.4 mmol) in 20 mL of DMF at 70° C. was added isobutyl nitrite (1.29 mL, 10.9 mmol) dropwise over ten minutes. After an additional 15 minutes the reaction was cooled to ambient temperature and poured into 600 mL of water. The product was extracted with ethyl acetate and the combined organics were washed with brine, dried over sodium sulfate, filtered and concentrated. The crude product was dissolved in dichloromethane, concentrated onto silica gel and purified by flash column chromatography, eluting with 20% ethyl acetate in hexanes to give ethyl 7-(4-(tert-butoxycarbonyl)phenoxy)-6,8-dichlorochroman-4-carboxylate (1.85 g, 90.9% yield) as a foam.

Step E: Preparation of 4-(6,8-dichloro-4-(ethoxycarbonyl)chroman-7-yloxy)benzoic acid:

To a solution of ethyl 7-(4-(tert-butoxycarbonyl)phenoxy)-6,8-dichlorochroman-4-carboxylate (1.85 g, 3.96 mmol) in 20 mL of DCM was added trifluoroacetic acid (10 mL). After stirring at ambient temperature for 1 hour, the mixture was concentrated to a sticky residue. The residue was dissolved in ethyl acetate and washed successively with saturated sodium bicarbonate and brine. The solution was dried over sodium sulfate and filtered. The filtrate was concentrated to give 4-(6,8-dichloro-4-(ethoxycarbonyl)chroman-7-yloxy)benzoic acid (1.85 g, 90.9% yield) as a powder. $^1$H NMR (400 MHz, CDCl$_3$) δ 8.07 (d, J=8.8 Hz, 2H), 7.35 (s, 1H), 6.90 (d, J=8.8 Hz, 1H), 4.36-4.48 (m, 2H), 4.25 (q, J=7.1 Hz, 2H), 3.80 (t, J=4.7 Hz, 1H), 2.37-2.43 (m, 1H), 2.11-2.20 (m, 1H), 1.32 (t, J=7.2 Hz, 3H).

Preparation B

4-(6-chloro-4-(ethoxycarbonyl)chroman-7-yloxy)benzoic acid

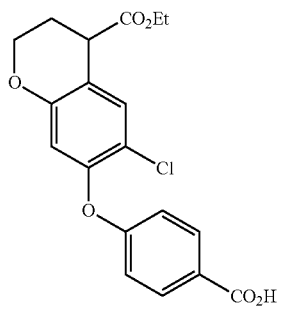 [SMILES: CCOC(=O)C1CCOc2cc(Oc3ccc(C(=O)O)cc3)c(Cl)cc21]

Step A: Preparation of 3-chloro-1-(5-chloro-2,4-dihydroxyphenyl)propan-1-one A 2-liter 4-neck round-bottom flask was charged with trifluoromethanesulfonic acid (500 g, 3.33 mol) and the flask contents were cooled below 10° C. 4-Chlororesorcinol (100 g, 0.69 mol) was added in portions over 20-30 minutes, maintaining the temperature at 4 to 8° C. The reaction mixture was stirred at or below 10° C. until a clear solution formed (40 minutes). 3-Chloropropanoic acid (78.8 g, 0.73 mol) was warmed until melted and then added in liquid form dropwise over 45 minutes to the flask, maintaining the temperature at or below 10° C. The reaction mixture was stirred for an additional 10 minutes at or below 10° C., then slowly heated to 50-55° C. and maintained there for 6 hours. The reaction mixture was cooled to ambient temperature and added dropwise to water (1.1 L) contained in a 3-liter 4-neck round-bottom flask. The resulting mixture was stirred at ambient temperature for 30 minutes. The resulting precipitate was collected by filtration, washed with water (3×540 mL), and dried in a fan dryer at 40° C. until the moisture content fell below 0.5%, to afford 3-chloro-1-(5-chloro-2,4-dihydroxyphenyl)propan-1-one as an orange solid (160 g, 98.4% yield).

Step B: Preparation of 6-chloro-7-hydroxychroman-4-one

A 20-liter 4-neck round-bottom flask was charged with water (10 L) and 3-chloro-1-(5-chloro-2,4-dihydroxyphenyl)propan-1-one (1.62 kg, 6.89 mol), and the resulting mixture was stirred and cooled to 10° C. A solution of sodium hydroxide (606.5 g, 15.16 mol) in water (2.96 L) was added dropwise over 40-60 minutes, maintaining the temperature at 10-15° C. The resulting mixture was stirred at ambient temperature for a further 30 minutes, then cooled to 5° C. Concentrated hydrochloric acid (1.31 L, 15.98 mol) was added dropwise over 30 minutes, maintaining the temperature at or below 10° C. The resulting mixture was stirred at ambient temperature for a further 30 minutes, and the resulting precipitate was collected by filtration, washed with water (3×5.5 L), and dried at 40° C. until the moisture content fell below 1%. This crude product (1.2 kg) was transferred to a 10-liter 4-neck round-bottom flask and stirred with acetonitrile (6.0 L) at ambient temperature for 2 hours, then cooled to 0-5° C. and stirred for an additional 2 hours. The resulting precipitate was collected by filtration, washed with 4:1 water:acetonitrile (1.5 L) and water (1.2 L), and dried in a fan dryer at 40° C. until the moisture content fell below 0.5%, to afford 6-chloro-7-hydroxychroman-4-one as an off-white solid (858 g, 62.7% yield).

Step C: Preparation of 6-chloro-4,7-bis(trimethylsilyloxy)chroman-4-carbonitrile (CAUTION: Hydrogen cyanide gas is produced in this reaction; take appropriate precautions). A 20-liter 4-neck round-bottom flask was charged with dichloromethane (12.5 L), iodine (32 g, 0.13 mol) and 6-chloro-7-hydroxychroman-4-one (1.25 kg, 6.30 mol). The resulting mixture was stirred under nitrogen and cooled to 10° C. Trimethylsilyl cyanide (2.36 L, 18.88 mol) was added dropwise over 30 minutes, maintaining the temperature at or below 10° C. The reaction mixture was stirred at ambient temperature for 10-11 hours, then cooled below 20° C. A solution of sodium thiosulfate (59.5 g, 0.38 mol) in water (500 mL) was added dropwise, maintaining the temperature below 20° C., and the resulting mixture was stirred for 20 minutes while maintaining the temperature below 20° C. Solid sodium sulfate anhydrous (3.75 kg) was added, and the resulting mixture was stirred for 30 minutes while maintaining the temperature below 20° C. The reaction mixture was filtered through a HyFlo™ bed, and the bed was washed with dichloromethane. The combined filtrate and washing were concentrated under reduced pressure at a temperature below 50° C. to afford 6-chloro-4,7-bis(trimethylsilyloxy)chroman-4-carbonitrile as a brown oil (2.2 kg, 94.5% yield).

Step D: Preparation of 6-chloro-7-hydroxychroman-4-carboxylic acid

A 20-liter 4-neck round-bottom flask was charged with glacial acetic acid (2.04 L), 6-chloro-4,7-bis(trimethylsilyloxy)chroman-4-carbonitrile (2.2 kg, 5.94 mol), and tin(II) chloride dihydrate (3.35 kg, 14.85 mol) and the resulting mixture was stirred at ambient temperature. Concentrated hydrochloric acid (5.0 L, 60 mol) was added, and the resulting mixture was stirred and heated to 80-85° C. for 12 hours. The reaction mixture was cooled to ambient temperature and water (3.6 L) was added, and stirring was continued at ambient temperature for 15 minutes. Isopropyl acetate (11.5 L) and water (5.8 L) were added, and stirring was continued at ambient temperature for 15 minutes. The layers were separated, and the aqueous layer was extracted with isopropyl acetate (2×2 L). The organic layers were combined and washed with brine (3×6 L), then dried over sodium sulfate and concentrated under reduced pressure at a temperature below 50° C. to afford crude 6-chloro-7-hydroxychroman-4-carboxylic acid as a brown semi-solid (1.70 kg, 125% yield).

Step E: Preparation of ethyl 6-chloro-7-hydroxychroman-4-carboxylate

A 20-liter 4-neck round-bottom flask was charged with ethanol (8.6 L) and crude 6-chloro-7-hydroxychroman-4-carboxylic acid (1.70 kg, 7.44 mol) and the resulting mixture was stirred at ambient temperature. Concentrated sulfuric acid (397 mL) was added over 10 minutes. The resulting mixture was stirred and heated to reflux for 16 hours. The reaction mixture was cooled to ambient temperature and diluted with ethyl acetate (9.0 mL). The resulting mixture was washed with brine (2×12 L). The brine washes were combined and extracted with ethyl acetate (4 L). The ethyl acetate layer was washed with brine (2 L). The organic layers were combined and dried over sodium sulfate, then concentrated under reduced pressure at a temperature below 50° C. The residue was purified by chromatography on silica gel (18 kg), eluting with 85:15 hexanes:ethyl acetate (235 L), to afford ethyl 6-chloro-7-hydroxychroman-4-carboxylate as a white powder (822 g, 43% yield). MS (apci) m/z=255.1 (M−H).

Step F: Preparation of ethyl 7-(4-(tert-butoxycarbonyl)phenoxy)-6-chlorochroman-4-carboxylate Tert-butyl 4-bromobenzoate (210.4 g, 818.2 mmol) was dissolved in 1 L of dioxane, which was previously degassed with argon, in a 4-neck 5 L round bottom flask equipped with a mechanical stirrer and a reflux condenser. Under argon flow and with stirring, ethyl 6-chloro-7-hydroxychroman-4-carboxylate (176.4 g, 687.2 mmol), N,N-dimethyl glycine hydrochloride (35.7 g, 346.2 mmol) and cuprous chloride (34.0 g, 342.9 mmol) were added via a funnel. Cesium carbonate then added and an additional 0.5 L of dioxane was added to the reaction mixture. The mixture was then heated at 95-97° C. for 20 hours. After cooling to ambient temperature, the reaction mixture was poured into 3 L of a 3:1 mixture of hexanes:ethyl acetate and activated charcoal (300 g) was added. After stirring periodically for 1 hour, the mixture was filtered thru GF/F paper, washing the filter cake with 2 L of a 3:1 mixture of hexanes:ethyl acetate. The resulting golden brown solution was concentrated to provide 304 g of crude ethyl 7-(4-(tert-butoxycarbonyl)-phenoxy)-6-chlorochroman-4-carboxylate. The crude product was dissolved in dichloromethane, concentrated onto silica gel and purified by flash column chromatography, eluting with a gradient of 10 to 25% ethyl acetate in hexanes to give ethyl 7-(4-(tert-butoxycarbonyl)phenoxy)-6-chlorochroman-4-carboxylate as a colorless, viscous oil (221 g, 74.3% yield). $^1$H NMR (400 MHz, CDCl$_3$) δ 7.96 (d, J=8.8 Hz, 2H), 7.37 (s, 1H), 6.94 (d, J=8.8 Hz, 2H), 6.54 (s, 1H), 4.21-4.29 (m, 4H), 3.74 (t, J=5.3 Hz, 1H), 2.30-2.36 (m, 1H), 2.05-2.14 (m, 1H), 1.58 (s, 9H), 1.31 (t, J=7.0 Hz, 3H).

Step G: Preparation of 4-(6-chloro-4-(ethoxycarbonyl)chroman-7-yloxy)benzoic acid Ethyl 7-(4-(tert-butoxycarbonyl)phenoxy)-6-chlorochroman-4-carboxylate (221 g, 0.511 mol) was dissolved in hydrogen chloride in ethyl acetate (2.4 N, 1.6 L, 3.84 mol) and the resulting solution was stirred at ambient temperature for 16 hours. The solution was concentrated to give 198 g of crude 4-(6-chloro-4-(ethoxycarbonyl)chroman-7-yloxy)benzoic acid. The crude product was recrystallized by dissolving in hot isopropyl acetate (0.5 L) and diluting with hexanes (1.1 L). After 48 hours, the crystals were collected and wash with hexanes. The resulting white solids were dried under high vacuum to give 4-(6-chloro-4-(ethoxycarbonyl)chroman-7-yloxy)benzoic acid (169 g, 88% yield). $^1$H NMR (400 MHz, CDCl$_3$) δ 8.08 (d, J=8.9 Hz, 2H), 7.38 (s, 1H), 6.98 (d, J=8.8 Hz, 2H), 6.60 (s, 1H), 4.21-4.31 (m, 4H), 3.75 (t, J=5.4 Hz, 1H), 2.31-2.37 (m, 1H), 2.08-2.15 (m, 1H), 1.32 (t, J=7.0 Hz, 3H).

EXAMPLE 1

7-(4-((5-(Trifluoromethyl)pyridin-2-yl)carbamoyl)phenoxy)-6-cyanochroman-4-carboxylic acid

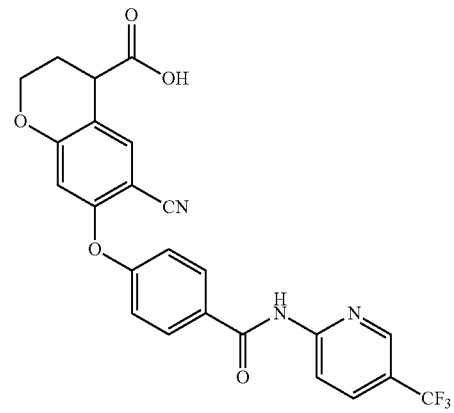 [SMILES: N#Cc1cc2c(cc1Oc1ccc(C(=O)Nc3ccc(C(F)(F)F)cn3)cc1)OCCC2C(=O)O]

Step A: Preparation of 7-fluoro-4-(trimethylsilyloxy)chroman-4-carbonitrile

7-Fluoro-2,3-dihydrochromen-4-one (470 mg, 2.829 mmol) and ZnI$_2$ (45.15 mg, 0.1414 mmol) was diluted with trimethylsilyl cyanide (1.413 mL, 11.32 mmol). The reaction was stirred for 4 hours at ambient temperature. The reaction was diluted with dichloromethane and washed with saturated sodium bicarbonate. The organic layer was dried over magnesium sulfate, filtered and concentrated to yield the title compound (750 mg, 99.92% yield).

Step B: Preparation of 7-fluoro-3,4-dihydro-2H-chromene-4-carboxylic acid

7-Fluoro-4-(trimethylsilyloxy)chroman-4-carbonitrile (750 mg, 2.83 mmol) and SnCl$_2$ dihydrate (2551 mg, 11.3 mmol) were diluted with glacial acetic acid (3 mL) and concentrated HCl (3 mL). The reaction was heated in an oil bath at 130° C. overnight. The reaction was cooled, then diluted with water and ethyl acetate. The layers were separated and the organic layer was dried over magnesium sulfate, filtered and concentrated to yield the title compound (465 mg, 83.9% yield).

Step C: Preparation of methyl 7-fluoro-3,4-dihydro-2H-chromene-4-carboxylate 7-Fluoro-3,4-dihydro-2H-chromene-4-carboxylic acid (346 mg, 1.76 mmol) was diluted with THF (2 mL), methanol (2 mL) and 4 drops of sulfuric acid. The reaction was heated at 55° C. and stirred for 12 hours. The reaction was cooled to ambient temperature, diluted with ethyl acetate and saturated sodium bicarbonate. The layers were separated and the organic layer was dried over magnesium sulfate, filtered and concentrated to yield the title compound (366 mg, 98.7% yield).

Step D: Preparation of methyl 6-bromo-7-fluoro-3,4-dihydro-2H-chromene-4-carboxylate Methyl 7-fluoro-3,4-dihydro-2H-chromene-4-carboxylate (336 mg, 1.60 mmol) was diluted with DMF (5 mL) followed by the addition of N-bromosuccinimide (313 mg, 1.76 mmol). The reaction was heated at 50° C. and stirred for 2.5 hours. The reaction was cooled, diluted with ethyl acetate and washed with water, saturated sodium bicarbonate, water, and brine. The organic layer was dried over magnesium sulfate, filtered and concentrated. The material was purified by silica gel chromatography using a Biotage 40M cartridge (gradient 5% ethyl acetate/hexane) to 50% to yield the title compound (415 mg, 89.8% yield).

Step E: Preparation of methyl 6-cyano-7-fluorochroman-4-carboxylate

Methyl 6-bromo-7-fluoro-3,4-dihydro-2H-chromene-4-carboxylate (415 mg, 1.44 mmol) was diluted with N-methylpyrrolidone (5 mL) followed by the addition of Cu(I)CN (643 mg, 7.18 mmol). The reaction was bubbled with argon for 20 minutes, then heated at 160° C. under a slight argon bubble for 6 hours. The reaction was cooled to ambient temperature and loaded directly onto a Biotage 25 column (silica gel), eluting with 5% ethyl acetate/hexanes to 100% ethyl acetate to yield the title compound (260 mg, 77.0% yield).

Step F: Preparation of methyl 7-(4-carbamoylphenoxy)-6-cyanochroman-4-carboxylate Methyl 6-cyano-7-fluorochroman-4-carboxylate (300 mg, 1.28 mmol), 4-hydroxybenzamide (227 mg, 1.66 mmol) and potassium carbonate (423 mg, 3.06 mmol) were diluted with dry NMP (4 mL). The reaction was bubbled with argon for 10 minutes and then heated at 110° C. for 12 hours. The reaction was cooled and loaded directly onto a biotage 40M cartridge (silica gel), eluting with 5% ethyl acetate/hexanes to 100% ethyl acetate to yield methyl 7-(4-carbamoylphenoxy)-6-cyanochroman-4-carboxylate (100 mg, 22.3% yield).

Step G: Preparation of 7-(4-((5-(trifluoromethyl)pyridin-2-yl)carbamoyl)phenoxy)-6-cyanochroman-4-carboxylate Methyl 7-(4-carbamoylphenoxy)-6-cyanochroman-4-carboxylate (58 mg, 0.17 mmol), 2-chloro-5-(trifluoromethyl)pyridine (0.021 mL, 0.17 mmol), cesium carbonate (75 mg, 0.23 mmol), (R)-(–)-1-[(S)-2-(dicyclohexylphosphino)ferrocenyl]ethyldi-t-butylphosphine (4.6 mg, 0.0083 mmol) and palladium(II) acetate (1.9 mg, 0.0083 mmol) were diluted with DME (1 mL). The reaction was heated at 90° C. and stirred for 5 hours. The reaction was loaded directly onto a biotage 25 cartridge (silica gel), eluting with 5% ethyl acetate/hexanes to 40% ethyl acetate/hexanes to afford methyl 7-(4-((5-(trifluoromethyl)pyridin-2-yl)carbamoyl)phenoxy)-6-cyanochroman-4-carboxylate (9 mg, 11% yield) as a white solid.

Step F: Preparation of 7-(4-((5-(trifluoromethyl)pyridin-2-yl)carbamoyl)phenoxy)-6-cyanochroman-4-carboxylic acid Methyl 7-(4-((5-(trifluoromethyl)pyridin-2-yl)carbamoyl)phenoxy)-6-cyanochroman-4-carboxylate (9 mg, 0.018 mmol) was diluted with THF (500 µL) followed by the addition of sodium hydroxide (0.11 mL, 0.11 mmol) and methanol (100 µL). After stirring for 2 hours, the reaction was diluted with ethyl acetate and 1N HCl. The layers were separated and the organic layer was dried over $MgSO_4$, filtered and concentrated. The material was purified using a reverse phase biotage 12iC18 column eluting with 0.1% TFA/5% ACN/95% water to 0.1% TFA/95% ACN/5% water to yield 7-(4-((5-(trifluoromethyl)pyridin-2-yl)carbamoyl)phenoxy)-6-cyanochroman-4-carboxylic acid (2.0 mg, 23% yield). MS (ESI)=484.0 (M+1).

EXAMPLE 2

7-(4-(5-Chloropyridin-2-ylcarbamoyl)phenoxy)-6-cyanochroman-4-carboxylic acid

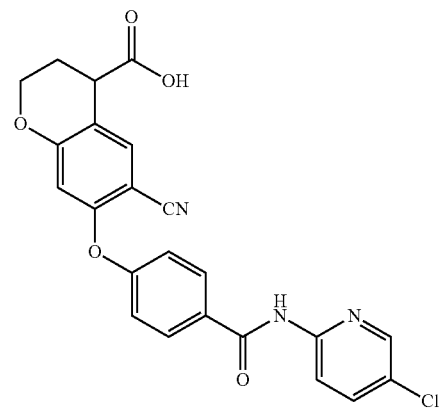 [SMILES: N#Cc1cc2c(cc1Oc1ccc(C(=O)Nc3ccc(Cl)cn3)cc1)OCCC2C(=O)O]

Step A: Preparation of 6-cyano-7-fluoro-3,4-dihydro-2H-chromene-4-carboxylic acid Methyl 6-cyano-7-fluoro-3,4-dihydro-2H-chromene-4-carboxylate (3.3 g, 14.0 mmol) and LiOH—$H_2O$ (5.89 g, 140 mmol) were stirred together in THF (25 mL) and water (25 mL) at ambient temperature for 1 hour. The reaction was diluted with ether and water, and filtered to remove undissolved solids. The filtrate was collected and the aqueous layer was washed with additional ether. The aqueous layer was acidified to pH 1-2 and the resulting solid was collected. The solid was then dissolved in ethyl acetate, dried, filtered and concentrated to provide the desired product (2.53 g, 81%) as a light yellow solid.

Step B: Preparation of tert-butyl 6-cyano-7-fluoro-3,4-dihydro-2H-chromene-4-carboxylate 6-Cyano-7-fluoro-3,4-dihydro-2H-chromene-4-carboxylic acid was dissolved in 10 mL of THF and treated with (Z)-tert-butyl N,N'-diisopropylcarbamimidate. After stirring for 3 hours, an additional 2 mL of (Z)-tert-butyl N,N'-diisopropylcarbamimidate was added and the reaction was stirred overnight. The reaction was diluted with ether, filtered, concentrated onto silica gel and flashed with 8:1 hexanes/ethyl acetate to provide the desired product (1.4 g, 64% yield) as a white solid.

Step C: Preparation of tert-Butyl 7-(4-carbamoylphenoxy)-6-cyanochroman-4-carboxylate tert-butyl 6-cyano-7-fluorochroman-4-carboxylate (290 mg, 1.05 mmol), 4-hydroxybenzamide (172 mg, 1.25 mmol) and potassium carbonate (347 mg, 2.51 mmol) were diluted with dry NMP (4 mL). The reaction was bubbled with argon for 10 minutes and then heated at 120° C. for 12 hours under a slight argon bubble. The reaction was cooled and loaded directly onto a biotage 40 M cartridge, eluting with 20% ethyl acetate/hexanes to 100% ethyl acetate to yield 1 g of the crude product which was found to contain NMP. The residue was taken up in ethyl acetate and washed twice with water and then brine. The organic layer was dried over magnesium sulfate, filtered and concentrated to provide the desired product (343 mg, 83.2% yield) as a white foam.

Step D: Preparation of tert-butyl 7-(4-(5-chloropyridin-2-ylcarbamoyl)phenoxy)-6-cyanochroman-4-carboxylate tert-Butyl 7-(4-carbamoylphenoxy)-6-cyanochroman-4-carboxylate (30 mg, 0.076 mmol), 2,5-dichloropyridine (12 mg, 0.084 mmol), XPHOS (7.3 mg, 0.015 mmol), palladium (II) acetate (1.7 mg, 0.0076 mmol) and cesium carbonate (62 mg, 0.19 mmol) were diluted with dioxane (600 μL) in a 1 mL vial. The reaction was purged with argon for 3 minutes, capped and heated at 80° C. for 12 hours. The reaction was cooled and loaded directly onto a biotage 25 column and eluted with 5% ethyl acetate/hexanes to 75% ethyl acetate/hexanes to yield tert-butyl 7-(4-(5-chloropyridin-2-ylcarbamoyl)phenoxy)-6-cyanochroman-4-carboxylate (5 mg, 0.0099 mmol, 13% yield).

Step E: Preparation of 7-(4-(5-chloropyridin-2-ylcarbamoyl)phenoxy)-6-cyanochroman-4-carboxylic acid tert-Butyl 7-(4-(5-chloropyridin-2-ylcarbamoyl)phenoxy)-6-cyanochroman-4-carboxylate (4 mg, 0.0079 mmol) was diluted with DCM (500 μL) and TFA (500 μL). After stirring for 2 hours, the reaction was concentrated and placed under high vacuum for 1 hour. The residue was purified by preparative TLC, eluting with 10% methanol/DCM to provide the desired product (2.5 mg, 0.0056 mmol, 70% yield) as a white solid. MS (ESI)=450.1 (M+1).

EXAMPLE 3

6-Cyano-7-(4-(quinolin-2-ylcarbamoyl)phenoxy)chroman-4-carboxylic acid

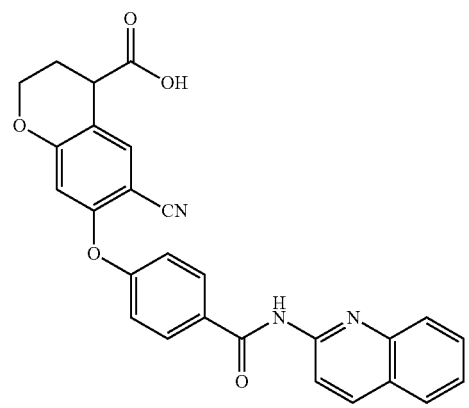 [SMILES: N#Cc1cc2c(cc1Oc1ccc(C(=O)Nc3ccc4ccccc4n3)cc1)OCCC2C(=O)O]

Prepared by the method of Example 2, using 2-chloroquinoline in place of 2,5-dichloropyridine in Step D. MS (ESI)=466.1 (M+1).

EXAMPLE 4

6-Cyano-7-(4-(quinoxalin-2-ylcarbamoyl)phenoxy)chroman-4-carboxylic acid

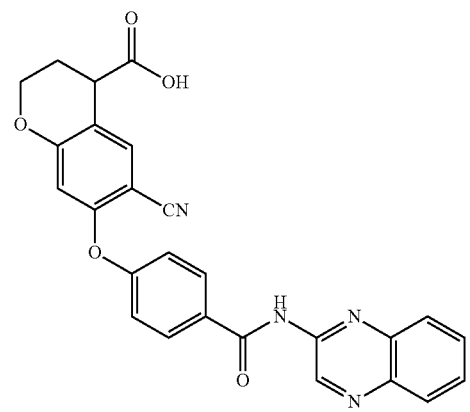 [SMILES: N#Cc1cc2c(cc1Oc1ccc(C(=O)Nc3cnc4ccccc4n3)cc1)OCCC2C(=O)O]

Prepared by the method of Example 2, using 2-chloroquinoxaline in place of 2,5-dichloropyridine in Step D. MS (ESI)= 467.0 (M+1).

EXAMPLE 5

7-(4-(6-Chloroquinolin-2-ylcarbamoyl)phenoxy)-6-cyanochroman-4-carboxylic acid

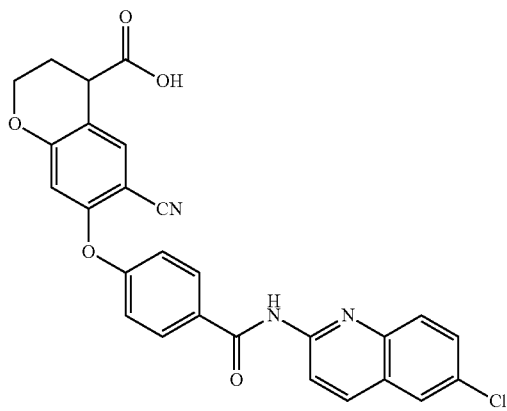 [SMILES: N#Cc1cc2c(cc1Oc1ccc(C(=O)Nc3ccc4cc(Cl)ccc4n3)cc1)OCCC2C(=O)O]

Prepared by the method of Example 2, using 2,6-dichloroquinoline in place of 2,5-dichloropyridine in Step D. MS (ESI)=500.1 (M+1).

EXAMPLE 6

7-(4-((6-(Trifluoromethyl)pyridin-3-yl)carbamoyl)phenoxy)-6-cyanochroman-4-carboxylic acid

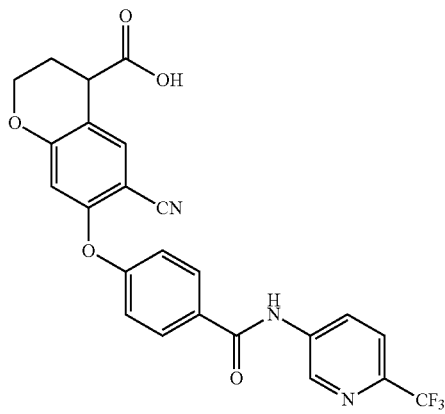 [SMILES: N#Cc1cc2c(cc1Oc1ccc(C(=O)Nc3ccc(C(F)(F)F)nc3)cc1)OCCC2C(=O)O]

Step A: Preparation of methyl 7-(4-(tert-butoxycarbonyl)phenoxy)-6-cyanochroman-4-carboxylate To methyl 6-cyano-7-fluoro-3,4-dihydro-2H-chromene-4-carboxylate (3.04 g, 12.9 mmol), tert-butyl 4-hydroxybenzoate (3.10 g, 16.0 mmol) and potassium carbonate (4.47 g, 32.3 mmol) in 20 mL of NMP was added oven dried powdered 4 Angstrom sieves (2.5 gm), the reaction was degassed with argon for 15 minutes then heated at 110° C. overnight. The reaction was diluted with ethyl acetate and water. The organic layer was dried, concentrated and the residue flashed with 4:1 hexanes/ethyl acetate to 3:1 hexanes/ethyl acetate to provide the desired product (2.3 g, 44%).

Step B: Preparation of 4-(6-cyano-4-(methoxycarbonyl)chroman-7-yloxy)benzoic acid Methyl 7-(4-(tert-butoxycarbonyl)phenoxy)-6-cyanochroman-4-carboxylate (350 mg, 0.855 mmol) was diluted with dichloromethane (2 mL) and treated with TFA (2 mL). After stirring for 3 hours, the reaction was concentrated. The crude material was purified using a biotage 40M cartridge eluting with 0.5% methanol/dichloromethane to 10% methanol/dichloromethane to yield 4-(6-cyano-4-(methoxycarbonyl)chroman-7-yloxy)benzoic acid (280 mg, 92.7% yield).

Step C: Preparation of methyl 7-(4-(((6-(trifluoromethyl)pyridin-3-yl)carbamoyl)phenoxy)-6-cyanochroman-4-carboxylate 4-(6-cyano-4-(methoxycarbonyl)chroman-7-yloxy)benzoic acid (100 mg, 0.283 mmol) was diluted with dichloromethane (1 mL) followed by the addition of oxalyl chloride in dichloromethane (2M) (0.156 mL, 0.311 mmol) and 1 drop of DMF. After stirring for 10 minutes, 3-amino-6-(trifluoromethyl)pyridine (91.8 mg, 0.566 mmol) and diisopropylethylamine (0.123 mL, 0.708 mmol) were added and the reaction was stirred for 5 hours. The reaction was loaded onto a biotage 25 column and eluted with 5% ethyl acetate/hexanes to 100% ethyl acetate to provide the desired product (141 mg, 100% yield).

Step D: Preparation of 7-(4-((6-(trifluoromethyl)pyridin-3-yl)carbamoyl)phenoxy)-6-cyanochroman-4-carboxylic acid Methyl 7-(4-((6-(trifluoromethyl)pyridin-3-yl)carbamoyl)phenoxy)-6-cyanochroman-4-carboxylate (141 mg, 0.283 mmol) was diluted with THF (1 mL) followed by the addition of sodium hydroxide (0.31 mL, 0.31 mmol) and methanol (300 µL). After stirring for 2 hours, the reaction was diluted with ethyl acetate and 1N HCl. The layers were separated and the organic layer was dried over magnesium sulfate, filtered and concentrated. The material was diluted with dichloromethane and a white precipitate formed which was filtered and rinsed with dichloromethane to provide the desired product (30 mg, 21.9% yield). MS (ESI)=484.1 (M+1).

EXAMPLE 7

6-Cyano-7-(4-(8-methoxyquinolin-3-ylcarbamoyl)phenoxy)chroman-4-carboxylic acid

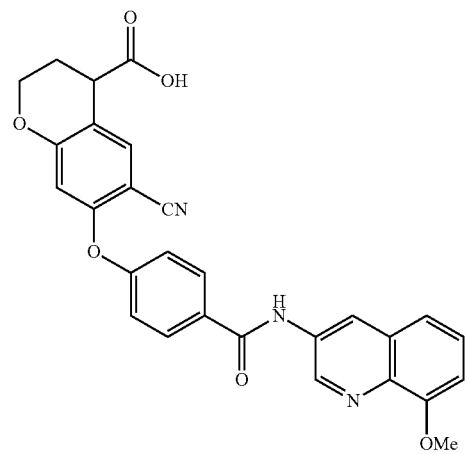 [SMILES: COc1cccc2cc(NC(=O)c3ccc(Oc4cc5c(cc4C#N)C(C(=O)O)CCO5)cc3)cnc12]

Step A: Preparation of methyl 6-cyano-7-(4-(8-methoxyquinolin-3-ylcarbamoyl)phenoxy)chroman-4-carboxylate Dissolved 4-(6-cyano-4-(methoxycarbonyl)chroman-7-yloxy)benzoic acid (0.10 g, 0.29 mmol), 8-methoxyquinolin-3-amine (0.050 g, 0.29 mmol), and HOAT (0.039 g, 0.29 mmol) in dry DMF (1 mL) at ambient temperature. EDCI (0.049 g, 0.32 mmol) was added and the mixture stirred at ambient temperature overnight. The reaction was diluted with excess water, acidified with 10% HCl and extracted with ethyl acetate. The combined organic layers were dried over sodium sulfate, filtered and concentrated. The crude material was purified by silica gel column chromatography eluting with 2-5% methanol/dichloromethane to provide the desired product (0.061 g, 42%) as a colorless foam.

Step B: Preparation of 6-cyano-7-(4-(8-methoxyquinolin-3-ylcarbamoyl)phenoxy)chroman-4-carboxylic acid To a solution of methyl 6-cyano-7-(4-(8-methoxyquinolin-3-ylcarbamoyl)phenoxy)chroman-4-carboxylate (0.061 g, 0.120 mmol) in THF (2 mL) was added LiOH—H$_2$O (0.239 mL, 0.239 mmol) and added a few drops of methanol to ensure a homogeneous solution. The reaction was stirred at ambient temperature for 3 hours. A few drops of acetic acid were added to the reaction and the solution concentrated to a yellow/white solid. The crude material was purified by silica gel column chromatography using 5% methanol/dichloromethane+0.1% acetic acid to provide the desired product (0.023 g, 39%). MS (APCI)=496.3 (M+1).

EXAMPLE 8

7-(4-(6-Chloroquinazolin-2-ylcarbamoyl)phenoxy)-6-cyanochroman-4-carboxylic acid

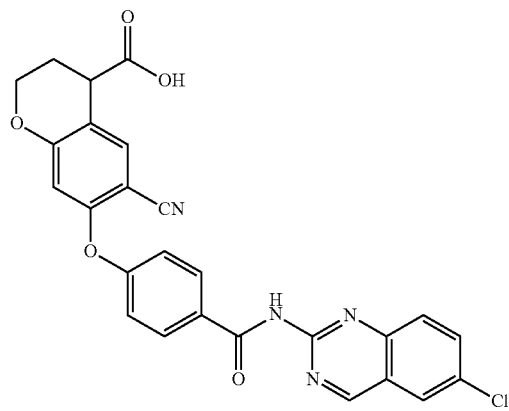 [SMILES: N#Cc1cc2c(cc1Oc1ccc(C(=O)Nc3ncc4cc(Cl)ccc4n3)cc1)OCCC2C(=O)O]

Prepared by the method of Example 6, using 6-chloroquinazolin-2-amine in place of 3-amino-6-(trifluoromethyl)pyridine in Step C. MS (ESI)=501.2 (M+1).

EXAMPLE 9

6-Cyano-7-(4-(isoquinolin-3-ylcarbamoyl)phenoxy)chroman-4-carboxylic acid

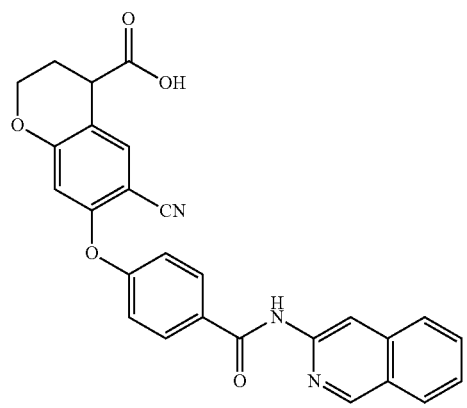 [SMILES: N#Cc1cc2c(cc1Oc1ccc(C(=O)Nc3cc4ccccc4cn3)cc1)OCCC2C(=O)O]

Prepared by the method of Example 6, using isoquinolin-3-amine in place of 3-amino-6-(trifluoromethyl)pyridine in Step C. MS (ESI)=466.2 (M+1).

EXAMPLE 10

6-Cyano-7-(4-(quinolin-3-ylcarbamoyl)phenoxy)chroman-4-carboxylic acid

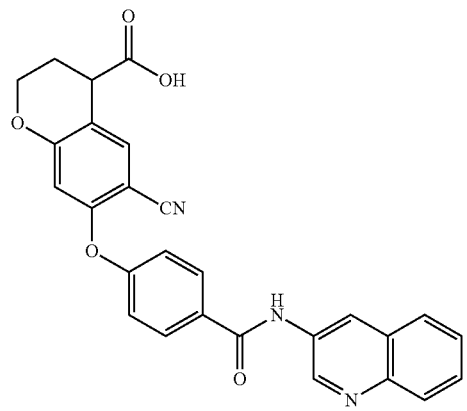 [SMILES: N#Cc1cc2c(cc1Oc1ccc(C(=O)Nc3cnc4ccccc4c3)cc1)OCCC2C(=O)O]

Prepared by the method of Example 6, using quinolin-3-amine in place of 3-amino-6-(trifluoromethyl)pyridine in Step C. MS (ESI)=466.2 (M+1).

EXAMPLE 11

6-Cyano-7-(4-(quinolin-3-ylcarbamoyl)phenoxy)chroman-4-carboxylic acid

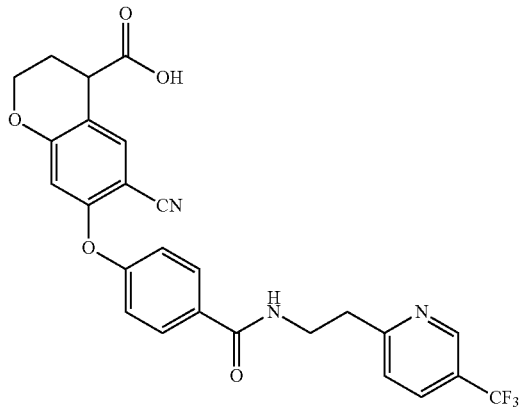 [SMILES: N#Cc1cc2c(cc1Oc1ccc(C(=O)NCCc3ccc(C(F)(F)F)cn3)cc1)OCCC2C(=O)O]

Prepared by the method of Example 7, using 2-(5-(trifluoromethyl)pyridin-2-yl)ethanamine dihydrochloride in place of 8-methoxyquinolin-3-amine in Step A. MS (APCI)=509.7 (M−1).

EXAMPLE 12

6-Cyano-7-(4-(2-(6-(trifluoromethyl)pyridin-3-yl)ethylcarbamoyl)phenoxy)chroman-4-carboxylic acid

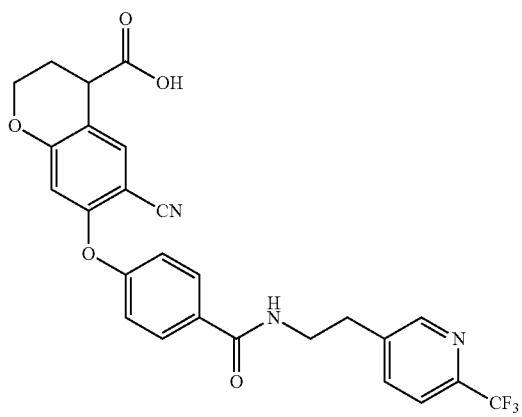 [SMILES: N#Cc1cc2c(cc1Oc1ccc(C(=O)NCCc3ccc(C(F)(F)F)nc3)cc1)OCCC2C(=O)O]

Prepared by the method of Example 7, using 2-(6-(trifluoromethyl)pyridin-3-yl)ethanamine in place of 8-methoxyquinolin-3-amine in Step A. MS (APCI)=512.1 (M+1).

EXAMPLE 13

6-Cyano-7-(4-(6-(3,4-dimethylphenyl)pyridin-2-ylcarbamoyl)phenoxy)chroman-4-carboxylic acid

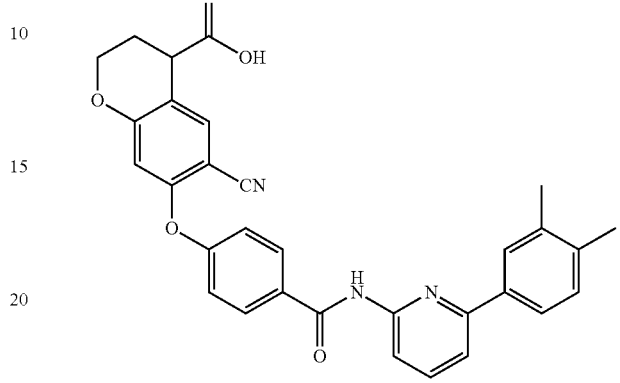

Step A: Preparation of methyl 7-(4-(6-bromopyridin-2-ylcarbamoyl)phenoxy)-6-cyanochroman-4-carboxylate To a solution of 4-(6-cyano-4-(methoxycarbonyl)chroman-7-yloxy)benzoic acid (1.00 g, 2.83 mmol) and a drop of DMF in DCE (10 ml) was added oxalyl chloride in dichloromethane (2M) (1.55 mL, 3.11 mmol). After stirring for 1 hour, 6-bromopyridin-2-amine (0.489 g, 2.83 mmol) and triethylamine (0.788 mL, 5.66 mmol) were added. After stirring overnight, the reaction was loaded onto silica gel and the product eluted to provide the desired product (0.939 g, 65%).

Step B: Preparation of methyl 6-cyano-7-(4-(6-(3,4-dimethylphenyl)pyridin-2-ylcarbamoyl)phenoxy)chroman-4-carboxylate A vial was charged with methyl 7-(4-(6-bromopyridin-2-ylcarbamoyl)phenoxy)-6-cyanochroman-4-carboxylate (51 mg, 0.100 mmol), 3,4-dimethylphenylboronic acid (19.5 mg, 0.130 mmol), $Na_2CO_3$ (31.9 mg, 0.300 mmol), toluene (1 mL) and water (0.1 mL). The mixture was degassed with Argon for few minutes, and then $Pd(PPh_3)_4$ (5.8 mg, 0.005 mmol) was added. The vial was sealed and heated at 100° C. for 16 hours. The reaction was cooled and the crude material was purified by silica gel column chromatography to provide the desired product (0.051 g, 95%).

Step C: Preparation of 6-cyano-7-(4-(6-(3,4-dimethylphenyl)pyridin-2-ylcarbamoyl)phenoxy)chroman-4-carboxylic acid A mixture of methyl 6-cyano-7-(4-(6-(3,4-dimethylphenyl)pyridin-2-ylcarbamoyl)phenoxy)chroman-4-carboxylate (51.1 mg, 0.096 mmol), LiOH—$H_2O$-1M–$H_2O$ (191.5 μL, 0.1915 mmol), and THF (1.5 mL) was stirred at ambient temperature for 3 days. The mixture was quenched with HCl (4M in dioxane) (71.83 μL, 0.287 mmol). The crude material was purified by silica gel column chromatography to provide the desired product (0.027 g). MS (APCI)=520.2 (M+1).

EXAMPLE 14

6-Cyano-7-(2-methyl-4-(6-(trifluoromethyl)pyridin-3-ylcarbamoyl)phenoxy)chroman-4-carboxylic acid

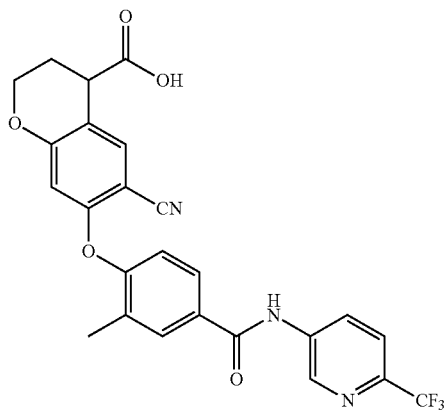 [SMILES: Cc1cc(C(=O)Nc2ccc(C(F)(F)F)nc2)ccc1Oc1cc2c(cc1C#N)C(C(=O)O)CCO2]

Step A: Preparation of methyl 7-(4-(tert-butoxycarbonyl)-2-methylphenoxy)-6-cyanochroman-4-carboxylate Methyl 6-cyano-7-fluorochroman-4-carboxylate (0.200 g, 0.850 mmol), tert-butyl 4-hydroxy-3-methylbenzoate (0.195 g, 0.935 mmol) and potassium carbonate (0.141 g, 1.02 mmol) were dissolved in 4 mL of dry DMSO and degassed with argon. The solution was heated in a microwave oven at 150° C. for 15 minutes, then at 170° C. for 15 additional minutes. The reaction was poured into 10% HCl/water (1 L), extracted with ethyl acetate, and the organic layer was washed with brine, dried over magnesium sulfate, filtered and concentrated to a yellow film. The crude product was adsorbed onto silica gel and purified by column using 20-30% ethyl acetate/hexanes to provide the desired product (0.133 g, 37%) as a light yellow foam.

Step B: Preparation of 4-(6-cyano-4-(methoxycarbonyl)chroman-7-yloxy)-3-methylbenzoic acid Methyl 7-(4-(tert-butoxycarbonyl)-2-methylphenoxy)-6-cyanochroman-4-carboxylate was taken up in dichloromethane (10 mL). To the solution was added 2 ml TFA and the solution was stirred at ambient temperature for 2 hours. The reaction was concentrated and the crude material was purified over silica gel, eluting with 2-3% methanol/dichloromethane, to provide the desired product (0.103 g, 89%).

Step C: Preparation of methyl 6-cyano-7-(2-methyl-4-(6-(trifluoromethyl)pyridin-3-ylcarbamoyl)phenoxy)chroman-4-carboxylate 4-(6-Cyano-4-(methoxycarbonyl)chroman-7-yloxy)-3-methylbenzoic acid (0.103 g, 0.280 mmol) was dissolved in 4 mL dry DCM at ambient temperature under nitrogen. Oxalyl chloride (0.0489 mL, 0.561 mmol) was added to the reaction followed by 10 μL DMF. The solution was stirred at ambient temperature for 1 hour. The solution was concentrated and the residue was taken up in 4 mL dry DCE. 6-(Trifluoromethyl)pyridin-3-amine (0.136 g, 0.841 mmol), pyridine (0.0567 mL, 0.701 mmol) and DMAP (0.0034 g, 0.0280 mmol) were added and the solution was stirred at ambient temperature overnight. The reaction was poured into water, extracted with ethyl acetate, dried over sodium sulfate, filtered and concentrated. The crude material was purified by silica gel column chromatography, eluting with 30-50% ethyl acetate/hexanes, followed by a second silica gel chromatography eluting with 30% acetone/hexanes to provide the desired product (0.097 g, 68%).

Step D: Preparation of 6-cyano-7-(2-methyl-4-(6-(trifluoromethyl)pyridin-3-ylcarbamoyl)phenoxy)chroman-4-carboxylic acid To a solution of methyl 6-cyano-7-(2-methyl-4-(6-(trifluoromethyl)pyridin-3-ylcarbamoyl)phenoxy)chroman-4-carboxylate (0.097 g, 0.190 mmol) in 2 mL of THF containing 200 μL methanol was added LiOH—H₂O (0.379 mL, 0.379 mmol) and the solution was stirred at ambient temperature for 12 hours. The reaction was quenched with 1 drop of glacial acetic acid and then concentrated to dryness. The crude material was purified by silica gel column chromatography, eluting with 2-5% methanol/dichloromethane+0.1% acetic acid to provide the desired product (0.04 g, 42%). MS (APCI)=498.1 (M+1).

EXAMPLE 15

6-Chloro-7-(4-(6-chloroquinoxalin-2-ylcarbamoyl)phenoxy)chroman-4-carboxylic acid

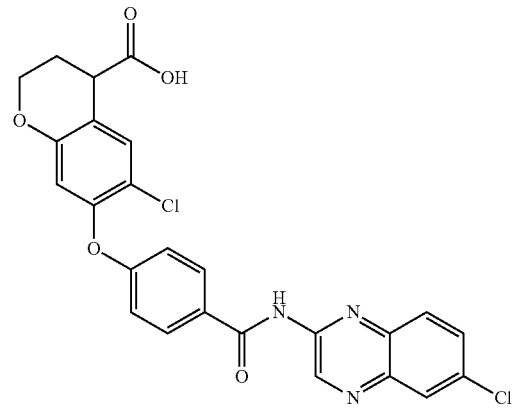 [SMILES: O=C(Nc1cnc2cc(Cl)ccc2n1)c1ccc(Oc2cc3c(cc2Cl)C(C(=O)O)CCO3)cc1]

Step A: Preparation of 3-chloro-1-(5-chloro-2,4-dihydroxyphenyl)propan-1-one A solution of 4-chlorobenzene-1,3-diol (100 g, 692 mmol) and 3-chloropropanoic acid (75.1 g, 692 mmol) in trifluoromethanesulfonic acid (295 mL) was stirred at 75° C. for 30 minutes. The reaction was cooled to ambient temperature and slowly poured into a 2 L beaker filled with ice. To the slurry was added ethyl acetate (1200 mL) with stirring until all solids dissolved. The mixture was poured into a reparatory funnel, the aqueous layer was removed and the organic layer was washed with water. The organic layer was dried over magnesium sulfate, filtered and concentrated. The crude material was purified by silica gel column chromatography eluting with a solvent system mixture of 15% ethyl acetate/hexanes to provide the desired product (162.6 g, 86%).

Step B: Preparation of 6-chloro-7-hydroxychroman-4-one

3-Chloro-1-(5-chloro-2,4-dihydroxyphenyl)propan-1-one (140 g, 596 mmol) was dissolved in a 2M aqueous NaOH solution (2085 mL) at 0° C., and then the reaction was warmed to ambient temperature over 2 hours. The reaction was acidified by the addition of 6M $H_2SO_4$ to a pH of ~2. The resulting solids were removed by filtration and dried under high vacuum. The resulting solid was dissolved in THF (600 mL) and washed with water. The organic layer and was dried over magnesium sulfate, filtered, and concentrated. The resulting solid was treated with a minimal amount of diethyl ether and sonicated until a homogeneous suspension resulted. The resulting solid was collected by filtration to provide the desired product (85.7 g, 73%).

Step C: Preparation of 6-chloro-7-hydroxy-4-(trimethylsilyloxy)chroman-4-carbonitrile To a solution of 6-chloro-7-hydroxychroman-4-one (85.7 g, 432 mmol) in trimethylsilanecarbonitrile (134 mL, 1008 mmol) was added zinc(II) iodide (6.89 g, 21.6 mmol). The reaction began to warm and was cooled with an ice bath as necessary. After stirring for 2 hours at ambient temperature the reaction was diluted with ethyl acetate (400 mL) and washed with saturated sodium bicarbonate solution. The organic layer was dried over magnesium sulfate, filtered and concentrated to provide the desired product (129 g, 100%).

Step D: Preparation of 6-chloro-7-hydroxychroman-4-carboxylic acid

A solution of 6-chloro-7-hydroxy-4-(trimethylsilyloxy)chroman-4-carbonitrile (129 g, 433 mmol) and $SnCl_2$ dihydrate (293 g, 1299 mmol) in concentrated HCl (435 mL) and glacial acetic acid (435 mL) was heated to 125° C. and stirred for 12 hours. The reaction was taken up in ethyl acetate (500 mL) and washed with water, dried over magnesium sulfate, filtered and concentrated to provide the desired product (99 g, 100%).

Step E: Preparation of 6-chloro-7-hydroxychroman-4-carboxylate

To a solution of 6-chloro-7-hydroxychroman-4-carboxylic acid (99 g, 433 mmol) in ethanol (650 mL) was added sulfuric acid (1.2 mL) and the reaction was stirred at 60° C. for 24 hours. The reaction was cooled to ambient temperature and the resulting solids were removed by filtration and discarded. The filtrate was diluted with ethyl acetate (700 mL), washed with water, dried over magnesium sulfate and concentrated. The crude material was purified by silica gel column chromatography eluting with a solvent system of 20% ethyl acetate/hexanes to give ethyl 6-chloro-7-hydroxychroman-4-carboxylate (46 g, 41%).

Step F: Preparation of ethyl 7-(4-carbamoyl-2-nitrophenoxy)-6-chlorochroman-4-carboxylate To a stirred solution of ethyl 6-chloro-7-hydroxychroman-4-carboxylate (6.40 g, 24.9 mmol) and 4-chloro-3-nitrobenzamide in N,N'-dimethylformamide (75 mL) at ambient temperature was added potassium carbonate (8.61 g, 62.3 mmol). An argon balloon with purge valve was attached, and the stirred mixture was evacuated and purged 5 times with argon. The mixture was stirred in an oil bath at 90° C. under argon. After 15 hours the reaction mixture was cooled to ambient temperature, then poured into a reparatory funnel containing water (1000 mL) and the extracted with ether (2×1000 mL). The organic layers were combined and dried over sodium sulfate, then evaporated to give 10.5 g of brown semi-solid. The crude material was purified by silica gel column chromatography, eluting with 99/1 chloroform/methanol followed by 98/2 chloroform/methanol to provide the desired product (7.74 g, 74%).

Step G: Preparation of ethyl 7-(2-amino-4-carbamoylphenoxy)-6-chlorochroman-4-carboxylate To a stirred solution of ethyl 7-(4-carbamoyl-2-nitrophenoxy)-6-chlorochroman-4-carboxylate (7.74 g, 18.4 mmol) in THF (130 mL) at ambient temperature was added zinc dust followed by saturated ammonium chloride solution (50 mL). The resulting mixture was stirred at ambient temperature. After 30 minutes the reaction was filtered through a glass microfibre filter and the insoluble material was washed twice with THF. The combined filtrate and washings were concentrated and the residue was diluted with ethyl acetate (250 mL) and water (125 mL). The organic layer was separated and washed with brine (75 mL), dried over sodium sulfate and evaporated to provide the desired product (5.95 g, 83%).

Step F: Preparation of ethyl 7-(4-carbamoylphenoxy)-6-chlorochroman-4-carboxylate To a solution of isobutyl nitrite (3.92 g, 15.2 mmol) in DMF (100 mL) at 66° C. was added a solution of ethyl 7-(2-amino-4-carbamoylphenoxy)-6-chlorochroman-4-carboxylate (5.94 g, 15.2 mmol) in DMF (30 mL) dropwise over 14 minutes. The temperature rose to 70° C. during the addition and gas began to evolve. After 37 minutes of stirring at 68-69° C. the resulting solution was cooled to ambient temperature and poured into a reparatory funnel containing water (1500 mL). The resulting mixture was extracted with ethyl acetate (250 mL) and the organic layer was washed with 1M HCl, and brine, dried over sodium sulfate and concentrated to give 5.39 g of brown solid. The solid was triturated with ether and filtered to provide the desired product (4.86 g, 85%).

Step G: Preparation of ethyl 6-chloro-7-(4-(6-chloroquinoxalin-2-ylcarbamoyl)phenoxy)chroman-4-carboxylate:

Ethyl 7-(4-carbamoylphenoxy)-6-chlorochroman-4-carboxylate (750 mg, 2.00 mmol), 2,6-dichloroquinoxaline (437 mg, 2.20 mmol), XPHOS (95.1 mg, 0.200 mmol), $Pd(OAc)_2$ (22.4 mg, 0.0998 mmol) and cesium carbonate (1626 mg, 4.99 mmol) were diluted with dioxane (6 mL) in a vial. The reaction was purged with argon for 3 minutes, capped and heated at 80° C. for 12 hours. The reaction was cooled and loaded directly onto a biotage 25 column (silica gel) and eluted with 5% ethyl acetate/hexanes to 75% ethyl acetate/hexanes to yield ethyl 6-chloro-7-(4-(6-chloroquinoxalin-2-ylcarbamoyl)phenoxy)chroman-4-carboxylate (540 mg, 1.00 mmol, 50.3% yield).

Step H: Preparation of 6-chloro-7-(4-(6-chloroquinoxalin-2-ylcarbamoyl)phenoxy)chroman-4-carboxylic acid Ethyl 6-chloro-7-(4-(6-chloroquinoxalin-2-ylcarbamoyl)phenoxy)chroman-4-carboxylate (540 mg, 1.00 mmol) was diluted with THF (8 mL) followed by the addition of NaOH (5015 µL, 5.02 mmol) and ethanol (4 mL). After stirring for 2 hours, the reaction was diluted with ethyl acetate and 0.5 M HCl. The layers were separated and the organic layer was dried over MgSO$_4$, filtered and concentrated. The material was triturated with DCM to provide the desired product (420 mg, 0.823 mmol, 82.1% yield). MS (ESI)=510.1 (M+1).

EXAMPLE 16

6-Chloro-7-(4-(6-(trifluoromethyl)quinolin-2-ylcarbamoyl)phenoxy)chroman-4-carboxylic acid

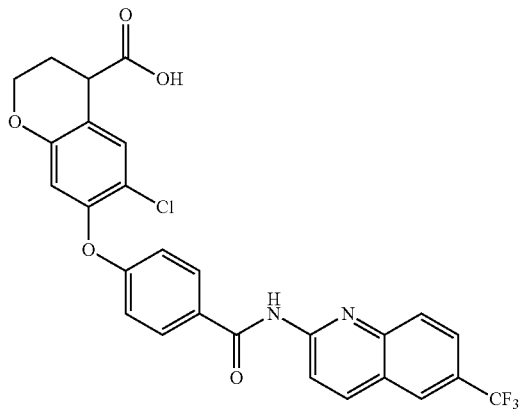 [SMILES: O=C(Nc1ccc2cc(C(F)(F)F)ccc2n1)c1ccc(Oc2cc3c(cc2Cl)C(C(=O)O)CCO3)cc1]

Prepared by the method of Example 15, using 2-chloro-6-(trifluoromethyl)quinoline in place of 2,6-dichloroquinoxaline in Step G. MS (ESI)=(M+1).

EXAMPLE 17

6-Chloro-7-(4-(7-chloroquinolin-2-ylcarbamoyl)phenoxy)chroman-4-carboxylic acid

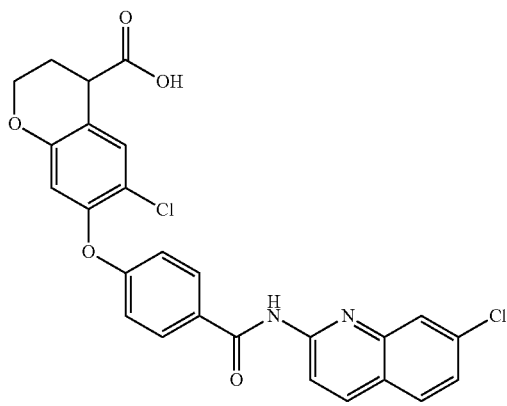 [SMILES: O=C(Nc1ccc2ccc(Cl)cc2n1)c1ccc(Oc2cc3c(cc2Cl)C(C(=O)O)CCO3)cc1]

Prepared by the method of Example 15, using 2,7-dichloroquinoline in place of 2,6-dichloroquinoxaline in Step G. MS (ESI)=509.2 (M+1).

EXAMPLE 18

6-Chloro-7-(4-(6-fluoroquinolin-2-ylcarbamoyl)phenoxy)chroman-4-carboxylic acid

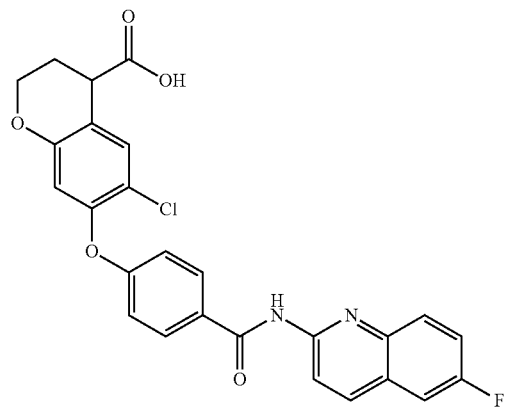 [SMILES: O=C(Nc1ccc2cc(F)ccc2n1)c1ccc(Oc2cc3c(cc2Cl)C(C(=O)O)CCO3)cc1]

Prepared by the method of Example 15, using 2-chloro-6-fluoroquinoline place of 2,6-dichloroquinoxaline in Step G. MS (ESI)=493.1 (M+1).

EXAMPLE 19

6-Chloro-7-(4-(5-chloroquinolin-2-ylcarbamoyl)phenoxy)chroman-4-carboxylic acid

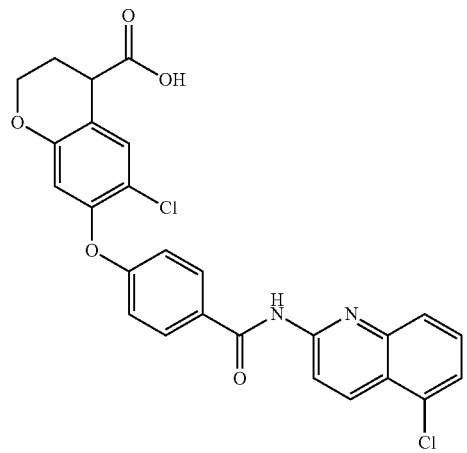 [SMILES: O=C(Nc1ccc2c(Cl)cccc2n1)c1ccc(Oc2cc3c(cc2Cl)C(C(=O)O)CCO3)cc1]

Prepared by the method of Example 15, using 2,5-dichloroquinoline in place of 2,6-dichloroquinoxaline in Step G. MS (APCI)=509.0 (M+1).

EXAMPLE 20

6-Chloro-7-(4-(7-chloroquinoxalin-2-ylcarbamoyl)phenoxy)chroman-4-carboxylic acid

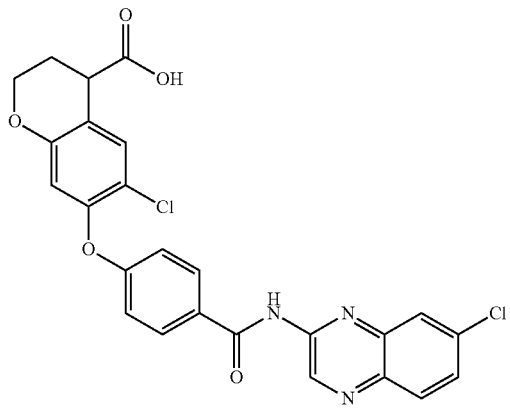 [SMILES: O=C(Nc1cnc2ccc(Cl)cc2n1)c1ccc(Oc2cc3c(cc2Cl)C(C(=O)O)CCO3)cc1]

Prepared by the method of Example 15, using 2,7-dichloroquinoloxaline in place of 2,6-dichloroquinoxaline in Step G. MS (ESI)=512.0 (M+1).

EXAMPLE 21

6-Chloro-7-(4-(4-methylquinolin-2-ylcarbamoyl)phenoxy)chroman-4-carboxylic acid

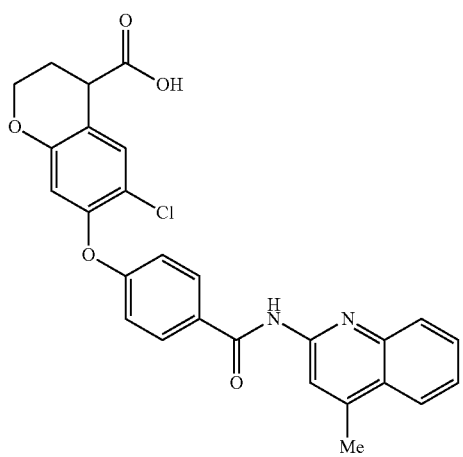 [SMILES: Cc1cc(NC(=O)c2ccc(Oc3cc4c(cc3Cl)C(C(=O)O)CCO4)cc2)nc2ccccc12]

Prepared by the method of Example 15, using 2-chloro-4-methylquinoline place of 2,6-dichloroquinoxaline in Step G. MS (APCI)=489.1 (M+1).

EXAMPLE 22

6-Chloro-7-(4-(6-methoxyquinolin-2-ylcarbamoyl)phenoxy)chroman-4-carboxylic acid

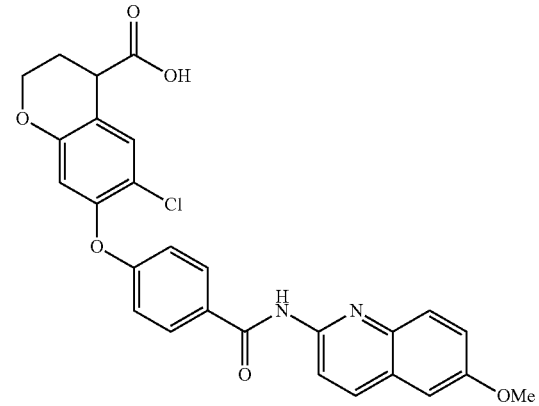 [SMILES: COc1ccc2nc(NC(=O)c3ccc(Oc4cc5c(cc4Cl)C(C(=O)O)CCO5)cc3)ccc2c1]

Prepared by the method of Example 15, using 2-chloro-6-methoxyquinoline in place of 2,6-dichloroquinoxaline in Step G. MS (APCI)=505.1 (M+1).

EXAMPLE 23

6-Chloro-7-(4-(quinolin-2-ylcarbamoyl)phenoxy)chroman-4-carboxylic acid

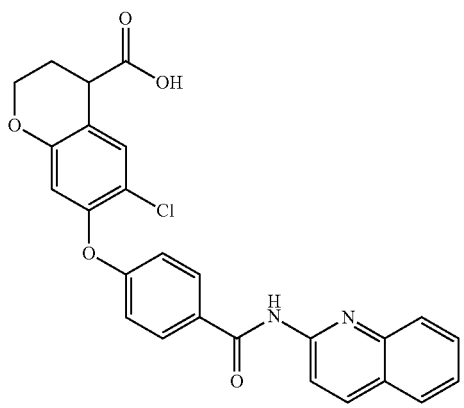 [SMILES: O=C(Nc1ccc2ccccc2n1)c1ccc(Oc2cc3c(cc2Cl)C(C(=O)O)CCO3)cc1]

Prepared by the method of Example 15, using 2,8-dichloroquinoline in place of 2,6-dichloroquinoxaline in Step G. The 8-chloro substituent was removed during the palladium coupling step. MS (ESI)=475.1 (M+1).

EXAMPLE 24

6-Chloro-7-(4-(8-methylquinolin-2-ylcarbamoyl)phenoxy)chroman-4-carboxylic acid

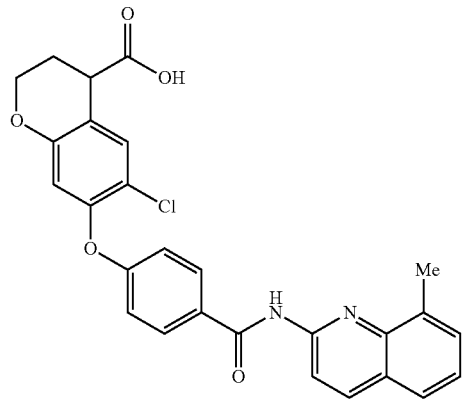 [SMILES: Cc1cccc2ccc(NC(=O)c3ccc(Oc4cc5c(cc4Cl)C(C(=O)O)CCO5)cc3)nc12]

Prepared by the method of Example 15, using 2-chloro-8-methylquinoline in place of 2,6-dichloroquinoxaline in Step G. MS (APCI)=489.1 (M+1).

EXAMPLE 26

6-Chloro-7-(4-(3-methylquinolin-2-ylcarbamoyl)phenoxy)chroman-4-carboxylic acid

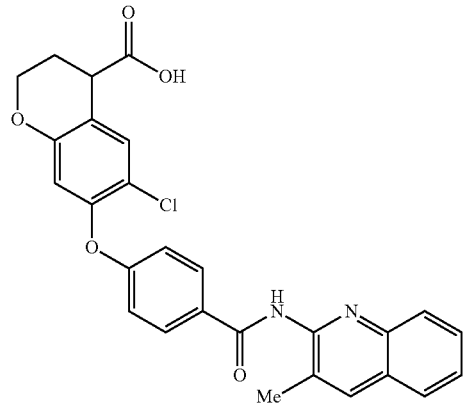

Prepared by the method of Example 15, using 2-chloro-3-methylquinoline in place of 2,6-dichloroquinoxaline in Step G. MS (ESI)=489.0 (M+1).

EXAMPLE 25

6-Chloro-7-(4-(8-chloroquinolin-2-ylcarbamoyl)phenoxy)chroman-4-carboxylic acid

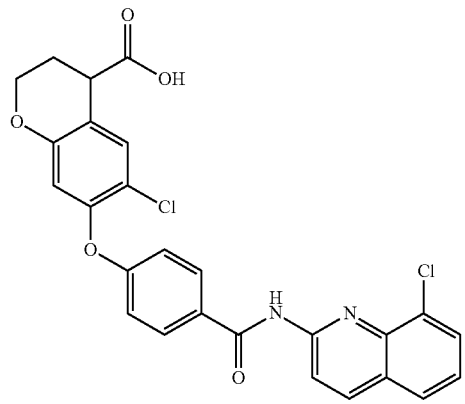 [SMILES: O=C(Nc1ccc2cccc(Cl)c2n1)c1ccc(Oc2cc3c(cc2Cl)C(C(=O)O)CCO3)cc1]

Prepared by the method of Example 15, using 2,8-dichloroquinoline in place of 2,6-dichloroquinoxaline in Step G. MS (ESI)=509.1 (M+1).

EXAMPLE 27

6-chloro-7-(4-(6-phenylpyridin-2-ylcarbamoyl)phenoxy)chroman-4-carboxylic acid

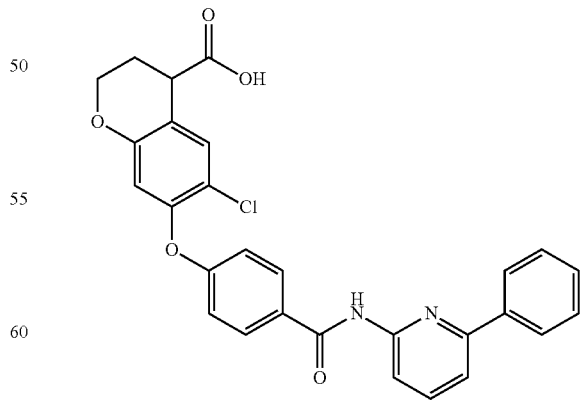

Prepared by the method of Example 15, using 2-chloro-6-phenylpyridine in place of 2,6-dichloroquinoxaline in Step G. MS (APCI)=501.2 (M+1).

EXAMPLE 28

6-Chloro-7-(4-(6-(trifluoromethyl)pyridin-2-ylcarbamoyl)phenoxy)chroman-4-carboxylic acid

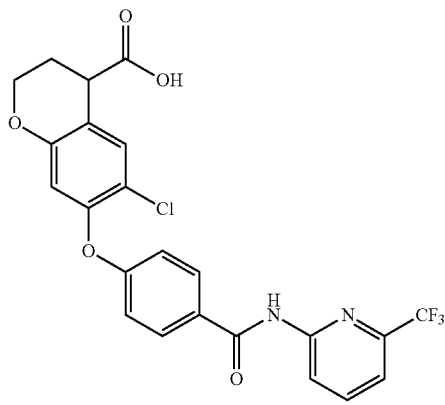 [SMILES: O=C(Nc1cccc(C(F)(F)F)n1)c1ccc(Oc2cc3c(cc2Cl)C(C(=O)O)CCO3)cc1]

Prepared by the method of Example 15, using 2-chloro-5-trifluoromethylpyridine in place of 2,6-dichloroquinoxaline in Step G. MS (ESI)=493.1 (M+1).

EXAMPLE 29

6-Chloro-7-(4-(6-(trifluoromethyl)pyridin-3-ylcarbamoyl)phenoxy)chroman-4-carboxylic acid

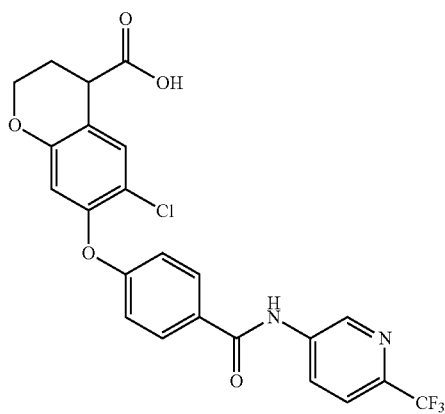 [SMILES: O=C(Nc1ccc(C(F)(F)F)nc1)c1ccc(Oc2cc3c(cc2Cl)C(C(=O)O)CCO3)cc1]

Prepared by the method of Example 15, using 3-chloro-6-trifluoromethylpyridine in place of 2,6-dichloroquinoxaline in Step G. MS (ESI)=493.1 (M+1).

EXAMPLE 30

6-Chloro-7-(4-(6-chloroquinolin-2-ylcarbamoyl)phenoxy)chroman-4-carboxylic acid

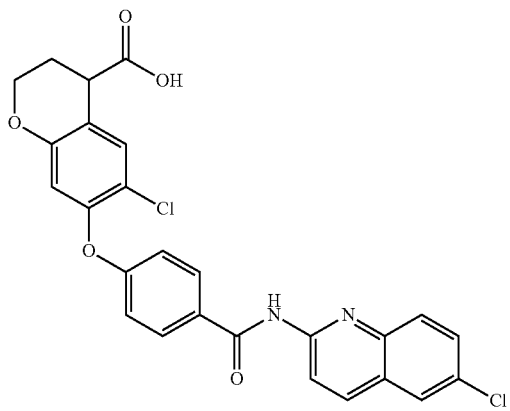 [SMILES: O=C(Nc1ccc2cc(Cl)ccc2n1)c1ccc(Oc2cc3c(cc2Cl)C(C(=O)O)CCO3)cc1]

Step A: Preparation of ethyl 7-(4-(tert-butoxycarbonyl)phenoxy)-6-chlorochroman-4-carboxylate tert-Butyl 4-iodobenzoate (25.9 g, 85.2 mmol) and 2,2,6,6-tetramethyl-3,5-heptanedione (7.01 mL, 34.1 mmol) were diluted with NMP (70 mL) and bubbled with Argon for 20 minutes. Copper (I) chloride (16.9 g, 170 mmol), ethyl 6-chloro-7-hydroxychroman-4-carboxylate (24.0 g, 93.7 mmol) and cesium carbonate (55.5 g, 170 mmol) were combined and added to the reaction using a small funnel which was rinsed with NMP (30 mL). The reaction was purged for an additional 10 minutes and then heated to 100° C. and stirred for 5 hours under Argon. The reaction was cooled and loaded directly onto a silica plug (2 kg) and eluted with 10% ethyl acetate/hexanes to yield 10 g of crude product. The crude material was purified by silica gel column chromatography, eluting with 5% ethyl acetate/hexanes to 50% ethyl acetate/hexanes to provide the desired product (14 g, 32.3 mmol, 38.0% yield) as a viscous oil.

Step B: Preparation of 4-(6-chloro-4-(ethoxycarbonyl)chroman-7-yloxy)benzoic acid Ethyl 7-(4-(tert-butoxycarbonyl)phenoxy)-6-chlorochroman-4-carboxylate (8.62 g, 19.91 mmol) was diluted with DCM (40 mL) followed by portionwise addition of TFA (30 mL). After stirring for 1 hour, the reaction was concentrated and placed under vacuum over the weekend. The residue was taken up in DCM and washed with saturated bicarbonate and 1N HCl. The organic layer was separated, dried over magnesium sulfate, filtered and concentrated to provide the desired product (7.278 g, 19.32 mmol, 97.00% yield).

Step C: Preparation of 6-chloro-7-(4-(6-chloroquinolin-2-ylcarbamoyl)phenoxy)chroman-4-carboxylate 4-(6-Chloro-4-(ethoxycarbonyl)chroman-7-yloxy)benzoic acid (1.00 g, 2.65 mmol) was diluted with DCE (10 mL) followed by the addition of oxalyl chloride in DCM (2M) (1.46 mL, 2.92 mmol) and DMF (1 drop). After stirring for 20 minutes, 6-chloroquinolin-2-amine (0.521 g, 2.92 mmol) and DIEA (1.16 mL, 6.64 mmol) were added and the reaction was stirred for 4 hours at 65° C. The reaction was cooled, diluted with DCM and washed with 0.5M HCl, saturated bicarbonate, dried over magnesium sulfate, filtered and concentrated. The residue was loaded onto a samplet with DCM and eluted with 5% ethyl acetate/hexanes to 60% ethyl acetate/hexanes to provide the desired product (1.13 g, 2.10 mmol, 79.2% yield) as a white foam.

Step D: Preparation of 6-chloro-7-(4-(6-chloroquinolin-2-ylcarbamoyl)phenoxy)chroman-4-carboxylic acid To ethyl 6-chloro-7-(4-(6-chloroquinolin-2-ylcarbamoyl)phenoxy)chroman-4-carboxylate (1.31 g, 2.44 mmol) in THF (12 mL) and ethanol (6 mL) was added NaOH (6.09 mL, 12.2 mmol) and the reaction stirred at ambient temperature for 3 hours. The reaction was diluted with ethyl acetate (25 mL) and 1N aqueous HCl (20 mL). THF was added as needed to keep the organic layer clear. The organic layer was separated, washed with brine, dried over magnesium sulfate and concentrated. The residue was triturated with DCM and the resulting solids were collected by filtration to provide the desired product (0.98 g, 1.92 mmol, 78.9% yield). MS (APCI)=509.0 (M+1).

EXAMPLE 32

6-Chloro-7-(4-(6-phenylpyrazin-2-ylcarbamoyl)phenoxy)chroman-4-carboxylic acid

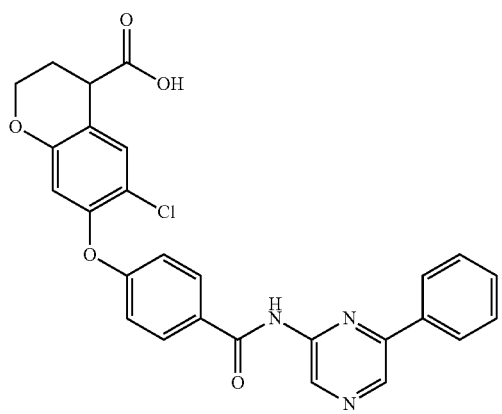

Prepared by the method of Example 15, using 2-chloro-6-phenylpyrazine in place of 2,6-dichloroquinoxaline in Step G. MS (APCI)=502.2 (M+1).

EXAMPLE 33

6-Chloro-7-(4-(6-(4-chlorophenyl)pyridin-2-ylcarbamoyl)phenoxy)chroman-4-carboxylic acid

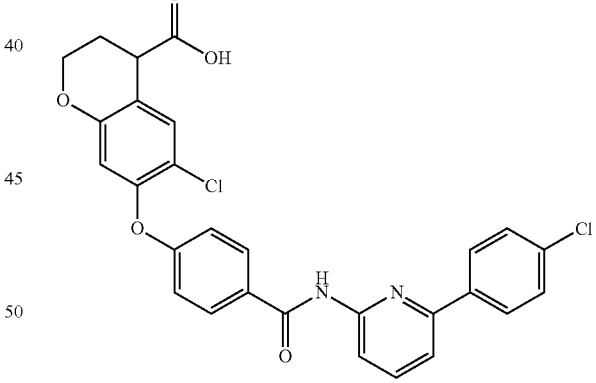

Step A: Preparation of ethyl 7-(4-(6-bromopyridin-2-ylcarbamoyl)phenoxy)-6-chlorochroman-4-carboxylate 4-(6-Chloro-4-(ethoxycarbonyl)chroman-7-yloxy)benzoic acid (1 g, 2.65 mmol) was diluted with DCM (10 mL) followed by the addition of oxalyl chloride in DCM (2M) (1.46 mL, 2.92 mmol) and DMF (1 drop). After stirring for 20 minutes, 6-bromopyridin-2-amine (0.505 g, 2.92 mmol) and DIEA (1.16 mL, 6.64 mmol) were added and the reaction was stirred overnight at ambient temperature. The reaction was

EXAMPLE 31

6-Chloro-7-(4-(4-(trifluoromethyl)pyridin-2-ylcarbamoyl)phenoxy)chroman-4-carboxylic acid

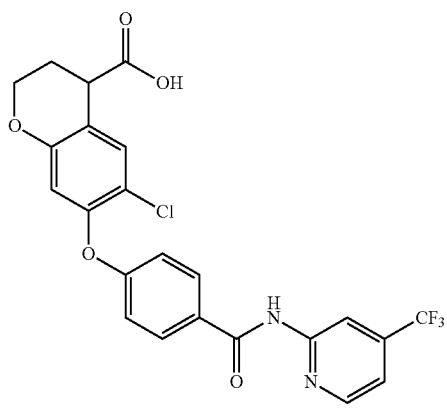 [SMILES: O=C(Nc1cc(C(F)(F)F)ccn1)c1ccc(Oc2cc3c(cc2Cl)C(C(=O)O)CCO3)cc1]

Prepared by the method of Example 30, using 2-amino-4-(trifluoromethyl)pyridine in place of 6-chloroquinolin-2-amine in Step C. MS (ESI)=493.2 (M+1).

loaded directly onto a biotage 40 cartridge and eluted with 5% ethyl acetate/hexanes to 70% ethyl acetate/hexanes to provide the desired product.

Step B: Preparation of 6-chloro-7-(4-(6-(4-chlorophenyl)pyridin-2-ylcarbamoyl)phenoxy)chroman-4-carboxylate Ethyl 7-(4-(6-bromopyridin-2-ylcarbamoyl)phenoxy)-6-chlorochroman-4-carboxylate (50 mg, 0.094 mmol), 4-chlorophenylboronic acid (19 mg, 0.12 mmol), $Na_2CO_3$ (30 mg, 0.28 mmol) and $Pd(PPh_3)_4$ (11 mg, 0.0094 mmol) were place in a 1 mL vial and diluted with toluene (600 μL) and water (60 μL). The vial was purged with argon, sealed and heated to 100° C. After stirring for 12 hours, the reaction was cooled and loaded directly onto a biotage 25 cartridge eluting with 5% ethyl acetate/hexanes to 60% ethyl acetate/hexanes to provide the desired product (40 mg, 0.071 mmol, 76% yield).

Step C: Preparation of 6-chloro-7-(4-(6-(4-chlorophenyl)pyridin-2-ylcarbamoyl)phenoxy)chroman-4-carboxylic acid Ethyl 6-chloro-7-(4-(6-(4-chlorophenyl)pyridin-2-ylcarbamoyl)phenoxy)chroman-4-carboxylate (50 mg, 0.089 mmol) was diluted with THF (1 mL) followed by the addition of NaOH (444 μL, 0.44 mmol) and ethanol (500 μL). After stirring for 2 hours, the reaction was diluted with ethyl acetate and 2N HCl. The layers were separated and the organics were dried over $MgSO_4$, filtered and concentrated to provide the desired product (30 mg, 0.056 mmol, 63% yield). MS (ESI)= 535.2 (M+1).

EXAMPLE 34

6-Chloro-7-(4-(6-(3-chlorophenyl)pyridin-2-ylcarbamoyl)phenoxy)chroman-4-carboxylic acid

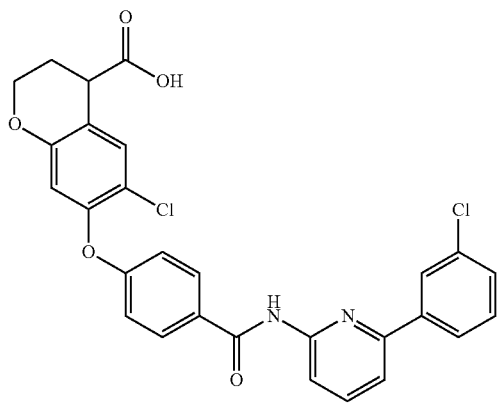 [SMILES: O=C(Nc1cccc(-c2cccc(Cl)c2)n1)c1ccc(Oc2cc3c(cc2Cl)C(C(=O)O)CCO3)cc1]

Prepared by the method of Example 33, using 3-chlorophenylboronic acid in place of 4-chlorophenylboronic acid in Step B. MS (ESI)=535.2 (M+1).

EXAMPLE 35

Sodium 6-chloro-7-(4-(6-chloroquinolin-2-ylcarbamoyl)phenoxy)chroman-4-carboxylate

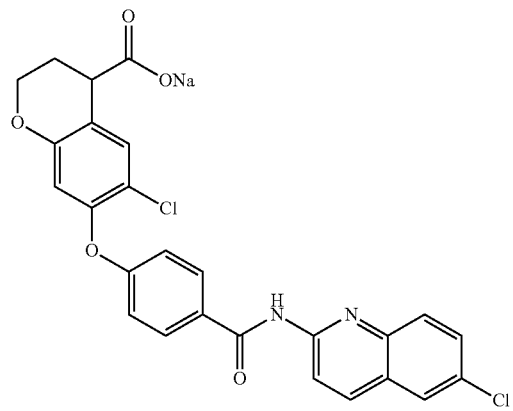

6-Chloro-7-(4-(6-chloroquinolin-2-ylcarbamoyl)phenoxy)chroman-4-carboxylic acid (0.050 g, 0.098 mmol) in THF (1.5 mL) was heated until a homogeneous solution resulted. The reaction was filtered and sodium 2-ethylhexanoate (0.020 g, 0.12 mmol) was added. The reaction was cooled to 0° C. Hexane was added in 0.5 mL portions and the solution was stored in the freezer overnight. The resulting solids were collected by filtration and dried to provide the desired product (0.043 g, 0.081 mmol, 82% yield). MS (ESI)= 509.1 (M+1).

EXAMPLE 36

6-Chloro-7-(4-(6-chloroquinolin-2-ylcarbamoyl)phenoxy)chroman-4-carboxylic acid, Enantiomer 1

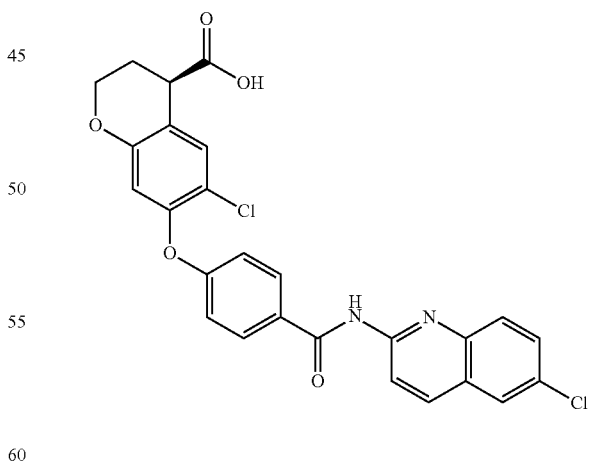

Step A: Preparation of tert-butyl 6-chloro-7-(4-(6-chloroquinolin-2-ylcarbamoyl)phenoxy)chroman-4-carboxylate To 6-chloro-7-(4-(6-chloroquinolin-2-ylcarbamoyl)phenoxy)chroman-4-carboxylic acid (0.980 g, 1.924 mmol) suspended in toluene (2 mL) was added N,N-dimethylformamide di-tert-butyl acetal (4.613 mL, 19.24 mmol) and the reaction heated to 60° C. for 2 hours under a positive pressure of nitrogen. The reaction was cooled and diluted with ethyl acetate (30 mL). The organic layer was washed with water (20 mL) and brine (20 mL). The organic layer was separated, dried over magnesium sulfate and concentrated. The resulting oil was loaded onto a silica gel samplet with DCM and the product eluted using a gradient of 5% to 40% ethyl acetate/hexanes to provide racemic tert-butyl 6-chloro-7-(4-(6-chloroquinolin-2-ylcarbamoyl)phenoxy)chroman-4-carboxylate (0.91 g, 1.609 mmol, 83.64% yield) as a foam. The enantiomers were separated by column chromatography using a cellulose tris(4-methylbenzoate) coated silica gel column (OJ column, 20 mm×250 mm; Chiral Technologies, West Chester, Pa.), eluting with 75% acetonitrile/25% methanol.

Step B: Preparation of 6-chloro-7-(4-(6-chloroquinolin-2-ylcarbamoyl)phenoxy)chroman-4-carboxylic acid, Enantiomer 1

To a solution of racemic tert-butyl 6-chloro-7-(4-(6-chloroquinolin-2-ylcarbamoyl)phenoxy)chroman-4-carboxylate, Enantiomer 1 (0.068 g, 0.12 mmol) in 2 mL of DCM was added 0.5 mL of TFA and the reaction was allowed to stand at ambient temperature. After stirring for 3 hours, the reaction was concentrated to a solid and taken up in 3 mL of DCM. Solid began to form after 5 min from the golden yellow solution. The supernatant was removed by pipet and dried to provide 6-chloro-7-(4-(6-chloroquinolin-2-ylcarbamoyl)phenoxy)chroman-4-carboxylic acid, Enantiomer 1 (0.061 g, 98%) as an off white powder.

EXAMPLE 37

6-Chloro-7-(4-(6-chloroquinolin-2-ylcarbamoyl)phenoxy)chroman-4-carboxylic acid, Enantiomer 2

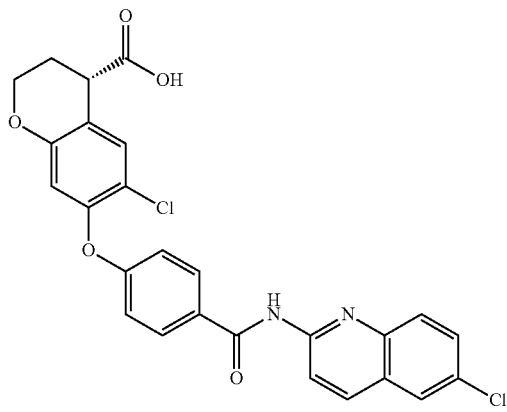 [SMILES: O=C(Nc1ccc2cc(Cl)ccc2n1)c1ccc(Oc2cc3c(cc2Cl)[C@@H](C(=O)O)CCO3)cc1]

Step A: Preparation of tert-butyl 6-chloro-7-(4-(6-chloroquinolin-2-ylcarbamoyl)phenoxy)chroman-4-carboxylate To 6-chloro-7-(4-(6-chloroquinolin-2-ylcarbamoyl)phenoxy)chroman-4-carboxylic acid (0.980 g, 1.924 mmol) suspended in toluene (2 mL) was added N,N-dimethylformamide di-tert-butyl acetal (4.613 mL, 19.24 mmol) and the reaction heated to 60° C. for 2 hours under a positive pressure of nitrogen. The reaction was cooled and diluted with ethyl acetate (30 mL). The organic layer was washed with water and brine. The organic layer was separated, dried over magnesium sulfate and concentrated. The resulting oil was loaded onto a silica gel samplet with DCM and the product eluted using a gradient of 5% to 40% ethyl acetate/hexanes to provide racemic tert-butyl 6-chloro-7-(4-(6-chloroquinolin-2-ylcarbamoyl)phenoxy)chroman-4-carboxylate (0.91 g, 1.609 mmol, 83.64%) as a foam. The enantiomers were separated by column chromatography using a cellulose tris(4-methylbenzoate) coated silica gel column (OJ column, 20 mm×250 mm; Chiral Technologies, West Chester, Pa.), eluting with 75% acetonitrile/25% methanol.

Step B: Preparation of 6-chloro-7-(4-(6-chloroquinolin-2-ylcarbamoyl)phenoxy)chroman-4-carboxylic acid, Enantiomer 2:

To a solution of racemic tert-butyl 6-chloro-7-(4-(6-chloroquinolin-2-ylcarbamoyl)phenoxy)chroman-4-carboxylate, Enantiomer 2 (0.087 g, 0.015 mmol) in 2 mL of DCM was added 0.5 mL of TFA and the reaction was allowed to stand at ambient temperature. After stirring for 3 hours, the reaction was concentrated to a solid and taken up in 3 mL of DCM. Solid began to form after 5 minutes from the golden yellow solution. The supernatant was removed by pipet and dried to provide 6-chloro-7-(4-(6-chloroquinolin-2-ylcarbamoyl)phenoxy)chroman-4-carboxylic acid, Enantiomer 2 (0.074 g, 94%) as an off white powder.

EXAMPLE 38

6-Cyano-7-(4-(2-(5-(trifluoromethyl)pyridin-2-yl)ethylcarbamoyl)phenoxy)chroman-4-carboxylic acid

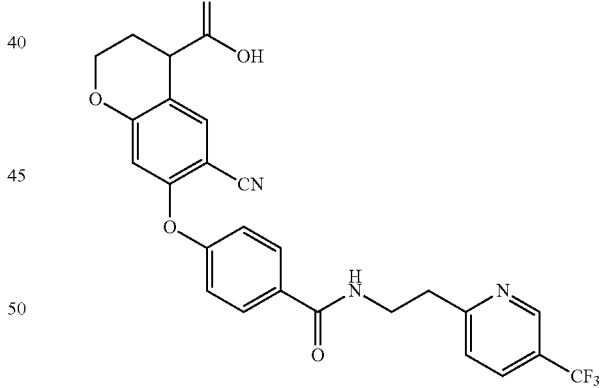

Step A: Preparation of methyl 6-cyano-7-(4-(2-(5-(trifluoromethyl)pyridin-2-yl)ethylcarbamoyl)phenoxy)chroman-4-carboxylate A mixture of 4-(6-cyano-4-(methoxycarbonyl)chroman-7-yloxy)benzoic acid (20 mg, 0.0566 mmol), 1-(3-(dimethylamino)propyl)-3-ethyl-carbodiimide hydrochloride (12.85 mg, 0.0670 mmol), 1-hydroxybenzotriazole monohydrate (10.26 mg, 0.0670 mmol), and 1,2-dichloroethane (1 mL) was stirred at ambient temperature for 20 minutes. 2-(5-(Trifluoromethyl)pyridin-2-yl)ethanamine dihydrochloride (19.23 mg, 0.0731 mmol) and triethylamine (84.91 µl, 0.6092 mmol) were added to the activated acid and the mixture was stirred for 18 hours at ambient temperature. The reaction mixture was purified on silica gel (MeOH in dichloromethane gradient) to provide 14.2 mg of the title compound as a thin film (48%).

Step B: Preparation of 6-cyano-7-(4-(2-(5-(trifluoromethyl)pyridin-2-yl)ethylcarbamoyl)phenoxy) chroman-4-carboxylic acid Methyl 6-cyano-7-(4-(2-(5-(trifluoromethyl)-pyridin-2-yl)ethylcarbamoyl)phenoxy)chroman-4-carboxylate (14.2 mg, 0.0270 mmol) was dissolved in THF (3 mL) and 1M solution of lithium hydroxide monohydrate in water (54.0 µl, 0.0540 mmol) was added. The mixture was stirred overnight at ambient temperature, then quenched with 4.0 M HCl solution in 1,4-dioxane (20.3 µl, 0.0811 mmol). The reaction mixture was purified on silica gel (MeOH in dichloromethane with 1% acetic acid gradient) to provide 5.1 mg of the title compound as a thin film (37%). MS (apci) m/z=509.7 (M−H).

EXAMPLE 39

6-Cyano-7-(4-(6-(3,4-dimethylphenyl)pyridin-2-ylcarbamoyl)phenoxy)chroman-4-carboxylic acid

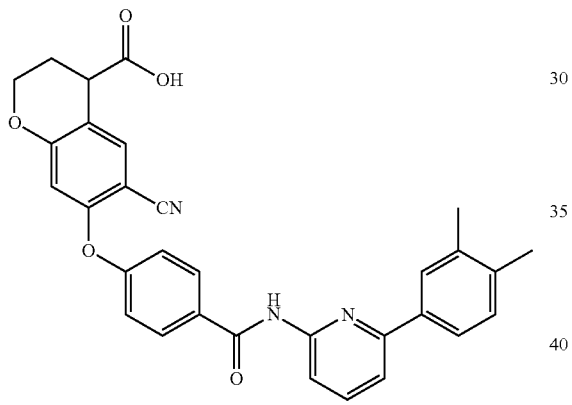

Step A: Preparation of methyl 7-(4-(6-bromopyridin-2-ylcarbamoyl)phenoxy)-6-cyanochroman-4-carboxylate To a solution of 4-(6-cyano-4-(methoxycarbonyl)chroman-7-yloxy)benzoic acid (1.00 g, 2.83 mmol) and a drop of DMF in 1,2-dichloroethane (10 mL) was added 2 M solution of oxalyl chloride in dichloromethane (1.556 ml, 3.113 mmol) and the mixture was stirred at ambient temperature for 1 hour. Gas evolution was observed. 6-Bromopyridin-2-amine (0.489 g, 2.8303 mmol) and triethylamine (0.789 ml, 5.66 mmol) were added to the acid chloride solution. The mixture was stirred at ambient temperature for 18 hours. The whole mixture was purified on silica gel (EtOAc/hexanes gradient) to provide 0.939 g of the title compound as a white solid (65.3%). MS (apci) m/z=508.0 (M+H).

Step B: Preparation of methyl 6-cyano-7-(4-(6-(3,4-dimethylphenyl)pyridin-2-ylcarbamoyl)phenoxy) chroman-4-carboxylate Methyl 7-(4-(6-bromopyridin-2-ylcarbamoyl)phenoxy)-6-cyanochroman-4-carboxylate (51 mg, 0.1003 mmol), 3,4-dimethylphenylboronic acid (19.562 mg, 0.1304 mmol), sodium carbonate (31.901 mg, 0.301 mmol), toluene (1 mL), and water (0.1 mL) were placed in a vial with a Teflon lined screw cap. Argon was bubbled through the mixture for 10 minutes. Palladium (0) tetrakistriphenylphosphine (5.797 mg, 0.00501 mmol) was added and the vial was sealed. The vial was placed in a preheated sand bath (100° C.) and the mixture was stirred for 16 hours at that temperature. The mixture was cooled to ambient temperature and whole mixture was purified on silica gel (EtOAc-hexanes gradient) to provide 51.1 mg of the title compound as a thin film (95.5%).

Step C: Preparation of 6-cyano-7-(4-(6-(3,4-dimethylphenyl)pyridin-2-ylcarbamoyl)phenoxy)chroman-4-carboxylic acid A mixture of methyl 6-cyano-7-(4-(6-(3,4-dimethylphenyl)pyridin-2-ylcarbamoyl)phenoxy)-chroman-4-carboxylate (51.1 mg, 0.09577 mmol), 1.0 M lithium hydroxide monohydrate solution in water (191.5 µl, 0.1915 mmol), and THF (1.5 ml) was stirred for 3 days at ambient temperature. The mixture was quenched with 4.0 M HCl solution in 1,4-dioxane (71.83 µl, 0.2873 mmol). The mixture was purified on silica gel (MeOH in dichloromethane gradient with 1% acetic acid) to provide 42.8 mg of the title compound was obtained as a thin film (86%). MS (apci) m/z=520.2 (M+H).

EXAMPLE 40

6-Cyano-7-(4-(6-(2,3-dimethylphenyl)pyridin-2-ylcarbamoyl)-phenoxy)-chroman-4-carboxylic acid

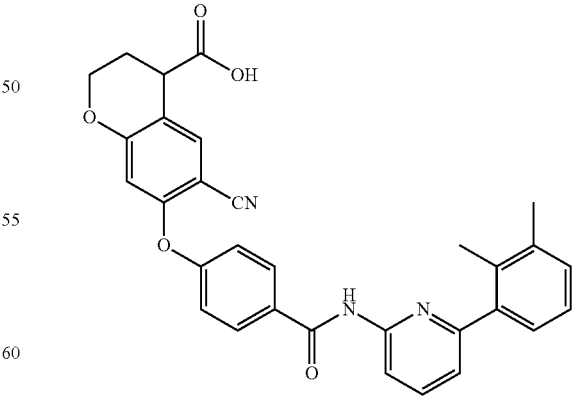

Prepared according to the method of Example 39, substituting 3,4-dimethylphenylboronic acid with 2,3-dimethylphenylboronic acid in Step B. MS (apci) m/z=520.2 (M+H).

EXAMPLE 41

6-Cyano-7-(4-(6-(3-(trifluoromethyl)phenyl)pyridin-2-ylcarbamoyl)-phenoxy)chroman-4-carboxylic acid

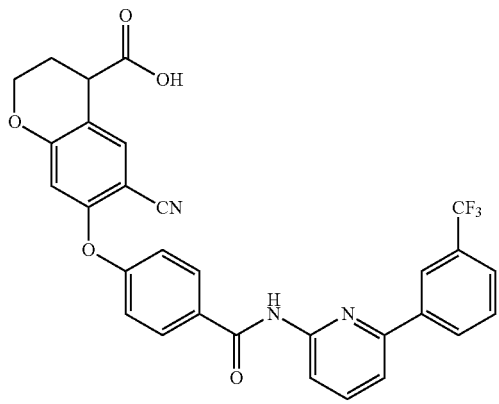 [SMILES: N#Cc1cc2c(cc1Oc1ccc(C(=O)Nc3cccc(-c4cccc(C(F)(F)F)c4)n3)cc1)OCCC2C(=O)O]

Prepared according to the method of Example 39, substituting 3,4-dimethylphenylboronic acid with 3-(trifluoromethyl)phenylboronic acid in Step B. MS (apci) m/z=560.1 (M+H).

EXAMPLE 42

6-Cyano-7-(4-(6-(4-(trifluoromethyl)phenyl)pyridin-2-ylcarbamoyl)-phenoxy)chroman-4-carboxylic acid

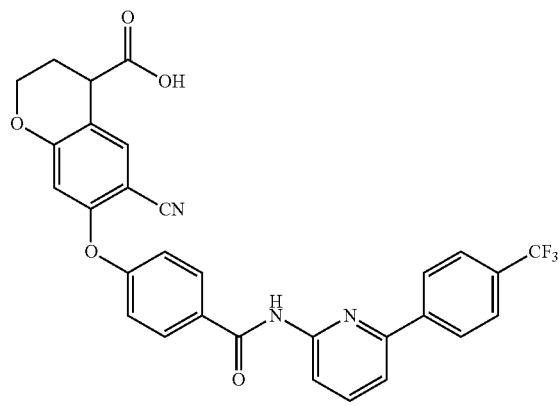 [SMILES: N#Cc1cc2c(cc1Oc1ccc(C(=O)Nc3cccc(-c4ccc(C(F)(F)F)cc4)n3)cc1)OCCC2C(=O)O]

Prepared according to the method of Example 39, substituting 3,4-dimethylphenylboronic acid with 4-(trifluoromethyl)phenylboronic acid in Step B. MS (apci) m/z=560.1 (M+H).

EXAMPLE 43

6-Cyano-7-(4-(6-(2,3-dihydrobenzofuran-5-yl)pyridin-2-ylcarbamoyl)-phenoxy)chroman-4-carboxylic acid

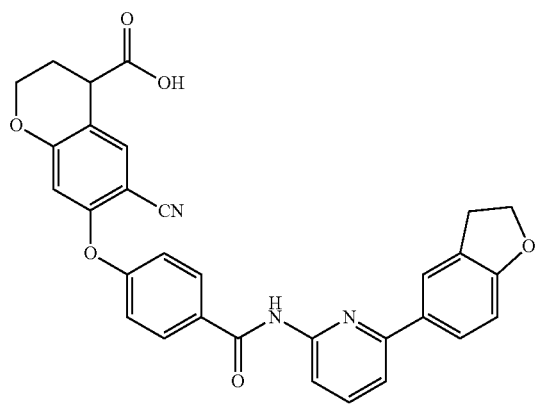 [SMILES: N#Cc1cc2c(cc1Oc1ccc(C(=O)Nc3cccc(-c4ccc5c(c4)CCO5)n3)cc1)OCCC2C(=O)O]

Prepared according to the method of Example 39, substituting 3,4-dimethylphenylboronic acid with 2,3-dihydrobenzofuran-5-ylboronic acid in Step B. MS (apci) m/z=534.2 (M+H).

EXAMPLE 44

Sodium 6-Chloro-7-(4-(6-(4-chlorophenyl)-5-fluoropyridin-2-ylcarbamoyl)phenoxy)chroman-4-carboxylate

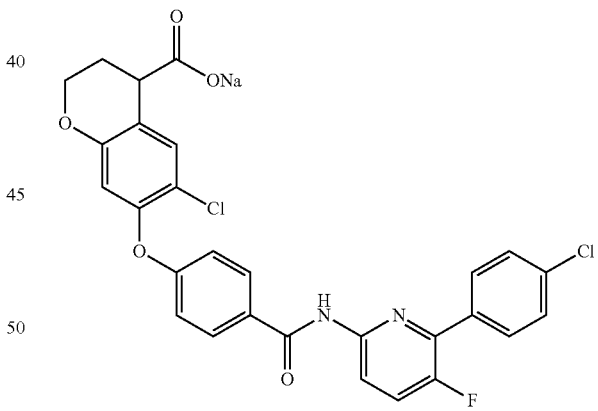

Step A: Preparation of 2-(4-chlorophenyl)-3-fluoropyridine

2-Chloro-3-fluoropyridine (0.4380 g, 3.33 mmol), 4-chlorophenylboronic acid (0.6248 g, 3.996 mmol), palladium tetrakistriphenylphosphine (0.1924 g, 0.1665 mmol), sodium carbonate (0.4235 g, 3.996 mmol), toluene (10 mL), and water (1 mL) were placed in a teflon lined vial. The vial was sealed and stirred at 125° C. for 21 hour. The mixture was cooled to ambient temperature and the whole mixture was purified on silica gel (EtOAc-hexanes gradient) to provide 569.4 mg of the title compound as white solid (82%).

Step B: Preparation of 2-(4-chlorophenol)-3-fluoropyridine 1-oxide

To a solution of 2-(4-chlorophenyl)-3-fluoropyridine (208 mg, 1.0018 mmol) in dichloromethane (3 mL) was added 3-chloroperbenzoic acid (370.44 mg, 1.5027 mmol, 70%) in one portion and the mixture was stirred at ambient temperature for 4 days. The mixture was diluted with dichloromethane, washed with 1N sodium hydroxide solution and brine, dried over anhydrous magnesium sulfate, filtered, and concentrated to provide 0.2173 g of the title compound as crude white solid, which was used for the next step without further purification.

Step C: Preparation of 6-chloro-2-(4-chlorophenol)-3-fluoropyridine

A mixture of 2-(4-chlorophenyl)-3-fluoropyridine 1-oxide (79.5 mg, 0.3555 mmol) and phosphorus oxychloride (5 ml, 54.620 mmol) was heated under reflux for 20 hours under nitrogen atmosphere. The mixture was cooled to ambient temperature and concentrated. The residue was dissolved in EtOAc (10 ml), washed with 1N sodium hydroxide, water, and brine, dried over anhydrous magnesium sulfate, filtered, and concentrated. The crude was purified on silica gel (EtOAc-hexanes gradient) to provide 22.8 mg of the title compound as white solid (26.5%).

Step D: Preparation of ethyl 6-chloro-7-(4-(6-(4-chlorophenyl)-5-fluoropyridin-2-ylcarbamoyl)-phenoxy)-chroman-4-carboxylate Prepared according to the method of Example 77, Step A, substituting 2-chloro-6-phenylpyrazine with 6-chloro-2-(4-chlorophenyl)-3-fluoropyridine. MS (apci) m/z=581.0 (M+H).

Step E: Preparation of 6-chloro-7-(4-(6-(4-chlorophenyl)-5-fluoropyridin-2-ylcarbamoyl)-phenoxy)-chroman-4-carboxylic acid Prepared according to the method of Example 77, Step B. MS (apci) m/z=553.0 (M+H).

Step F: Preparation of Sodium 6-chloro-7-(4-(6-(4-chlorophenyl)-5-fluoropyridin-2-ylcarbamoyl)phenoxy)-chroman-4-carboxylate 6-Chloro-7-(4-(6-(4-chlorophenyl)-5-fluoropyridin-2-yl-carbamoyl)phenoxy)-chroman-4-carboxylic acid (16.1 mg, 0.0291 mmol) was dissolved in MeOH-THF (0.5 mL-0.5 mL) and 0.5 M sodium methoxide solution in methanol (58.19 µl, 0.0291 mmol) was added. The mixture was stirred at ambient temperature for 1 hour and concentrated. The residue was chased with dichloromethane multiple times and dried under high vacuum to provide 17.0 mg of the title compound as white solid (101.6%). MS (apci) m/z=553.0 (M+2H—Na).

EXAMPLE 45

6-Chloro-7-(4-(8-methylquinolin-2-ylcarbamoyl) phenoxy)chroman-4-carboxylic acid

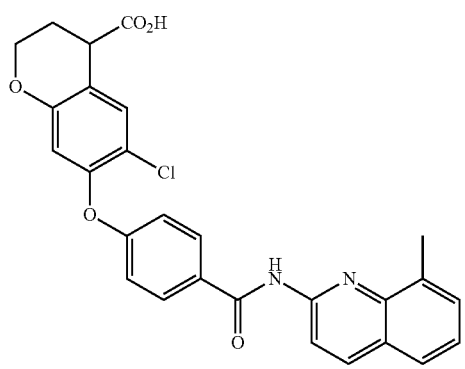 [SMILES: Cc1cccc2ccc(NC(=O)c3ccc(Oc4cc5c(cc4Cl)C(C(=O)O)CCO5)cc3)nc12]

Step A: Preparation of ethyl 7-(4-carbamoylphenoxy)-6-chlorochroman-4-carboxylate To a solution of 4-(6-chloro-4-(ethoxycarbonyl)chroman-7-yloxy)benzoic acid (Preparation B; 2.46 g, 6.529 mmol) in dichloromethane (32 ml) was added DMF (2 drops) and oxalyl chloride (0.6835 ml, 7.835 mmol). The reaction was stirred for 90 minutes. To this, anhydrous ammonia gas was bubbled into the reaction for 90 minutes. The reaction was stirred an additional hour, then diluted with EtOAc and washed twice with 1M hydrochloric acid, then with saturated sodium bicarbonate and saturated sodium chloride. The organic layer was dried over anhydrous sodium sulfate, filtered, and concentrated. The crude material was purified by recrystallization from EtOAc/hexanes to yield the desired compound (1.5 g, 3.991 mmol, 61.14% yield).

Step B: Preparation of 8-methylquinoline 1-oxide

To a solution of 8-methylquinoline (1.00 g, 6.98 mmol) in DCM (21 ml) was added 3-chlorobenzoperoxoic acid (2.35 g, 10.5 mmol), and the reaction was stirred for 16 hours at ambient temperature. The reaction was diluted with EtOAc and washed with 20% sodium sulfite, saturated sodium bicarbonate, and saturated sodium chloride. The organic layer was dried over anhydrous sodium sulfate, filtered, and concentrated. The residue was purified on the silica gel eluting with a gradient of 1-10% MeOH/DCM to yield the desired compound (0.440 g, 2.76 mmol, 39.6% yield).

Step C: Preparation of 2-chloro-8-methylquinoline

To a solution of 8-methylquinoline 1-oxide (0.440 g, 2.764 mmol) in toluene (10 ml) was added phosphoryl trichloride (1.265 ml, 13.82 mmol), and the reaction was heated to 80° C. for 2 hours. The reaction was cooled to ambient temperature and concentrated. The crude material was taken up in EtOAc and washed with saturated sodium bicarbonate and saturated sodium chloride. The organic layer was dried over anhydrous sodium sulfate, filtered, and concentrated to yield the desired compound (0.4 g, 2.252 mmol, 81.47% yield).

Step D: Preparation of ethyl 6-chloro-7-(4-(8-methylquinolin-2-ylcarbamoyl)phenoxy)chroman-4-carboxylate To a solution of ethyl 7-(4-carbamoylphenoxy)-6-chlorochroman-4-carboxylate (0.025 g, 0.0665 mmol), 2-chloro-8-methylquinoline (0.0130 g, 0.0732 mmol), X-PHOS (0.0238 g, 0.0732 mmol), and dicyclohexyl(2',4',6'-triisopropylbiphenyl-2-yl)phosphine (0.00634 g, 0.0133 mmol) in THF (0.6 ml) was added tris(dibenzylideneacetone)dipalladium (0.0030 g, 0.0033 mmol), and the reaction was heated to 60° C. for 16 hours. The reaction was loaded directly onto silica gel and eluted with a gradient of 5-70% EtOAc/hexanes to yield the desired compound (0.024 g, 0.0464 mmol, 69.8% yield).

Step E: Preparation of 6-chloro-7-(4-(8-methylquinolin-2-ylcarbamoyl)phenoxy)chroman-4-carboxylic acid To a solution of ethyl 6-chloro-7-(4-(8-methylquinolin-2-ylcarbamoyl)phenoxy)chroman-4-carboxylate (0.024 g, 0.0464 mmol) in 3:1 THF/MeOH (1 ml) was added 1M sodium hydroxide (0.0511 ml, 0.0511 mmol), and the reaction was stirred for 16 hours at ambient temperature. The reaction was concentrated to dryness and acidified with diluted hydrochloric acid. The reaction was extracted with EtOAc twice, and the combined organics were dried over anhydrous sodium sulfate, filtered, and concentrated to yield the desired compound (0.02 g, 0.0409 mmol, 88.1% yield). MS (apci) m/z=489.1 (M+H).

EXAMPLE 46

6-Chloro-7-(4-(4-methylquinolin-2-ylcarbamoyl)phenoxy)chroman-4-carboxylic acid

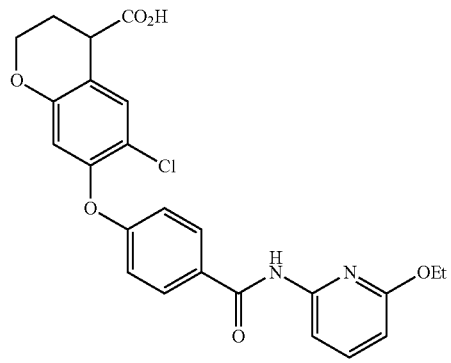 [SMILES: CCOc1cccc(NC(=O)c2ccc(Oc3cc4c(cc3Cl)C(C(=O)O)CCO4)cc2)n1]

Prepared according to the method of Example 45, substituting 4-methylquinoline for 8-methylquinoline. MS (apci) m/z=489.1 (M+H).

EXAMPLE 47

6-Chloro-7-(4-(5-chloroquinolin-2-ylcarbamoyl)phenoxy)chroman-4-carboxylic acid

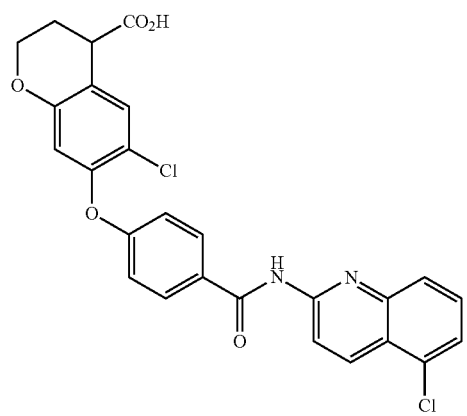 [SMILES: O=C(Nc1ccc2c(Cl)cccc2n1)c1ccc(Oc2cc3c(cc2Cl)C(C(=O)O)CCO3)cc1]

Prepared according to the method of Example 45, substituting reagent 5-chloroquinoline for 8-methylquinoline. MS (apci) m/z=509.0 (M+H).

EXAMPLE 48

6-Chloro-7-(4-(6-phenylpyridin-2-ylcarbamoyl)phenoxy)chroman-4-carboxylic acid

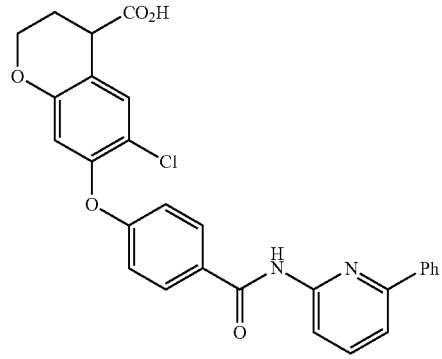 [SMILES: O=C(Nc1cccc(-c2ccccc2)n1)c1ccc(Oc2cc3c(cc2Cl)C(C(=O)O)CCO3)cc1]

Prepared according to the method of Example 45, substituting 2-chloro-6-phenylpyridine for 8-methylquinoline. MS (apci) m/z=501.1 (M+H).

EXAMPLE 49

6-Cyano-7-(4-(6-(2,4-dichlorophenyl)pyridin-2-yl-carbamoyl)phenoxy)chroman-4-carboxylic acid

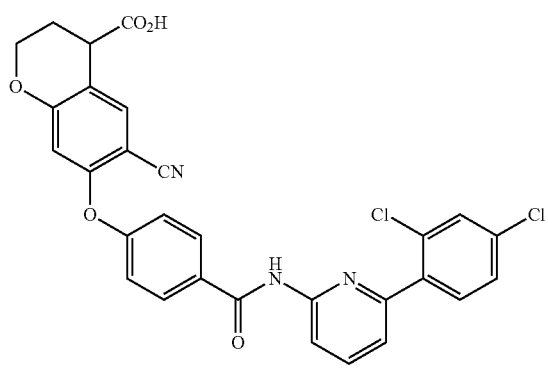

Prepared according to the method of Example 39, substituting 2,4-dichlorophenylboronic acid for 3,4-dimethylphenylboronic acid. MS (apci) m/z=560.1 (M+H).

EXAMPLE 50

7-(4-(6-(3-Chlorophenyl)pyridin-2-ylcarbamoyl)phenoxy)-6-cyanochroman-4-carboxylic acid

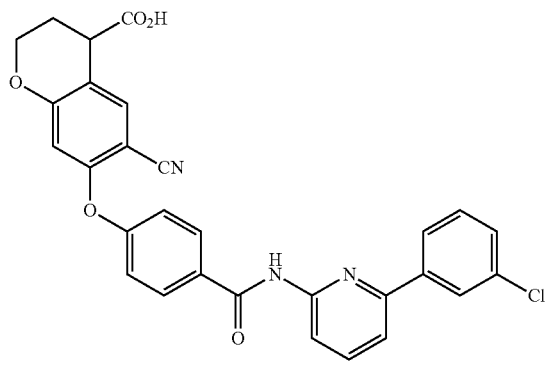 [SMILES: N#Cc1cc2c(cc1Oc1ccc(C(=O)Nc3cccc(-c4cccc(Cl)c4)n3)cc1)OCCC2C(=O)O]

Prepared according to the method of Example 39, substituting 3-chlorophenylboronic acid for 3,4-dimethylphenylboronic acid. MS (apci) m/z=560.1 (M+H).

EXAMPLE 51

7-(4-(6-(4-Chlorophenyl)pyridin-2-ylcarbamoyl)phenoxy)-6-cyanochroman-4-carboxylic acid

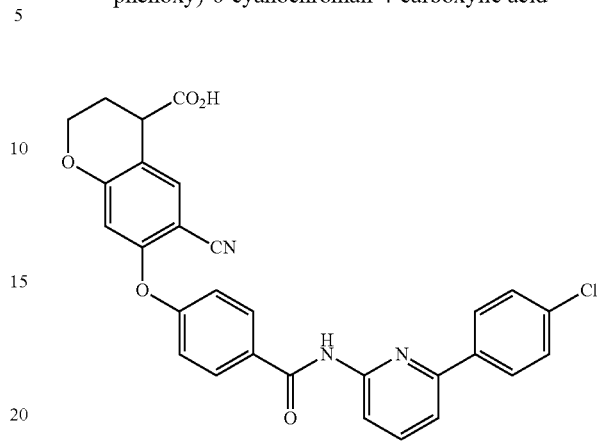

Prepared according to the method of Example 39, substituting 4-chlorophenylboronic acid for 3,4-dimethylphenylboronic acid. MS (apci) m/z=560.1 (M+H).

EXAMPLE 52

6-Chloro-7-(4-(6-(3,4-dichlorophenyl)pyridin-2-ylcarbamoyl)phenoxy)chroman-4-carboxylic acid

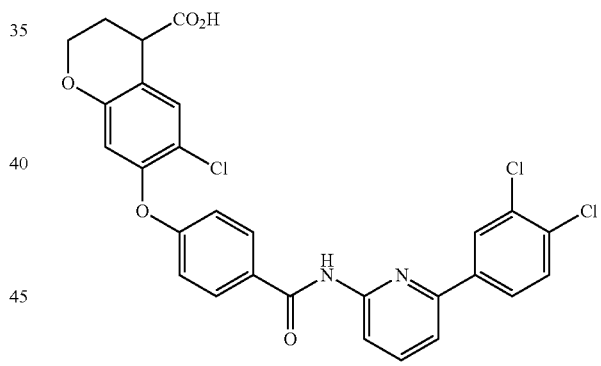

Step A: Preparation of ethyl 7-(4-(6-bromopyridin-2-ylcarbamoyl)phenoxy)-6-chlorochroman-4-carboxylate To a solution of 4-(6-chloro-4-(ethoxycarbonyl)chroman-7-yloxy)benzoic acid (Preparation B; 1.00 g, 2.654 mmol) in dichloroethane (2.6 ml) and DMF (1 drop) was added oxalyl chloride (0.2778 ml, 3.185 mmol), and the reaction was stirred at ambient temperature for 2 hours. The reaction was diluted with pyridine (10 ml), and 6-bromopyridin-2-amine (0.9183 g, 5.308 mmol) was added. The reaction was heated to 80° C. for 16 hours, then cooled to ambient temperature and diluted with EtOAc. The reaction was washed with 1M hydrochloric acid, saturated sodium bicarbonate, and saturated sodium chloride. The organic layer was dried over anhydrous sodium sulfate, filtered, and concentrated. The crude material was purified on silica gel eluting with a linear gradient of 5-70% EtOAc/hexanes to yield the desired compound (1.2 g, 2.257 mmol, 85.02% yield).

Step B: Preparation of ethyl 6-chloro-7-(4-(6-(3,4-dichlorophenyl)pyridin-2-ylcarbamoyl)phenoxy)chroman-4-carboxylate To a solution of ethyl 7-(4-(6-bromopyridin-2-ylcarbamoyl)phenoxy)-6-chlorochroman-4-carboxylate (0.050 g, 0.094 mmol), 3,4-dichlorophenylboronic acid (0.023 g, 0.12 mmol), and sodium carbonate (0.030 g, 0.28 mmol) in toluene (1 ml) and water (0.1 ml) degassed with argon was added tetrakis(triphenylphosphine)palladium (0.0054 g, 0.0047 mmol), and the reaction was heated to 100° C. for 16 hours. The reaction was loaded directly onto silica gel and eluted with a linear gradient of 5-70% EtOAc/hexanes to yield the desired compound (0.051 g, 0.085 mmol, 91% yield).

Step C: Preparation of 6-chloro-7-(4-(6-(3,4-dichlorophenyl)pyridin-2-ylcarbamoyl)phenoxy)chroman-4-carboxylic acid To a solution of ethyl 6-chloro-7-(4-(6-(3,4-dichlorophenyl)pyridin-2-ylcarbamoyl)phenoxy)chroman-4-carboxylate (0.051 g, 0.085 mmol) in 3:1 v/v THF/ethanol (1 ml) was added 1M sodium hydroxide (0.20 ml, 0.20 mmol), and the reaction was stirred for 16 hours. The reaction was concentrated, taken up in water, and acidified with 1M hydrochloric acid. The reaction was extracted twice with EtOAc, and the combined organic layers were dried over anhydrous sodium sulfate, filtered, and concentrated. The crude material was purified by silica gel preparative thin-layer chromatography, eluting with 95:5:1 DCM/MeOH/glacial acetic acid to yield the desired compound (0.032 g, 0.056 mmol, 66% yield). MS (apci) m/z=569.0 (M+H).

EXAMPLE 53

6-Chloro-7-(4-(6-(4-chloro-3-(trifluoromethyl)phenyl)pyridin-2-ylcarbamoyl)phenoxy)chroman-4-carboxylic acid

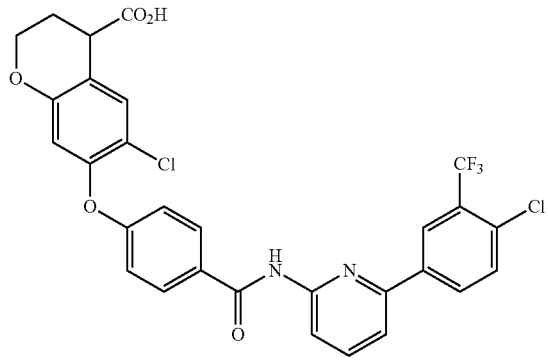 [SMILES: O=C(Nc1cccc(-c2ccc(Cl)c(Cl)c2)n1)c1ccc(Oc2cc3c(cc2Cl)C(C(=O)O)CCO3)cc1]

Prepared according to the method of Example 52 substituting 3-(trifluoromethyl)-4-chlorophenylboronic acid for 3,4-dichlorophenylboronic acid. MS (apci) m/z=603.0 (M+H).

EXAMPLE 54

Sodium 6-chloro-7-(4-(6'-methoxy-2,3'-bipyridin-6-ylcarbamoyl)phenoxy)chroman-4-carboxylate

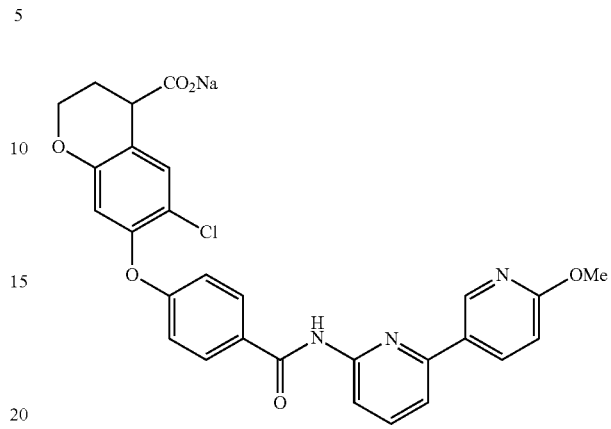

Step A: Preparation of 6-chloro-7-(4-(6'-methoxy-2,3'-bipyridin-6-ylcarbamoyl)phenoxy)chroman-4-carboxylic acid Prepared according to the method of Example 52, substituting 6-methoxypyridin-3-ylboronic acid for 3,4-dichlorophenylboronic acid.

Step B: Preparation of sodium 6-chloro-7-(4-(6'-methoxy-2,3'-bipyridin-6-ylcarbamoyl)phenoxy)chroman-4-carboxylate To a solution of 6-chloro-7-(4-(6'-methoxy-2,3'-bipyridin-6-ylcarbamoyl)phenoxy)chroman-4-carboxylic acid (0.080 g, 0.150 mmol) in 1:1 THF/methanol (2 ml) was added a 0.5 M solution of sodium methoxide in methanol (0.301 ml, 0.150 mmol), and the reaction was stirred for 2 hours, then concentrated to yield the desired compound (0.080 g, 0.144 mmol, 96.0% yield). MS (apci) m/z=532.2 (M-Na+2H).

EXAMPLE 55

Sodium 6-chloro-7-(4-(2',6'-dimethoxy-2,3'-bipyridin-6-ylcarbamoyl)phenoxy)chroman-4-carboxylate

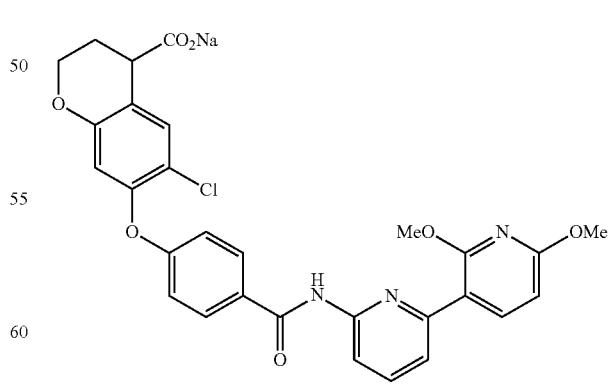

Prepared according to the method of Example 54, substituting 2,6-dimethoxypyridin-3-ylboronic acid for 6-methoxypyridin-3-ylboronic acid. MS (apci) m/z=562.2 (M-Na+2H).

EXAMPLE 56

6-Chloro-7-(4-(6-(2-chlorophenyl)pyridin-2-ylcarbamoyl)phenoxy)chroman-4-carboxylic acid

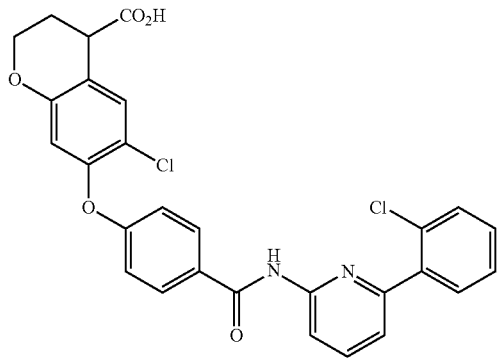 [SMILES: O=C(Nc1cccc(-c2ccccc2Cl)n1)c1ccc(Oc2cc3c(cc2Cl)C(C(=O)O)CCO3)cc1]

Step A: Preparation of ethyl 6-chloro-7-(4-(6-(2-chlorophenyl)pyridin-2-ylcarbamoyl)phenoxy)chroman-4-carboxylate Prepared according to the method of Example 82, substituting 2-chlorophenylboronic acid for 2,4-difluorophenylboronic acid.

Step B: Preparation of 6-chloro-7-(4-(6-(2-chlorophenyl)pyridin-2-ylcarbamoyl)phenoxy)chroman-4-carboxylic acid To a solution of ethyl 6-chloro-7-(4-(6-(2-chlorophenyl)pyridin-2-ylcarbamoyl)phenoxy)chroman-4-carboxylate (0.010 g, 0.0177 mmol) in 3:1 THF/ethanol (1 ml) was added 1M sodium hydroxide (0.0373 ml, 0.0373 mmol), and the reaction was stirred for 16 hours at ambient temperature. The reaction was concentrated and diluted with water. The reaction was acidified with 1M hydrochloric acid and extracted twice with EtOAc. The combined organic layers were dried over anhydrous sodium sulfate, filtered, and concentrated. The crude material was purified by silica gel preparative thin-layer chromatography eluting with 95:5:1 DCM/MeOH/glacial acetic acid to yield the desired compound (0.007 g, 0.0124 mmol, 70.0% yield). MS (apci) m/z=535.1 (M+H).

EXAMPLE 57

6-Chloro-7-(4-(6-p-tolylpyridin-2-ylcarbamoyl)phenoxy)chroman-4-carboxylic acid

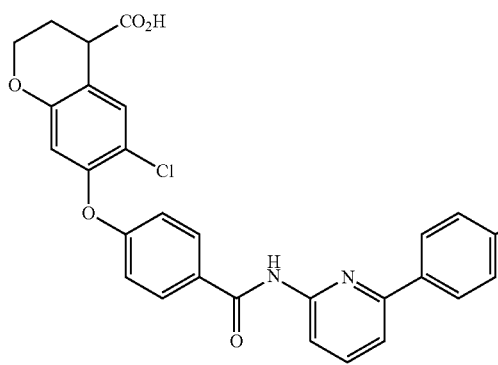

Step A: Preparation of 6-p-tolylpyridin-2-amine hydrochloride

To a solution of 6-bromopyridin-2-amine (0.500 g, 2.89 mmol) in toluene (10 ml) was added benzaldehyde (0.313 g, 2.95 mmol), and the reaction was stirred for 30 minutes. To this, p-tolylboronic acid (0.471 g, 3.47 mmol), sodium carbonate (0.368 g, 3.47 mmol), and water (10 ml) were added, and the reaction was degassed with argon. Tetrakis(triphenylphosphine)palladium (0.167 g, 0.144 mmol) was added, and the reaction was heated to 100° C. for 60 hours. The reaction was diluted with 10 ml of toluene and 10 ml of water, and the organic layer was collected. The organic layer was treated with 4M hydrogen chloride in dioxane (1.44 ml, 5.78 mmol) dropwise with vigorous stirring. The resulting solid was collected via filtration to yield pure 6-p-tolylpyridin-2-amine hydrochloride (0.564 g, 2.56 mmol, 88.4% yield).

Step B: Preparation of ethyl 6-chloro-7-(4-(6-p-tolylpyridin-2-ylcarbamoyl)phenoxy)chroman-4-carboxylate To a solution of 4-(6-chloro-4-(ethoxycarbonyl)chroman-7-yloxy)benzoic acid (Preparation B; 56 mg, 0.1486 mmol) in 1,2-dichloroethane (0.15 ml) and DMF (1 drop) was added oxalyl chloride (15.56 μl, 0.1783 mmol), and the reaction was stirred for 2 hours. To this, pyridine (0.6 ml) and 6-p-tolylpyridin-2-amine hydrochloride (36.08 mg, 0.1635 mmol) were added, and the reaction was heated to 80° C. for 16 hours. The reaction was diluted with EtOAc and washed with 10% citric acid, saturated sodium bicarbonate, and saturated sodium chloride. The organic layer was dried over anhydrous sodium sulfate, filtered, and concentrated. The crude material was purified by silica gel chromatography, eluting with a gradient of 5-70% EtOAc/hexanes to yield the desired compound (49 mg, 0.09024 mmol, 60.72% yield).

Step C: Preparation of 6-chloro-7-(4-(6-p-tolylpyridin-2-ylcarbamoyl)phenoxy)chroman-4-carboxylic acid To a solution of ethyl 6-chloro-7-(4-(6-p-tolylpyridin-2-ylcarbamoyl)phenoxy)chroman-4-carboxylate (0.049 g, 0.090 mmol) in 3:1 THF/ethanol (1 ml) was added 1M sodium hydroxide (0.19 ml, 0.19 mmol), and the reaction was stirred at ambient temperature for 16 hours. The reaction was concentrated to dryness and acidified with 1M hydrochloric acid. The reaction was diluted with water and extracted twice with EtOAc. The combined organic layers were dried over anhydrous sodium sulfate, filtered, and concentrated to yield the desired compound (0.035 g, 0.068 mmol, 75% yield). MS (apci) m/z=515.1 (M+H).

EXAMPLE 58

6-Chloro-7-(4-(6-(4-methoxyphenyl)pyridin-2-ylcarbamoyl)phenoxy)chroman-4-carboxylic acid

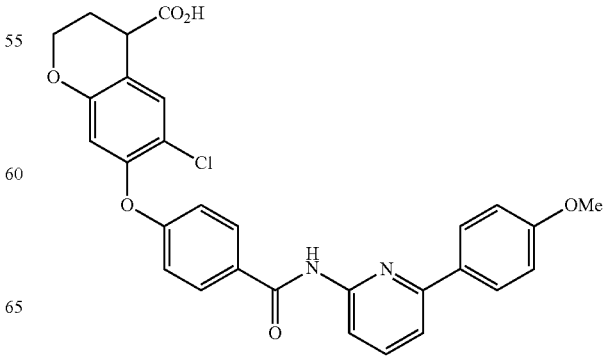

Prepared according to the method of Example 57, substituting 4-methoxyphenylboronic acid for 4-methylboronic acid. MS (apci) m/z=531.1 (M+H).

EXAMPLE 59

Sodium 6-chloro-7-(4-(6-(2-chloro-4-(trifluoromethyl)phenyl)pyridazin-3-ylcarbamoyl)phenoxy)chroman-4-carboxylate

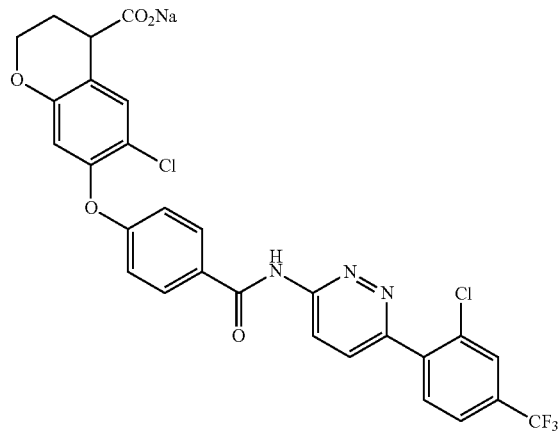

Step A: Preparation of ethyl 6-chloro-7-(4-(6-chloropyridazin-3-ylcarbamoyl)phenoxy)chroman-4-carboxylate To a solution of 4-(6-chloro-4-(ethoxycarbonyl)chroman-7-yloxy)benzoic acid (Preparation B; 0.500 g, 1.334 mmol) in 1,2-dichloroethane (1.3 ml) and DMF (1 drop) was added oxalyl chloride (0.1396 ml, 1.601 mmol), and the reaction was stirred for 1 hour at ambient temperature. The reaction was diluted with pyridine (5 ml) and 6-chloropyridazin-3-amine (0.2592 g, 2.001 mmol) was added. The reaction was heated to 80° C. for 16 hours, then diluted with EtOAc and washed with 1M hydrochloric acid, sodium bicarbonate, and saturated sodium chloride. The organic layer was dried over anhydrous sodium sulfate, filtered, and concentrated. The crude material was purified by silica gel chromatography eluting with a linear gradient of 5-70% EtOAc/hexanes to yield the desired compound (0.5 g, 1.028 mmol, 77.07% yield).

Step B: Preparation of ethyl 6-chloro-7-(4-(6-(2-chloro-4-(trifluoromethyl)phenyl)pyridazin-3-ylcarbamoyl)phenoxy)chroman-4-carboxylate A solution of ethyl 6-chloro-7-(4-(6-chloropyridazin-3-ylcarbamoyl)phenoxy)chroman-4-carboxylate (0.131 g, 0.268 mmol), 2-chloro-4-(trifluoromethyl)phenylboronic acid (0.0903 g, 0.402 mmol), and 20% aqueous sodium carbonate (0.426 ml, 0.805 mmol) in toluene (2 ml) was degassed with argon, then tetrakis(triphenylphosphine)palladium (0.0155 g, 0.0134 mmol) was added and the reaction was heated to 110° C. for 16 hours. The reaction mixture was loaded directly onto silica gel and purified eluting with a linear gradient of 5-70% EtOAc/hexanes to yield the desired compound (0.034 g, 0.0538 mmol, 20.0% yield).

Step C: Preparation of 6-chloro-7-(4-(6-(2-chloro-4-(trifluoromethyl)phenyl)pyridazin-3-ylcarbamoyl)phenoxy)chroman-4-carboxylic acid To a solution of ethyl 6-chloro-7-(4-(6-(2-chloro-4-(trifluoromethyl)phenyl)pyridazin-3-ylcarbamoyl)phenoxy)chroman-4-carboxylate (0.034 g, 0.054 mmol) in 3:1 THF/EtOH (1 ml) was added 1M sodium hydroxide (0.22 ml, 0.22 mmol), and the reaction was stirred at ambient temperature for 16 hours. The reaction was concentrated to dryness, taken up in water, and acidified with 1M hydrochloric acid. The reaction was extracted twice with EtOAc, and the combined organic layers were washed with saturated sodium chloride, dried over anhydrous sodium sulfate, filtered, and concentrated to yield the desired compound (0.030 g, 0.050 mmol, 92% yield).

Step D: Preparation of sodium 6-chloro-7-(4-(6-(2-chloro-4-(trifluoromethyl)phenyl)pyridazin-3-ylcarbamoyl)phenoxy)chroman-4-carboxylate To a solution of 6-chloro-7-(4-(6-(2-chloro-4-(trifluoromethyl)phenyl)pyridazin-3-ylcarbamoyl)phenoxy)chroman-4-carboxylic acid (0.030 g, 0.050 mmol) in MeOH (2 ml) was added a 0.5M solution of sodium methoxide in methanol (0.099 ml, 0.050 mmol), and the reaction was stirred for 2 hours. The reaction was concentrated to yield the desired compound (0.030 g, 0.048 mmol, 96% yield). MS (apci) m/z=603.9 (M-Na+2H).

EXAMPLE 60

Sodium 6-chloro-7-(4-(6-(3-chloro-4-(trifluoromethyl)phenyl)pyridazin-3-ylcarbamoyl)phenoxy)chroman-4-carboxylate

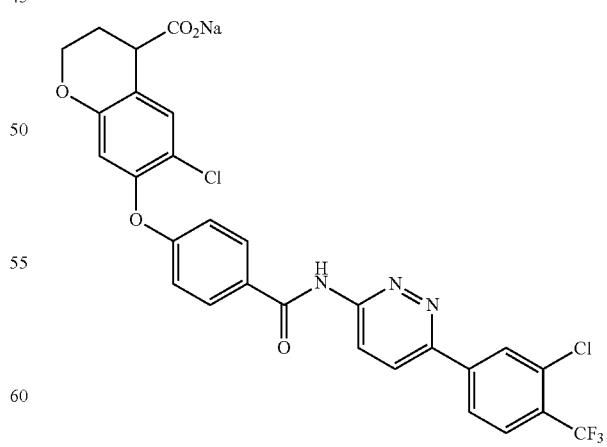

Prepared according to the method of Example 59, substituting 3-chloro-4-(trifluoromethyl)phenylboronic acid for 2-chloro-4-(trifluoromethyl)phenylboronic acid. MS (apci) m/z=603.9 (M-Na+2H).

EXAMPLE 61

Sodium 6-chloro-7-(4-(5-(4-(trifluoromethyl)phenyl)pyrazin-2-ylcarbamoyl)phenoxy)chroman-4-carboxylate

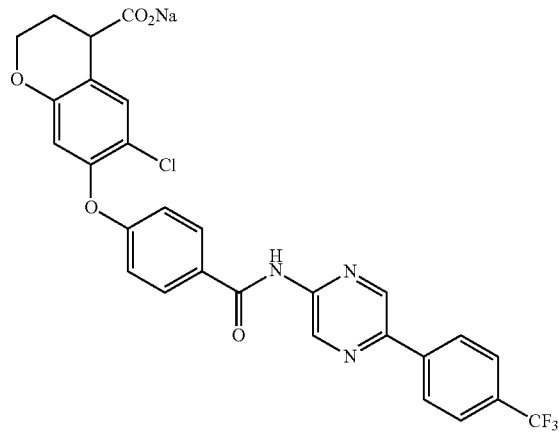

Step A: Preparation of ethyl 7-(4-(5-bromopyrazin-2-ylcarbamoyl)phenoxy)-6-chlorochroman-4-carboxylate Prepared according to the method of Example 59, step A, using 2-amino-5-bromopyrazine in place of 6-chloropyridazin-3-amine.

Step B: Preparation of sodium 6-chloro-7-(4-(5-(4-(trifluoromethyl)phenyl)pyrazin-2-ylcarbamoyl)phenoxy)chroman-4-carboxylate Prepared from ethyl 7-(4-(5-bromopyrazin-2-ylcarbamoyl)phenoxy)-6-chlorochroman-4-carboxylate according to the method of Example 59, steps B-D, using 4-trifluoromethylphenylboronic acid in place of 2-chloro-4-(trifluoromethyl)phenylboronic acid. MS (apci) m/z=570.0 (M-Na+2H).

EXAMPLE 62

Sodium 6-chloro-7-(4-(6-p-tolylpyridazin-3-ylcarbamoyl)phenoxy)chroman-4-carboxylate

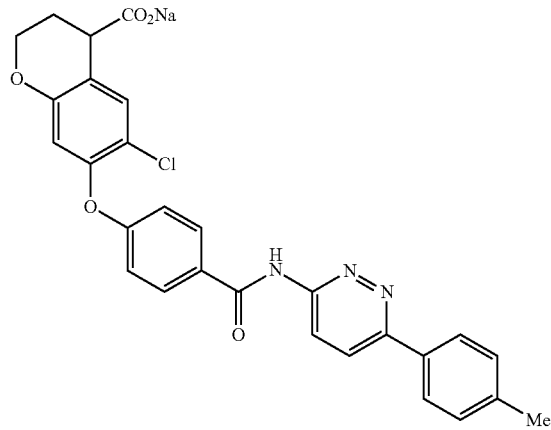

Prepared according to the method of Example 59, substituting 4-methylphenylboronic acid for 2-chloro-4-(trifluoromethyl)phenylboronic acid. MS (apci) m/z=516.0 (M-Na+2H).

EXAMPLE 63

Sodium 6-chloro-7-(4-(6-(4-methoxyphenyl)pyridazin-3-ylcarbamoyl)phenoxy)chroman-4-carboxylate

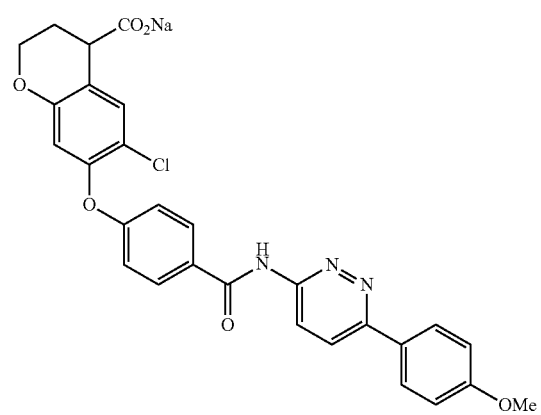

Prepared according to the method of Example 59, substituting 4-methoxyphenylboronic acid for 2-chloro-4-(trifluoromethyl)phenylboronic acid. MS (apci) m/z=532.1 (M-Na+2H).

EXAMPLE 64

Sodium 6-chloro-7-(4-(6-(4-(methylthio)phenyl)pyridazin-3-ylcarbamoyl)phenoxy)chroman-4-carboxylate

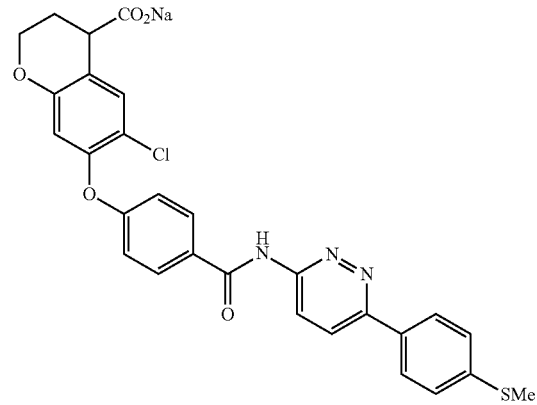

Prepared according to the method of Example 59, substituting 4-thiomethylphenylboronic acid for 2-chloro-4-(trifluoromethyl)phenylboronic acid. MS (apci) m/z=548.1 (M-Na+2H).

EXAMPLE 65

Sodium 6-chloro-7-(4-(6-(3,4-dichlorophenyl)pyridazin-3-ylcarbamoyl)phenoxy)chroman-4-carboxylate

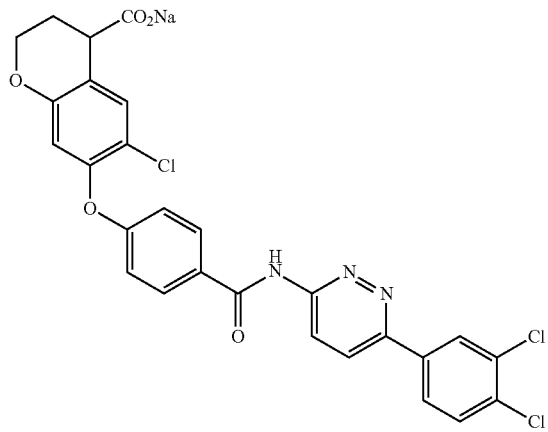

Prepared according to the method of Example 59, substituting 3,4-dichlorophenylboronic acid for 2-chloro-4-(trifluoromethyl)phenylboronic acid. MS (apci) m/z=570.0 (M-Na+2H).

EXAMPLE 66

Sodium 6-chloro-7-(4-(6-(4-fluorophenyl)pyridazin-3-ylcarbamoyl)phenoxy)chroman-4-carboxylate

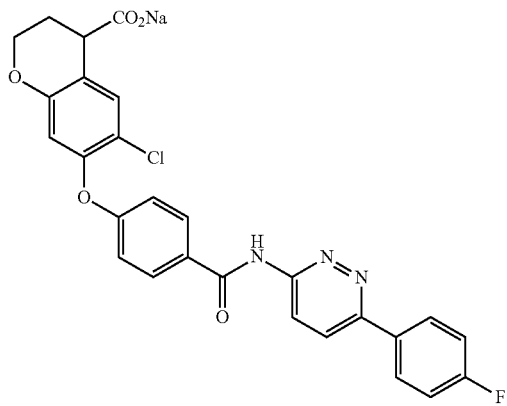

Prepared according to the method of Example 59, substituting 4-fluorophenylboronic acid for 2-chloro-4-(trifluoromethyl)phenylboronic acid. MS (apci) m/z=520.1 (M-Na+2H).

EXAMPLE 67

Sodium 6-chloro-7-(4-(6-(4-chloro-3-fluorophenyl)pyridazin-3-ylcarbamoyl)phenoxy)chroman-4-carboxylate

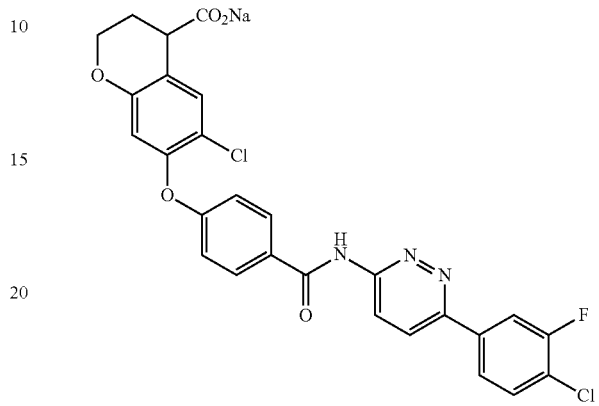

Prepared according to the method of Example 59, substituting 3-fluoro-4-chlorophenylboronic acid for 2-chloro-4-(trifluoromethyl)phenylboronic acid. MS (apci) m/z=544.0 (M-Na+2H).

EXAMPLE 68

Sodium 6-chloro-7-(4-(6-(6-methoxypyridin-3-yl)pyridazin-3-ylcarbamoyl)phenoxy)chroman-4-carboxylate

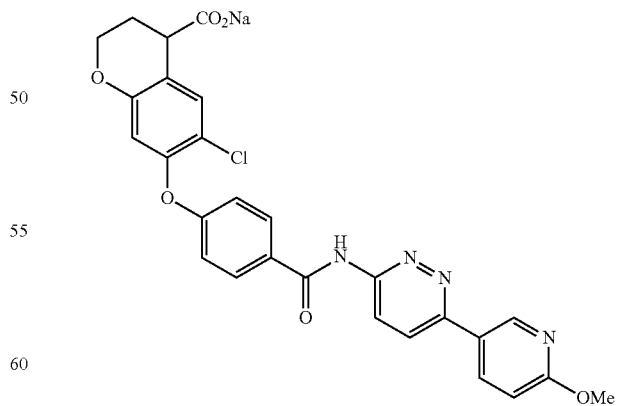

Prepared according to the method of Example 59, substituting 6-methoxypyridin-3-ylboronic acid for 2-chloro-4-(trifluoromethyl)phenylboronic acid. MS (apci) m/z=533.0 (M-Na+2H).

EXAMPLE 69

Sodium 6-chloro-7-(4-(6-(2,6-dimethoxypyridin-3-yl)pyridazin-3-ylcarbamoyl)phenoxy)chroman-4-carboxylate

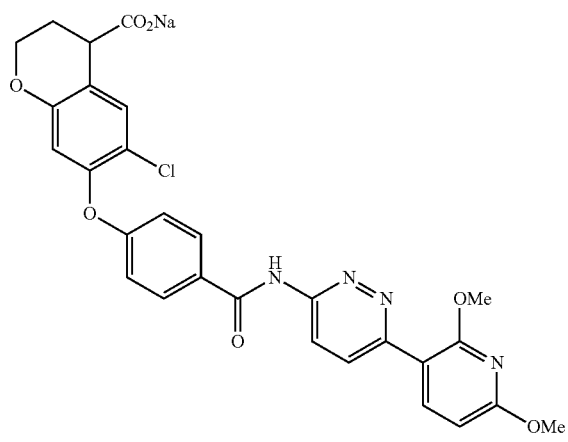

Prepared according to the method of Example 59, substituting 2,6-dimethoxypyridin-3-ylboronic acid for 2-chloro-4-(trifluoromethyl)phenylboronic acid. MS (apci) m/z=563.0 (M-Na+2H).

EXAMPLE 70

Sodium 6-chloro-7-(4-(6-(2-fluoro-4-(trifluoromethyl)phenyl)pyridazin-3-ylcarbamoyl)phenoxy)chroman-4-carboxylate

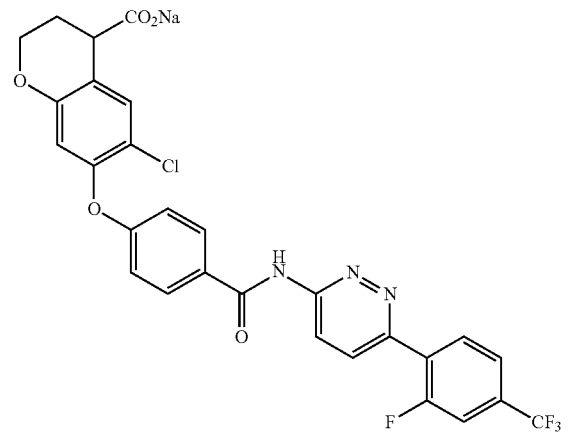

Step A: Preparation of 6-(2-fluoro-4-(trifluoromethyl)phenyl)pyridazin-3-amine

To a solution of 6-chloropyridazin-3-amine (0.300 g, 2.32 mmol), 2-fluoro-4-(trifluoromethyl)phenylboronic acid (0.626 g, 3.01 mmol), cesium fluoride (0.915 g, 6.02 mmol), and N-ethyl-N-isopropylpropan-2-amine (0.449 g, 3.47 mmol) in propanol (17 ml) degassed with argon was added (dppf)palladium(II) chloride dichloromethane adduct (0.0953 g, 0.116 mmol), and the reaction was heated to 100° C. in a sealed tube for 3 hours. The reaction was cooled to ambient temperature, diluted with EtOAc, and washed with water and saturated sodium chloride. The organic layer was dried over anhydrous sodium sulfate, filtered, and concentrated. The crude material was purified by flash chromatography on silica gel, eluting with a linear gradient of 0-10% methanol/EtOAc to yield the desired compound (0.086 g, 0.334 mmol, 14.4% yield).

Step B: Preparation of 6-chloro-7-(4-(6-(2-fluoro-4-(trifluoromethyl)phenyl)pyridazin-3-ylcarbamoyl)phenoxy)chroman-4-carboxlic acid Prepared from 6-(2-fluoro-4-(trifluoromethyl)pyridazin-3-amine using the procedure of Example 57, steps B and C.

Step C: Preparation of sodium 6-chloro-7-(4-(6-(2-fluoro-4-(trifluoromethyl)phenyl)pyridazin-3-ylcarbamoyl)phenoxy)chroman-4-carboxylate To a solution of 6-chloro-7-(4-(6-(2-fluoro-4-(trifluoromethyl)phenyl)pyridazin-3-ylcarbamoyl)phenoxy)chroman-4-carboxylic acid (0.071 g, 0.12 mmol) in 1:1 THF/methanol (2 ml) was added a 0.5M solution of sodium methoxide in methanol (0.24 ml, 0.12 mmol), and the reaction was stirred at ambient temperature for 2 hours. The reaction was concentrated to yield the desired compound (0.071 g, 0.12 mmol, 96% yield). MS (apci) m/z=588.0 (M-Na+2H).

EXAMPLE 71

Sodium 6-chloro-7-(4-(6-(2,4-difluorophenyl)pyridazin-3-ylcarbamoyl)phenoxy)chroman-4-carboxylate

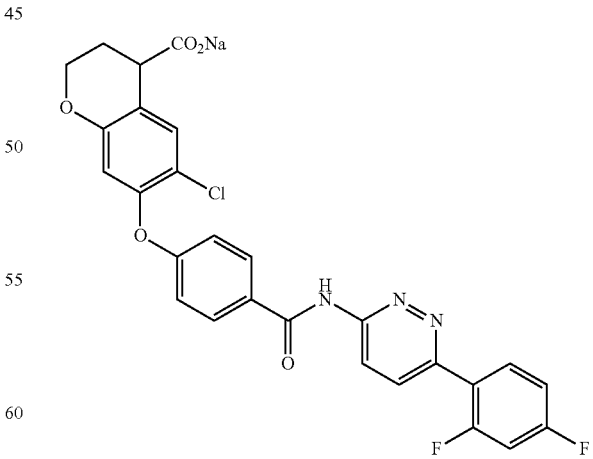

Prepared according to the method of Example 70, substituting 2,4-difluorophenylboronic acid for 2-fluoro-4-(trifluoromethyl)phenylboronic acid. MS (apci) m/z=538.0 (M-Na+2H).

EXAMPLE 72

Sodium 6-chloro-7-(4-(6-(4-chloro-2-fluorophenyl)pyridazin-3-ylcarbamoyl)phenoxy)chroman-4-carboxylate

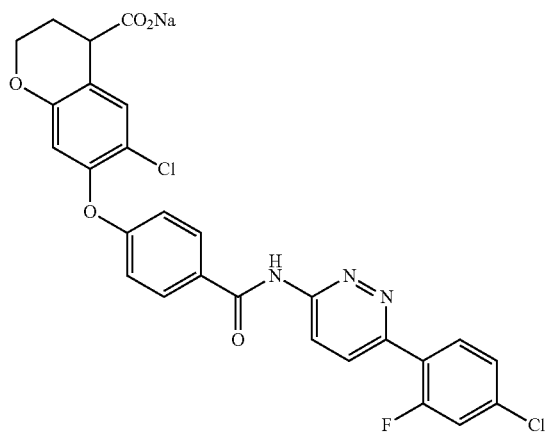

Prepared according to the method of Example 70, substituting 2-fluoro-4-chlorophenylboronic acid for 2-fluoro-4-(trifluoromethyl)phenylboronic acid. MS (apci) m/z=554.0 (M-Na+2H).

EXAMPLE 73

Sodium 6-chloro-7-(4-(6'-methoxy-3,3'-bipyridin-6-ylcarbamoyl)phenoxy)chroman-4-carboxylate

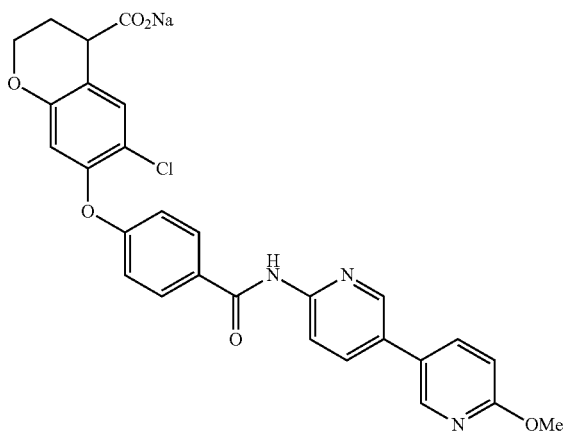

Steps A and B: Preparation of 6-chloro-7-(4-(6'-methoxy-3,3'-bipyridin-6-ylcarbamoyl)phenoxy)chroman-4-carboxylic acid Prepared according to the procedure for Example 52 using 5-bromopyridin-2-amine in place of 6-chloropyridin-2-amine, and using 6-methoxypyridin-3-ylboronic acid in place of 3,4-dichlorophenylboronic acid in Step B.

Step C: Preparation of sodium 6-chloro-7-(4-(6'-methoxy-3,3'-bipyridin-6-ylcarbamoyl)phenoxy)chroman-4-carboxylate To a solution of 6-chloro-7-(4-(6'-methoxy-3,3'-bipyridin-6-ylcarbamoyl)phenoxy)chroman-4-carboxylic acid (0.040 g, 0.0752 mmol) in 1:1 THF/MeOH (2 ml) was added a 0.5M solution of sodium methoxide in methanol (0.150 ml, 0.0752 mmol), and the reaction was stirred for 2 hours at ambient temperature. The reaction was concentrated to yield the desired compound (0.040 g, 0.0722 mmol, 96.0% yield). MS (apci) m/z=532.2 (M-Na+2H).

EXAMPLE 74

Sodium 6-chloro-7-(4-(2',6'-dimethoxy-3,3'-bipyridin-6-ylcarbamoyl)phenoxy)chroman-4-carboxylate

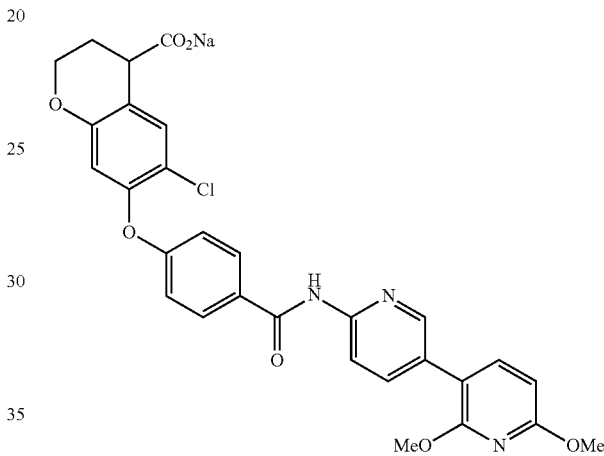

Prepared according to the method of Example 73, substituting 2,6-dimethoxypyridin-3-ylboronic acid for 6-methoxypyridin-3-ylboronic acid. MS (apci) m/z=562.2 (M-Na+2H).

EXAMPLE 75

6-Chloro-7-(4-(6-(3-(trifluoromethyl)phenyl)pyridin-3-ylcarbamoyl)phenoxy)chroman-4-carboxylic acid

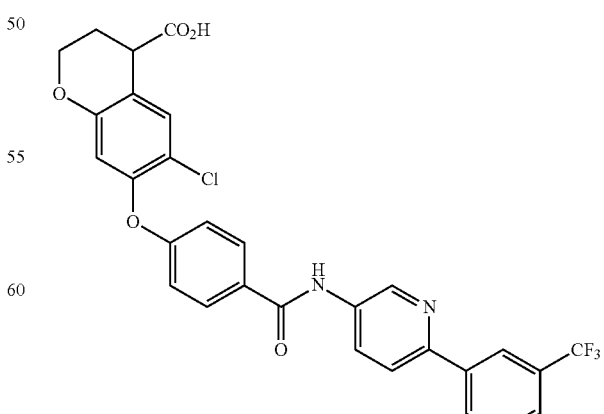

Prepared according to the procedure for Example 52 with the following modifications: In Step A, 6-bromopyridin-3-amine was used in place of 6-chloropyridin-2-amine, and using 3-(trifluoromethyl)phenylboronic acid in place of 3,4-dichlorophenylboronic acid in Step B. MS (apci) m/z=569 (M+H).

EXAMPLE 76

Sodium 6-chloro-7-(4-(6-(4-(trifluoromethyl)phenyl)pyridin-3-ylcarbamoyl)phenoxy)chroman-4-carboxylate

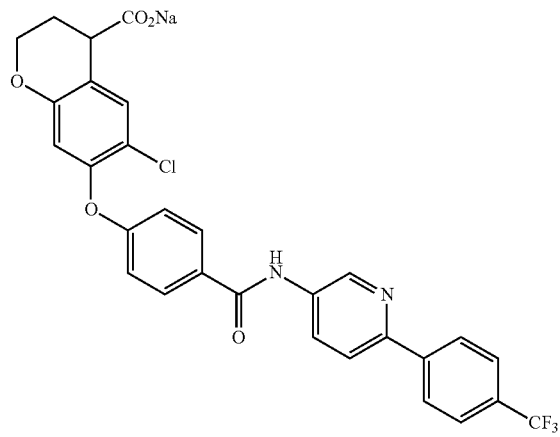

Steps A and B: Preparation of 6-chloro-7-(4-(6-(4-(trifluoromethyl)phenyl)pyridin-3-ylcarbamoyl)phenoxy)chroman-4-carboxylic acid Prepared according to the procedure for Example 52 with the following modifications: In Step A, 6-bromopyridin-3-amine, was used in place of 6-chloropyridin-2-amine, and in Step B, 4-(trifluoromethyl)phenylboronic acid was used in place of 3,4-dichlorophenylboronic acid.

Step C: Preparation of sodium 6-chloro-7-(4-(6-(4-(trifluoromethyl)phenyl)pyridin-3-ylcarbamoyl)phenoxy)chroman-4-carboxylate Prepared according to the procedure for Example 73, Step C. MS (apci) m/z=569.2 (M-Na+2H).

EXAMPLE 77

6-Chloro-7-(4-(6-phenylpyrazin-2-ylcarbamoyl)phenoxy)chroman-4-carboxylic acid

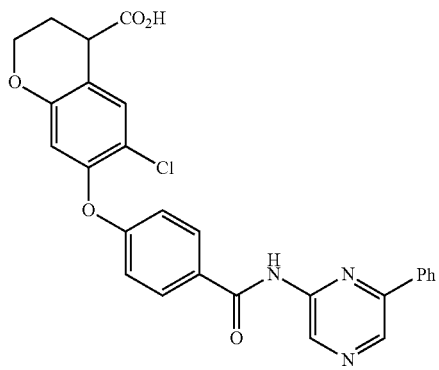 [SMILES: O=C(Nc1cncc(-c2ccccc2)n1)c1ccc(Oc2cc3c(cc2Cl)C(C(=O)O)CCO3)cc1]

Step A: Ethyl 6-chloro-7-(4-(6-phenylpyrazin-2-ylcarbamoyl)phenoxy)chroman-4-carboxylate Argon was bubbled through a tetrahydrofuran (665 µl) solution of ethyl 7-(4-carbamoylphenoxy)-6-chlorochroman-4-carboxylate (50 mg, 0.133 mmol; Example 45, step A) and 2-chloro-6-phenylpyrazine (25.4 mg, 0.133 mmol) at ambient temperature in a vial. Cesium carbonate (47.7 mg, 0.146 mmol), XPHOS ligand (12.7 mg, 0.0266 mmol), and tris(dibenzylideneacetone)dipalladium (0) (6.09 mg, 0.0066 mmol) were added. Argon was bubbled through the reaction for two minutes and the vial was capped. The reaction was heated to 60° C. (oil bath temperature) for 18 hours. The reaction was cooled to ambient temperature and applied to silica gel. Elution with a gradient of ethyl acetate/hexanes (20 to 85%) provided the title compound (65 mg, 92%) as an off-white solid.

Step B: Preparation of 6-chloro-7-(4-(6-phenylpyrazin-2-lcarbamoyl)phenoxy)chroman-4-carboxylic acid Ethyl 6-chloro-7-(4-(6-phenylpyrazin-2-ylcarbamoyl)phenoxy)chroman-4-carboxylate (31 mg, 0.0585 mmol) in 2:1 THF-Ethanol (1.2 ml) was treated with 1.0 N aqueous sodium hydroxide (87.7 µl, 0.0877 mmol) at ambient temperature. After 18 hours, the reaction was diluted with ethyl acetate and acidified with 1.0 N aqueous hydrogen chloride (117 µl, 0.117 mmol. The reaction was transferred to a separatory funnel and was washed with brine. The organic layer was dried with sodium sulfate, filtered, and concentrated in vacuo to provide the title compound (26 mg, 89%) as an off-white solid. MS (apci) m/z=502.2 (M+H).

EXAMPLE 78

6-Chloro-7-(4-(6-ethoxypyridin-2-ylcarbamoyl)phenoxy)chroman-4-carboxylic acid

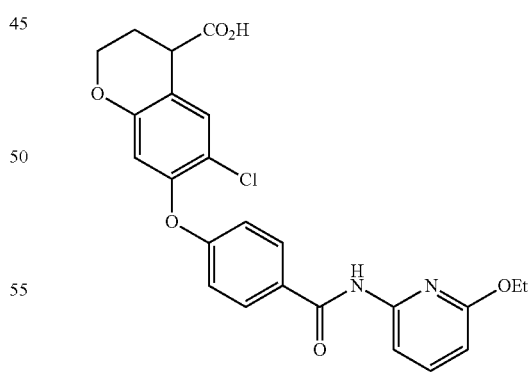

Step A: Ethyl 6-chloro-7-(4-(6-ethoxypyridin-2-ylcarbamoyl)phenoxy)chroman-4-carboxylate Prepared according to Example 77, Step A, replacing 2-chloro-6-phenylpyrazine with 2-chloro-6-ethoxypyridine, to provide 57 mg (81%) of the title compound.

Step B: Preparation of 6-chloro-7-(4-(6-ethoxypyridin-2-ylcarbamoyl)phenoxy)chroman-4-carboxylic acid Prepared according to Example 77, Step B to provide the title compound (49 mg, 91%) as a white solid. MS (apci) m/z=469.1 (M+H).

EXAMPLE 79

6-chloro-7-(4-(6-(4-chlorophenyl)pyrazin-2-ylcarbamoyl)phenoxy)chroman-4-carboxylic acid

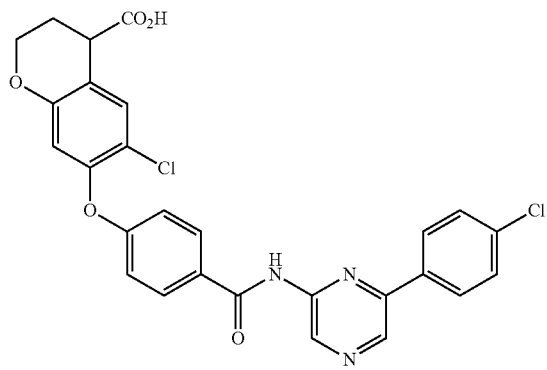 [SMILES: O=C(Nc1cncc(-c2ccc(Cl)cc2)n1)c1ccc(Oc2cc3c(cc2Cl)C(C(=O)O)CCO3)cc1]

Step A: Preparation of 2-chloro-6-(4-chlorophenyl)pyrazine:

2,6-Dichloropyrazine (779 mg, 5.23 mmol), 4-chlorophenylboronic acid (899 mg, 5.75 mmol), and potassium carbonate (2876 µl of a 2 M solution, 5.75 mmol) in toluene-ethanol (4:1, 17 ml) were sparged with argon for 5 minutes. Pd(PPh$_3$)$_4$ (604 mg, 0.52 mmol) was added and the mixture was sparged an additional 2 minutes. The reaction was heated to 65° C. for 16 hours, then cooled to ambient temperature, concentrated in vacuo, and dissolve in 25 ml ethyl acetate. The ethyl acetate solution was washed with saturated aqueous sodium bicarbonate and brine solution, dried with sodium sulfate, filtered, concentrated, and purified on silica gel. Elution with a gradient of 2-30% ethyl acetate-hexanes provided the title compound (389 mg, 33%) as a white solid.

Step B: Preparation of ethyl 6-chloro-7-(4-(6-(4-chlorophenyl)pyrazin-2-ylcarbamoyl)phenoxy)chroman-4-carboxylate Prepared according to Example 77, Step A wherein 2-chloro-6-phenylpyrazine was replaced with 2-chloro-6-(4-chlorophenyl)pyrazine to provide 68 mg (91%) of the title compound.

Step C: Preparation of 6-chloro-7-(4-(6-(4-chlorophenyl)pyrazin-2-ylcarbamoyl)phenoxy)chroman-4-carboxylic acid Prepared according to Example 77, Step B to provide the title compound (29 mg, 45%) as a white solid. MS (apci) m/z=536.1 (M+H).

EXAMPLE 80

Sodium 6-chloro-7-(4-(2-(2-methoxy-6-(trifluoromethyl)pyridin-3-yl)ethylcarbamoyl)phenoxy)chroman-4-carboxylate

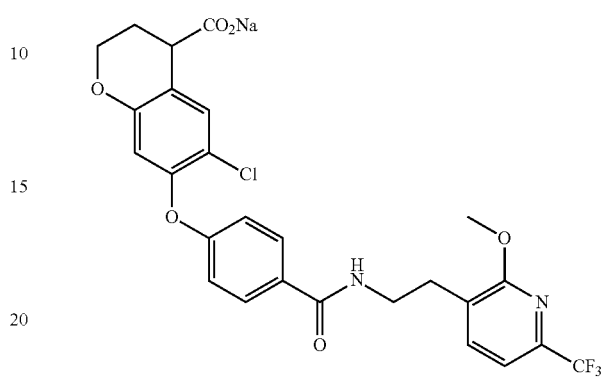

Step A: Preparation of 2-methoxy-3-(2-nitrovinyl)-6-(trifluoromethyl)pyridine 2-methoxy-6-(trifluoromethyl)nicotinaldehyde (300 mg, 1.46 mmol) (Example 139, Step A) was treated with nitromethane (790 µl, 14.6 mmol) at ambient temperature. Solid methylamine hydrochloride (77.0 mg, 1.14 mmol) and sodium acetate (93.6 mg, 1.14 mmol) were added and the colorless reaction mixture was stirred rapidly at ambient temperature for 14 hours. The reaction mixture was applied directly to silica gel and eluted with 2 to 20% ethyl acetate-hexanes to provide the desired compound (193 mg, 0.778 mmol, 53.2% yield) as a yellow solid.

Step B: Preparation of 2-(2-methoxy-6-(trifluoromethyl)pyridin-3-yl)ethanamine To a suspension of lithium borohydride (71.2 mg, 3.27 mmol) in tetrahydrofuran (5 ml) was added chlorotrimethylsilane (826 µl, 6.53 mmol) at ambient temperature (exothermic reaction) and the reaction was allowed to stir for 30 minutes. 2-Methoxy-3-(2-nitrovinyl)-6-(trifluoromethyl)pyridine (193 mg, 0.778 mmol) was added, and the reaction was heated to reflux for 6 hours. The reaction was cooled to ambient temperature and quenched by the addition of 1M HCl (9 ml). After 15 minutes, the reaction was diluted with water and washed with ether and hexanes. The aqueous layer was adjust to pH 13 with 5 N aqueous sodium hydroxide and extracted with ethyl acetate (2×25 ml). The combined ethyl acetate extractions were dried over Na$_2$SO$_4$, filtered, and concentrated to yield the desired compound (143 mg, 0.649 mmol, 83.5% yield).

Step C: Preparation of ethyl 6-chloro-7-(4-(2-(2-methoxy-6-(trifluoromethyl)pyridin-3-yl)ethylcarbamoyl)phenoxy)chroman-4-carboxylate 2-(2-Methoxy-6-(trifluoromethyl)pyridin-3-yl)ethanamine (140 mg, 0.637 mmol) in dichloromethane (1 ml) was treated sequentially with 4-(6-chloro-4-(ethoxycarbonyl)chroman-7-yloxy)benzoic acid (Preparation B; 240 mg, 0.637 mmol), N1-((ethylimino)methylene)-N3,N3-dimethylpropane-1,3-diamine hydrochloride (147 mg, 0.764 mmol), and 4-(dimethylamino)pyridine (7.78 mg, 0.0637 mmol) at ambient temperature. After 14 hours, the reaction was applied directly to silica gel. Elution with ethyl acetate (50-80%) provided the desired compound (264 mg, 0.456 mmol, 71.6% yield) as a white solid.

Step D: Preparation of 6-chloro-7-(4-(2-(2-methoxy-6-(trifluoromethyl)pyridin-3-yl)ethylcarbamoyl)phenoxy)chroman-4-carboxylic acid Prepared according to Example 77, Step B to provide the title compound (266 mg, 105%) as a white solid.

Step E: Preparation of sodium 6-chloro-7-(4-(2-(2-methoxy-6-(trifluoromethyl)pyridin-3-yl)ethylcarbamoyl)phenoxy)chroman-4-carboxylate 6-Chloro-7-(4-(2-(2-methoxy-6-(trifluoromethyl)pyridin-3-yl)ethylcarbamoyl)phenoxy)chroman-4-carboxylic acid (255 mg, 0.463 mmol) in 2:1 THF-MeOH (2 ml) was treated with 0.5 N sodium methoxide in methanol (926 µl, 0.463 mmol) at ambient temperature. After 15 minutes, the reaction was concentrated in vacuo. The material was suspended in ethyl acetate and concentrated to a solid. The solid was suspended in ethyl acetate, hexanes were added, and the mixture was concentrated in vacuo to a solid. The material was suspended in dichloromethane, hexanes were added, and the suspension concentrated to provide the desired compound (268 mg, 0.468 mmol, 101% yield) as a solid. MS (apci) m/z=551.0 (M-Na+2H).

EXAMPLE 81

6-Chloro-7-(4-(6-(3,4-difluorophenyl)pyridin-2-ylcarbamoyl)phenoxy)chroman-4-carboxylic acid

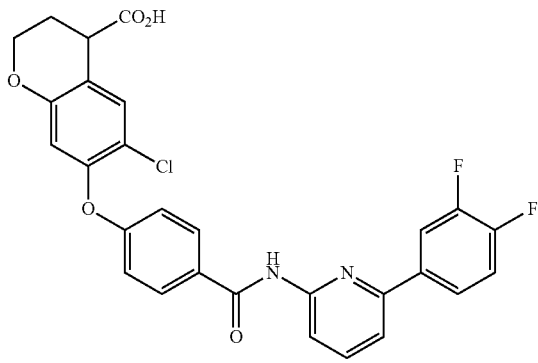

Step A: Preparation of ethyl 6-chloro-7-(4-(6-(2,4-difluorophenyl)pyridin-2-ylcarbamoyl)phenoxy)chroman-4-carboxylate Prepared according to Example 52, Step B substituting the boronic acid of that example with 3,4-difluorophenylboronic acid to provide the title compound (32 mg, 75%).

Step B: Preparation of 6-chloro-7-(4-(6-(3,4-difluorophenyl)pyridin-2-ylcarbamoyl)phenoxy)chroman-4-carboxylic acid Prepared according to Example 52, Step B to provide the title compound (28 mg, 91%) as a white solid. MS (apci) m/z=537.1 (M+H).

EXAMPLE 82

6-Chloro-7-(4-(6-(2,4-difluorophenyl)pyridin-2-ylcarbamoyl)phenoxy)chroman-4-carboxylic acid

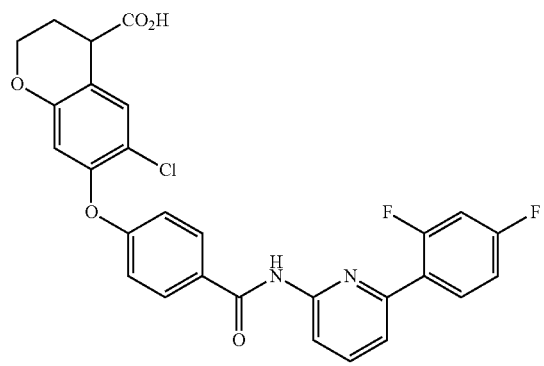 [SMILES: O=C(Nc1cccc(-c2ccc(F)cc2F)n1)c1ccc(Oc2cc3c(cc2Cl)C(C(=O)O)CCO3)cc1]

Step A: Preparation of ethyl 6-chloro-7-(4-(6-(2,4-difluorophenyl)pyridin-2-ylcarbamoyl)phenoxy)chroman-4-carboxylate Ethyl 7-(4-(6-bromopyridin-2-ylcarbamoyl)phenoxy)-6-chlorochroman-4-carboxylate (Example 52, Step A, 40 mg, 0.0752 mmol), 2,4-difluorophenylboronic acid (15.4 mg, 0.0978 mmol), and cesium fluoride (29.7 mg, 0.196 mmol) in i-PrOH (1 ml) were sparged with argon for 2 minutes in a vial. Dichloro[1,1'-bis(diphenylphosphino)ferrocene]palladium (II) dichloromethane adduct (3.09 mg, 0.00376 mmol) and triethylamine (15.7 µl, 0.113 mmol) were added and the vial capped. The reaction was heated to 105° C. for 90 minutes. The reaction was applied directly to a silica gel column and eluted with 20 to 80% ethyl acetate/hexanes gradient to provide the title compound (30 mg, 0.0531 mmol, 70.6% yield) as a white foam.

Step B: Preparation of 6-chloro-7-(4-(6-(2,4-difluorophenyl)pyridin-2-ylcarbamoyl)phenoxy)chroman-4-carboxylic acid Prepared according to Example 77, Step B to provide the title compound (29 mg, 80%) as a white solid. MS (apci) m/z=537.1 (M+H).

The following compounds were also made according to the method of Example 82.

| Ex. # | Structure | Name | MS (apci) |
|---|---|---|---|
| 83 | 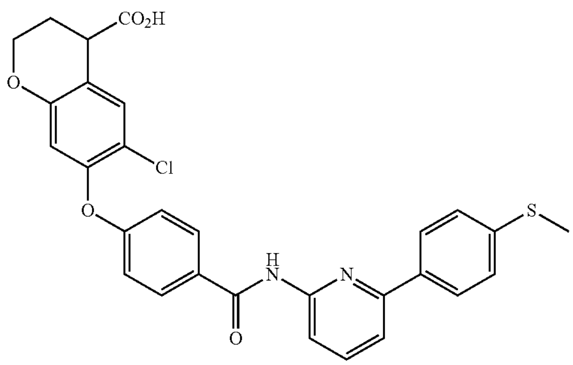 [SMILES: CSc1ccc(-c2cccc(NC(=O)c3ccc(Oc4cc5c(cc4Cl)C(C(=O)O)CCO5)cc3)n2)cc1] | 6-Chloro-7-(4-(6-(4-(methylthio)phenyl)pyridin-2-ylcarbamoyl)phenoxy)chroman-4-carboxylic acid | m/z = 547.1 (M + H). |
| 84 | 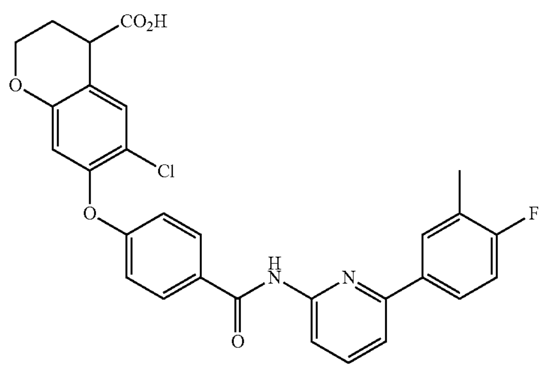 [SMILES: Cc1cc(-c2cccc(NC(=O)c3ccc(Oc4cc5c(cc4Cl)C(C(=O)O)CCO5)cc3)n2)ccc1F] | 6-Chloro-7-(4-(6-(4-fluoro-3-methylphenyl)pyridin-2-ylcarbamoyl)phenoxy)chroman-4-carboxylic acid | m/z = 533.1 (M + H). |
| 85 | 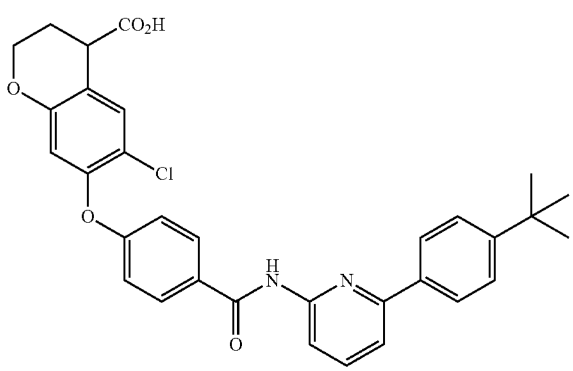 [SMILES: CC(C)(C)c1ccc(-c2cccc(NC(=O)c3ccc(Oc4cc5c(cc4Cl)C(C(=O)O)CCO5)cc3)n2)cc1] | 7-(4-(6-(4-tert-Butylphenyl)pyridin-2-ylcarbamoyl)phenoxy)-6-chlorochroman-4-carboxylic acid | m/z = 557.2 (M + H). |
| 86 | 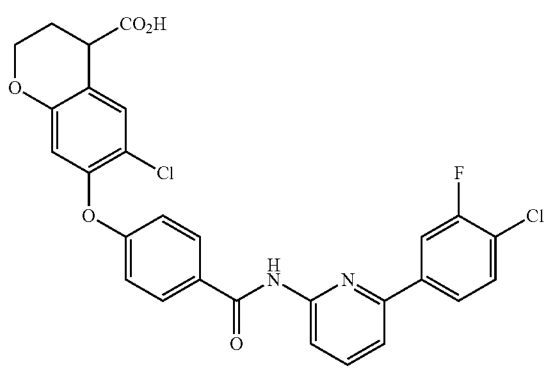 [SMILES: O=C(Nc1cccc(-c2ccc(Cl)c(F)c2)n1)c1ccc(Oc2cc3c(cc2Cl)C(C(=O)O)CCO3)cc1] | 6-Chloro-7-(4-(6-(4-chloro-3-fluorophenyl)pyridin-2-ylcarbamoyl)phenoxy)chroman-4-carboxylic acid | m/z = 553.0 (M + H). |

-continued

| Ex. # | Structure | Name | MS (apci) |
|---|---|---|---|
| 87 | 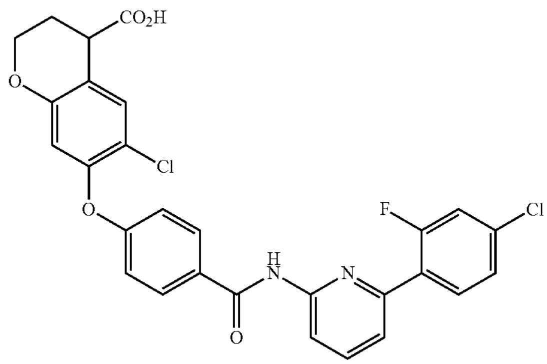 [SMILES: O=C(Nc1cccc(-c2ccc(Cl)cc2F)n1)c1ccc(Oc2cc3c(cc2Cl)C(C(=O)O)CCO3)cc1] | 6-chloro-7-(4-(6-(4-chloro-2-fluorophenyl)pyridin-2-ylcarbamoyl)phenoxy)chroman-4-carboxylic acid | m/z = 553.0 (M + H). |
| 88 | 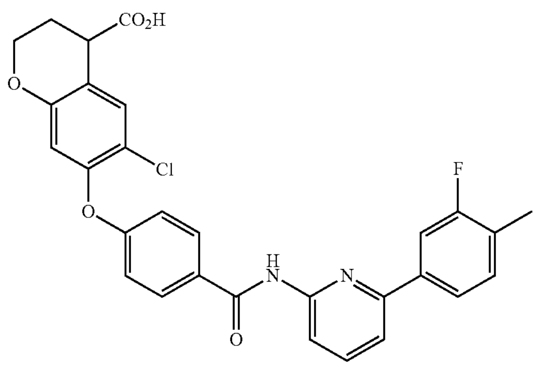 [SMILES: Cc1ccc(-c2cccc(NC(=O)c3ccc(Oc4cc5c(cc4Cl)C(C(=O)O)CCO5)cc3)n2)cc1F] | 6-Chloro-7-(4-(6-(3-fluoro-4-methylphenyl)pyridin-2-ylcarbamoyl)phenoxy)chroman-4-carboxylic acid | m/z = 533.1 (M + H). |
| 89 | 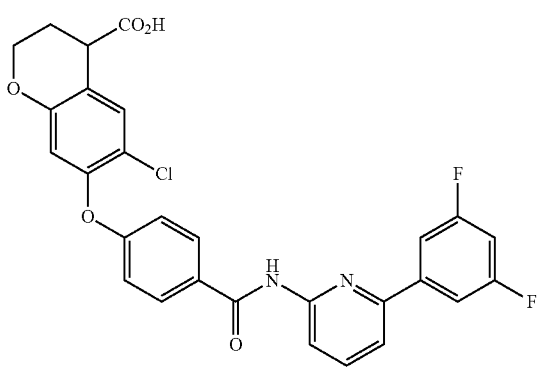 [SMILES: O=C(Nc1cccc(-c2cc(F)cc(F)c2)n1)c1ccc(Oc2cc3c(cc2Cl)C(C(=O)O)CCO3)cc1] | 6-chloro-7-(4-(6-(3,5-difluorophenyl)pyridin-2-ylcarbamoyl)phenoxy)chroman-4-carboxylic acid | m/z = 537.1 (M + H). |
| 90 | 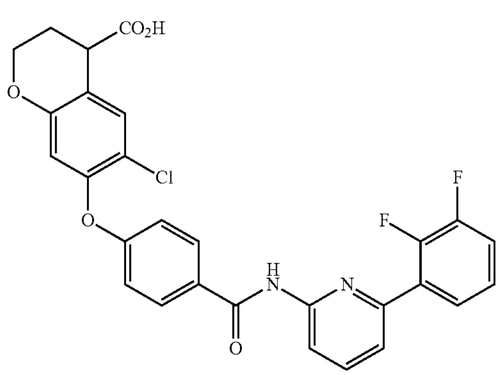 [SMILES: O=C(Nc1cccc(-c2cccc(F)c2F)n1)c1ccc(Oc2cc3c(cc2Cl)C(C(=O)O)CCO3)cc1] | 6-chloro-7-(4-(6-(2,3-difluorophenyl)pyridin-2-ylcarbamoyl)phenoxy)chroman-4-carboxylic acid | m/z = 537.1 (M + H). |

EXAMPLE 91

7-(4-(6-(tert-Butylthio)pyridin-2-ylcarbamoyl)phenoxy)-6-chlorochroman-4-carboxylic acid

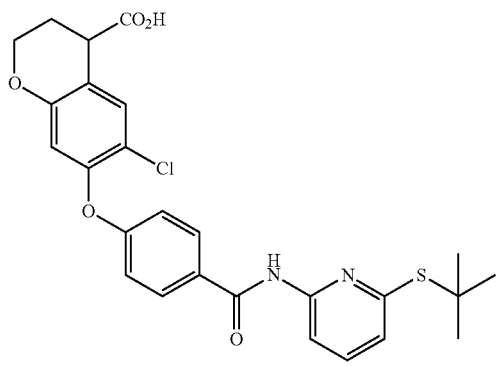 [SMILES: CC(C)(C)Sc1cccc(NC(=O)c2ccc(Oc3cc4c(cc3Cl)C(C(=O)O)CCO4)cc2)n1]

Step A: Preparation 2-(tert-butylthio)-6-chloropyridine

A suspension of sodium 2-methylpropane-2-thiolate (188 mg, 1.68 mmol) in DMF was treated with 2,6-dichloropyridine (4865 µl, 1.46 mmol) at ambient temperature in a vial. The vial was capped and heated to 80° C. with rapid stirring of the colorless solution. After 12 hours, the reaction was cooled to ambient temperature and diluted with ethyl acetate. The ethyl acetate solution was washed with brine solution, dried with sodium sulfate, filtered, concentrated and purified on silica gel. Elution with 2% to 10% ethyl acetate/hexanes provided the title compound (271 mg, 1.34 mmol, 92.0% yield) as a light yellow oil.

Step B-C: Preparation of 7-(4-(6-(tert-butylthio)pyridin-2-ylcarbamoyl)phenoxy)-6-chlorochroman-4-carboxylic acid Prepared according to the method of Example 77, Steps A-B to provide the title compound. MS (apci) m/z=512.9 (M+H).

EXAMPLE 92

6-Chloro-7-(4-(6-(3-chlorophenyl)pyrazin-2-ylcarbamoyl)phenoxy)chroman-4-carboxylic acid

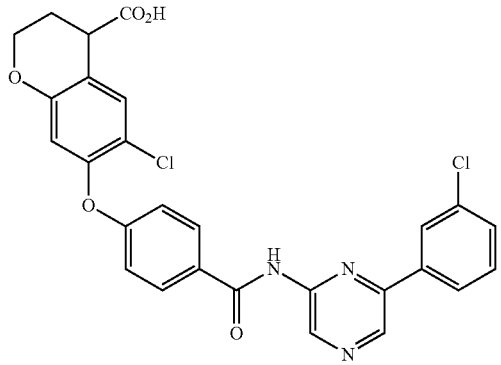 [SMILES: O=C(Nc1cncc(-c2cccc(Cl)c2)n1)c1ccc(Oc2cc3c(cc2Cl)C(C(=O)O)CCO3)cc1]

Step A: Preparation of ethyl 6-chloro-7-(4-(6-chloropyrazin-2-ylcarbamoyl)phenoxy)chroman-4-carboxylate Prepared according to the method of Example 52, Step A, substituting the 6-bromopyridin-2-amine with 2-amino-6-chloropyrazine to provide the title compound (260 mg, 87%) as a white solid.

Steps B-C: Preparation of 6-chloro-7-(4-(6-(3-chlorophenyl)pyrazin-2-ylcarbamoyl)phenoxy)chroman-4-carboxylic acid Prepared according to the method of Example 82, Steps A-B to provide the title compound (31 mg, 82%). MS (apci) m/z=536.1 (M+H).

EXAMPLE 93

6-Chloro-7-(4-(6-(4-(trifluoromethyl)phenyl)pyrazin-2-ylcarbamoyl)phenoxy)chroman-4-carboxylic acid

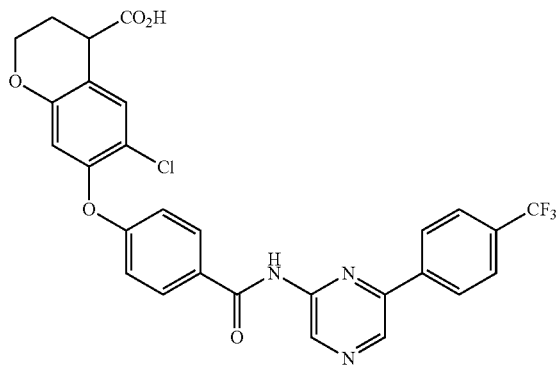 [SMILES: O=C(Nc1cncc(-c2ccc(C(F)(F)F)cc2)n1)c1ccc(Oc2cc3c(cc2Cl)C(C(=O)O)CCO3)cc1]

Prepared according to the method of Example 92. MS (apci) m/z=570.1 (M+H).

EXAMPLE 94

6-chloro-7-(4-(6-(3-(trifluoromethyl)phenyl)pyrazin-2-ylcarbamoyl)phenoxy)chroman-4-carboxylic acid

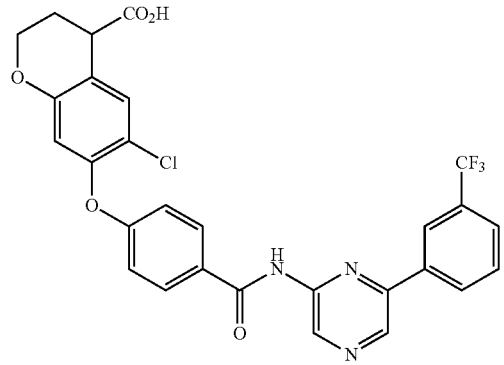

Prepared according to the method of Example 92. MS (apci) m/z=570.1 (M+H).

EXAMPLE 95

6-Chloro-7-(4-(5-(4-chlorophenyl)pyrazin-2-ylcarbamoyl)phenoxy)chroman-4-carboxylic acid

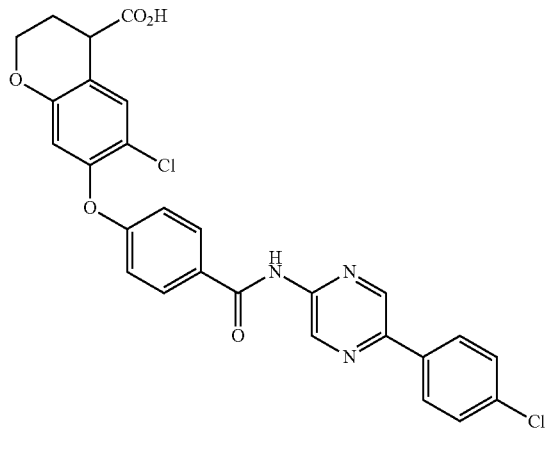 [SMILES: O=C(Nc1cnc(-c2ccc(Cl)cc2)cn1)c1ccc(Oc2cc3c(cc2Cl)C(C(=O)O)CCO3)cc1]

Step A: Preparation of ethyl 6-chloro-7-(4-(6-chloropyrazin-2-ylcarbamoyl)phenoxy)chroman-4-carboxylate Prepared according to the method of Example 52, Step A, substituting the 6-bromopyridin-2-amine with 2-amino-5-bromopyrazine to provide the title compound (556 mg, 89%) as a white solid.

Steps B-C: Preparation of 6-chloro-7-(4-(5-(4-chlorophenyl)pyrazin-2-ylcarbamoyl)phenoxy)chroman-4-carboxylic acid Prepared according to the method of Example 82, Steps A-B to provide the title compound. MS (apci) m/z=536.1 (M+H).

EXAMPLE 96

6-Chloro-7-(4-(5-(3-chlorophenyl)pyrazin-2-ylcarbamoyl)phenoxy)chroman-4-carboxylic acid

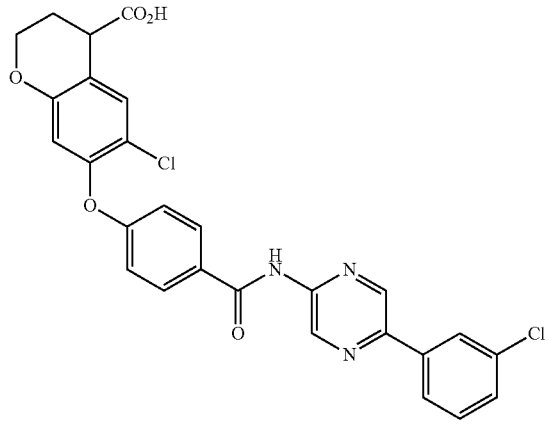 [SMILES: O=C(Nc1cnc(-c2cccc(Cl)c2)cn1)c1ccc(Oc2cc3c(cc2Cl)C(C(=O)O)CCO3)cc1]

Prepared according to the method of Example 95. MS (apci) m/z=536.1 (M+H).

EXAMPLE 97

6-Chloro-7-(4-(6-(3-chlorophenyl)pyridazin-3-ylcarbamoyl)phenoxy)chroman-4-carboxylic acid

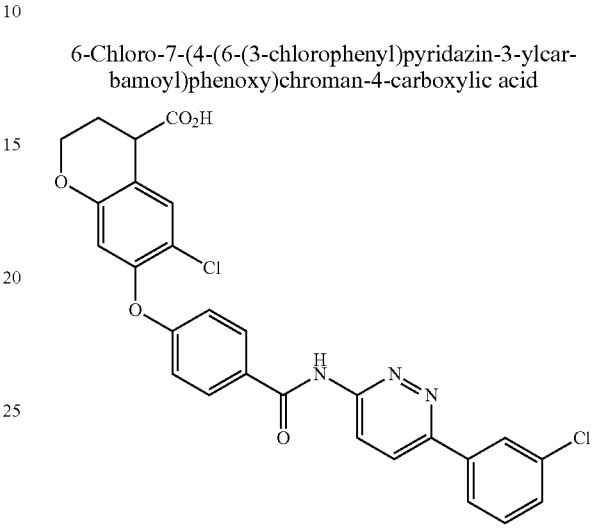

Prepared according to the method of Example 59, steps A-C. MS (apci) m/z=535.9 (M+H).

EXAMPLE 98

Sodium 6-chloro-7-(4-(6-(4-(trifluoromethyl)phenyl)pyridazin-3-ylcarbamoyl)phenoxy)chroman-4-carboxylate

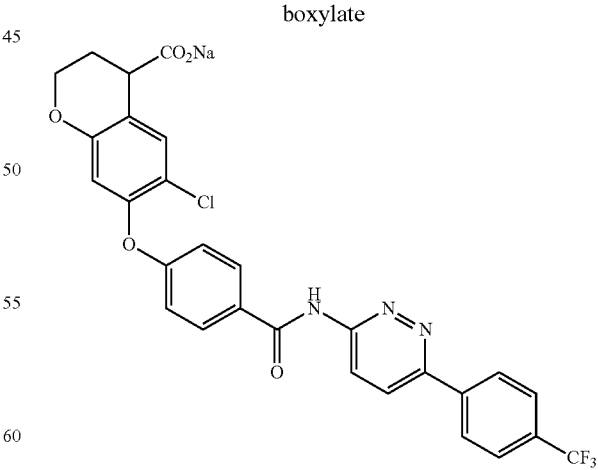

Prepared according to the method of Example 59. MS (apci) m/z=569.9 (M-Na+2H).

EXAMPLE 99

Sodium 6-chloro-7-(4-(6-(3-(trifluoromethyl)phenyl)pyridazin-3-ylcarbamoyl)phenoxy)chroman-4-carboxylate

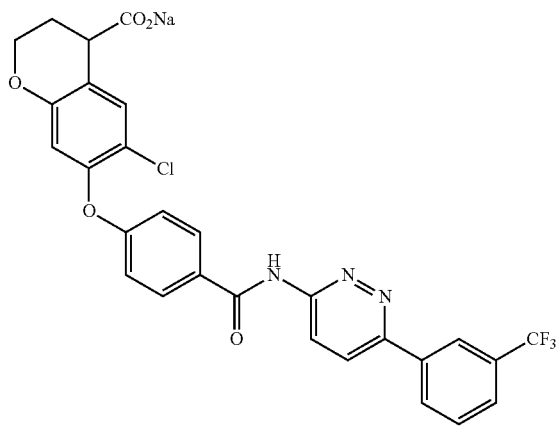

Prepared according to the method of Example 59. MS (apci) m/z=570.0 (M-Na+2H).

EXAMPLE 100

Sodium 6-chloro-7-(4-(2-(4-chlorophenyl)pyrimidin-4-ylcarbamoyl)phenoxy)chroman-4-carboxylate

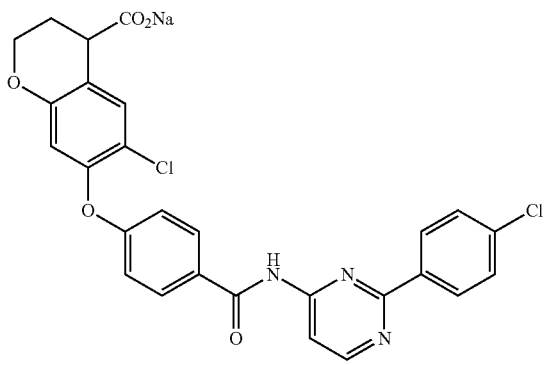

Step A: Preparation of 2-(4-chlorophenyl)-4-methoxypyrimidine

2-Chloro-4-methoxypyrimidine (509 mg, 3.52 mmol), 4-chlorophenylboronic acid (826 mg, 5.28 mmol), and sodium carbonate (3732 μl, 7.04 mmol) in toluene (17 ml) were sparged with argon for 2 minutes in a glass vial. Pd(PPh$_3$)$_4$ (203 mg, 0.176 mmol) was added and the reaction mixture was sparged an additional 1 minute. The vial was capped and the reaction heated to 115° C. for 19 hours. The reaction was cooled to ambient temperature and diluted with ethyl acetate. The organic layer was washed with water and brine, dried with sodium sulfate, filtered, concentrated and purified on silica gel. Elution with a 2-20% ethyl acetate/hexanes gradient provided the title compound (161 mg, 0.730 mmol, 20.7% yield) as a white foam.

Step B: Preparation of 2-(4-chlorophenyl)pyrimidin-4(3H)-one 2-(4-Chlorophenyl)-4-methoxypyrimidine (161 mg, 0.730 mmol) in water (1.5 ml) was treated with concentrated hydrochloric acid (608 μl, 7.30 mmol) at ambient temperature. The suspension was heated to reflux during which the reaction became a clear solution. After 12 hours, the reaction was cooled to ambient temperature and the resulting white suspension was diluted with water and filtered. The solids were washed with water and dried under high vacuum to provide the title compound (100 mg, 0.484 mmol, 66.3% yield) as a white solid.

Step C: Preparation of 4-chloro-2-(4-chlorophenyl)pyrimidine 2-(4-chlorophenyl)pyrimidin-4(3H)-one (100 mg, 0.4840 mmol), suspended in toluene (2 ml), was treated with phosphoryl trichloride (443.0 μl, 4.840 mmol) at ambient temperature. The suspension was heated to reflux at which point the reaction became a colorless solution. After 4 hours, the reaction was cooled to ambient temperature and concentrated in vacuo to afford a white solid. The reaction was diluted with dichloromethane and washed with saturated aqueous sodium bicarbonate. The organics were dried with sodium sulfate, filtered, concentrated, and purified on silica gel. Elution with 2-20% ethyl acetate/hexanes provided the title compound (99 mg, 0.4399 mmol, 90.89% yield) as a white solid.

Steps D-E: Preparation of 6-chloro-7-(4-(2-(4-chlorophenyl)pyrimidin-4-ylcarbamoyl)phenoxy)chroman-4-carboxylic acid Prepared according to the method of Example 77, Steps A-B to provide the title compound as a white solid.

Step F: Preparation of sodium 6-chloro-7-(4-(2-(4-chlorophenyl)pyrimidin-4-ylcarbamoyl)phenoxy)chroman-4-carboxylate Prepared according to the method of Example 59, Step D. MS (apci) m/z=536.0 (M-Na+2H).

EXAMPLE 101

Sodium 6-chloro-7-(4-(6-(4-chlorophenyl)-2-methylpyrimidin-4-ylcarbamoyl)phenoxy)chroman-4-carboxylate

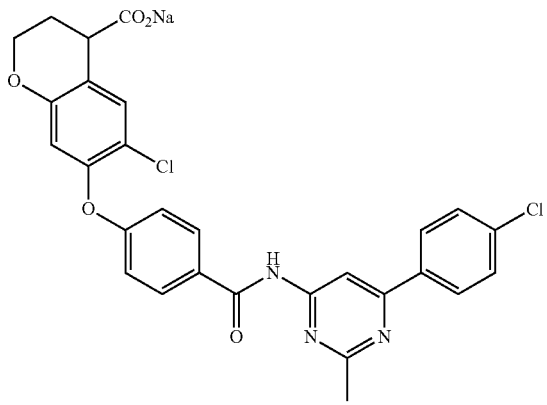

Prepared according to the method of Example 100. MS (apci) m/z=550.0 (M-Na+2H).

EXAMPLE 102

Sodium 6-chloro-7-(4-(6-methyl-2-(4-(trifluoromethyl)phenyl)pyrimidin-4-ylcarbamoyl)phenoxy)chroman-4-carboxylate

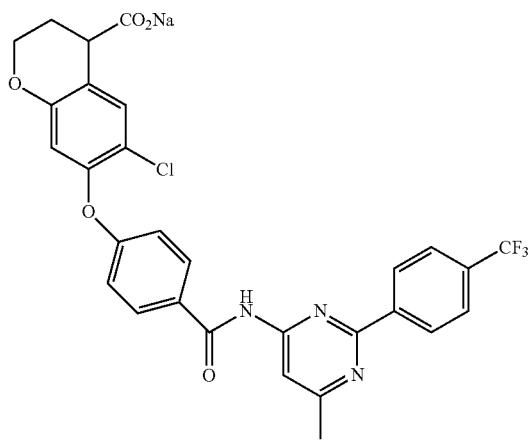

Prepared according to the method of Example 100. MS (apci) m/z=584.0 (M-Na+2H).

EXAMPLE 103

Sodium 6-chloro-7-(4-(6-(2,4-dichlorophenyl)pyridin-2-ylcarbamoyl)phenoxy)chroman-4-carboxylate

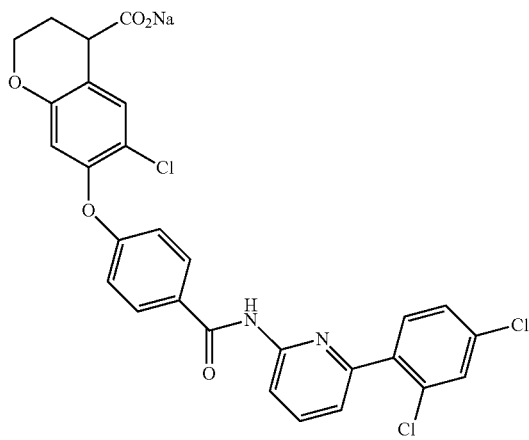

Prepared according to the methods of Example 82 and Example 59, Step A. MS (apci) m/z=571.0 (M-Na+2H).

EXAMPLE 104

Sodium 6-chloro-7-(4-(6-(4-chloro-2-methoxyphenyl)pyridin-2-ylcarbamoyl)phenoxy)chroman-4-carboxylate

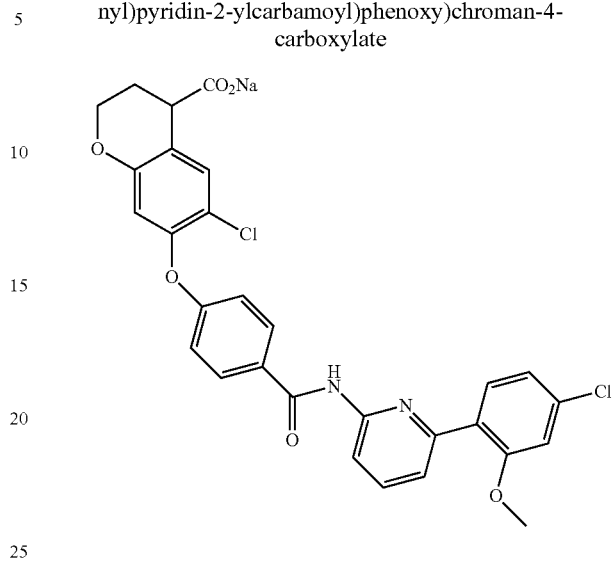

Prepared according to the method of Example 103. MS (apci) m/z=565.1 (M-Na+2H).

EXAMPLE 105

6-Chloro-7-(4-(6-isobutylpyridin-2-ylcarbamoyl)phenoxy)chroman-4-carboxylic acid

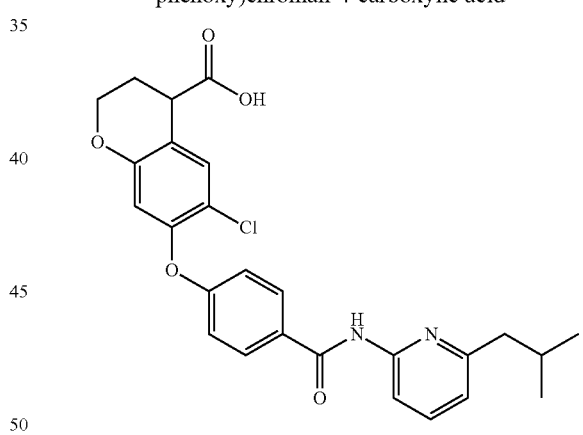

To ethyl 7-(4-(6-bromopyridin-2-ylcarbamoyl)phenoxy)-6-chlorochroman-4-carboxylate (Example 52, Step A, 0.021 g, 0.039 mmol) in THF (0.5 ml) was added 0.5 isobutylzinc bromide in THF (0.12 ml, 0.059 mmol) followed by bis(tri-t-butylphosphine)palladium (0) (0.0010 g, 0.0020 mmol) and the reaction was stirred at ambient temperature for 1 hour. The reaction was loaded onto silica gel and the product eluted using 3:1 hexanes/ethyl acetate. The resulting oil was dissolved in THF/MeOH/1N NaOH (0.5 ml/0.5 ml/0.25 ml) and stirred at ambient temperature for 3 hours. The reaction was diluted with DCM (35 ml) and washed with water with made acidic (pH=5) with 1N HCl. The organic layer was washed with brine (10 ml), dried over magnesium sulfate and concentrated to give the title compound (0.013 g, 0.027 mmol, 68% yield) as a white solid. MS (ESI) m/z=481.31 (M+H).

EXAMPLE 106

Sodium 8-bromo-6-chloro-7-(4-(6-(4-chlorophenyl)pyridin-2-ylcarbamoyl)phenoxy)chroman-4-carboxylate

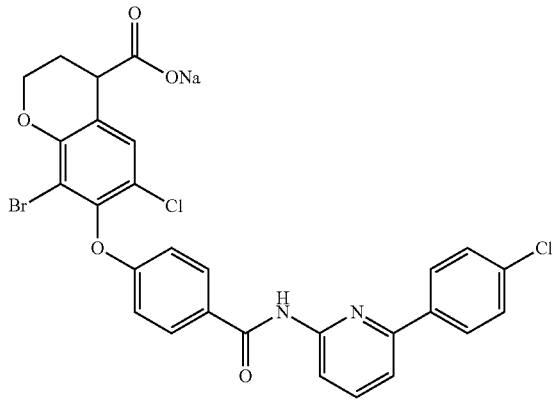

Step A: Preparation of ethyl 8-bromo-6-chloro-7-hydroxychroman-4-carboxylate To a stirred solution of ethyl 6-chloro-7-hydroxychroman-4-carboxylate (5.14 g, 20.0 mmol) in glacial acetic acid (50 mL) at ambient temperature was added bromine (1.2 mL, 24 mmol) in six equal portions, waiting 30-60 seconds between each addition for the bromine color to be discharged. Following completion of addition, the solution was concentrated and the residue concentrated from toluene, then partitioned between ethyl acetate (200 mL) and 5% sodium bisulfite (100 mL). The organic was layer dried over sodium sulfate, then stirred with activated charcoal (2 g) at ambient temperature for 20 minutes. The charcoal was removed by filtration through a glass microfibre filter and the filtrate was concentrated to afford ethyl 8-bromo-6-chloro-7-hydroxychroman-4-carboxylate as a light brown oil (6.05 g, 90% yield).

Step B: Preparation of ethyl 8-bromo-7-(4-(tert-butoxycarbonyl)-2-nitrophenoxy)-6-chlorochroman-4-carboxylate To a stirred solution of ethyl 8-bromo-6-chloro-7-hydroxychroman-4-carboxylate (4.00 g, 11.9 mmol) and tert-butyl 4-fluoro-3-nitrobenzoate (3.16 g, 13.1 mmol) in N,N-dimethylformamide (66 mL) at ambient temperature was added solid potassium carbonate (2.64 g, 19.1 mmol). The resulting mixture was stirred in an oil bath set to 90° C. for 30 minutes. The mixture was cooled to ambient temperature and poured into a separatory funnel containing water (600 mL). Chloroform (300 mL) was added, followed by 1M hydrochloric acid (100 mL). The organic layer was dried over sodium sulfate and concentrated. The residue was purified by chromatography on silica gel, eluting with 90/10 hexanes/ethyl acetate to afford the desired compound as a light yellow glass (4.33 g, 65% yield).

Step C: Preparation of ethyl 7-(2-amino-4-(tert-butoxycarbonyl)phenoxy)-8-bromo-6-chlorochroman-4-carboxylate To a stirred solution of ethyl 8-bromo-7-(4-(tert-butoxycarbonyl)-2-nitrophenoxy)-6-chlorochroman-4-carboxylate (2.00 g, 3.59 mmol) in tetrahydrofuran (15 mL) at ambient temperature was added zinc dust (4.70 g, 71.8 mmol), followed by saturated ammonium chloride solution (7.5 mL). The resulting mixture was stirred at ambient temperature for 1 hour. The mixture was filtered through a glass microfibre filter to remove the insoluble zinc solids, and the solids were washed twice with tetrahydrofuran. The combined filtrate and washings were concentrated to remove most of the tetrahydrofuran, and the residue was partitioned between ethyl acetate (100 mL) and water (50 mL). The organic layer was washed with brine (50 mL), then dried over sodium sulfate and concentrated to afford the desired compound as a light brown glass (1.61 g, 85% yield).

Step D: Preparation of ethyl 8-bromo-7-(4-(tert-butoxycarbonyl)phenoxy)-6-chlorochroman-4-carboxylate N,N-dimethylformamide (20 mL) was heated in an oil bath set to 70° C. Isobutyl nitrite (0.90 mL, 7.6 mmol) was added, and to the resulting stirred solution at 68° C. was added a solution of ethyl 7-(2-amino-4-(tert-butoxycarbonyl)phenoxy)-8-bromo-6-chlorochroman-4-carboxylate (1.6 g, 6.0 mmol) in N,N-dimethylformamide (6 mL), dropwise over 5 minutes. The resulting solution was stirred at 70° C. for 30 minutes. The resulting red solution was cooled to ambient temperature and partitioned between water (600 mL) and ethyl acetate (50 mL). The organic layer was washed with 1M hydrochloric acid (10 mL) and brine (10 mL), then dried over sodium sulfate and concentrated. The residue was purified by chromatography on silica gel, eluting with 95/5 to 85/15 hexanes/ethyl acetate, to afford ethyl 8-bromo-7-(4-(tert-butoxycarbonyl)phenoxy)-6-chlorochroman-4-carboxylate as an orange oil (0.27 g, 17% yield).

Step E: Preparation of 4-(8-bromo-6-chloro-4-(ethoxycarbonyl)chroman-7-yloxy)benzoic acid To a stirred solution of ethyl 8-bromo-7-(4-(tert-butoxycarbonyl)phenoxy)-6-chlorochroman-4-carboxylate (0.26 g, 0.51 mmol) in dichloromethane (5 mL) at ambient temperature was added trifluoroacetic acid (5 mL). The resulting solution was stirred at ambient temperature for 30 minutes. The solution was concentrated and the residual glassy solid was redissolved in ethyl acetate (2 mL). Hexanes (10 mL) were added, and after mixing for a few minutes, the product solidified. The mixture was concentrated to afford the desired compound as a light brown powder (0.23 g, 99% yield).

Step F: Preparation of ethyl 8-bromo-6-chloro-7-(4-(6-(4-chlorophenyl)pyridin-2-ylcarbamoyl)phenoxy)chroman-4-carboxylate A solution of 4-(8-bromo-6-chloro-4-(ethoxycarbonyl)chroman-7-yloxy)benzoic acid (0.18 g, 0.40 mmol) in thionyl chloride (5 mL) was stirred and heated to gentle reflux for 30 minutes. The solution was cooled to ambient temperature and concentrated. The residual light yellow solid was dissolved in dichloromethane (4 mL). To the resulting stirred solution at ambient temperature was added 6-(4-chlorophenyl)pyridin-2-amine hydrochloride (96.6 mg, 0.40 mmol), followed by N,N-diisopropylethylamine (0.28 mL, 1.60 mmol). A solution formed, and stirring was continued at ambient temperature for 3 hours. The solution was diluted with ethyl acetate (20 mL) and 1M hydrochloric acid (10 mL), then transferred to a separatory funnel. After shaking, the organic layer was washed successively with 10 mL portions of water, 10% sodium carbonate, and brine, dried over sodium sulfate and evaporated. The residual oil was purified by chromatography on silica gel, eluting with 80/20 hexanes/ethyl acetate, to afford the desired compound as a colorless oil (0.15 g, 58% yield).

Step G: Preparation of sodium 8-bromo-6-chloro-7-(4-(6-(4-chlorophenyl)pyridin-2-ylcarbamoyl)phenoxy)chroman-4-carboxylate To a stirred solution of ethyl 8-bromo-6-chloro-7-(4-(6-(4-chlorophenyl)pyridin-2-ylcarbamoyl)phenoxy)chroman-4-carboxylate (28 mg, 0.044 mmol) in a mixture of tetrahydrofuran (0.5 mL) and ethanol (0.25 mL) at ambient temperature was added 1M sodium hydroxide (0.17 mL, 0.17 mmol). The resulting slightly cloudy mixture was vigorously stirred at ambient temperature for 1 hour. The reaction mixture was partitioned between ethyl acetate (4 mL) and 1M hydrochloric acid (2 mL). The organic layer was dried over sodium sulfate and concentrated to afford the carboxylic acid as a colorless oil (21 mg, 78% yield). To convert to the sodium salt, the oil was dissolved in methanol (1 mL) and treated with a 25% (w/v) solution of sodium methoxide in methanol (7.8 µL, 0.034 mmol). The resulting solution was concentrated, and the residue was concentrated twice from ether to afford the desired compound as a light yellow solid (21 mg, 78% yield). MS (apci) m/z=613.0 (M+2H—Na).

EXAMPLE 107

Sodium 7-(4-(6-(4-chlorophenyl)pyridin-2-ylcarbamoyl)phenoxy)-6,8-dicyclopropylchroman-4-carboxylate

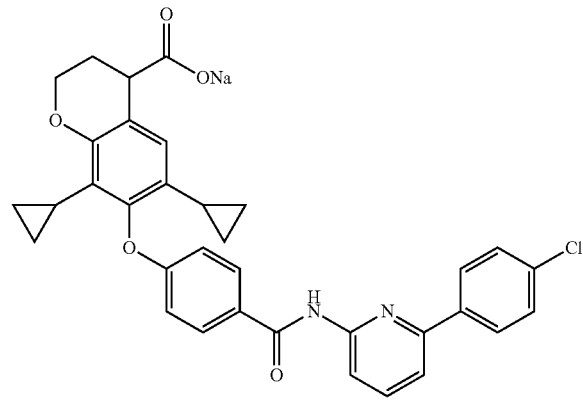

Step A: Preparation of ethyl 7-(4-(tert-butoxycarbonyl)-2-nitrophenoxy)-6,8-dicyclopropylchroman-4-carboxylate To a stirred solution of ethyl 8-bromo-7-(4-(tert-butoxycarbonyl)-2-nitrophenoxy)-6-chlorochroman-4-carboxylate (Example 106, Step B) (0.56 g, 1.0 mmol) in xylenes (6 mL) was added successively water (0.3 mL), potassium phosphate (1.27 g, 6.0 mmol), tricyclohexylphosphine (0.11 g, 0.40 mmol), and cyclopropylboronic acid (0.34 g, 4.0 mmol). The resulting mixture was stirred and a balloon of nitrogen with a three-way purge valve was attached, and the flask was evacuated and refilled five times with nitrogen. Palladium(II) acetate (0.045 g, 0.20 mmol) was added, and again the flask was evacuated and refilled five times with nitrogen. The mixture was stirred in an oil bath set to 140° C. under the nitrogen balloon for 2 hours. The mixture was cooled to ambient temperature, and diluted with ethyl acetate (25 mL) and water (15 mL). The organic layer was dried over sodium sulfate and concentrated. The residue was purified by chromatography on silica gel, eluting with 90/10 hexanes/ethyl acetate, to afford the desired compound as a light yellow glass (0.24 g, 46%).

Step B: Preparation of sodium 7-(4-(6-(4-chlorophenyl)pyridin-2-ylcarbamoyl)phenoxy)-6,8-dicyclopropylchroman-4-carboxylate Prepared according to the method of Steps C through G of Example 106, substituting ethyl 7-(4-(tert-butoxycarbonyl)-2-nitrophenoxy)-6,8-dicyclopropylchroman-4-carboxylate for the desired compound. MS (apci) m/z=581.1 (M+2H—Na).

EXAMPLE 108

Sodium 6-chloro-7-(4-(6-(4-chlorophenyl)pyridin-2-ylcarbamoyl)phenoxy)-8-cyclopropylchroman-4-carboxylate

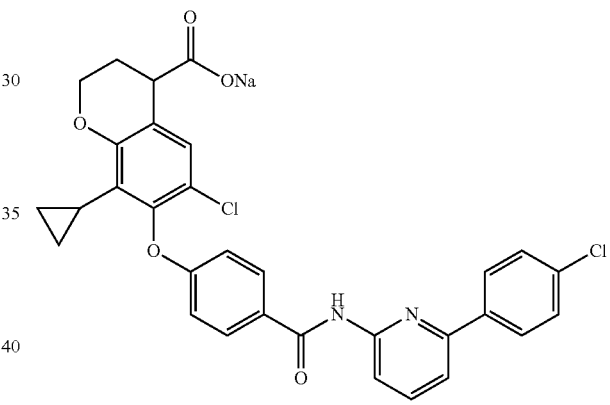

Step A: Preparation of ethyl 7-(4-(tert-butoxycarbonyl)-2-nitrophenoxy)-6-chloro-8-cyclopropylchroman-4-carboxylate To a stirred solution of ethyl 8-bromo-7-(4-(tert-butoxycarbonyl)-2-nitrophenoxy)-6-chlorochroman-4-carboxylate (Example 106, Step B) (0.59 g, 1.05 mmol) in toluene (6 mL) was added successively water (0.3 mL), potassium phosphate (0.67 g, 3.2 mmol), tricyclohexylphosphine (0.12 g, 0.42 mmol), and cyclopropylboronic acid (0.18 g, 2.1 mmol). The resulting mixture was stirred and a balloon of nitrogen with a three-way purge valve was attached, and the flask was evacuated and refilled five times with nitrogen. Palladium(II) acetate (0.047 g, 0.21 mmol) was added, and again the flask was evacuated and refilled five times with nitrogen. The mixture was stirred in an oil bath set to 100° C. under the nitrogen balloon for 1.5 hours. The mixture was cooled to ambient temperature, and diluted with ethyl acetate (25 mL) and water (15 mL). The organic layer was dried over sodium sulfate and concentrated. The residue was purified by chromatography on silica gel, eluting with 85/15 hexanes/ethyl acetate, to afford the desired compound as a yellow oil (0.28 g, 51%).

Step B: Preparation of sodium 6-chloro-7-(4-(6-(4-chlorophenyl)pyridin-2-ylcarbamoyl)phenoxy)-8-cyclopropylchroman-4-carboxylate Prepared according to the method of Steps C through G of Example 106, substituting ethyl 7-(4-(tert-butoxycarbonyl)-2-nitrophenoxy)-6-chloro-8-cyclopropylchroman-4-carboxylate for ethyl 8-bromo-7-(4-(tert-butoxycarbonyl)-2-nitrophenoxy)-6-chlorochroman-4-carboxylate. MS (apci) m/z=575.1 (M+2H—Na).

EXAMPLE 109

6-Chloro-7-(4-(6-(4-fluorophenyl)pyridin-2-ylcarbamoyl)phenoxy)chroman-4-carboxylic acid

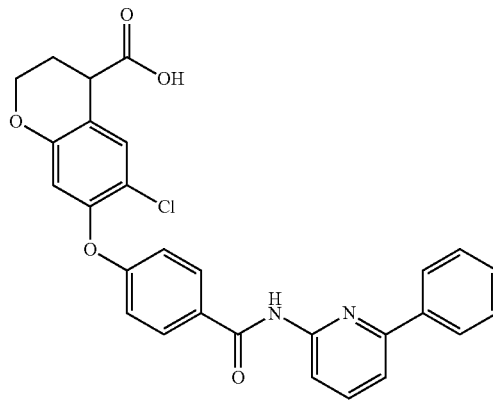

Prepared according to the method of Example 33, replacing 4-chlorophenylboronic acid in Step C with 4-fluorophenylboronic acid. MS (ESI)=519.2 (M+H)

EXAMPLE 110

6-Chloro-7-(4-(6-(4-(trifluoromethyl)phenyl)pyridin-2-ylcarbamoyl)phenoxy)chroman-4-carboxylic acid

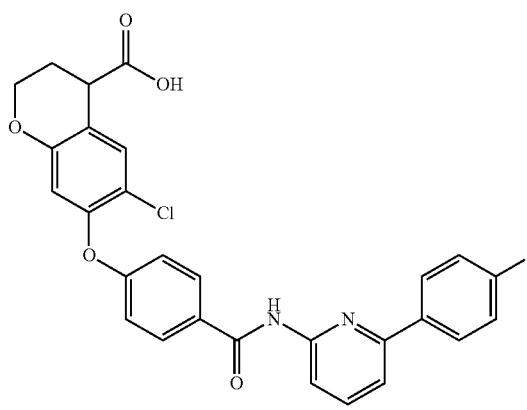

Prepared according to the method of Example 33, replacing 4-chlorophenylboronic acid in Step C with 4-(trifluoromethyl)phenylboronic acid. MS (ESI)=569.2 (M+H)

EXAMPLE 111

6-Chloro-7-(4-(6-cyclopropylpyridin-2-ylcarbamoyl)phenoxy)chroman-4-carboxylic acid

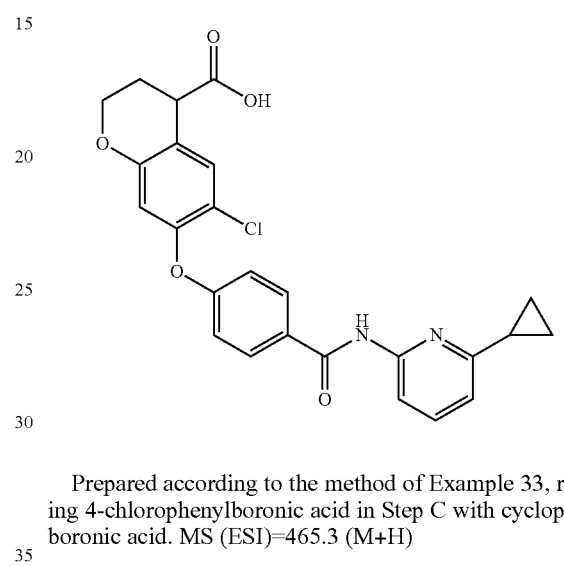

Prepared according to the method of Example 33, replacing 4-chlorophenylboronic acid in Step C with cyclopropylboronic acid. MS (ESI)=465.3 (M+H)

EXAMPLE 112

6-Chloro-7-(4-(6-(3-(trifluoromethyl)phenyl)pyridin-2-ylcarbamoyl)phenoxy)chroman-4-carboxylic acid

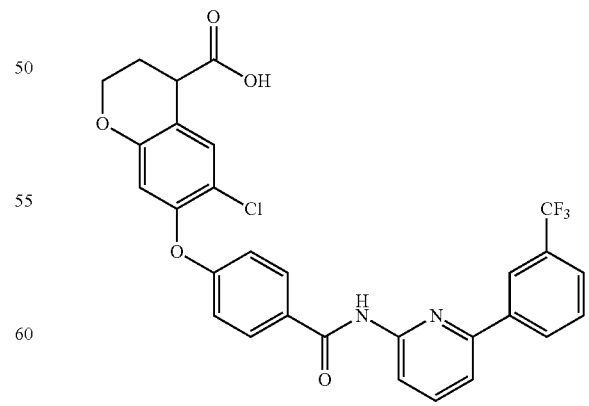

Prepared according to the method of Example 33, replacing 4-chlorophenylboronic acid in Step C with 3-(trifluoromethyl)phenylboronic acid. MS (ESI)=569.1 (M+H)

EXAMPLE 113

6-Chloro-7-(4-(2'-(trifluoromethyl)-2,4'-bipyridin-6-ylcarbamoyl)phenoxy)chroman-4-carboxylic acid

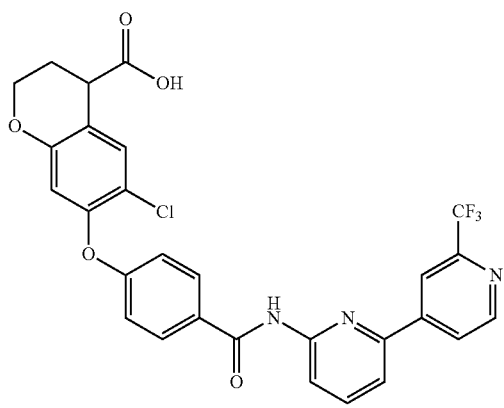 [SMILES: O=C(Nc1cccc(-c2ccnc(C(F)(F)F)c2)n1)c1ccc(Oc2cc3c(cc2Cl)C(C(=O)O)CCO3)cc1]

Prepared according to the method of Example 33, replacing 4-chlorophenylboronic acid in Step C with 2-(trifluoromethyl)pyridin-4-ylboronic acid. MS (ESI)=570.1 (M+H)

EXAMPLE 114

7-(4-(6-tert-Butylpyridin-2-ylcarbamoyl)phenoxy)-6-chlorochroman-4-carboxylic acid

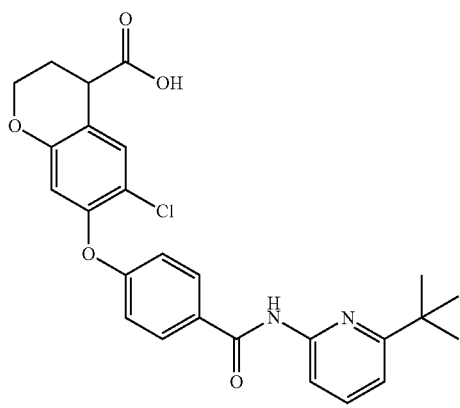 [SMILES: CC(C)(C)c1cccc(NC(=O)c2ccc(Oc3cc4c(cc3Cl)C(C(=O)O)CCO4)cc2)n1]

Step A: Preparation of ethyl 7-(4-(6-tert-butylpyridin-2-ylcarbamoyl)phenoxy)-6-chlorochroman-4-carboxylate Ethyl 7-(4-(6-bromopyridin-2-ylcarbamoyl)phenoxy)-6-chlorochroman-4-carboxylate (Example 52, Step A; 30 mg, 0.056 mmol) and bis(tri-t-butylphosphine)palladium (0) (14 mg, 0.028 mmol) were diluted with tert-butylzinc bromide (113 µl, 0.056 mmol) and stirred for 1 hour. The reaction was loaded onto silica gel and eluted with 5% ethyl acetate/hexanes to 70% ethyl acetate/hexanes to yield the desired compound (8 mg, 0.016 mmol, 56% yield).

Step B: 7-(4-(6-tert-butylpyridin-2-ylcarbamoyl)phenoxy)-6-chlorochroman-4-carboxylic acid Ethyl 7-(4-(6-tert-butylpyridin-2-ylcarbamoyl)phenoxy)-6-chlorochroman-4-carboxylate (10 mg, 0.020 mmol) was diluted with THF (200 µL) followed by the addition of NaOH (98 µL, 0.098 mmol) and ethanol (100 µL). After stirring for 3 hours, the reaction was diluted with 0.5N HCl and ethyl acetate. The layers were separated and the organic layer was dried over MgSO$_4$, filtered and concentrated. The material was purified using a 0.5 mm preparative TLC plate, eluting with 10% methanol/DCM to yield the desired compound (0.8 mg, 0.0017 mmol, 8.5% yield). MS (ESI)=481.2 (M+H).

EXAMPLE 115

6-Chloro-7-(4-(5-(4-chlorophenyl)pyridin-2-ylcarbamoyl)phenoxy)chroman-4-carboxylic acid

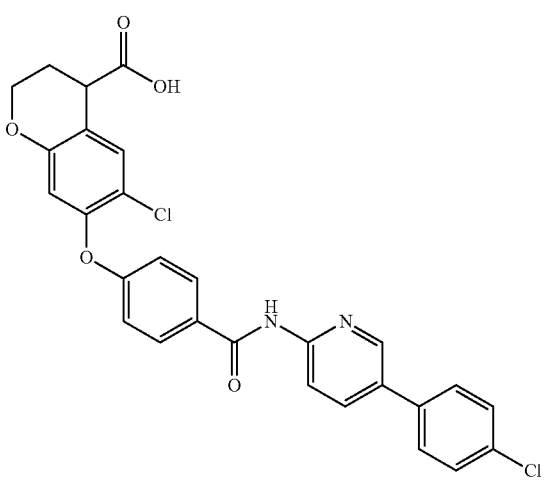 [SMILES: O=C(Nc1ccc(-c2ccc(Cl)cc2)cn1)c1ccc(Oc2cc3c(cc2Cl)C(C(=O)O)CCO3)cc1]

Step A: Preparation of ethyl 7-(4-(5-bromopyridin-2-ylcarbamoyl)phenoxy)-6-chlorochroman-4-carboxylate 4-(6-Chloro-4-(ethoxycarbonyl)chroman-7-yloxy)benzoic acid (Preparation B; 460 mg, 1.22 mmol) was diluted with DCM (5 mL) followed by the addition of oxalyl chloride in DCM (2M) (671 µL, 1.34 mmol) and DMF (1 drop). 5-Bromopyridin-2-amine (634 mg, 3.66 mmol) and pyridine (966 mg, 12.2 mmol) were added and the reaction was stirred at ambient temperature for 2 hours. The reaction was diluted with ethyl acetate and washed with 2N HCl, water, dried over MgSO$_4$, filtered and concentrated. The material was purified on silica gel eluting with 5% ethyl acetate/hexanes to 70% ethyl acetate/hexanes to yield the desired compound (450 mg, 0.846 mmol, 69.3% yield).

Step B: Preparation of ethyl 6-chloro-7-(4-(5-(4-chlorophenyl)pyridin-2-ylcarbamoyl)phenoxy)chroman-4-carboxylate Ethyl 7-(4-(5-bromopyridin-2-ylcarbamoyl)phenoxy)-6-chlorochroman-4-carboxylate (50 mg, 0.094 mmol), 4-chlorophenylboronic acid (15 mg, 0.094 mmol), Na$_2$CO$_3$ (25 mg, 0.24 mmol) and Pd(PPh$_3$)$_4$ (11 mg, 0.0094 mmol) were placed in a 1 mL vial and diluted with toluene (800 µL) and water (80 μL). The vial was purged with argon, sealed and heated to 100° C. After stirring for 36 hours, the reaction was loaded onto silica gel eluting with 5% ethyl acetate/hexanes to 70% ethyl acetate/hexanes to yield the desired compound (30 mg, 0.053 mmol, 57% yield).

Step C: Preparation of 6-chloro-7-(4-(5-(4-chlorophenyl)pyridin-2-ylcarbamoyl)phenoxy)chroman-4-carboxylic acid Ethyl 6-chloro-7-(4-(5-(4-chlorophenyl)pyridin-2-ylcarbamoyl)phenoxy)chroman-4-carboxylate (30 mg, 0.053 mmol) was diluted with THF (500 μL) followed by the addition of NaOH (266 μl, 0.27 mmol) and ethanol (200 μL). After stirring for 2 hours, the reaction was diluted with ethyl acetate and 0.5N HCl. The layers were separated and the organic layer was dried over MgSO$_4$, filtered and concentrated to yield the desired compound (27 mg, 0.050 mmol, 95% yield). MS (ESI)=535.1 (M+H).

The following compounds were also made according to Example 115, using the appropriate amine in Step A and replacing 4-chlorophenylboronic acid in Step B with the appropriate boronic acid.

| Ex. # | Structure | Name | MS (ESI) |
|---|---|---|---|
| 116 | 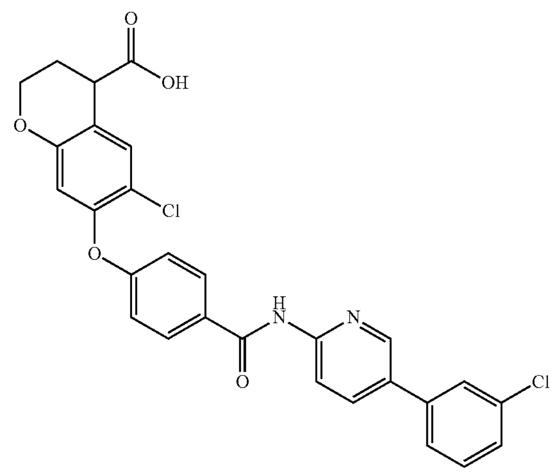 | 6-Chloro-7-(4-(5-(3-chlorophenyl)pyridin-2-ylcarbamoyl)phenoxy)chroman-4-carboxylic acid | 535.0 (M + H). |
| 117 | 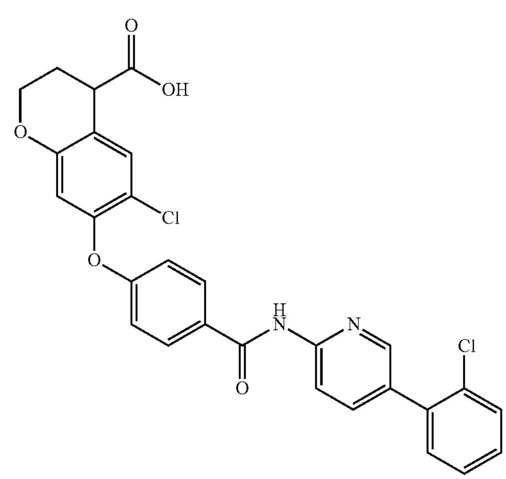 [SMILES: O=C(Nc1ccc(-c2ccccc2Cl)cn1)c1ccc(Oc2cc3c(cc2Cl)C(C(=O)O)CCO3)cc1] | 6-Chloro-7-(4-(5-(2-chlorophenyl)pyridin-2-ylcarbamoyl)phenoxy)chroman-4-carboxylic acid | 535.0 (M + H). |

-continued

| Ex. # | Structure | Name | MS (ESI) |
|---|---|---|---|
| 118 | 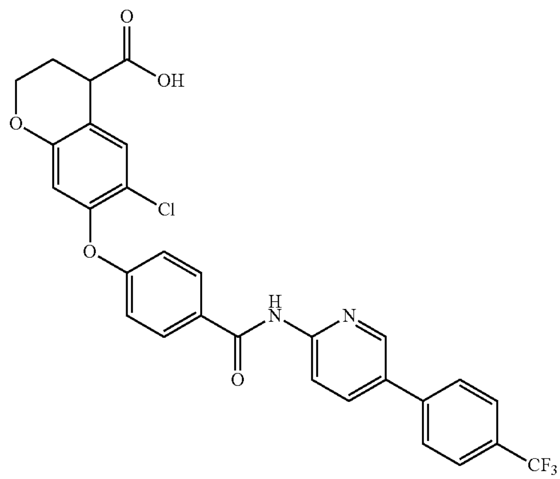 [SMILES: O=C(Nc1ccc(-c2ccc(C(F)(F)F)cc2)cn1)c1ccc(Oc2cc3c(cc2Cl)C(C(=O)O)CCO3)cc1] | 6-Chloro-7-(4-(5-(4-(trifluoromethyl)phenyl)pyridin-2-ylcarbamoyl)phenoxy)chroman-4-carboxylic acid | 569.1 (M + H). |
| 119 | 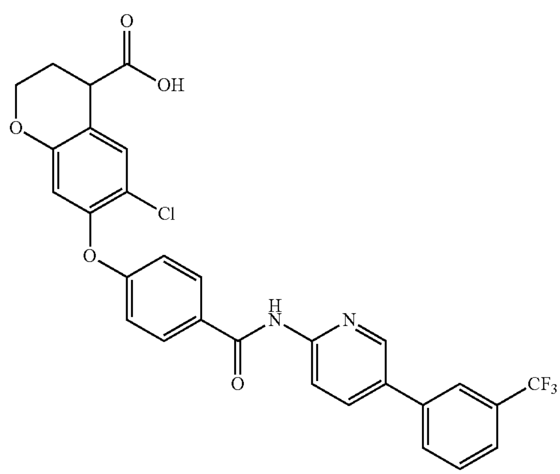 [SMILES: O=C(Nc1ccc(-c2cccc(C(F)(F)F)c2)cn1)c1ccc(Oc2cc3c(cc2Cl)C(C(=O)O)CCO3)cc1] | 6-Chloro-7-(4-(5-(3-trifluoromethyl)phenyl)pyridin-2-ylcarbamoyl)phenoxy)chroman-4-carboxylic acid | 569.1 (M + H) |
| 120 | 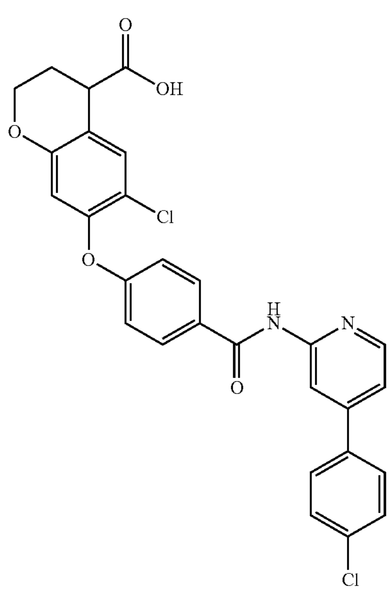 [SMILES: O=C(Nc1cc(-c2ccc(Cl)cc2)ccn1)c1ccc(Oc2cc3c(cc2Cl)C(C(=O)O)CCO3)cc1] | 6-Chloro-7-(4-(4-(4-chlorophenyl)pyridin-2-ylcarbamoyl)phenoxy)chroman-4-carboxylic acid | 535.1 (M + H) |

| Ex. # | Structure | Name | MS (ESI) |
|---|---|---|---|
| 121 | 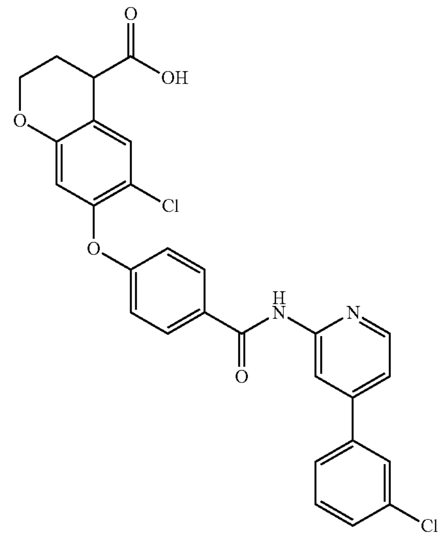 [SMILES: O=C(Nc1cc(-c2cccc(Cl)c2)ccn1)c1ccc(Oc2cc3c(cc2Cl)C(C(=O)O)CCO3)cc1] | 6-Chloro-7-(4-(4-(3-chlorophenyl)pyridin-2-ylcarbamoyl)phenoxy)chroman-4-carboxylic acid | 535.1 (M + H). |
| 122 | 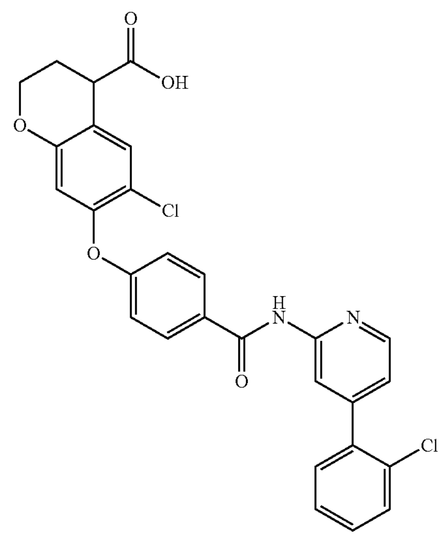 [SMILES: O=C(Nc1cc(-c2ccccc2Cl)ccn1)c1ccc(Oc2cc3c(cc2Cl)C(C(=O)O)CCO3)cc1] | 6-Chloro-7-(4-(4-(2-chlorophenyl)pyridin-2-ylcarbamoyl)phenoxy)chroman-4-carboxylic acid | 535.1 (M + H) |
| 123 | 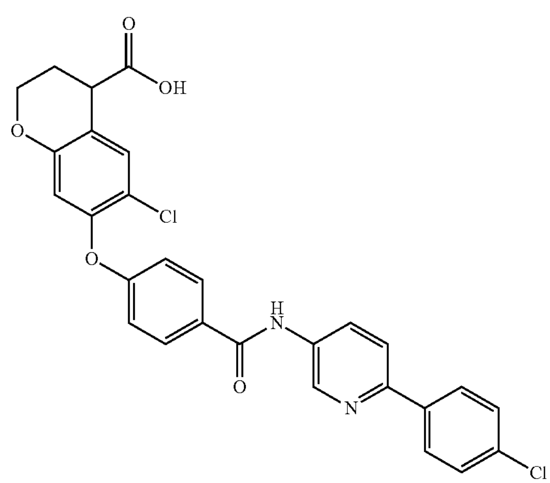 [SMILES: O=C(Nc1ccc(-c2ccc(Cl)cc2)nc1)c1ccc(Oc2cc3c(cc2Cl)C(C(=O)O)CCO3)cc1] | 6-Chloro-7-(4-(6-(4-chlorophenyl)pyridin-3-ylcarbamoyl)phenoxy)chroman-4-carboxylic acid | 535.3 (M + H) |

| Ex. # | Structure | Name | MS (ESI) |
|---|---|---|---|
| 124 | 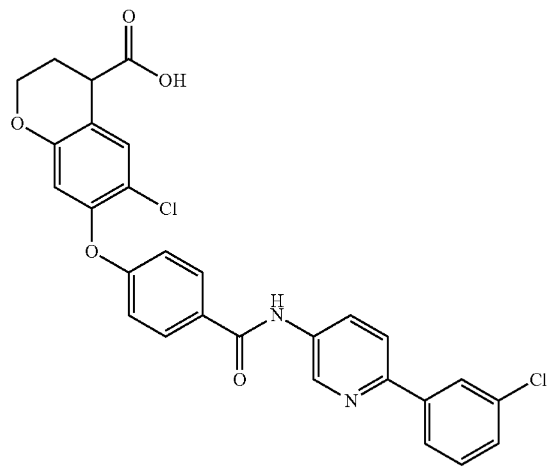 [SMILES: O=C(Nc1ccc(-c2cccc(Cl)c2)nc1)c1ccc(Oc2cc3c(cc2Cl)C(C(=O)O)CCO3)cc1] | 6-Chloro-7-(4-(6-(3-chlorophenyl)pyridin-3-ylcarbamoyl)phenoxy)chroman-4-carboxylic acid | 535.3 (M + H) |
| 125 | 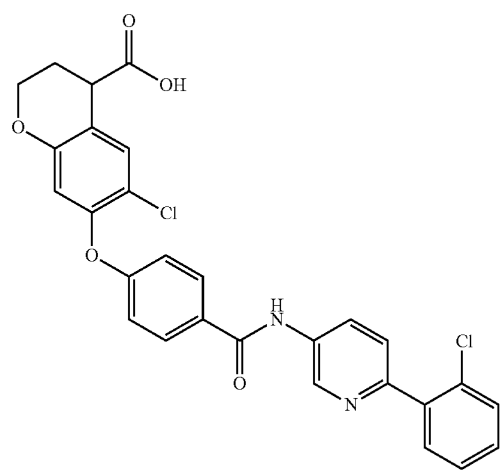 [SMILES: O=C(Nc1ccc(-c2ccccc2Cl)nc1)c1ccc(Oc2cc3c(cc2Cl)C(C(=O)O)CCO3)cc1] | 6-Chloro-7-(4-(6-(2-chlorophenyl)pyridin-3-ylcarbamoyl)phenoxy)chroman-4-carboxylic acid | 535.3 (M + H) |
| 126 | 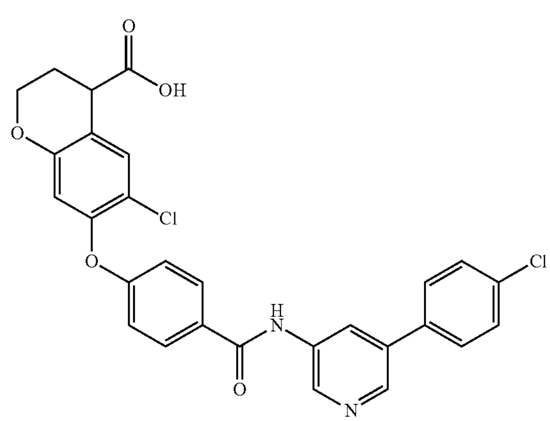 [SMILES: O=C(Nc1cncc(-c2ccc(Cl)cc2)c1)c1ccc(Oc2cc3c(cc2Cl)C(C(=O)O)CCO3)cc1] | 6-Chloro-7-(4-(5-(4-chlorophenyl)pyridin-3-ylcarbamoyl)phenoxy)chroman-4-carboxylic acid | 535.3 (M + H). |

-continued

| Ex. # | Structure | Name | MS (ESI) |
|---|---|---|---|
| 127 | 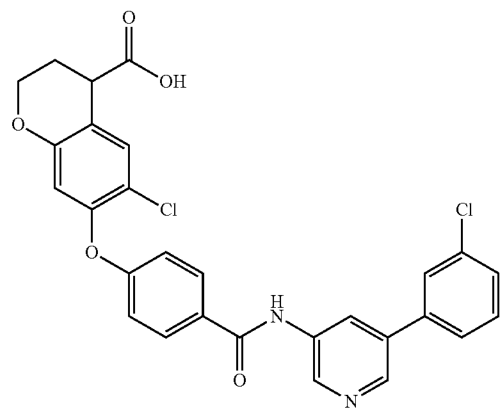 [SMILES: O=C(Nc1cncc(-c2cccc(Cl)c2)c1)c1ccc(Oc2cc3c(cc2Cl)C(C(=O)O)CCO3)cc1] | 6-Chloro-7-(4-(5-(3-chlorophenyl)pyridin-3-ylcarbamoyl)phenoxy)chroman-4-carboxylic acid | 535.3 (M + H) |
| 128 | 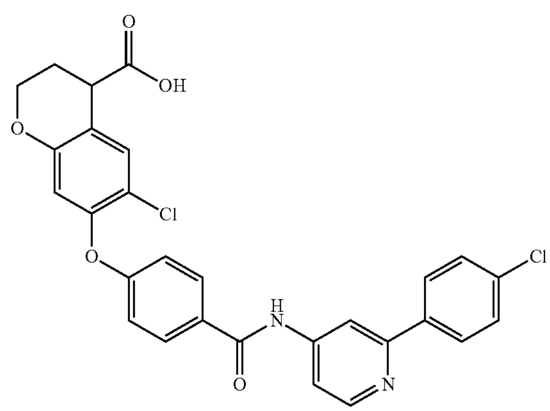 [SMILES: O=C(Nc1ccnc(-c2ccc(Cl)cc2)c1)c1ccc(Oc2cc3c(cc2Cl)C(C(=O)O)CCO3)cc1] | 6-Chloro-7-(4-(2-(4-chlorophenyl)pyridin-4-ylcarbamoyl)phenoxy)chroman-4-carboxylic acid | 535.1 (M + H) |
| 129 | 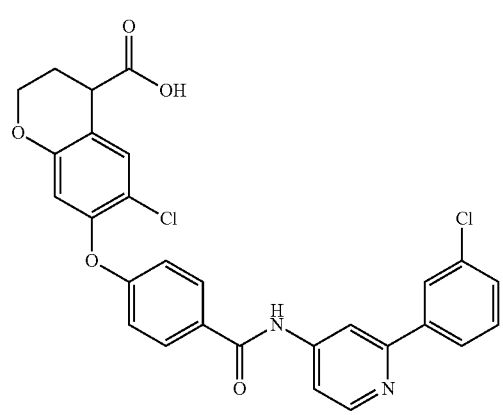 [SMILES: O=C(Nc1ccnc(-c2cccc(Cl)c2)c1)c1ccc(Oc2cc3c(cc2Cl)C(C(=O)O)CCO3)cc1] | 6-Chloro-7-(4-(2-(3-chlorophenyl)pyridin-4-ylcarbamoyl)phenoxy)chroman-4-carboxylic acid | 535.1 (M + H) |

EXAMPLE 130

6-Chloro-7-(4-(4-(4-(trifluoromethyl)phenyl)pyrimidin-2-ylcarbamoyl)phenoxy)chroman-4-carboxylic acid

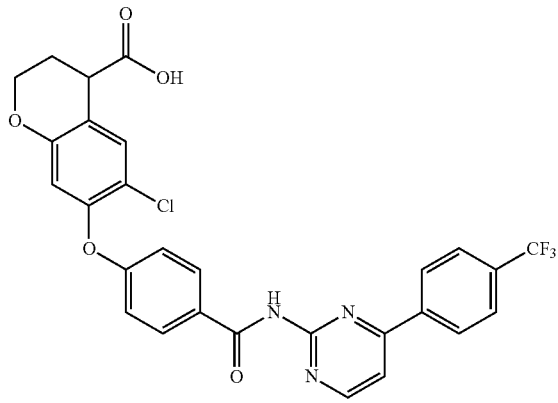 [SMILES: O=C(Nc1nccc(-c2ccc(C(F)(F)F)cc2)n1)c1ccc(Oc2cc3c(cc2Cl)C(C(=O)O)CCO3)cc1]

Step A: Preparation of 2-chloro-4-(4-(trifluoromethyl)phenyl)pyrimidine 4-(trifluoromethyl)phenylboronic acid (319 mg, 1.68 mmol), 2,4-dichloropyrimidine (250 mg, 1.68 mmol), $Na_2CO_3$ (445 mg, 4.20 mmol) and $Pd(PPh_3)_4$ (97.0 mg, 0.0839 mmol) were combined in a 5 mL reaction vial and diluted with toluene (3 mL) and water (300 µL). The reaction was purged with argon, heated to 60° C. and stirred overnight. The reaction was loaded directly onto silica gel and eluted with 5% ethyl acetate/hexanes to 60% ethyl acetate/hexanes to yield the desired compound (120 mg, 0.464 mmol, 27.6% yield).

Step B: Preparation of ethyl 6-chloro-7-(4-(4-(4-(trifluoromethyl)phenyl)pyrimidin-2-ylcarbamoyl)phenoxy)chroman-4-carboxylate Ethyl 7-(4-carbamoylphenoxy)-6-chlorochroman-4-carboxylate (Example 45, Step A; 75 mg, 0.20 mmol) 2-chloro-4-(4-(trifluoromethyl)phenyl)pyrimidine (52 mg, 0.20 mmol), XPHOS (9.5 mg, 0.020 mmol), $Pd_2dba_3$ (9.1 mg, 0.0100 mmol) and $Cs_2CO_3$ (130 mg, 0.40 mmol) were diluted with THF (0.6 mL) and purged with Argon for 2 minutes. The reaction was capped, heated to 50° C. and stirred overnight. The reaction was loaded directly onto silica gel and eluted with 50% ethyl acetate/hexanes to 100% ethyl acetate/hexanes to yield the desired compound (50 mg, 0.084 mmol, 42% yield).

Step C: Preparation of 6-chloro-7-(4-(4-(4-(trifluoromethyl)phenyl)pyrimidin-2-ylcarbamoyl)phenoxy)chroman-4-carboxylic acid Ethyl 6-chloro-7-(4-(4-(4-(trifluoromethyl)phenyl)pyrimidin-2-ylcarbamoyl)phenoxy)chroman-4-carboxylate (50 mg, 0.084 mmol) was diluted with THF (1 mL) followed by the addition of NaOH (502 µL, 0.50 mmol) and ethanol (500 µL). After stirring for 2 hours, the reaction was diluted with ethyl acetate and 2N HCl. The layers were separated and the organic layer was dried over $MgSO_4$, filtered and concentrated. The residue was purified using a 0.5 mm preparative TLC plate eluting with 10% methanol/DCM to yield the desired compound (5 mg, 0.0088 mmol, 10% yield). MS (ESI)=570.1 (M+H)

EXAMPLE 131

6-Chloro-7-(4-(4-(3-(trifluoromethyl)phenyl)pyrimidin-2-ylcarbamoyl)phenoxy)chroman-4-carboxylic acid

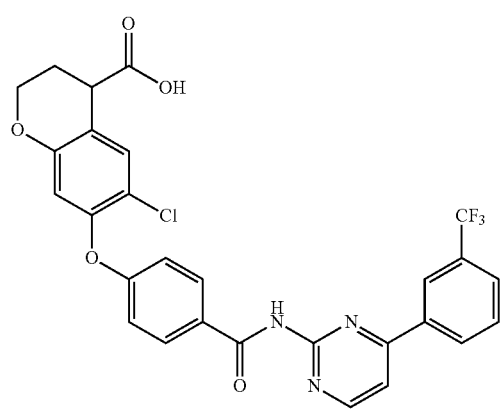

Prepared according to the method of Example 130, replacing 4-(trifluoromethyl)phenylboronic acid in Step A with 3-(trifluoromethyl)phenylboronic acid. MS (ESI)=570.1 (M+H).

EXAMPLE 132

6-Chloro-7-(4-(4-(4-chlorophenyl)pyrimidin-2-ylcarbamoyl)phenoxy)chroman-4-carboxylic acid

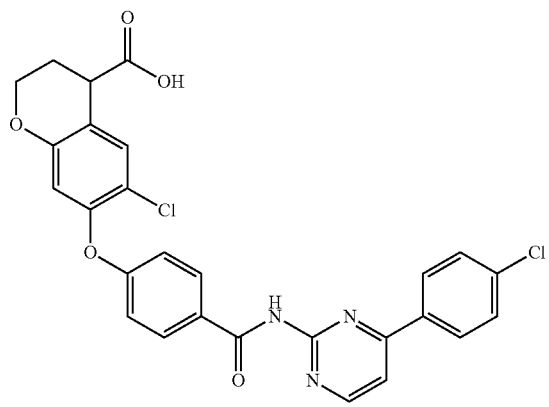 [SMILES: O=C(Nc1nccc(-c2ccc(Cl)cc2)n1)c1ccc(Oc2cc3c(cc2Cl)C(C(=O)O)CCO3)cc1]

Prepared according to the method of Example 130, replacing 4-(trifluoromethyl)phenylboronic acid in Step A with 4-chlorophenylboronic acid. MS (ESI)=536.1 (M+H).

EXAMPLE 133

6-Chloro-7-(4-(4-(3-chlorophenyl)pyrimidin-2-ylcarbamoyl)phenoxy)chroman-4-carboxylic acid

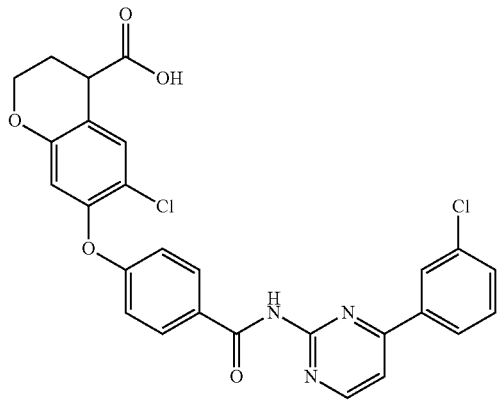 [SMILES: O=C(Nc1nccc(-c2cccc(Cl)c2)n1)c1ccc(Oc2cc3c(cc2Cl)C(C(=O)O)CCO3)cc1]

Prepared according to the method of Example 130, replacing 4-(trifluoromethyl)phenylboronic acid in Step A with 3-chlorophenylboronic acid. MS (ESI)=536.1 (M+H).

EXAMPLE 134

6-Chloro-7-(4-(5-(3-chlorophenyl)pyrimidin-2-ylcarbamoyl)phenoxy)chroman-4-carboxylic acid

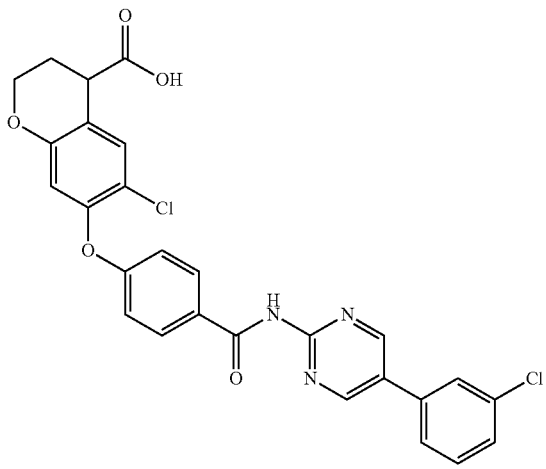 [SMILES: O=C(Nc1ncc(-c2cccc(Cl)c2)cn1)c1ccc(Oc2cc3c(cc2Cl)C(C(=O)O)CCO3)cc1]

Prepared according to the method of Example 130, replacing 2,4-dichloropyrimidine with 5-bromo-2-chloropyrimidine. MS (ESI)=536.1 (M+H).

EXAMPLE 135

6-Chloro-7-(4-(2-(3-chlorophenyl)pyrimidin-5-ylcarbamoyl)phenoxy)chroman-4-carboxylic acid

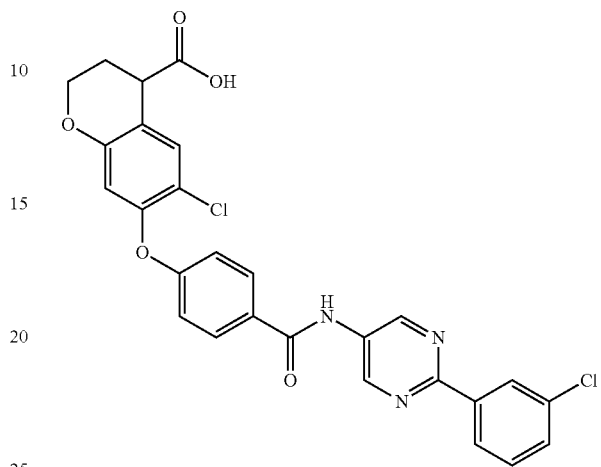

Step A: Preparation of 2-(3-chlorophenyl)-5-nitropyrimidine 2-(3-Chlorophenyl)-5-nitropyrimidine (100 mg, 0.424 mmol, 45.1% yield), 3-chlorophenylboronic acid (147 mg, 0.940 mmol), $Na_2CO_3$ (249 mg, 2.35 mmol) and $Pd(PPh_3)_4$ (54.3 mg, 0.0470 mmol) were combined in a vial, diluted with toluene (2 mL) and water (200 µL), purged with Argon, sealed and heated to 100° C. and stirred for 3 hours. The reaction was loaded directly onto silica gel and eluted with 5% ethyl acetate/hexanes to 50% ethyl acetate/hexanes to yield the desired compound (100 mg, 0.424 mmol, 45.1% yield).

Step B: Preparation of 2-(3-chlorophenyl)pyrimidin-5-amine 2-(3-Chlorophenyl)-5-nitropyrimidine (100 mg, 0.424 mmol) was diluted with THF (1 mL) followed by the addition of Zn dust (27.8 mg, 0.424 mmol) and sat $NH_4Cl$ (1 mL). After stirring for 3 hours, the reaction was diluted with ethyl acetate and 10% sodium carbonate. The layers were separated and the organic layer was dried over $MgSO_4$, filtered and concentrated. The material was purified using a 0.5 mm preparative TLC plate eluting with 10% methanol/DCM to yield the desired compound (25 mg, 0.122 mmol, 28.6% yield).

Step C: Preparation of ethyl 6-chloro-7-(4-(2-(3-chlorophenyl)pyrimidin-5-ylcarbamoyl)phenoxy)chroman-4-carboxylate 4-(6-Chloro-4-(ethoxycarbonyl)chroman-7-yloxy)benzoic acid (Preparation B; 45 mg, 0.12 mmol) was diluted with DCM (1 mL) followed by the addition of oxalyl chloride in DCM (2M) (66 µl, 0.13 mmol) and DMF (1 drop). 2-(3-chlorophenyl)pyrimidin-5-amine (25 mg, 0.12 mmol) and DIEA (52 µl, 0.30 mmol) were added and the reaction was stirred at ambient temperature for 4 hours. The reaction was loaded directly onto silica gel and eluted with 5% ethyl acetate/hexanes to 70% ethyl acetate/hexanes to yield the desired compound (45 mg, 0.080 mmol, 67% yield).

Step D: 6-Chloro-7-(4-(2-(3-chlorophenyl)pyrimidin-5-ylcarbamoyl)phenoxy)chroman-4-carboxylic acid Ethyl 6-chloro-7-(4-(2-(3-chlorophenyl)pyrimidin-5-ylcarbamoyl)phenoxy)chroman-4-carboxylate (45 mg, 0.080 mmol) was diluted with THF (1 mL) followed by the addition of NaOH (399 μl, 0.40 mmol) and ethanol (500 uL). After stirring for 2 hours, the reaction was diluted with ethyl acetate and 2N HCl. The layers were separated and the organic layer was dried over MgSO$_4$, filtered and concentrated. The residue was purified using a 0.5 mm preparative TLC plate eluting with 10% methanol/DCM to yield the desired compound (15 mg, 0.028 mmol, 35% yield) MS (ESI)=536.1 (M+H).

EXAMPLE 136

6,8-Dichloro-7-(4-(6-(4-chlorophenyl)pyrazin-2-ylcarbamoyl)phenoxy)chroman-4-carboxylic acid

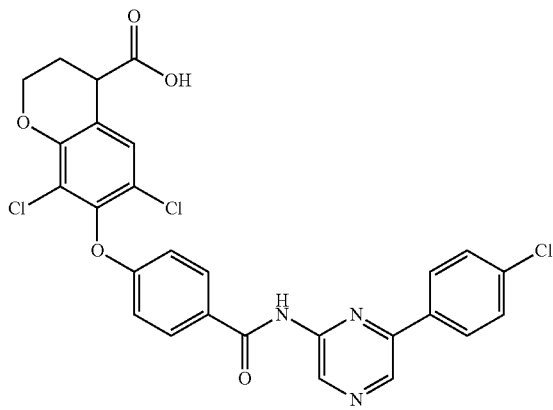 [SMILES: O=C(Nc1cncc(-c2ccc(Cl)cc2)n1)c1ccc(Oc2c(Cl)cc3c(c2Cl)OCCC3C(=O)O)cc1]

Prepared according to the method of Example 79, replacing ethyl 7-(4-carbamoylphenoxy)-6-chlorochroman-4-carboxylate with ethyl 7-(4-carbamoylphenoxy)-6,8-dichlorochroman-4-carboxylate (synthesis shown below). MS (ESI)=570.0 (M+H)

Preparation of ethyl 7-(4-carbamoylphenoxy)-6,8-dichlorochroman-4-carboxylate 4-(6,8-Dichloro-4-(ethoxycarbonyl)chroman-7-yloxy)benzoic acid (Preparation A; 150 mg, 0.365 mmol) was diluted with DCM (1.5 mL) followed by the addition of oxalyl chloride in DCM (2M) (201 μl, 0.401 mmol) and DMF (1 drop). Ammonia (6.21 mg, 0.365 mmol) was bubbled in for 10 minutes. The reaction was placed under nitrogen and stirred for 3 hours. The reaction was diluted with ethyl acetate and washed with water. The organic layer was concentrated, loaded onto silica gel and eluted with neat ethyl acetate to yield ethyl 7-(4-carbamoylphenoxy)-6,8-dichlorochroman-4-carboxylate (120 mg, 0.293 mmol, 80.2% yield) as a white solid.

EXAMPLE 137

6,8-Dichloro-7-(4-(2-(4-chlorophenyl)pyrimidin-4-ylcarbamoyl)phenoxy)chroman-4-carboxylic acid

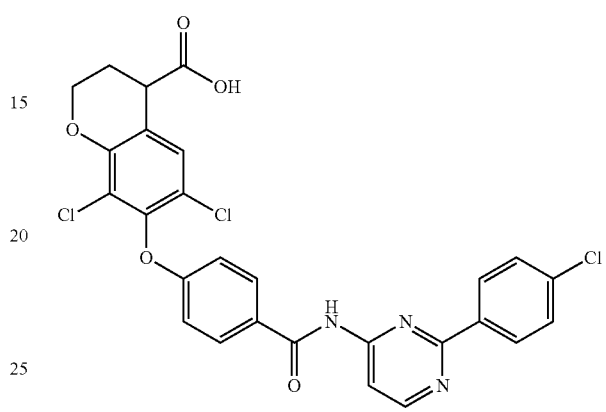

Prepared according to the method of Example 136 replacing 2-chloro-6-(4-chlorophenyl)pyrazine with 4-chloro-2-(4-chlorophenyl)pyrimidine). MS (ESI)=570.0 (M+H).

EXAMPLE 138

Sodium 6-chloro-7-(4-(2-(3,5-dichloropyridin-2-yl)ethylcarbamoyl)phenoxy)chroman-4-carboxylate

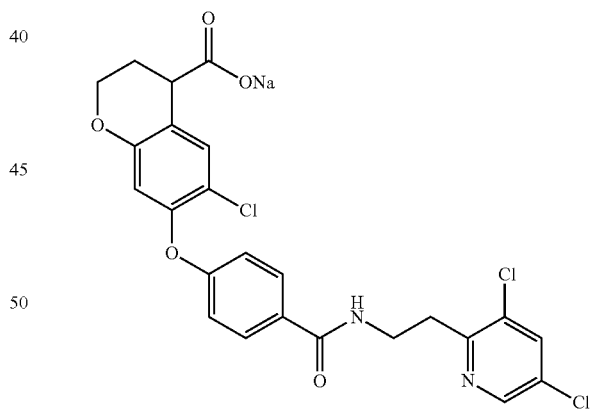

Step A: Preparation of methyl 2-cyano-2-(3,5-dichloropyridin-2-yl)acetate

NMP (7 mL) was added to a round bottom, placed under nitrogen and cooled to 0° C. NaH (1.16 g, 29.1 mmol) was added portionwise followed by the addition of methyl cyanoacetate (1.31 ml, 14.5 mmol) (in 3 mL of NMP) dropwise. After stirring for 30 minutes at 0° C., 2-bromo-3,5-dichloropyridine (3.0 g, 13.2 mmol) was added and the reaction was heated to 130° C. for 5 hours. The reaction was allowed to cool, poured into ice and extracted twice with ethyl acetate. The ethyl acetate was combined, dried over MgSO$_4$, filtered and concentrated. The amorphous material was crystallized from methanol to afford the desired compound (700 mg, 2.86 mmol, 21.6% yield) as light brown needles.

Step B: Preparation of 2-(3,5-dichloropyridin-2-yl)acetonitrile

Methyl 2-cyano-2-(3,5-dichloropyridin-2-yl)acetate (120 mg, 0.490 mmol) was diluted with DMSO (1 mL) and water (40 uL) followed by the addition of sodium chloride (14.3 mg, 0.245 mmol). The reaction was heated to 130° C. and stirred for 3 hours. The reaction was allowed to cool, loaded onto silica gel and eluted with 5% ethyl acetate/hexanes to 50% ethyl acetate/hexanes to yield the desired compound (70 mg, 0.374 mmol, 76.4% yield).

Step C: Preparation of tert-butyl 2-(3,5-dichloropyridin-2-yl)ethylcarbamate

To a solution of 2-(3,5-dichloropyridin-2-yl)acetonitrile (70 mg, 0.37 mmol) in methanol (1.5 mL) was added cobalt (II) chloride hexahydrate (98 mg, 0.41 mmol) and tert-butyl 2-(3,5-dichloropyridin-2-yl)ethylcarbamate (55 mg, 0.19 mmol, 50% yield). The solution was cooled to 0° C. followed by the portionwise addition of NaBH$_4$ (85 mg, 2.2 mmol). After stirring for 5 hours, the reaction was loaded directly onto silica gel and eluted with 5% ethyl acetate/hexanes to 50% ethyl acetate/hexanes to yield the desired compound (55 mg, 0.19 mmol, 50% yield).

Step D: Preparation of 2-(3,5-dichloropyridin-2-yl)ethanamine

Tert-butyl 2-(3,5-dichloropyridin-2-yl)ethylcarbamate (50 mg, 0.17 mmol) was diluted with DCM (500 uL) followed by the addition of TFA (500 μl). After stirring for 2 hours, the reaction was concentrated and placed under vacuum to yield the desired compound (32 mg, 0.17 mmol, 98% yield).

Step E: Preparation of ethyl 6-chloro-7-(4-(2-(3,5-dichloropyridin-2-yl)ethylcarbamoyl)phenoxy)chroman-4-carboxylate 4-(6-chloro-4-(ethoxycarbonyl)chroman-7-yloxy)benzoic acid (Preparation B; 60 mg, 0.16 mmol) was diluted with DCM (1 mL) followed by the addition of oxalyl chloride in DCM (2M) (88 μl, 0.18 mmol) and DMF (1 drop). After stirring for 10 minutes, 2-(3,5-dichloropyridin-2-yl)ethanamine (30 mg, 0.16 mmol) and DIEA (111 μl, 0.64 mmol) were added. The reaction was stirred for 2 hours. The reaction was loaded onto silica gel and eluted with a gradient of 5%-75% ethyl acetate/hexanes to yield the desired compound (40 mg, 0.073 mmol, 46% yield).

Step F: Preparation of ethyl 6-chloro-7-(4-(2-(3,5-dichloropyridin-2-yl)ethylcarbamoyl)phenoxy)chroman-4-carboxylic acid Ethyl 6-chloro-7-(4-(2-(3,5-dichloropyridin-2-yl)ethylcarbamoyl)phenoxy)chroman-4-carboxylate (40 mg, 0.073 mmol) was diluted with THF (500 μl) followed by the addition of NaOH (364 μl, 0.36 mmol) and ethanol (300 μl). After stirring for 3 hours, the reaction was diluted with ethyl acetate and 2N HCl. The layers were separated and the organic layer was dried over MgSO$_4$, filtered and concentrated to yield the desired compound (38 mg, 0.073 mmol, 100% yield).

Step G: Preparation of sodium 6-chloro-7-(4-(2-(3,5-dichloropyridin-2-yl)ethylcarbamoyl)phenoxy)chroman-4-carboxylate 6-Chloro-7-(4-(2-(3,5-dichloropyridin-2-yl)ethylcarbamoyl)phenoxy)chroman-4-carboxylic acid (38 mg, 0.073 mmol) was diluted with THF (500 μl) followed by the addition of NaOMe (146 μl, 0.073 mmol). After stirring for 1 hour, the reaction was concentrated to yield 6-chloro-7-(4-(2-(3,5-dichloropyridin-2-yl)ethylcarbamoyl)phenoxy)chroman-4-carboxylic acid (35 mg, 0.067 mmol, 92% yield) as a white foam. MS (ESI)=521.0 (M+H).

EXAMPLE 139

Sodium 6-chloro-7-(4-(2-(2-(dimethylamino)-6-(trifluoromethyl)pyridin-3-yl)ethylcarbamoyl)phenoxy)chroman-4-carboxylate

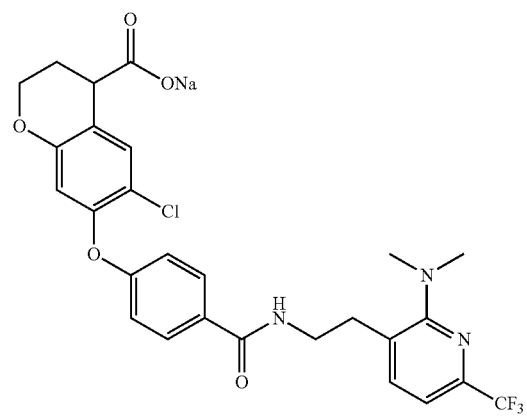

Step A: Preparation of 2-chloro-6-(trifluoromethyl)nicotinaldehyde

2-Chloro-6-(trifluoromethyl)nicotinonitrile (340 mg, 1.65 mmol) was diluted with toluene (2.0 mL), placed under nitrogen and cooled to −78° C. DIBAL-H (3292 μl, 3.29 mmol) was added dropwise and the reaction was stirred for 1 hour. The reaction was warmed to 0° C. and acetic acid (1 mL) was added followed by 5 mL of water. After stirring for 2 hours, the reaction was extracted twice with ethyl acetate, washed with Rochelle's salt, dried over MgSO$_4$, filtered and concentrated. The material was loaded onto silica gel and eluted with 5% ethyl acetate/hexanes to 30% ethyl acetate/hexanes to yield the desired compound (115 mg, 0.549 mmol, 33.3% yield) as a clear oil.

Step B: Preparation of 2-(dimethylamino)-6-(trifluoromethyl)nicotinaldehyde

To a stirred solution of 2-chloro-6-(trifluoromethyl)nicotinaldehyde (115 mg, 0.549 mmol) in THF (1 mL) was added dimethylamine (823 μl, 1.65 mmol). The reaction was heated to 50° C. and stirred for 3 hours. The reaction was loaded onto silica gel and eluted with 5% ethyl acetate/hexanes to 50% ethyl acetate/hexanes to yield the desired compound (50 mg, 0.229 mmol, 41.8% yield).

Step C: Preparation of (E)-N,N-dimethyl-3-(2-nitrovinyl)-6-(trifluoromethyl)pyridin-2-amine 2-(dimethylamino)-6-(trifluoromethyl)nicotinaldehyde (50 mg, 0.229 mmol) was diluted with nitromethane (86.9 μl, 1.60 mmol) followed by the addition of methylamine hydrochloride (9.28 mg, 0.138 mmol) and sodium acetate (11.3 mg, 0.138 mmol). After stirring for 5 hours, the reaction was loaded directly onto silica gel and eluted with 5% ethyl acetate/hexanes to 50% ethyl acetate hexanes to yield the desired compound (40 mg, 0.153 mmol, 66.8% yield).

Step D: Preparation of 3-(2-aminoethyl)-N,N-dimethyl-6-(trifluoromethyl)pyridin-2-amine LiBH4 (13.3 mg, 0.613 mmol) was diluted with THF (1 mL) followed by the dropwise addition of chlorotrimethylsilane (155 μl, 1.23 mmol). After stirring for 15 minutes, argon was bubbled through the reaction mixture for 2 minutes to eliminate any trimethylsilane in the reaction. (E)-N,N-dimethyl-3-(2-nitrovinyl)-6-(trifluoromethyl)pyridin-2-amine (40 mg, 0.153 mmol) was added (in 500 μL of THF, gas evolution occurred). The reaction was heated to reflux for 2 hours, cooled to 0° C. and carefully quenched with methanol (300 μl). The reaction mixture was concentrated, diluted with DCM and 20% KOH. The layers were separated and the organic layer was dried over MgSO4, filtered and concentrated to yield the desired compound (20 mg, 0.0858 mmol, 56.0% yield).

Steps E-G: Preparation of sodium 6-chloro-7-(4-(2-(2-(dimethylamino)-6-(trifluoromethyl)pyridin-3-yl)ethylcarbamoyl)phenoxy)chroman-4-carboxylate Prepared according to the method of Example 138, replacing 2-(3,5-dichloropyridin-2-yl)ethanamine with 3-(2-aminoethyl)-N,N-dimethyl-6-(trifluoromethyl)pyridin-2-amine. MS (ESI)=564.2 (M+H).

EXAMPLE 140

Sodium 6-chloro-7-(4-(2-(2,6-dimethoxypyridin-3-yl)ethylcarbamoyl)phenoxy)chroman-4-carboxylate

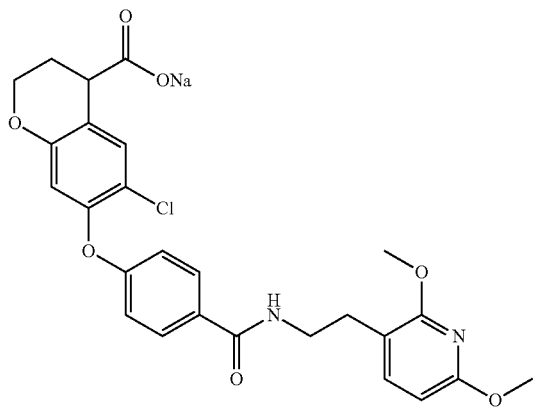

Prepared according to the method of Example 139, replacing 2-(dimethylamino)-6-(trifluoromethyl)nicotinaldehyde with 2,6-dimethoxynicotinaldehyde. MS (ESI)=513.3 (M+H).

EXAMPLE 141

6-Chloro-7-(4-(6-(4-chlorophenyl)pyridin-2-ylcarbamoyl)phenoxy)chroman-4-carboxylic acid, Enantiomer 1

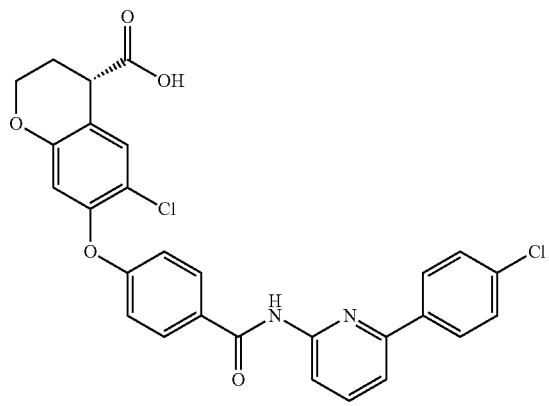

Prepared according to the method of Example 36, starting from 6-chloro-7-(4-(6-(4-chlorophenyl)pyridin-2-ylcarbamoyl)phenoxy)chroman-4-carboxylic acid (Example 33). MS (ESI)=535.0 (M+H).

EXAMPLE 142

6-Chloro-7-(4-(6-(4-chlorophenyl)pyridin-2-ylcarbamoyl)phenoxy)chroman-4-carboxylic acid, Enantiomer 2

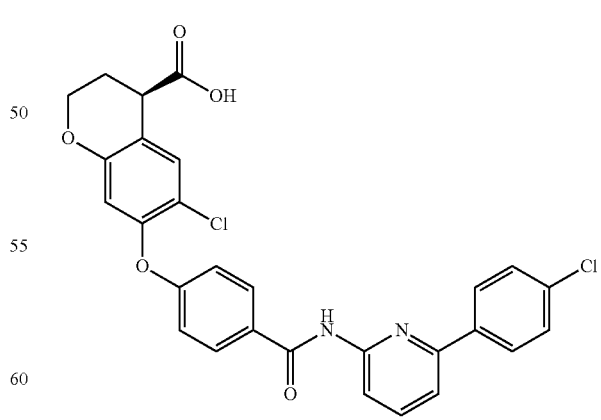

Prepared according to the method of Example 37, starting from 6-chloro-7-(4-(6-(4-chlorophenyl)pyridin-2-ylcarbamoyl)phenoxy)chroman-4-carboxylic acid (Example 33). MS (ESI)=535.0 (M+H).

EXAMPLE 143

Sodium 6,8-dichloro-7-(4-(6-(4-chlorophenyl)pyridin-2-ylcarbamoyl)phenoxy)-chroman-4-carboxylate

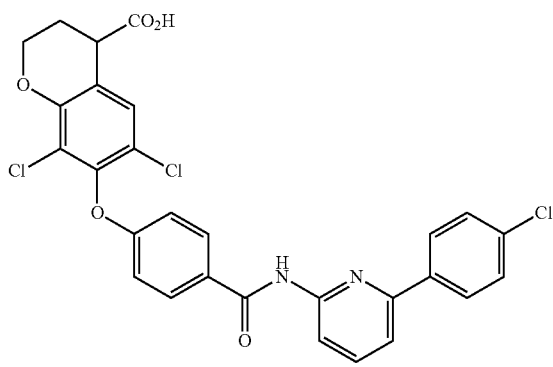 [SMILES: O=C(Nc1cccc(-c2ccc(Cl)cc2)n1)c1ccc(Oc2c(Cl)cc3c(c2Cl)OCCC3C(=O)O)cc1]

Step A: Preparation of 6,8-dichloro-7-(4-(6-(4-chlorophenyl)pyridin-2-ylcarbamoyl)phenoxy)chroman-4-carboxylic acid Prepared according to the method of Example 115, substituting 6-(4-chlorophenyl)pyridin-2-amine for 5-bromopyridin-2-amine. MS (apci) m/z=569 (M+H).

Step B: Preparation of sodium 6,8-dichloro-7-(4-(6-chloroquinolin-2-ylcarbamoyl)-phenoxy)chroman-4-carboxylate Prepared according to the method of Example 138, step G. MS (apci) m/z=569 (M+2H—Na).

EXAMPLE 144

Sodium 6,8-dichloro-7-(4-(6-chloroquinolin-2-ylcarbamoyl)phenoxy)chroman-4-carboxylate

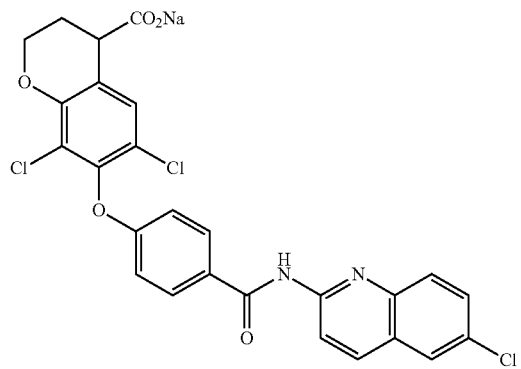

Step A: Preparation of 6,8-dichloro-7-(4-(6-chloroquinolin-2-ylcarbamoyl)phenoxy)-chroman-4-carboxylic acid Prepared according to the method of Example 115, substituting 6-chloroquinolin-2-amine for 5-bromopyridin-2-amine. MS (apci) m/z=543 (M+H).

Step B: Preparation of sodium 6,8-dichloro-7-(4-(6-chloroquinolin-2-ylcarbamoyl)-phenoxy)chroman-4-carboxylate Prepared according to the method of Example 204, step G. MS (apci) m/z=543 (M+2H—Na).

EXAMPLE 145

Sodium 6,8-dichloro-7-(4-(6-(3-chlorophenyl)pyridin-3-ylcarbamoyl)phenoxy)-chroman-4-carboxylate

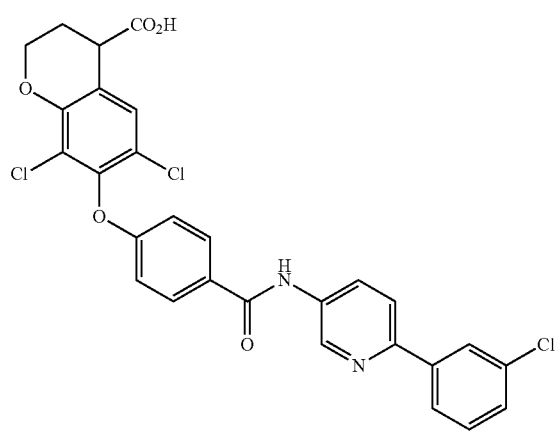 [SMILES: O=C(Nc1ccc(-c2cccc(Cl)c2)nc1)c1ccc(Oc2c(Cl)cc3c(c2Cl)OCCC3C(=O)O)cc1]

Step A: Preparation of 6,8-dichloro-7-(4-(6-(3-chlorophenyl)pyridin-3-ylcarbamoyl)-phenoxy)chroman-4-carboxylic acid Prepared according to the method of Example 115, substituting 6-(3-chlorophenyl)pyridin-3-amine for 5-bromopyridin-2-amine. MS (apci) m/z=569 (M+H).

Step B: Preparation of sodium 6,8-dichloro-7-(4-(6-(3-chlorophenyl)pyridin-3-ylcarbamoyl)phenoxy)chroman-4-carboxylate Prepared according to the method of Example 138, step G. MS (apci) m/z=569 (M+2H—Na).

EXAMPLE 146

6-Cyano-7-(4-(5-phenyl-1,3,4-thiadiazol-2-ylcarbamoyl)phenoxy)chroman-4-carboxylic acid

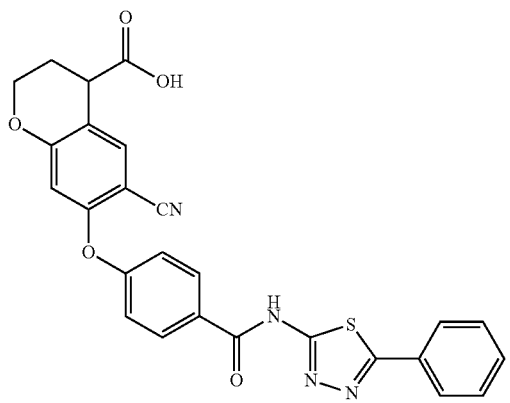 [SMILES: N#Cc1cc2c(cc1Oc1ccc(C(=O)Nc3nnc(-c4ccccc4)s3)cc1)OCCC2C(=O)O]

Step A: Preparation of methyl 6-cyano-7-(4-(5-phenyl-1,3,4-thiadiazol-2-ylcarbamoyl)phenoxy)chroman-4-carboxylate 4-(6-cyano-4-(methoxycarbonyl)chroman-7-yloxy)benzoic acid (20 mg, 0.057 mmol) was diluted with DCM (1 ml) followed by the addition of oxalyl chloride in DCM (2M) (31 μl, 0.062 mmol) and DMF (1 drop). After stirring for 15 minutes, 2-amino-5-phenyl-[1,3,4]-thiadiazole (10 mg, 0.057 mmol) and DIEA (25 μl, 0.14 mmol) were added. After stirring for 12 hours, the reaction was loaded directly onto a biotage 25 column and eluted with 5% ethyl acetate/hexanes to 100% ethyl acetate to yield methyl 6-cyano-7-(4-(5-phenyl-1,3,4-thiadiazol-2-ylcarbamoyl)phenoxy)chroman-4-carboxylate (17 mg, 0.033 mmol, 59% yield).

Step B: Preparation of 6-cyano-7-(4-(5-phenyl-1,3,4-thiadiazol-2-ylcarbamoyl)phenoxy)chroman-4-carboxylic acid Methyl 6-cyano-7-(4-(5-phenyl-1,3,4-thiadiazol-2-ylcarbamoyl)phenoxy)chroman-4-carboxylate (17 mg, 0.033 mmol) was diluted with THF (500 μL) followed by the addition of NaOH (166 μL, 0.17 mmol) and methanol (200 μL). After stirring for 2 hours, the reaction was diluted with ethyl acetate and 2N HCl. The layers were separated and the organic layer was dried over MgSO$_4$, filtered and concentrated to yield 6-cyano-7-(4-(5-phenyl-1,3,4-thiadiazol-2-ylcarbamoyl)phenoxy)chroman-4-carboxylic acid (10 mg, 0.020 mmol, 60% yield). MS (APCI)=498.9 (M+1).

EXAMPLE 147

7-(4-(5-(4-chlorophenyl)-1,3,4-thiadiazol-2-ylcarbamoyl)phenoxy)-6-cyanochroman-4-carboxylic acid

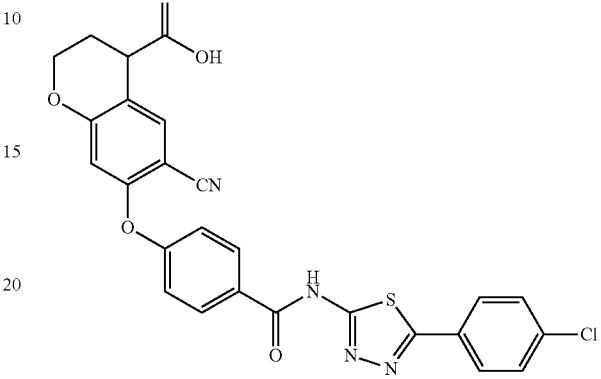

Prepared by the method of Example 146, using 5-(4-chlorophenyl)-1,3,4-thiadiazol-2-amine in place of 2-amino-5-phenyl-[1,3,4]-thiadiazole in Step A. MS (ESI)=533.0 (M+1).

EXAMPLE 148

6-chloro-7-(4-(5-phenyl-1,3,4-thiadiazol-2-ylcarbamoyl)phenoxy)chroman-4-carboxylic acid

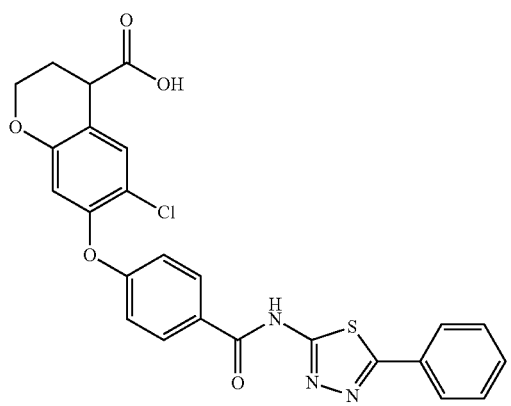 [SMILES: O=C(Nc1nnc(-c2ccccc2)s1)c1ccc(Oc2cc3c(cc2Cl)C(C(=O)O)CCO3)cc1]

Step A: Preparation of 3-chloro-1-(5-chloro-2,4-dihydroxyphenyl)propan-1-one

A solution of 4-chlorobenzene-1,3-diol (100 g, 692 mmol) and 3-chloropropanoic acid (75.1 g, 692 mmol) in trifluoromethanesulfonic acid (295 ml) was stirred at 75° C. for 30 minutes. The reaction was cooled to ambient temperature and slowly poured into a 2 L beaker filled with ice. To the slurry was added ethyl acetate with stirring until all solids dissolved. The mixture was poured into a separatory funnel, the aqueous layer was removed and the resulting organic layer was washed with water. The organic layer was dried over magnesium sulfate, filtered and concentrated. The residue was purified by column chromatograph (silica) eluting with a solvent system mixture of 15% ethyl acetate/hexanes to provide the desired product (162.6 g, 86%).

Step B: Preparation of 6-chloro-7-hydroxychroman-4-one 3-chloro-1-(5-chloro-2,4-dihydroxyphenyl)propan-1-one (140 g, 596 mmol) was dissolved in a 2M aqueous NaOH solution (2085 ml) at 0° C. then allowed to warm up to ambient temperature over the next 2 hours. The reaction was acidified by the addition of 6M $H_2SO_4$ to a pH of ~2. The resulting solids were removed by filtration and dried under high vacuum. The resulting solid was dissolved in THF (600 ml) and washed with water. The organic layer and was dried over magnesium sulfate, filtered, and concentrated. The resulting solid was treated with a minimal amount of diethyl ether and sonicated until a homogeneous suspension resulted. The resulting solid was collected by filtration to give the desired compound (85.7 g, 73%).

Step C: Preparation of 6-chloro-7-hydroxy-4-(trimethylsilyloxy)chroman-4-carbonitrile To a solution of 6-chloro-7-hydroxychroman-4-one (85.7 g, 432 mmol) in trimethylsilanecarbonitrile (134 ml, 1008 mmol) was added zinc(II) iodide (6.89 g, 21.6 mmol). The reaction began to warm and was cooled with an ice bath as necessary. After 2 hours at ambient temperature the reaction was diluted with ethyl acetate (400 ml) and washed with saturated sodium bicarbonate solution (2×400 ml). The organic layer was dried over magnesium sulfate, filtered and concentrated to give the desired compound (129 g, 100%).

Step D: Preparation of 6-chloro-7-hydroxychroman-4-carboxylic acid

A solution of 6-chloro-7-hydroxy-4-(trimethylsilyloxy)chroman-4-carbonitrile (129 g, 433 mmol) and SnCl2 dihydrate (293 g, 1299 mmol) in concentrated HCl (435 ml) and glacial acetic acid (435 ml) was heated to 125° C. and stirred for 12 hours. The reaction was taken up in ethyl acetate (500 ml) and washed with water (3×500 ml), dried over magnesium sulfate, filtered and concentrated to give the desired compound (99 g, 100%).

Step E: Preparation of 6-chloro-7-hydroxychroman-4-carboxylate

To a solution of 6-chloro-7-hydroxychroman-4-carboxylic acid (99 g, 433 mmol) in ethanol (650 ml) was added sulfuric acid (1.2 ml) and the reaction stirred at 60° C. for 24 hours. The reaction was cooled to ambient temperature and the resulting solids were removed by filtration and discarded. Thefiltrate was diluted with ethyl acetate (700 ml), washed with water (50 ml), dried over magnesium sulfate and concentrated. The residue was purified by silica gel chromatography, eluting with a solvent system of 20% ethyl acetate/hexanes to give the desired compound (46 g, 41%).

Step F: Preparation of ethyl 7-(4-(tert-butoxycarbonyl)phenoxy)-6-chlorochroman-4-carboxylate tert-Butyl 4-iodobenzoate (25.9 g, 85.2 mmol) and 2,2,6,6-tetramethyl-3,5-heptanedione (7.01 ml, 34.1 mmol) were diluted with NMP (70 ml) and bubbled with Argon for 20 minutes. Copper (I) chloride (16.9 g, 170 mmol), ethyl 6-chloro-7-hydroxychroman-4-carboxylate (24.0 g, 93.7 mmol) and cesium carbonate (55.5 g, 170 mmol) were combined and added to the reaction using a small funnel which was rinsed with NMP (30 ml). The reaction was purged for an additional 10 minutes and then heated to 100° C. and stirred for 5 hours under Argon. The reaction was allowed to cool and loaded directly onto a silica plug (2 kg) and eluted with 10% ethyl acetate/hexanes to yield about 10 g of product. The product was further purified using a biotage 65, eluting with 5% ethyl acetate/hexanes to 50% ethyl acetate/hexanes to yield the desired compound (14 g, 32.3 mmol, 38.0% yield) as a viscous oil.

Step G: Preparation of 4-(6-chloro-4-(ethoxycarbonyl)chroman-7-yloxy)benzoic acid Ethyl 7-(4-(tert-butoxycarbonyl)phenoxy)-6-chlorochroman-4-carboxylate (8.62 g, 19.91 mmol) was diluted with DCM (40 ml) followed by the portion wise addition of TFA (30 ml). After stirring for 1 hour, the reaction was concentrated and placed under vacuum over the weekend. The residue was taken up in DCM and washed with saturated bicarbonate and 1N HCl. The organic layer was separated, dried over magnesium sulfate, filtered and concentrated to yield the desired compound (7.278 g, 19.32 mmol, 97.00% yield) as a nice white foam.

Step H: Preparation of 6-chloro-7-(4-(5-phenyl-1,3,4-thiadiazol-2-ylcarbamoyl)phenoxy)chroman-4-carboxylate 4-(6-chloro-4-(ethoxycarbonyl)chroman-7-yloxy)benzoic acid (30 mg, 0.080 mmol) was diluted with DCM (1 ml) followed by the addition of oxalyl chloride in DCM (2M) (44 μl, 0.088 mmol) and DMF (1 drop). After stirring for 15 minutes, 2-amino-5-phenyl-[1,3,4]-thiadiazole (14 mg, 0.080 mmol) and DIEA (35 μL, 0.20 mmol) were added. After stirring for 12 hours, the reaction was loaded directly onto a biotage 25 column and eluted with 5% ethyl acetate/hexanes to 100% ethyl acetate to yield the desired compound (17 mg, 0.032 mmol, 40% yield).

Step I: Preparation of 6-chloro-7-(4-(5-phenyl-1,3,4-thiadiazol-2-ylcarbamoyl)phenoxy)chroman-4-carboxylic acid Ethyl 6-chloro-7-(4-(5-phenyl-1,3,4-thiadiazol-2-ylcarbamoyl)phenoxy)chroman-4-carboxylate (17 mg, 0.032 mmol) was diluted with THF (500 μL) followed by the addition of NaOH (159 μL, 0.16 mmol) and ethanol (200 μL). After stirring for 4 hours, the reaction was diluted with ethyl acetate and 1N HCl, the layers were separated and the organic layer was dried over $MgSO_4$, filtered and concentrated. The material was purified using a 0.5 mm preparative TLC plate eluting with 10% methanol/DCM to yield the desired compound (5 mg, 0.0098 mmol, 31% yield). MS (ESI)=508.1 (M+1).

EXAMPLE 149

6-chloro-7-(4-(5-(4-chlorophenyl)-1,3,4-thiadiazol-2-ylcarbamoyl)phenoxy)chroman-4-carboxylic acid

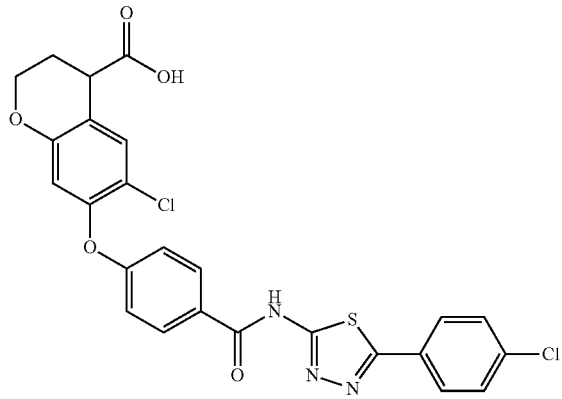 [SMILES: O=C(Nc1nnc(-c2ccc(Cl)cc2)s1)c1ccc(Oc2cc3c(cc2Cl)C(C(=O)O)CCO3)cc1]

Prepared by the method of Example 148, using 5-(4-chlorophenyl)-1,3,4-thiadiazol-2-amine in place of 2-amino-5-phenyl-[1,3,4]-thiadiazole in Step A. MS (ESI)=542.1 (M+1).

EXAMPLE 150

7-(4-(4-tert-butylthiazol-2-ylcarbamoyl)phenoxy)-6-chlorochroman-4-carboxylic acid

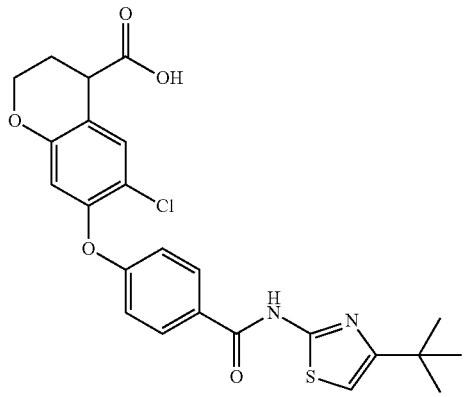 [SMILES: CC(C)(C)c1csc(NC(=O)c2ccc(Oc3cc4c(cc3Cl)C(C(=O)O)CCO4)cc2)n1]

Step A: Preparation of ethyl 7-(4-(4-tert-butylthiazol-2-ylcarbamoyl)phenoxy)-6-chlorochroman-4-carboxylate 4-(6-chloro-4-(ethoxycarbonyl)chroman-7-yloxy)benzoic acid (53 mg, 0.141 mmol) and 2-amino-4-tert-butylthiazole (44.0 mg, 0.281 mmol) in DMA were treated with 1-(3-dimethylaminopropyl)-3-ethylcarbodiimide hydrochloride (53.9 mg, 0.281 mmol) followed by 1-hydroxy-7-azabenzotriazole (19.1 mg, 0.141 mmol) at ambient temperature. The reaction was heated to 50° C. for 14 hours. The reaction was diluted with ethyl acetate, washed with 1 N HCl, saturated aqueous bicarbonate, and brine. The ethyl acetate layer was dried with sodium sulfate and the product purified on SP1 (20 to 65% Ethyl acetate/hexane) to provide the desired compound (47 mg).

Step B: Preparation of 7-(4-(4-tert-butylthiazol-2-ylcarbamoyl)phenoxy)-6-chlorochroman-4-carboxylic acid Ethyl 7-(4-(4-tert-butylthiazol-2-ylcarbamoyl)phenoxy)-6-chlorochroman-4-carboxylate (408 µl, 0.0408 mmol) in 2:1 THF-Ethanol was treated with 1N sodium hydroxide (0.061 ml, 0.061 mmol) at ambient temperature. After 18 hours, the reaction was diluted with ethyl acetate and acidified with hydrogen chloride (81.6 µl, 0.0816 mmol). The reaction was washed with brine, dried with sodium sulfate, filtered, and concentrated in vacuo to give the desired product (0.015 g, 76%) as a white solid. MS (APCI)=487.1 (M+1).

The following compounds were prepared according to the method of Example 150 using the appropriate starting materials.

| Ex. # | Structure | Name | MS Data |
|---|---|---|---|
| 151 | 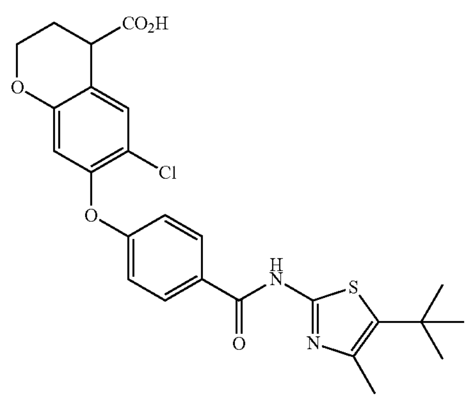 [SMILES: Cc1nc(NC(=O)c2ccc(Oc3cc4c(cc3Cl)C(C(=O)O)CCO4)cc2)sc1C(C)(C)C] | 7-(4-(5-tert-butyl-4-methylthiazol-2-ylcarbamoyl)phenoxy)-6-chlorochroman-4-carboxylic acid | (apci) 501.1 (M + H) |

| Ex. # | Structure | Name | MS Data |
|---|---|---|---|
| 152 | 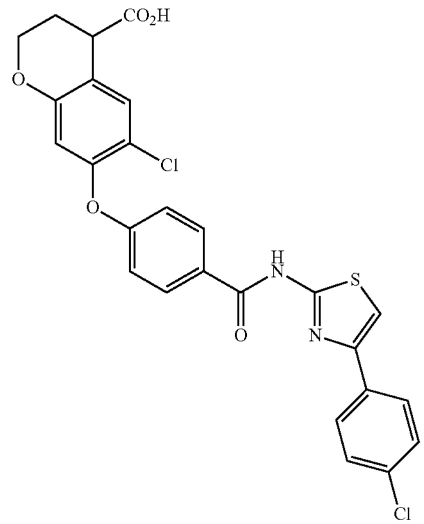 [SMILES: O=C(Nc1nc(-c2ccc(Cl)cc2)cs1)c1ccc(Oc2cc3c(cc2Cl)C(C(=O)O)CCO3)cc1] | 6-chloro-7-(4-(4-(4-chlorophenyl)thiazol-2-ylcarbamoyl)phenoxy)chroman-4-carboxylic acid | (apci) 540.9 (M + H) |
| 153 | 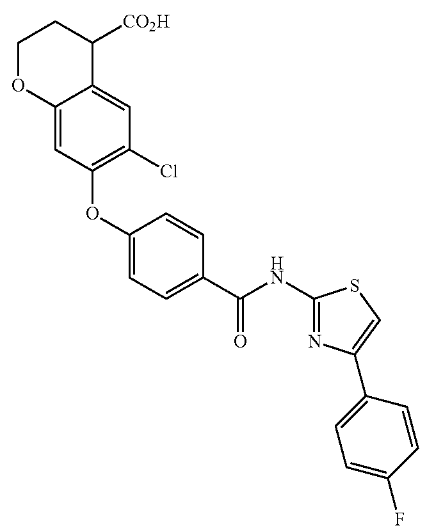 [SMILES: O=C(Nc1nc(-c2ccc(F)cc2)cs1)c1ccc(Oc2cc3c(cc2Cl)C(C(=O)O)CCO3)cc1] | 6-chloro-7-(4-(4-(4-fluorophenyl)thiazol-2-ylcarbamoyl)phenoxy)chroman-4-carboxylic acid | (apci) 525.0 (M + H) |
| 154 | 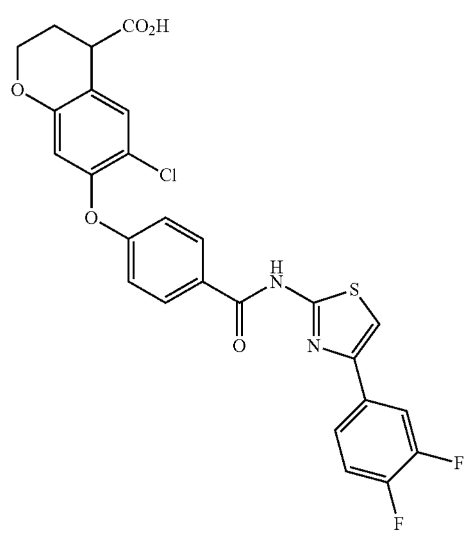 [SMILES: O=C(Nc1nc(-c2ccc(F)c(F)c2)cs1)c1ccc(Oc2cc3c(cc2Cl)C(C(=O)O)CCO3)cc1] | 6-chloro-7-(4-(4-(3,4-difluorophenyl)thiazol-2-ylcarbamoyl)phenoxy)chroman-4-carboxylic acid | (apci) 542.9 (M + H) |

| Ex. # | Structure | Name | MS Data |
|---|---|---|---|
| 155 | 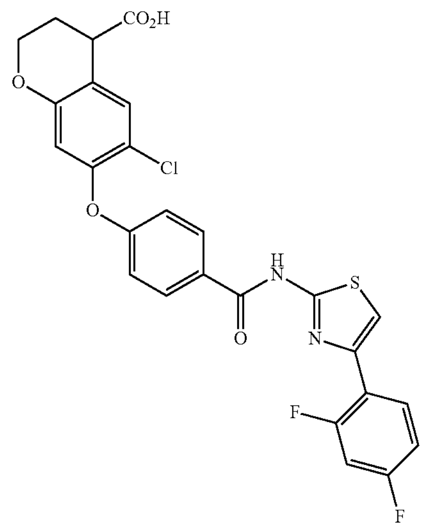 [SMILES: O=C(Nc1nc(-c2ccc(F)cc2F)cs1)c1ccc(Oc2cc3c(cc2Cl)C(C(=O)O)CCO3)cc1] | 6-chloro-7-(4-(4-(2,4-difluorophenyl)thiazol-2-ylcarbamoyl)phenoxy)chroman-4-carboxylic acid | (apci) 542.9 (M + H) |
| 156 | 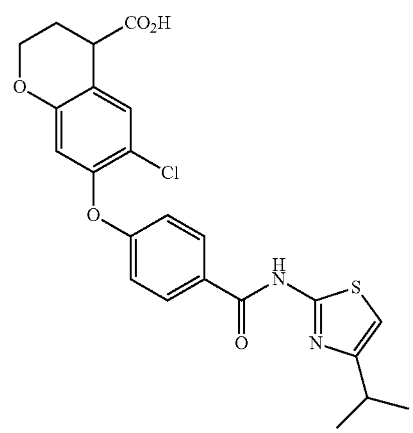 [SMILES: CC(C)c1csc(NC(=O)c2ccc(Oc3cc4c(cc3Cl)C(C(=O)O)CCO4)cc2)n1] | 6-chloro-7-(4-(4-isopropylthiazol-2-ylcarbamoyl)phenoxy)chroman-4-carboxylic acid | (apci) 473.0 (M + H) |
| 157 | 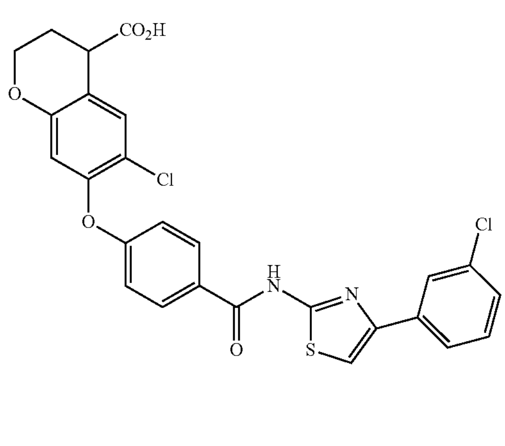 [SMILES: O=C(Nc1nc(-c2cccc(Cl)c2)cs1)c1ccc(Oc2cc3c(cc2Cl)C(C(=O)O)CCO3)cc1] | 6-chloro-7-(4-(4-(3-chlorophenyl)thiazol-2-ylcarbamoyl)phenoxy)chroman-4-carboxylic acid | (apci) 540.9 (M + H) |

| Ex. # | Structure | Name | MS Data |
|---|---|---|---|
| 158 | 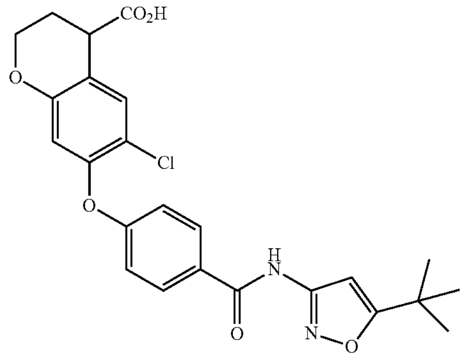 [SMILES: CC(C)(C)c1cc(NC(=O)c2ccc(Oc3cc4c(cc3Cl)C(C(=O)O)CCO4)cc2)no1] | 7-(4-(5-tert-butylisoxazol-3-ylcarbamoyl)phenoxy)-6-chlorochroman-4-carboxylic acid | (apci) 471.0 (M + H) |
| 159 | 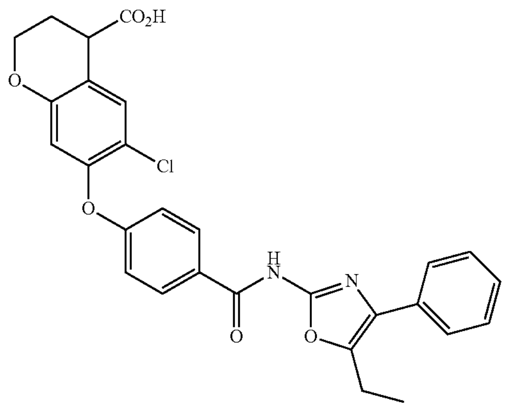 [SMILES: CCc1oc(NC(=O)c2ccc(Oc3cc4c(cc3Cl)C(C(=O)O)CCO4)cc2)nc1-c1ccccc1] | 6-chloro-7-(4-(5-ethyl-4-phenyloxazol-2-ylcarbamoyl)phenoxy)chroman-4-carboxylic acid | (apci) 519.0 (M + H) |
| 160 | 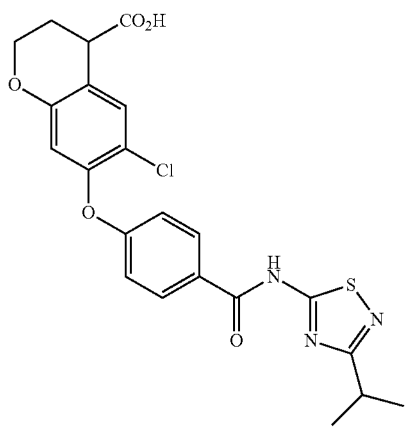 [SMILES: CC(C)c1nsc(NC(=O)c2ccc(Oc3cc4c(cc3Cl)C(C(=O)O)CCO4)cc2)n1] | 6-chloro-7-(4-(3-isopropyl-1,2,4-thiadiazol-5-ylcarbamoyl)phenoxy)chroman-4-carboxylic acid | (apci) 473.9 (M + H) |
| 161 | 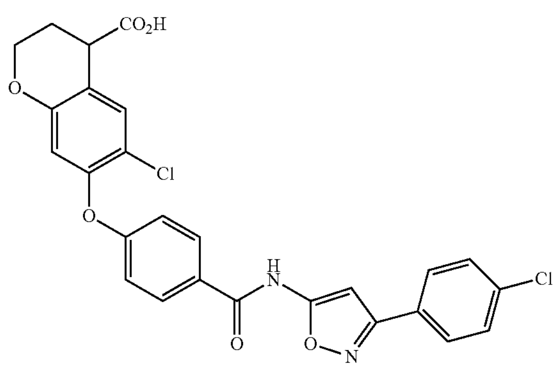 [SMILES: O=C(Nc1cc(-c2ccc(Cl)cc2)no1)c1ccc(Oc2cc3c(cc2Cl)C(C(=O)O)CCO3)cc1] | 6-chloro-7-(4-(3-(4-chlorophenyl)isoxazol-5-ylcarbamoyl)phenoxy)chroman-4-carboxylic acid | (apci) 526.8 (M + H) |

-continued

| Ex. # | Structure | Name | MS Data |
|---|---|---|---|
| 162 | 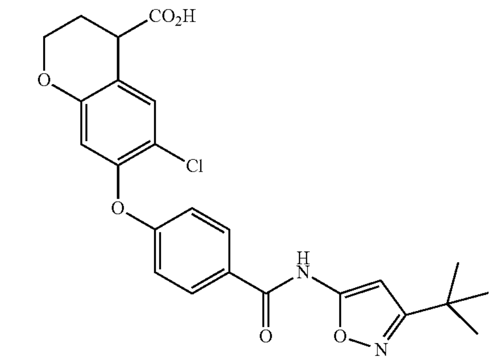 [SMILES: CC(C)(C)c1cc(NC(=O)c2ccc(Oc3cc4c(cc3Cl)C(C(=O)O)CCO4)cc2)on1] | 7-(4-(3-tert-butylisoxazol-5-ylcarbamoyl)phenoxy)-6-chlorochroman-4-carboxylic acid | (apci) 471.0 (M + H) |
| 163 | 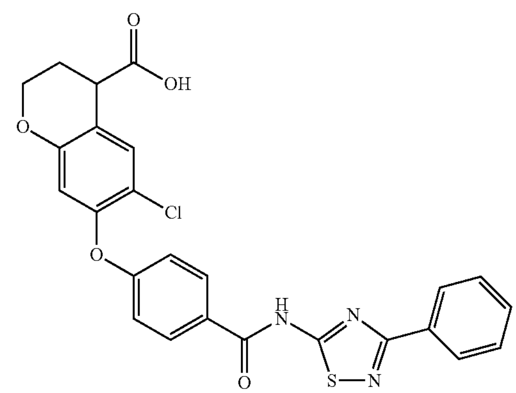 [SMILES: O=C(Nc1nc(-c2ccccc2)ns1)c1ccc(Oc2cc3c(cc2Cl)C(C(=O)O)CCO3)cc1] | 6-chloro-7-(4-(3-phenyl-1,2,4-thiadiazol-5-ylcarbamoyl)phenoxy)chroman-4-carboxylic acid | (apci) 508.0 (M + H) |

EXAMPLE 164

Sodium 6-chloro-7-(4-(1-(3-chlorophenyl)-1H-pyrazol-4-ylcarbamoyl)phenoxy)chroman-4-carboxylate

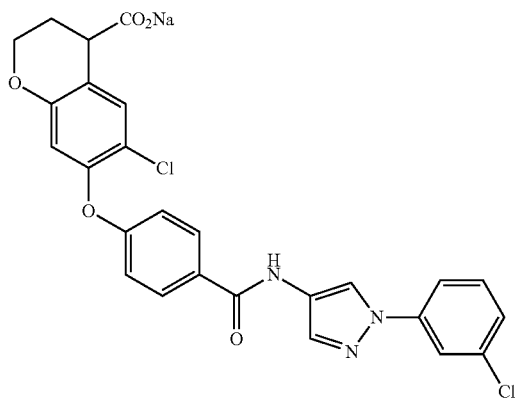

Step A: Preparation of N-(1,3-dioxopropan-2-yl)benzamide 2-phenyloxazole-4-carbaldehyde (5.0 g, 28.9 mmol) and 2.0 M aqueous sodium hydroxide solution (50 ml) were heated to 70° C. in a 250 mL Erlenmeyer flask until dissolved. Some insoluble dark material remained which was removed by filtration. The reaction was cooled in an ice bath and acidified (sulfuric acid) with swirling. The resulting solid was collected by filtration, washed with water, and dried under vacuum to provide the title compound (4.85 g, 88%).

Step B: Preparation of N-(1-(3-chlorophenyl)-1H-pyrazol-4-yl)benzamide

N-(1,3-dioxopropan-2-yl)benzamide (1 g, 5.2 mmol) and (3-chlorophenyl)hydrazine hydrochloride (0.94 g, 5.2 mmol) were mixed with 1N HCl (5 mL), ethanol (40 mL) and concentrated HCl was added (1 mL). The reaction was heated to boiling for 10 minutes and then allowed to cool. The solvent was removed by rotary evaporation. To the resulting residue was added water (20 mL) and dilute ammonium hydroxide (10%) to pH 11. The solids were collected by filtration and washed with water, then dried under vacuum to provide the title compound (1.34 g, 88%).

Step C: Preparation of 1-(3-chlorophenyl)-1H-pyrazol-4-amine

N-(1-(3-chlorophenyl)-1H-pyrazol-4-yl)benzamide (1.34 g, 4.5 mmol) was heated with 68% sulfuric acid (24 mL) at 100° C. for 2 hours and then at 110° C. for 3 hours. The reaction was diluted with water (100 mL) and basified with sodium hydroxide solution. The aqueous mixture was extracted with ethyl acetate. The combined extracts were dried (sodium sulfate), filtered and evaporated. The solid were dried under high vacuum to provide the title compound (0.82 g; 94%) as a brown solid.

Step D: Preparation of ethyl 6-chloro-7-(4-(1-(3-chlorophenyl)-1H-pyrazol-4-ylcarbamoyl)phenoxy)chroman-4-carboxylate Prepared according to the method of Example 148, Step H wherein 2-amino-5-phenyl-[1,3,4]-thiadiazole was replaced by 1-(3-chlorophenyl)-1H-pyrazol-4-amine to provide the title compound (293 mg, 100%).

Step E: Preparation of 6-chloro-7-(4-(1-(3-chlorophenyl)-1H-pyrazol-4-ylcarbamoyl)phenoxy)chroman-4-carboxylic acid Ethyl 6-chloro-7-(4-(1-(3-chlorophenyl)-1H-pyrazol-4-ylcarbamoyl)phenoxy)chroman-4-carboxylate (280 mg, 0.5 mmol) was dissolved in 2:1 tetrahydrofuran/ethanol (3 mL) and treated with sodium hydroxide (2 ml of a 1 N solution, 2.0 mmol) at ambient temperature. After 3 hours, the reaction was diluted with water (20 mL), acidified with 2N HCl (2 mL) and extracted with ethyl acetate. The combined organic phases were dried (sodium sulfate), filtered and the solvent removed under vacuum to provide the title compound (270 mg, 102%).

Step F: Preparation of sodium 6-chloro-7-(4-(1-(3-chlorophenyl)-1H-pyrazol-4-ylcarbamoyl)phenoxy)chroman-4-carboxylate 6-chloro-7-(4-(1-(3-chlorophenyl)-1H-pyrazol-4-ylcarbamoyl)phenoxy)chroman-4-carboxylic acid (250 mg, 0.48 mmol) was dissolved in methanol (5 ml) and treated with 0.5 N sodium methoxide in methanol (0.954 ml, 0.48 mmol) at ambient temperature. After 30 minutes, the reaction was concentrated in vacuo, triturated with ethyl acetate and hexanes, and dried under high vacuum to provide the title compound (240 mg, 92%) as a white solid. MS (apci)=526.0 (M-Na+2H)

EXAMPLE 165

Sodium 6,8-dichloro-7-(4-(1-(3-chlorophenyl)-1H-pyrazol-4-ylcarbamoyl)phenoxy)chroman-4-carboxylate

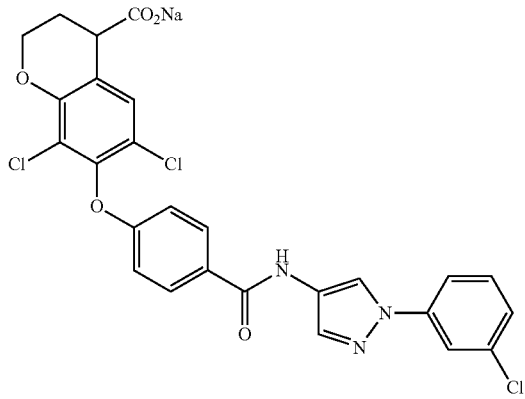

Step A: Preparation of ethyl 6,8-dichloro-7-hydroxychroman-4-carboxylate

To a solution of ethyl 6-chloro-7-hydroxychroman-4-carboxylate (5.04 g, 19.6 mmol) in 50 mL of DMF was added of n-chlorosuccinimide (2.74 g, 20.5 mmol). The resulting mixture was heated at 60° C. for 40 minutes and poured into water. The product was extracted with ethyl acetate and the combined organics were washed with brine, dried over sodium sulfate, filtered and concentrated. The crude product was dissolved in dichloromethane, concentrated onto silica gel and purified by flash column chromatography, eluting with 25% ethyl acetate in hexanes to give the desired product (3.5 g, 61.2% yield) as a an oil which was used directly in the next step.

Step B: Preparation of ethyl 7-(4-(tert-butoxycarbonyl)-2-nitrophenoxy)-6,8-dichlorochroman-4-carboxylate A mixture of ethyl 6,8-dichloro-7-hydroxychroman-4-carboxylate (2.50 g, 8.59 mmol), tert-butyl 4-fluoro-3-nitrobenzoate (2.20 g, 9.12 mmol) and potassium carbonate (1.8 g, 13 mmol) in 50 mL of NMP was degassed with argon for 10 minutes and was then heated at 80° C. overnight. After stirring overnight the reaction mixture was cooled to ambient temperature and diluted with 600 mL of water. The pH was adjusted to 1-2 with 1 N HCl and the resulting solids were collected by filtration. The solids were then dissolved in ethyl acetate and the solution was washed with brine, dried over sodium sulfate, filtered and concentrated. The crude product was purified by flash column chromatography, eluting with 20% ethyl acetate in hexanes to give the desired product (2.74 g, 62.3% yield) as an oil.

Step C: Preparation of ethyl 7-(2-amino-4-(tert-butoxycarbonyl)phenoxy)-6,8-dichlorochroman-4-carboxylate To a mixture of ethyl 7-(4-(tert-butoxycarbonyl)-2-nitrophenoxy)-6,8-dichlorochroman-4-carboxylate (2.70 g, 5.27 mmol) in 25 mL of THF and 25 mL of saturated ammonium chloride was added zinc dust (3.45 g, 52.7 mmol) under argon. After 1 hour at ambient temperature, the reaction was diluted with ethyl acetate and filtered. The biphasic filtrate was separated and the organic layer was washed with brine. The organic layer was dried over sodium sulfate, filtered and concentrated. The crude product was dissolved in dichloromethane, concentrated onto silica gel and purified by flash column chromatography, eluting with 20% ethyl acetate in hexanes to give ethyl the desired product (2.20 g, 86.5% yield) as a white foam. MS (ESI) m/z=482 (M+H).

Step D: Preparation of ethyl 7-(4-(tert-butoxycarbonyl)phenoxy)-6,8-dichlorochroman-4-carboxylate To a solution of ethyl 7-(2-amino-4-(tert-butoxycarbonyl)phenoxy)-6,8-dichlorochroman-4-carboxylate (2.1 g, 4.4 mmol) in 20 mL of DMF at 70° C. was added isobutyl nitrite (1.29 mL, 10.9 mmol) dropwise over ten minutes. After an additional 15 minutes the reaction was cooled to ambient temperature and poured into 600 mL of water. The product was extracted with ethyl acetate and the combined organics were washed with brine, dried over sodium sulfate, filtered and concentrated. The crude product was dissolved in dichloromethane, concentrated onto silica gel and purified by flash column chromatography, eluting with 20% ethyl acetate in hexanes to give the desired product (1.85 g, 90.9% yield) as a foam.

Step E: Preparation of 4-(6,8-dichloro-4-(ethoxycarbonyl)chroman-7-yloxy)benzoic acid To a solution of ethyl 7-(4-(tert-butoxycarbonyl)phenoxy)-6,8-dichlorochroman-4-carboxylate (1.85 g, 3.96 mmol) in 20 mL of DCM was added trifluoroacetic acid (10 mL). After stirring at ambient temperature for 1 hour, the mixture was concentrated to a sticky residue. The residue was dissolved in ethyl acetate and washed successively with saturated sodium bicarbonate and brine. The solution was then dried over sodium sulfate and filtered. The filtrate was concentrated to give the desired product (1.85 g, 90.9% yield) as a powder.

Step F-H: Preparation of sodium 6,8-dichloro-7-(4-(1-(3-chlorophenyl)-1H-pyrazol-4-ylcarbamoyl)phenoxy)chroman-4-carboxylate Prepared according to the method of Example 164, Steps D-F, replacing 4-(6-chloro-4-(ethoxycarbonyl)chroman-7-yloxy)benzoic acid with 4-(6,8-dichloro-4-(ethoxycarbonyl)chroman-7-yloxy)benzoic acid, to provide the title compound. MS (apci)=558.0 (M-Na+2H)

EXAMPLE 166

6-chloro-7-(4-(1-(3,4-difluorophenyl)-1H-pyrazol-3-ylcarbamoyl)phenoxy)chroman-4-carboxylic acid

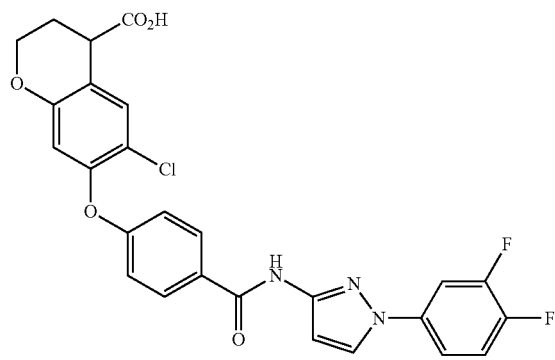 [SMILES: O=C(Nc1ccn(-c2ccc(F)c(F)c2)n1)c1ccc(Oc2cc3c(cc2Cl)C(C(=O)O)CCO3)cc1]

Step A: Preparation of 1-(3,4-difluorophenyl)-1H-pyrazol-3-amine

To ethanol (28 ml) was added sodium (0.407 g, 17.7 mmol), and the mixture was stirred about 30 minutes. To this, (3,4-difluorophenyl)hydrazine hydrochloride (1.00 g, 5.54 mmol) and (E)-3-ethoxyacrylonitrile (0.912 ml, 8.86 mmol) were added, and the reaction was heated to reflux for 16 hours. The reaction was diluted with water (30 ml) and acidified to pH 3 with 5M hydrochloric acid. The reaction was allowed to stir at ambient temperature for another 2 hours and was then neutralized (pH 7) by the addition of 5M sodium hydroxide. The reaction was concentrated to remove most of the ethanol. The resulting suspension was extracted twice with EtOAc, and the combined organic layers were dried over anhydrous sodium sulfate, filtered, and concentrated. The crude product was purified by silica gel chromatography, eluting with a linear gradient of 20-100% EtOAc/hexanes to yield the desired product (0.250 g, 1.28 mmol, 23.1% yield).

Step B: Preparation of ethyl 6-chloro-7-(4-(1-(3,4-difluorophenyl)-1H-pyrazol-3-ylcarbamoyl)phenoxy)chroman-4-carboxylate To a solution of 4-(6-chloro-4-(ethoxycarbonyl)chroman-7-yloxy)benzoic acid (0.050 g, 0.13 mmol), 1-(3,4-difluorophenyl)-1H-pyrazol-3-amine (0.028 g, 0.15 mmol), and 3H-[1,2,3]triazolo[4,5-b]pyridin-3-ol (0.018 g, 0.13 mmol) in DMF (0.7 ml) was added 1-(3-dimethylaminopropyl)-3-ethylcarbodiimide hydrochloride (0.028 g, 0.15 mmol), and the reaction was allowed to stir at ambient temperature for 60 hours. The reaction was diluted with EtOAc and washed with 10% citric acid, saturated sodium bicarbonate, and saturated sodium chloride. The combined organic layers were dried over anhydrous sodium sulfate, filtered, and concentrated. The residue was purified by silica gel chromatography, eluting with a linear gradient of 5-70% EtOAc/hexanes to yield the desired product (0.067 g, 0.12 mmol, 91% yield).

Step C: Preparation of 6-chloro-7-(4-(1-(3,4-difluorophenyl)-1H-pyrazol-3-ylcarbamoyl)phenoxy)chroman-4-carboxylic acid To a solution of ethyl 6-chloro-7-(4-(1-(3,4-difluorophenyl)-1H-pyrazol-3-ylcarbamoyl)phenoxy)chroman-4-carboxylate (0.067 g, 0.121 mmol) in 3:1 THF/MeOH (1 ml) was added 1M sodium hydroxide (0.133 ml, 0.133 mmol), and the reaction was allowed to stir for 16 hours. The reaction was concentrated, acidified with dilute HCl, and extracted twice with EtOAc. The combined organics were dried over anhydrous sodium sulfate, filtered, and concentrated to yield the desired product (0.039 g, 0.0742 mmol, 61.3% yield). MS (apci): m/z=526.1 (M+H).

The following compounds were prepared according to the method of Example 166 using the appropriate starting materials.

| Ex. # | Structure | Name | MS Data |
|---|---|---|---|
| 167 | (chroman carboxylic acid linked via phenoxy-benzamide to pyrazole bearing 3-chloro-4-fluorophenyl) | 6-chloro-7-(4-(1-(3-chloro-4-fluorophenyl)-1H-pyrazol-3-ylcarbamoyl)phenoxy)chroman-4-carboxylic acid | (apci) 542.1 (M + H) |

| Ex. # | Structure | Name | MS Data |
|---|---|---|---|
| 168 | 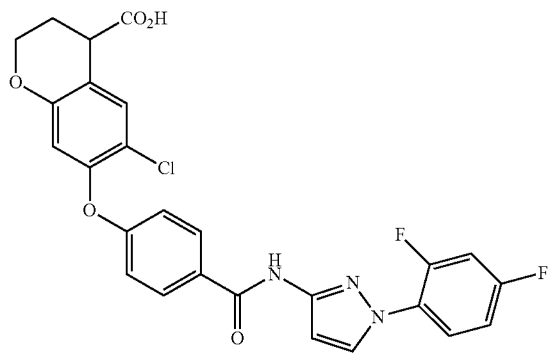 [SMILES: O=C(Nc1ccn(-c2ccc(F)cc2F)n1)c1ccc(Oc2cc3c(cc2Cl)C(C(=O)O)CCO3)cc1] | 6-chloro-7-(4-(1-(2,4-difluorophenyl)-1H-pyrazol-3-ylcarbamoyl)phenoxy)chroman-4-carboxylic acid | (apci) 526.1 (M + H) |
| 169 | 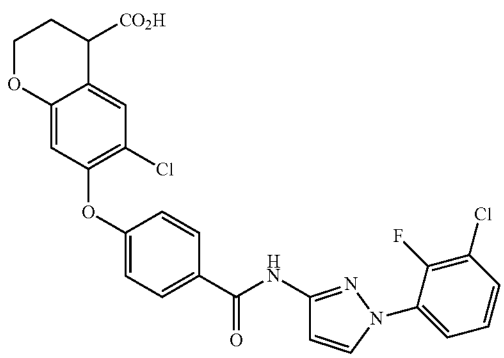 [SMILES: O=C(Nc1ccn(-c2cccc(Cl)c2F)n1)c1ccc(Oc2cc3c(cc2Cl)C(C(=O)O)CCO3)cc1] | 6-chloro-7-(4-(1-(3-chloro-2-fluorophenyl)-1H-pyrazol-3-ylcarbamoyl)phenoxy)chroman-4-carboxylic acid | (apci) 542.1 (M + H) |
| 170 | 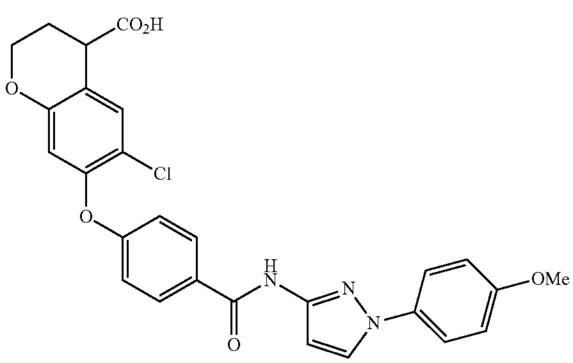 [SMILES: COc1ccc(-n2ccc(NC(=O)c3ccc(Oc4cc5c(cc4Cl)C(C(=O)O)CCO5)cc3)n2)cc1] | 6-chloro-7-(4-(1-(4-methoxyphenyl)-1H-pyrazol-3-ylcarbamoyl)phenoxy)chroman-4-carboxylic acid | (apci) 520.2 (M + H) |
| 171 | 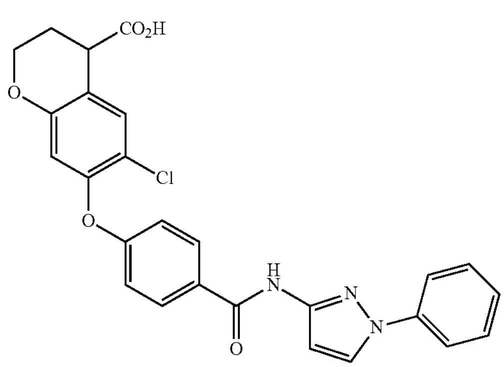 [SMILES: O=C(Nc1ccn(-c2ccccc2)n1)c1ccc(Oc2cc3c(cc2Cl)C(C(=O)O)CCO3)cc1] | 6-chloro-7-(4-(1-(1-phenyl)-1H-pyrazol-3-ylcarbamoyl)phenoxy)chroman-4-carboxylic acid | (apci) 490.2 (M + H) |

| Ex. # | Structure | Name | MS Data |
|---|---|---|---|
| 172 | 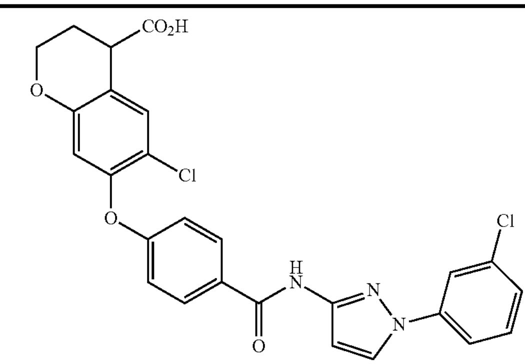 | 6-chloro-7-(4-(1-(3-chlorophenyl)-1H-pyrazol-3-ylcarbamoyl)phenoxy)chroman-4-carboxylic acid | (apci) 524.2 (M + H) |
| 173 | 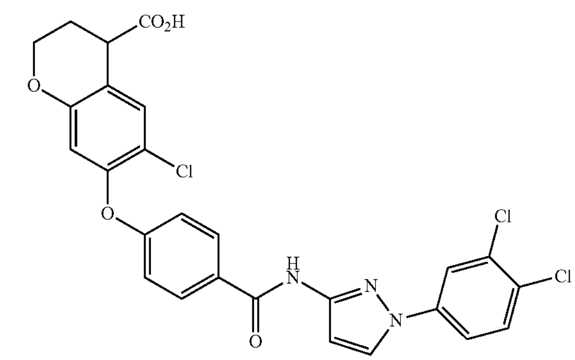 [SMILES: O=C(Nc1ccn(-c2ccc(Cl)c(Cl)c2)n1)c1ccc(Oc2cc3c(cc2Cl)C(C(=O)O)CCO3)cc1] | 6-chloro-7-(4-(1-(3,4-dichlorophenyl)-1H-pyrazol-3-ylcarbamoyl)phenoxy)chroman-4-carboxylic acid | (apci) 558.1 (M + H) |
| 174 | 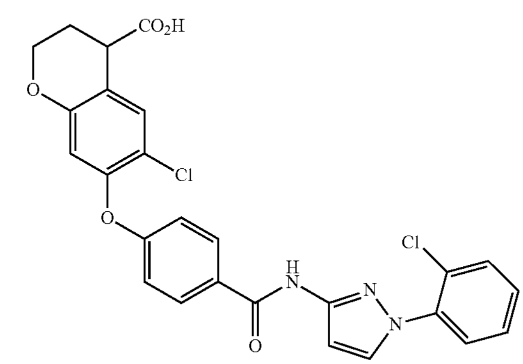 [SMILES: O=C(Nc1ccn(-c2ccccc2Cl)n1)c1ccc(Oc2cc3c(cc2Cl)C(C(=O)O)CCO3)cc1] | 6-chloro-7-(4-(1-(2-chlorophenyl)-1H-pyrazol-3-ylcarbamoyl)phenoxy)chroman-4-carboxylic acid | (apci) 524.1 (M + H) |
| 175 | 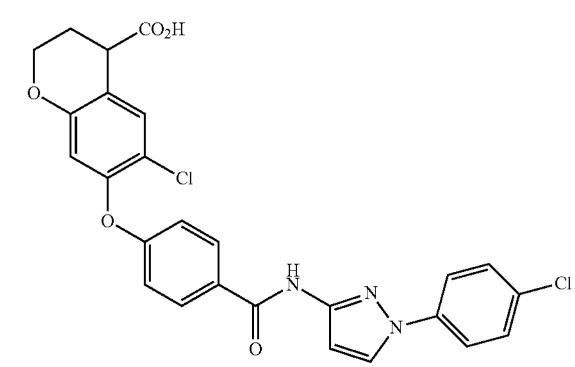 [SMILES: O=C(Nc1ccn(-c2ccc(Cl)cc2)n1)c1ccc(Oc2cc3c(cc2Cl)C(C(=O)O)CCO3)cc1] | 6-chloro-7-(4-(1-(4-chlorophenyl)-1H-pyrazol-3-ylcarbamoyl)phenoxy)chroman-4-carboxylic acid | (apci) 524.1 (M + H) |

The following compounds were prepared according to the method of Example 166, Steps B-C, using the appropriate starting materials.

| Ex. # | Structure | Name | MS Data |
|---|---|---|---|
| 176 | 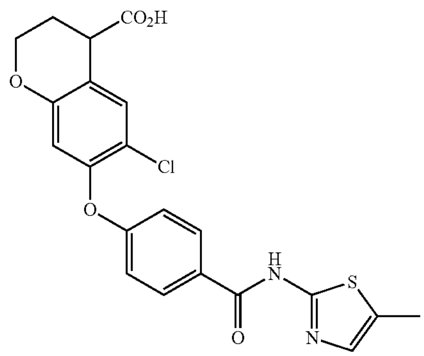 | 6-cyano-7-(4-(5-methylthiazol-2-ylcarbamoyl)phenoxy)chroman-4-carboxylic acid | (apci) 436.0 (M + H) |
| 177 | 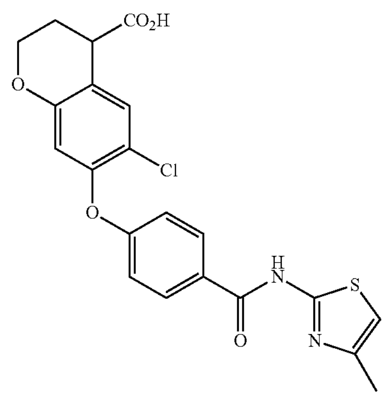 | 6-cyano-7-(4-(4-methylthiazol-2-ylcarbamoyl)phenoxy)chroman-4-carboxylic acid | (apci) 436.0 (M + H) |
| 178 | 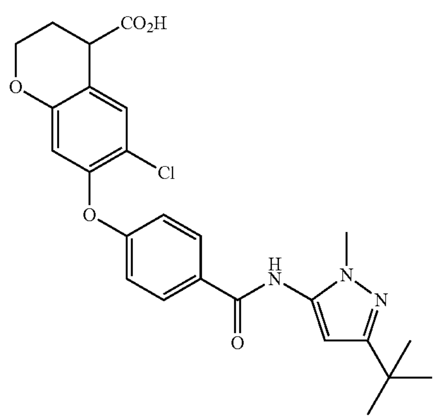 [SMILES: Cn1nc(C(C)(C)C)cc1NC(=O)c1ccc(Oc2cc3c(cc2Cl)C(C(=O)O)CCO3)cc1] | 7-(4-(3-tert-butyl-1-methyl-1H-pyrazol-5-ylcarbamoyl)phenoxy)-6-chlorochroman-4-carboxylic acid | (apci) 484.2 (M + H) |
| 179 | 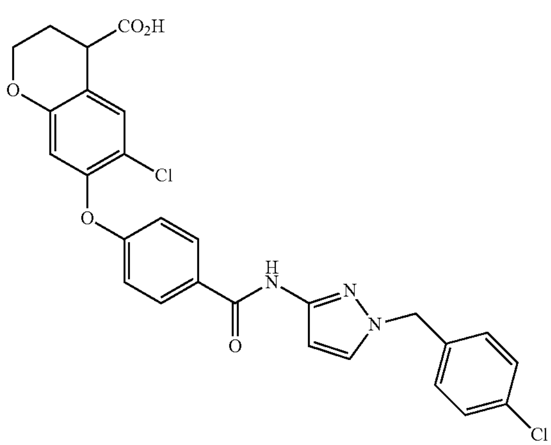 [SMILES: O=C(Nc1ccn(Cc2ccc(Cl)cc2)n1)c1ccc(Oc2cc3c(cc2Cl)C(C(=O)O)CCO3)cc1] | 6-chloro-7-(4-(1-(4-chlorobenzyl)-1H-pyrazol-3-ylcarbamoyl)phenoxy)chroman-4-carboxylic acid | (apci) 538.0 (M + H) |

EXAMPLE 180

6-Chloro-7-(4-(3-(4-chlorophenyl)-1H-pyrazol-5-ylcarbamoyl)phenoxy)chroman-4-carboxylic acid

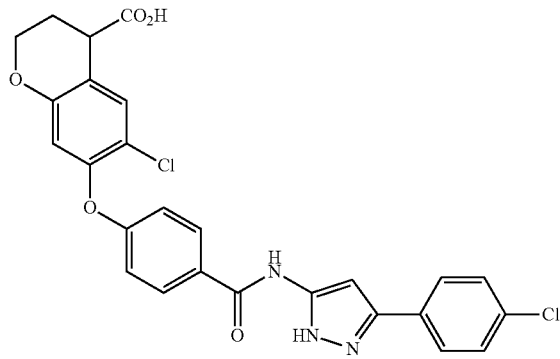 [SMILES: O=C(Nc1cc(-c2ccc(Cl)cc2)n[nH]1)c1ccc(Oc2cc3c(cc2Cl)C(C(=O)O)CCO3)cc1]

Prepared according to the method of Example 39, substituting 4-(6-cyano-4-(methoxycarbonyl)chroman-7-yloxy)benzoic acid in Step A with 4-(6-chloro-4-(ethoxycarbonyl)chroman-7-yloxy)benzoic acid and 6-bromopyridin-2-amine with 3-(4-chlorophenyl)-1H-pyrazol-5-amine. MS (apci) m/z=524.1 (M+H).

EXAMPLE 181

6-Chloro-7-(4-(3-(4-fluorophenyl)-1H-pyrazol-5-ylcarbamoyl)phenoxy)chroman-4-carboxylic acid

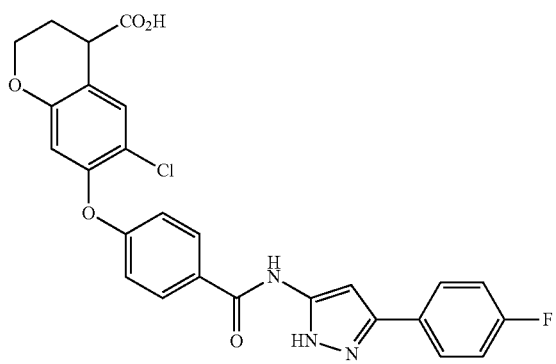 [SMILES: O=C(Nc1cc(-c2ccc(F)cc2)n[nH]1)c1ccc(Oc2cc3c(cc2Cl)C(C(=O)O)CCO3)cc1]

Prepared according to the method of Example 39, substituting 4-(6-cyano-4-(methoxycarbonyl)chroman-7-yloxy)benzoic acid in Step A with 4-(6-chloro-4-(ethoxycarbonyl)chroman-7-yloxy)benzoic acid and 6-bromopyridin-2-amine with 3-(4-fluorophenyl)-1H-pyrazol-5-amine. MS (apci) m/z=508.2 (M+H).

EXAMPLE 182

Enantiomer 2 of 6-Chloro-7-(4-(6-(4-chlorophenyl)pyridin-2-ylcarbamoyl)phenoxy)chroman-4-carboxylic acid

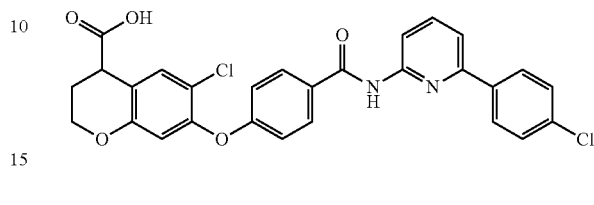

Step A: Preparation of Ethyl 7-(4-(6-bromopyridin-2-ylcarbamoyl)phenoxy)-6-chlorochroman-4-carboxylate 4-(6-Chloro-4-(ethoxycarbonyl)chroman-7-yloxy)benzoic acid (Preparation B; 1.0 g, 2.65 mmol) was diluted with dichloromethane (10 mL) followed by the addition of oxalyl chloride in dichloromethane (2M) (1.46 mL, 2.92 mmol) and DMF (1 drop). After stirring for 20 minutes, 6-bromopyridin-2-amine (0.505 g, 2.92 mmol) and diisopropyl ethylamine (1.16 ml, 6.64 mmol) were added and the reaction was stirred overnight at ambient temperature, then heated to 70° C. for 4 hours. The reaction mixture was cooled, then loaded directly onto a Biotage 40 cartridge, eluting with 5% ethyl acetate/hexanes to 70% ethyl acetate/hexanes to yield ethyl 7-(4-(6-bromopyridin-2-ylcarbamoyl)phenoxy)-6-chlorochroman-4-carboxylate (500 mg, 0.940 mmol, 35.4% yield).

Step B: Preparation of Ethyl 6-chloro-7-(4-(6-(4-chlorophenyl)pyridin-2-ylcarbamoyl)phenoxy)chroman-4-carboxylate Ethyl 7-(4-(6-bromopyridin-2-ylcarbamoyl)phenoxy)-6-chlorochroman-4-carboxylate (50 mg, 0.094 mmol), 4-chlorophenylboronic acid (59 mg, 0.38 mmol), Na$_2$CO$_3$ (30 mg, 0.28 mmol) and Pd(PPh$_3$)$_4$ (11 mg, 0.0094 mmol) were place in a 1 mL vial and diluted with toluene (800 μL) and water (80 μL). The vial was purged with argon, sealed and heated to 100° C. After stirring for 12 hours, the reaction was cooled and loaded directly onto a biotage 25 cartridge eluting with 5% ethyl acetate/hexanes to 60% ethyl acetate/hexanes to yield ethyl 6-chloro-7-(4-(6-(4-chlorophenyl)pyridin-2-ylcarbamoyl)phenoxy)chroman-4-carboxylate (50 mg, 0.089 mmol, 94% yield).

Step C: Preparation of 6-chloro-7-(4-(6-(2-chlorophenyl)pyridin-3-ylcarbamoyl)phenoxy)chroman-4-carboxylic acid Ethyl 6-chloro-7-(4-(6-(4-chlorophenyl)pyridin-2-ylcarbamoyl)phenoxy)chroman-4-carboxylate (50 mg, 0.089 mmol) was diluted with THF (1 mL) followed by the addition of 1 N aq. NaOH (444 μL, 0.44 mmol) and ethanol (500 μL). After stirring for 4 hours, the reaction was diluted with ethyl acetate and 1N aq. HCl. The layers were separated and the organic layer was dried over MgSO$_4$, filtered and concentrated to yield 6-chloro-7-(4-(6-(4-chlorophenyl)pyridin-2- ylcarbamoyl)phenoxy)chroman-4-carboxylic acid (45 mg, 0.084 mmol, 95% yield). MS (ESI, positive) m/z=535.3.

Step D: Preparation of tert-butyl 6-chloro-7-(4-(6-(4-chlorophenyl)pyridin-2-ylcarbamoyl)phenoxy)chroman-4-carboxylate and separation of enantiomers 6-Chloro-7-(4-(6-(4-chlorophenyl)pyridin-2-ylcarbamoyl)phenoxy)chroman-4-carboxylic acid (45 mg, 0.0841 mmol) was diluted with toluene (600 µL) followed by the addition of N,N-dimethylformamide di-tert-butyl acetal (202 µL, 0.841 mmol). The reaction was heated to 60° C. and stirred for 24 hours. The reaction was loaded directly onto a Biotage 25 cartridge eluting with 5% ethyl acetate/hexanes to 40% ethyl acetate/hexanes to yield tert-butyl 6-chloro-7-(4-(6-(4-chlorophenyl)pyridin-2-ylcarbamoyl)phenoxy)chroman-4-carboxylate (45 mg, 0.0761 mmol, 90.5% yield). The material was resolved via supercritical fluid chromatography employing a CHIRALCEL® OJ-H column (3×15 cm) eluting with 35% ethanol/carbon dioxide at 100 bar, using 3 mL injections and a flow rate of 140 mL/min. Collection of fractions containing peak 2 and removal of volatiles provided Enantiomer 2 of 6-chloro-7-(4-(6-(4-chlorophenyl)pyridin-2-ylcarbamoyl)phenoxy)chroman-4-carboxylic acid.

Step E: Preparation of Enantiomer 2 of 6-chloro-7-(4-(6-(4-chlorophenyl)pyridin-2-ylcarbamoyl)phenoxy)chroman-4-carboxylic acid Enantiomer 2 of tert-butyl 6-chloro-7-(4-(6-(4-chlorophenyl)pyridin-2-ylcarbamoyl)phenoxy)chroman-4-carboxylate (10 mg, 0.017 mmol) was diluted with dichloromethane (100 µL) followed by the addition of trifluoroacetic acid (100 µL). After stirring for 2 hours, the reaction was concentrated to yield Enantiomer 2 of 6-chloro-7-(4-(6-(4-chlorophenyl)pyridin-2-ylcarbamoyl)phenoxy)chroman-4-carboxylic acid (9.0 mg, 0.017 mmol, 99% yield). MS (apci, positive) m/z=535.1. $^1$H NMR (400 MHz, CDCl$_3$) δ 9.03 (br s, 1H), 8.35 (d, 1H), 7.96 (d, 2H), 7.90-7.85 (m, 4H), 7.48-7.42 (m, 4H), 7.05 (d, 2H), 6.60 (s, 1H), 4.29-4.23 (m, 2H), 3.82 (t, 1H), 2.36 (dd, 1H), 2.19-2.10 (m, 1H).

EXAMPLE 183

6-Chloro-7-(4-(6-(trifluoromethyl)benzo[d]thiazol-2-ylcarbamoyl)phenoxy)chroman-4-carboxylic acid

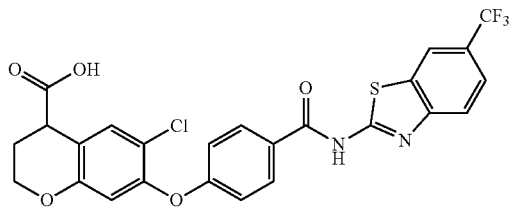 [SMILES: O=C(Nc1nc2ccc(C(F)(F)F)cc2s1)c1ccc(Oc2cc3c(cc2Cl)C(C(=O)O)CCO3)cc1]

Step A: Preparation of ethyl 6-chloro-7-(4-(6-(trifluoromethyl)benzo[d]thiazol-2-ylcarbamoyl)phenoxy)chroman-4-carboxylate 4-(6-Chloro-4-(ethoxycarbonyl)chroman-7-yloxy)benzoic acid (Preparation B; 100 mg, 0.265 mmol) was diluted with dichloromethane (5 mL) followed by the addition of oxalyl chloride in dichloromethane (2M) (146 µL, 0.292 mmol) and dimethylformamide (1 drop). After stirring for 30 minutes a small aliquot was diluted with methanol for 5 minutes. Thin layer chromatography of this aliquot showed complete conversion to methyl ester. 6-(Trifluoromethyl)benzo[d]thiazol-2-amine (63.7 mg, 0.292 mmol) and diisopropyl ethylamine (116 µL, 0.664 mmol) were added and the reaction was stirred at 35° C. for 1 hour. The reaction was loaded directly onto a Biotage 25 cartridge and eluted with 5% ethyl acetate/hexanes to 70% ethyl acetate/hexanes to yield ethyl 6-chloro-7-(4-(6-(trifluoromethyl)benzo[d]thiazol-2-ylcarbamoyl)phenoxy)chroman-4-carboxylate (50 mg, 0.0867 mmol, 32.7% yield).

Step B: Preparation of 6-Chloro-7-(4-(6-(trifluoromethyl)benzo[d]thiazol-2-ylcarbamoyl)phenoxy)chroman-4-carboxylic acid Ethyl 6-chloro-7-(4-(6-(trifluoromethyl)benzo[d]thiazol-2-ylcarbamoyl)phenoxy)chroman-4-carboxylate (50 mg, 0.087 mmol) was diluted with THF (500 µL) followed by the addition of aqueous NaOH (433 µL, 0.43 mmol) and ethanol (100 µL). After stirring for 2 hours, the reaction was diluted with ethyl acetate and 0.5N aqueous HCl. The layers were separated and the organic layer was concentrated to yield 6-chloro-7-(4-(6-(trifluoromethyl)benzo[d]thiazol-2-ylcarbamoyl)phenoxy)chroman-4-carboxylic acid (35 mg, 0.064 mmol, 74% yield). MS (apci, positive) m/z=548.8. $^1$H NMR (400 MHz, D6 DMSO) δ 13.06 (br s, 1H), 8.54 (s, 1H), 8.19 (d, 2H), 7.95 (d, 1H), 7.86 (dd, 1H), 7.49 (s, 1H), 7.06 (d, 2H), 6.76 (s, 1H), 4.30-4.26 (m, 1H), 4.10 (dt, 1H), 3.86 (t, 1H), 2.26-2.20 (m, 1H), 2.11-2.02 (m, 1H).

EXAMPLE 184

Sodium 6-Chloro-7-(4-(2-(6-cyclopropyl-2-methoxypyridin-3-yl)ethylcarbamoyl)phenoxy)chroman-4-carboxylate

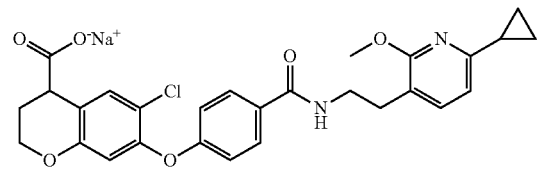

Step A: Preparation of 2-(6-cyclopropyl-2-methoxypyridin-3-yl)ethanamine

Step A1: 2,6-Dichloronicotinaldehyde (1 g, 5.68 mmol) was diluted with sodium methoxide (11.4 mL, 5.68 mmol) (solution in methanol) and heated to 55° C. After stirring for 3 hours, the reaction was loaded directly onto a silica gel column and eluted with 5% ethyl acetate/hexanes to 50% ethyl acetate/hexanes to yield 6-chloro-2-methoxynicotinaldehyde (0.695 g, 4.05 mmol, 71.3% yield).

Step A2: 6-Chloro-2-methoxynicotinaldehyde (200 mg, 1.17 mmol), cyclopropylboronic acid (200 mg, 2.33 mmol), sodium carbonate (371 mg, 3.50 mmol) and tetrakis(triphenylphosphine)palladium (0) (67.3 mg, 0.0583 mmol) were combined, diluted with toluene (2 mL) and water (200 µL). The reaction vial was purged with argon, heated to 90° C. and stirred for 12 hours. The reaction was cooled, loaded onto silica gel and eluted with 5% ethyl acetate/hexanes to 50% ethyl acetate/hexanes to yield 6-cyclopropyl-2-methoxynicotinaldehyde (121 mg, 0.683 mmol, 58.6% yield).

Step A3: 6-Cyclopropyl-2-methoxynicotinaldehyde (121 mg, 0.683 mmol) was diluted with nitromethane (259 µL, 4.78 mmol) followed by the addition of methylamine hydrochloride (27.7 mg, 0.410 mmol) and sodium acetate (33.6 mg, 0.410 mmol). After stirring for 4 hours, the reaction was loaded directly onto a silica gel column and eluted with 5% ethyl acetate/hexanes to 50% ethyl acetate hexanes to yield (E)-6-cyclopropyl-2-methoxy-3-(2-nitrovinyl)pyridine (135 mg, 0.613 mmol, 89.8% yield).

Step A4: To a stirred solution of lithium borohydride (1226 µL, 2.45 mmol) in THF was added chlorotrimethylsilane (622 µl, 4.90 mmol) dropwise. After stirring for 15 minutes, argon was bubbled through the reaction mixture for 2 minutes to eliminate any trimethylsilane in the reaction mixture. (E)-6-cyclopropyl-2-methoxy-3-(2-nitrovinyl)pyridine (135 mg, 0.613 mmol) was added (in 1 mL of THF). The reaction was heated to reflux for 2 hours, cooled to 0° C. and carefully quenched with methanol (1 mL). The reaction mixture was concentrated, diluted with dichloromethane and 20% aqueous KOH. The layers were separated and the organic layer was dried over sodium sulfate, filtered and concentrated to yield 2-(6-cyclopropyl-2-methoxypyridin-3-yl)ethanamine (118 mg, 0.614 mmol, 100% yield).

Step B: Preparation of ethyl 6-chloro-7-(4-(2-(6-cyclopropyl-2-methoxypyridin-3-yl)ethylcarbamoyl)phenoxy)chroman-4-carboxylate To a stirred solution of 4-(6-chloro-4-(ethoxycarbonyl)chroman-7-yloxy)benzoic acid (200 mg, 0.531 mmol) and 1-hydroxybenzotriazole monohydrate (89.4 mg, 0.584 mmol) was added 2-(6-cyclopropyl-2-methoxypyridin-3-yl)ethanamine (117 mg, 0.610 mmol) (in dimethylformamide, 3 mL). 1-Ethyl-(3-dimethylaminopropyl)carbodiimide hydrochloride (112 mg, 0.584 mmol) was added and the reaction was stirred for 5 hours. The reaction was loaded onto silica gel and eluted with 5% ethyl acetate/hexanes to 75% ethyl acetate/hexanes to yield ethyl 6-chloro-7-(4-(2-(6-cyclopropyl-2-methoxypyridin-3-yl)ethylcarbamoyl)phenoxy)chroman-4-carboxylate (136 mg, 0.247 mmol, 46.5% yield). MS (apci+es, positive) m/z=552.2.

Step C: Preparation of 6-chloro-7-(4-(2-(6-cyclopropyl-2-methoxypyridin-3-yl)ethylcarbamoyl)phenoxy)chroman-4-carboxylic acid Ethyl 6-chloro-7-(4-(2-(6-cyclopropyl-2-methoxypyridin-3-yl)ethylcarbamoyl)phenoxy)chroman-4-carboxylate (133 mg, 0.241 mmol) was diluted with tetrahydrofuran (2 mL) followed by the addition of aqueous NaOH (603 µL, 1.21 mmol) and ethanol (1 mL). After stirring for 2 hours, the reaction was diluted with ethyl acetate and 2N aqueous HCl. The layers were separated and the organic layer was dried over MgSO$_4$, filtered and concentrated to yield 6-chloro-7-(4-(2-(6-cyclopropyl-2-methoxypyridin-3-yl)ethylcarbamoyl)phenoxy)chroman-4-carboxylic acid (70 mg, 0.134 mmol, 55.5% yield). MS (es+apci, positive) m/z=523.2. $^1$H NMR (400 MHz, CDCl$_3$) δ 7.71 (d, 2H), 7.42 (s, 1H), 7.35 (d, 1H), 6.96 (d, 2H), 6.54 (s, 1H), 6.47 (d, 1H), 4.25 (dd, 2H), 3.74 (t, 1H), 3.68 (t, 2H), 3.02 (t, 2H), 2.38-2.32 (m, 1H), 2.19-2.08 (m, 2H), 1.13-1.09 (m, 2H), 0.93-0.89 (m, 2H).

Step D: Preparation of 6-Chloro-7-(4-(2-(2-ethoxypyridin-3-yl)ethylcarbamoyl)phenoxy)chroman-4-carboxylic acid sodium salt 6-Chloro-7-(4-(2-(6-cyclopropyl-2-methoxypyridin-3-yl)ethylcarbamoyl)phenoxy)chroman-4-carboxylic acid (70 mg, 0.13 mmol) was diluted with methanol (1 mL) followed by the addition of NaOMe (268 µL, 0.13 mmol). After stirring for 2 hours, the reaction was concentrated and dried under high vacuum pressure for 2 hours. The material was diluted with hexanes, sonicated and concentrated to afford 6-chloro-7-(4-(2-(6-cyclopropyl-2-methoxypyridin-3-yl)ethylcarbamoyl)phenoxy)chroman-4-carboxylic acid sodium salt (40 mg, 0.076 mmol, 57% yield). MS (es+apci, positive) m/z=523.2.]

EXAMPLE 185

Enantiomer 2 of sodium 6-chloro-7-(4-(6-(4-(trifluoromethyl)phenyl)pyridazin-3-ylcarbamoyl)phenoxy)chroman-4-carboxylate

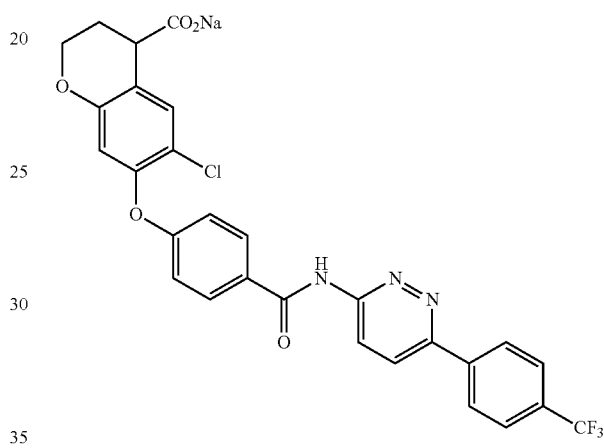

Step A: Preparation of 6-(4-(trifluoromethyl)phenyl)pyridazin-3-amine

To a solution of 6-chloropyridazin-3-amine (3.00 g, 23.2 mmol), 4-(trifluoromethyl)phenylboronic acid (5.72 g, 30.1 mmol), cesium fluoride (9.15 g, 60.2 mmol), triethylamine (4.84 mL, 34.7 mmol) in n-propanol (100 mL) degassed with argon was added dichloro[1,1'-bis(diphenylphosphino)ferrocene]palladium (II) dichloromethane adduct (0.953 g, 1.16 mmol), and the reaction was heated to reflux for 3 hours. Water was added to precipitate solids, which were collected by filtrations. The solids were purified on a SP1 system (0-10% MeOH in EtOAc) to yield 6-(4-(trifluoromethyl)phenyl)pyridazin-3-amine (1.5 g, 6.27 mmol, 27.1% yield).

Step B: Preparation of Ethyl 6-chloro-7-(4-(6-(4-(trifluoromethyl)phenyl)pyridazin-3-ylcarbamoyl)phenoxy)chroman-4-carboxylate To a solution of 4-(6-chloro-4-(ethoxycarbonyl)chroman-7-yloxy)benzoic acid (Preparation B; 2.137 g, 5.701 mmol) in DCE (6 mL) and DMF (1 drop) was added oxalyl dichloride (0.5968 mL, 6.841 mmol), and the reaction was allowed to stir at ambient temperature for 1 hour. The evolution of gases slowed several times, and 3 more drops of DMF were added over the course of this activation step. Pyridine (24 mL) and 6-(4-(trifluoromethyl)phenyl)pyridazin-3-amine (1.5 g, 6.271 mmol) were added, and the reaction was heated to 80° C. overnight. The reaction mixture was diluted with EtOAc and washed with 10% citric acid, sodium bicarbonate and brine. The organic layer was dried over Na₂SO₄, filtered, and concentrated. The crude material was precipitated from EtOAc/hexanes to yield ethyl 7-chloro-6-(4-(6-(4-(trifluoromethyl)phenyl)pyridazin-3-ylcarbamoyl)phenoxy)-1,2,3,4-tetrahydronaphthalene-1-carboxylate (1.83 g, 3.070 mmol, 53.86% yield). MS (apci, positive) m/z=597.9.

Step C: Preparation of 6-chloro-7-(4-(6-(4-(trifluoromethyl)phenyl)pyridazin-3-ylcarbamoyl)phenoxy)chroman-4-carboxylic acid and separation of enantiomers:

To a solution of ethyl 6-chloro-7-(4-(6-(4-(trifluoromethyl)phenyl)pyridazin-3-ylcarbamoyl)phenoxy)chroman-4-carboxylate (1.83 g, 3.07 mmol) in 40 mL of 3:1 THF/EtOH was added sodium hydroxide (12.3 ml, 12.3 mmol). The reaction was stirred for 3 hours, then concentrated. The crude material was combined with 1M HCl (50 mL) and stirred for 3 hours. The material was resolved via supercritical fluid chromatography employing a CHIRALCEL® OJ-H column (3×15 cm) eluting with 35% ethanol/carbon dioxide at 100 bar, using 3 mL injections and a flow rate of 140 mL/min. Collection of fractions containing peak 2 and removal of volatiles provided Enantiomer 2 of 6-chloro-7-(4-(6-(4-(trifluoromethyl)phenyl)pyridazin-3-ylcarbamoyl)phenoxy)chroman-4-carboxylic acid (0.730 g, 1.29 mmol, 41.9% yield) as a white solid. MS (apci, positive) m/z=569.9.

Step D: Preparation of Enantiomer 2 of 6-Chloro-7-(4-(6-(4-(trifluoromethyl)phenyl)pyridazin-3-ylcarbamoyl)phenoxy)chroman-4-carboxylic acid sodium salt To a suspension of Enantiomer 2 of 7-chloro-6-(4-(6-(4-(trifluoromethyl)phenyl)pyridazin-3-ylcarbamoyl)phenoxy)-1,2,3,4-tetrahydronaphthalene-1-carboxylic acid (0.035 g, 0.0616 mmol) in MeOH (2 mL) was added sodium methoxide (0.123 mL, 0.0616 mmol), and the reaction was allowed to stir at ambient temperature for 2 hours. The reaction mixture was concentrated to yield the sodium salt of Enantiomer 2 of 7-chloro-6-(4-(6-(4-(trifluoromethyl)phenyl)pyridazin-3-ylcarbamoyl)phenoxy)-1,2,3,4-tetrahydronaphthalene-1-carboxylate. MS (apci, positive) m/z=570.0. ¹H NMR (400 MHz, D6 DMSO) δ 11.60 (br s, 1H), 8.52 (d, 1H), 8.41-8.36 (m, 3H), 8.13 (d, 2H), 7.93 (d, 2H), 7.59 (s, 1H), 6.99) d, 2H), 6.62 (s, 1H), 4.26-4.13 (m, 2H), 3.27 (m, 1H), 2.24-2.21 (m, 1H), 1.83-1.76 (m, 1H).

EXAMPLE 186

Sodium 6-Chloro-7-(4-(2-(2-cyclopropyl-6-(trifluoromethyl)pyridin-3-yl)ethylcarbamoyl)phenoxy)chroman-4-carboxylate

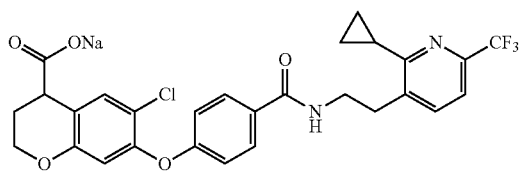

Step A: Preparation of 2-(2-cyclopropyl-6-(trifluoromethyl)pyridin-3-yl)ethanamine Step A1: 2-Chloro-6-(trifluoromethyl)nicotinonitrile (1.0 g, 4.84 mmol) was diluted with toluene (5.0 mL), placed under nitrogen and cooled to −78° C. DIBAL-H (9.68 mL, 9.68 mmol) was added dropwise and the reaction was stirred for 1 hour. The reaction was warmed to 0° C. and acetic acid (2 mL in 8 mL of water) was added dropwise. After stirring for 2 hours, the reaction was extracted twice with ethyl acetate, washed with Rochelle's salt, dried over MgSO₄, filtered and concentrated. The material was loaded onto silica gel and eluted with 5% ethyl acetate/hexanes to 30% ethyl acetate/hexanes to yield 2-chloro-6-(trifluoromethyl)nicotinaldehyde (337 mg, 1.61 mmol, 33.2% yield) as a clear oil.

Step A2: 2-Chloro-6-(trifluoromethyl)nicotinaldehyde (176 mg, 0.840 mmol), cyclopropylboronic acid (152 mg, 1.76 mmol), sodium carbonate (267 mg, 2.52 mmol) and tetrakis(triphenylphosphine)palladium (0) (48.5 mg, 0.0420 mmol) were combined, diluted with toluene (2 mL) and water (200 µL). The reaction vial was purged with argon, heated to 90° C. and stirred for 24 hours. The reaction was allowed to cool, loaded onto silica gel and eluted with 5% ethyl acetate/hexanes to 50% ethyl acetate/hexanes to yield 2-cyclopropyl-6-(trifluoromethyl)nicotinaldehyde (130 mg, 0.604 mmol, 71.9% yield).

Step A3: 2-Cyclopropyl-6-(trifluoromethyl)nicotinaldehyde (130 mg, 0.604 mmol) was diluted with nitromethane (229 µL, 4.23 mmol) followed by the addition of methylamine hydrochloride (24.5 mg, 0.363 mmol) and sodium acetate (29.7 mg, 0.363 mmol). After stirring for 4 hours, the reaction was loaded onto silica gel and eluted with 5% ethyl acetate/hexanes to 50% ethyl acetate/hexanes to yield (E)-2-cyclopropyl-3-(2-nitrovinyl)-6-(trifluoromethyl)pyridine (26 mg, 0.101 mmol, 16.7% yield).

Step A4: To a stirred solution of lithium borohydride (232 µL, 0.465 mmol) in THF was added chlorotrimethylsilane (118 µL, 0.930 mmol) dropwise. After stirring for 15 minutes, argon was bubbled through the reaction mixture for 2 minutes to eliminate any trimethylsilane in the reaction mixture. (E)-2-cyclopropyl-3-(2-nitrovinyl)-6-(trifluoromethyl)pyridine (30 mg, 0.116 mmol) was added (in 1 mL of THF). The reaction was heated to reflux for 2 hours, cooled to 0° C. and carefully quenched with methanol (1 mL). The reaction mixture was concentrated, diluted with dichloromethane and 20% aqueous KOH. The layers were separated and the organic layer was dried over sodium sulfate, filtered and concentrated to yield 2-(2-cyclopropyl-6-(trifluoromethyl)pyridin-3-yl)ethanamine (26 mg, 0.113 mmol, 97.2% yield).

Step B: Preparation of ethyl 6-chloro-7-(4-(2-(2-cyclopropyl-6-(trifluoromethyl)pyridin-3-yl)ethylcarbamoyl)phenoxy)chroman-4-carboxylate 4-(6-Chloro-4-(ethoxycarbonyl)chroman-7-yloxy)benzoic acid (Preparation B; 50 mg, 0.13 mmol) was diluted with dichloromethane (2 mL) followed by the addition of oxalyl chloride in dichloromethane (2M) (73 µL, 0.15 mmol) and DMF (1 drop). After stirring for 15 minutes, 2-(2-cyclopropyl-6-(trifluoromethyl)pyridin-3-yl)ethanamine (31 mg, 0.13 mmol) and diisopropyl ethylamine (69 µL, 0.40 mmol) were added. After stirring for 1 hour, the reaction was loaded onto silica gel and eluted with 100% ethyl acetate to yield ethyl 6-chloro-7-(4-(2-(2-cyclopropyl-6-(trifluoromethyl)pyridin-3-yl)ethylcarbamoyl)phenoxy)chroman-4-carboxylate (15 mg, 0.025 mmol, 19% yield). MS (es+apci, positive) m/z=589.2.

Step C: Preparation of 6-chloro-7-(4-(2-(2-cyclopropyl-6-(trifluoromethyl)pyridin-3-yl)ethylcarbamoyl)phenoxy)chroman-4-carboxylic acid Ethyl 6-chloro-7-(4-(2-(2-cyclopropyl-6-(trifluoromethyl)pyridin-3-yl)ethylcarbamoyl)phenoxy)chroman-4-carboxylate (15 mg, 0.025 mmol) was diluted with THF (200 µL) followed by the addition of aq. 1N NaOH (127 µL, 0.13 mmol) and ethanol (100 µL). After stirring for 2 hours, the reaction was diluted with ethyl acetate and 2N aqueous HCl. The layers were separated and the organic layer was dried over MgSO$_4$, filtered and concentrated to yield 6-chloro-7-(4-(2-(2-cyclopropyl-6-(trifluoromethyl)pyridin-3-yl)ethylcarbamoyl)phenoxy)chroman-4-carboxylic acid (14 mg, 0.025 mmol, 98% yield).

Step D: Preparation of 6-chloro-7-(4-(2-(2-cyclopropyl-6-(trifluoromethyl)pyridin-3-yl)ethylcarbamoyl)phenoxy)chroman-4-carboxylic acid sodium salt 6-Chloro-7-(4-(2-(2-cyclopropyl-6-(trifluoromethyl)pyridin-3-yl)ethylcarbamoyl)phenoxy)chroman-4-carboxylic acid (15 mg, 0.027 mmol) was diluted with methanol (1 mL) followed by the addition of NaOMe in methanol (53 µL, 0.027 mmol). After stirring for 2 hours, the reaction was concentrated and dried under high vacuum pressure for 2 hours. The material was diluted with hexanes, sonicated and concentrated to afford 6-chloro-7-(4-(2-(2-cyclopropyl-6-(trifluoromethyl)pyridin-3-yl)ethylcarbamoyl)phenoxy)chroman-4-carboxylic acid sodium salt (15 mg, 0.027 mmol, 100% yield) as a white solid. MS (es+apci, positive) m/z=561.1. $^1$H NMR (400 MHz, D6 DMSO) δ 8.59 (br s, 1H), 7.81 (d, 2H), 7.75 (d, 1H), 7.54 (d, 1H), 7.49 (s, 1H), 6.95 (d, 2H), 6.57 (s, 1H), 4.17 (br s, 2H), 3.55-3.53 (m, 3H), 3.35-3.31 (m, 4H), 3.11-3.09 (m, 2H), 2.47-2.43 (m, 1H), 2.21-2.17 (m, 1H), 1.92-1.87 (m, 1H).

EXAMPLE 187

6-Chloro-7-(4-(2-(6-cyclopropyl-2-(dimethylamino)pyridin-3-yl)ethylcarbamoyl)phenoxy)chroman-4-carboxylic acid

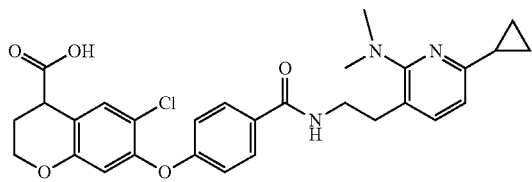 [SMILES: CN(C)c1nc(C2CC2)ccc1CCNC(=O)c1ccc(Oc2cc3c(cc2Cl)C(C(=O)O)CCO3)cc1]

Step A: Preparation of 3-(2-aminoethyl)-6-cyclopropyl-N,N-dimethylpyridin-2-amine Step A1: 2,6-Dichloronicotinaldehyde (500 mg, 2.84 mmol) was diluted with dimethylamine (3125 µL, 6.25 mmol) and heated to 50° C. After stirring for 3 hours, the reaction was loaded onto a silica gel column and eluted with 5% ethyl acetate/hexanes to 50% ethyl acetate/hexanes to yield 6-chloro-2-(dimethylamino)nicotinaldehyde (155 mg, 0.840 mmol, 29.6% yield).

Step A2: 6-chloro-2-(dimethylamino)nicotinaldehyde (155 mg, 0.840 mmol), sodium carbonate (267 mg, 2.52 mmol), cyclopropylboronic acid (108 mg, 1.26 mmol) and palladium tetrakis(triphenylphosphine) (0) (48.5 mg, 0.0420 mmol) were diluted with toluene (2 mL) and water (200 µL). The reaction was purged with argon, sealed and heated to 90° C. After stirring for 4 hours, the reaction was cooled, loaded onto silica gel and eluted with 5% ethyl acetate/hexanes to 75% ethyl acetate/hexanes to yield 6-cyclopropyl-2-(dimethylamino)nicotinaldehyde (100 mg, 0.526 mmol, 62.6% yield).

Step A3: 6-cyclopropyl-2-(dimethylamino)nicotinaldehyde (100 mg, 0.526 mmol) was diluted with nitromethane (199 µL, 3.68 mmol) followed by the addition of methylamine hydrochloride (21.3 mg, 0.315 mmol) and sodium acetate (25.9 mg, 0.315 mmol). After stirring for 4 hours, the reaction was loaded directly onto a silica gel column and eluted with 5% ethyl acetate/hexanes to 100% ethyl acetate hexanes to yield (E)-6-cyclopropyl-N,N-dimethyl-3-(2-nitrovinyl)pyridin-2-amine (123 mg, 0.527 mmol, 100% yield).

Step A4: To a stirred solution of lithium borohydride (1055 µL, 2.11 mmol) (in 2 mL of THF) was added chlorotrimethylsilane (535 µL, 4.22 mmol) dropwise. After stirring for 15 minutes, Argon was bubbled through the reaction mixture for 2 minutes to eliminate any trimethylsilane in the reaction mixture. (E)-6-Cyclopropyl-N,N-dimethyl-3-(2-nitrovinyl)pyridin-2-amine (123 mg, 0.527 mmol) was added (in 1 mL of THF). The reaction was heated to reflux for 2 hours, cooled to 0° C. and carefully quenched with methanol (1 mL). The reaction mixture was concentrated, diluted with dichloromethane and 20% aqueous KOH. The layers were separated and the organic layer was dried over sodium sulfate, filtered and concentrated to yield 3-(2-aminoethyl)-6-cyclopropyl-N,N-dimethylpyridin-2-amine (107 mg, 0.521 mmol, 98.8% yield).

Step B: Preparation of ethyl 6-chloro-7-(4-(2-(6-cyclopropyl-2-(dimethylamino)pyridin-3-yl)ethylcarbamoyl)phenoxy)chroman-4-carboxylate 4-(6-Chloro-4-(ethoxycarbonyl)chroman-7-yloxy)benzoic acid (Preparation B; 200 mg, 0.531 mmol) was diluted with dichloromethane (2 mL) followed by the addition of oxalyl chloride in dichloromethane (2M) (292 µL, 0.584 mmol) and dimethylformamide (1 drop). After stirring for 15 minutes, 3-(2-aminoethyl)-6-cyclopropyl-N,N-dimethylpyridin-2-amine (109 mg, 0.531 mmol) and diisopropyl ethylamine (277 µL, 1.59 mmol) were added. After stirring for 2 hours, the reaction was loaded onto silica gel and eluted with 5% ethyl acetate/hexanes to 100% ethyl acetate to yield ethyl 6-chloro-7-(4-(2-(6-cyclopropyl-2-(dimethylamino)pyridin-3-yl)ethylcarbamoyl)phenoxy)chroman-4-carboxylate (77 mg, 0.137 mmol, 25.7% yield).

Step C: Preparation of 6-chloro-7-(4-(2-(6-cyclopropyl-2-(dimethylamino)pyridin-3-yl)ethylcarbamoyl)phenoxy)chroman-4-carboxylic acid Ethyl 6-chloro-7-(4-(2-(6-cyclopropyl-2-(dimethylamino)pyridin-3-yl)ethylcarbamoyl)phenoxy)chroman-4-carboxylate (77 mg, 0.14 mmol) was diluted with terahydrofuran (1 mL) followed by the addition of aq. NaOH (341 µL, 0.68 mmol) and ethanol (500 µL). After stirring for 2 hours, the reaction was diluted with ethyl acetate and 2N aqueous HCl. The pH of the aqueous layer was adjusted to 6 with 1N aqueous NaOH and extracted with ethyl acetate. The ethyl acetate layer was dried over MgSO$_4$, filtered and concentrated to yield 6-chloro-7-(4-(2-(6-cyclopropyl-2-(dimethylamino)pyridin-3-yl)ethylcarbamoyl)phenoxy)chroman-4-carboxylic acid (70 mg, 0.13 mmol, 96% yield).

Step D: Preparation of 6-chloro-7-(4-(2-(6-cyclopropyl-2-(dimethylamino)pyridin-3-yl)ethylcarbamoyl)phenoxy)chroman-4-carboxylic acid sodium salt 6-Chloro-7-(4-(2-(6-cyclopropyl-2-(dimethylamino)pyridin-3-yl)ethylcarbamoyl)phenoxy)chroman-4-carboxylic acid (77 mg, 0.14 mmol) was diluted with THF (500 μL) followed by the addition of NaOMe in methanol (287 μL, 0.14 mmol). After stirring for 2 hours, the reaction was concentrated to yield 6-chloro-7-(4-(2-(6-cyclopropyl-2-(dimethylamino)pyridin-3-yl)ethylcarbamoyl)phenoxy)chroman-4-carboxylic acid (50 mg, 0.093 mmol, 65% yield). MS (es+apci, positive) m/z=536.2. $^1$H NMR (400 MHz, D6 DMSO) δ 8.51 (t, 1H), 7.82 (dd, 2H), 7.55 (d, 1H), 7.22 (dd, 1H), 6.92 (dd, 2H), 6.50 (d, 1H), 6.32 (dd. 1H), 4.21 (t, 1H), 4.11-4.08 (m, 1H), 3.62-3.59 (m, 1H), 3.41-3.36 (m, 2H), 3.20 (br s, 1H), 2.92 (s, 3H), 2.92 (s, 3H), 2.83 (t, 1H), 2.22-2.18 (m, 1H), 1.78-1.75 (m, 2H), 1.25 (br s, 1H), 0.96-0.93 (m, 1H), 0.88-0.79 (m, 2H).

Additional compounds made according to the methods described herein are shown in the following Table.

| Ex. # | Structure | Name | Data |
| --- | --- | --- | --- |
| 188 | 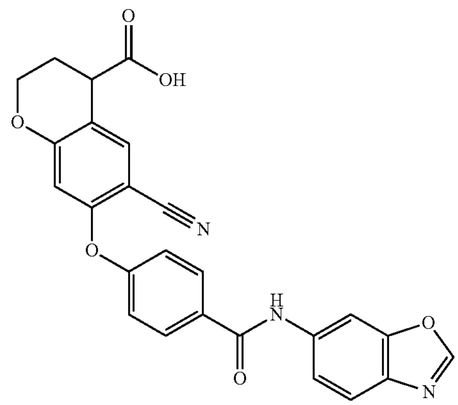 [SMILES: N#Cc1cc2c(cc1Oc1ccc(C(=O)Nc3ccc4ncoc4c3)cc1)OCCC2C(=O)O] | 7-(4-(benzo[d]oxazol-6-ylcarbamoyl)phenoxy)-6-cyanochroman-4-carboxylic acid | m/z = 456.0 (esi, pos) |
| 189 | 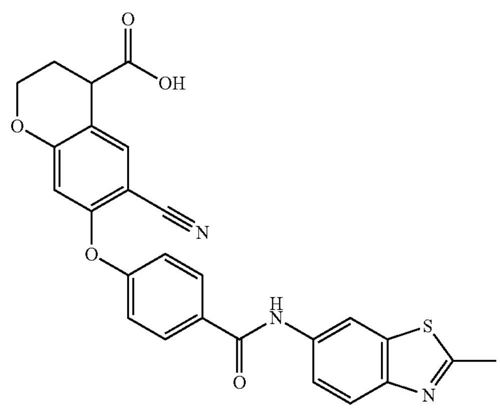 [SMILES: Cc1nc2ccc(NC(=O)c3ccc(Oc4cc5c(cc4C#N)C(C(=O)O)CCO5)cc3)cc2s1] | 6-cyano-7-(4-(2-methylbenzo[d]thiazol-6-ylcarbamoyl)phenoxy)chroman-4-carboxylic acid | m/z = 486.2 (esi, pos) |
| 190 | 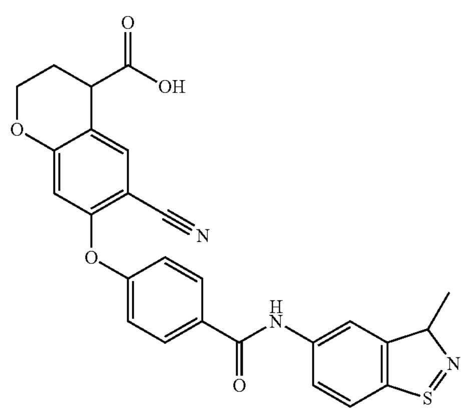 | 6-cyano-7-(4-(3-methylbenzo[d]isothiazol-5-ylcarbamoyl)phenoxy)chroman-4-carboxylic acid | m/z = 486.1 (esi, pos) |

-continued

| Ex. # | Structure | Name | Data |
|---|---|---|---|
| 191 | 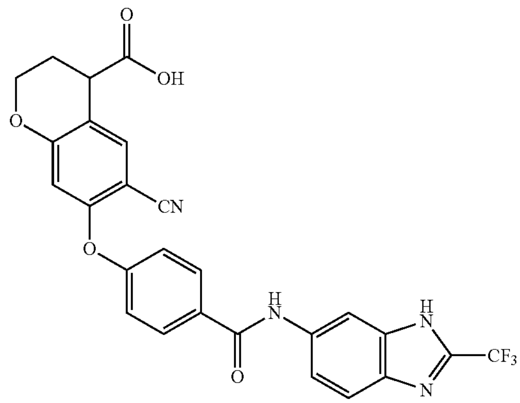 [SMILES: N#Cc1cc2c(cc1Oc1ccc(C(=O)Nc3ccc4nc(C(F)(F)F)[nH]c4c3)cc1)OCCC2C(=O)O] | 6-cyano-7-(4-(2-(trifluoromethyl)-1H-benzo[d]imidazol-6-ylcarbamoyl)phenoxy)chroman-4-carboxylic acid | m/z = 523.2 (esi, pos) |
| 192 | 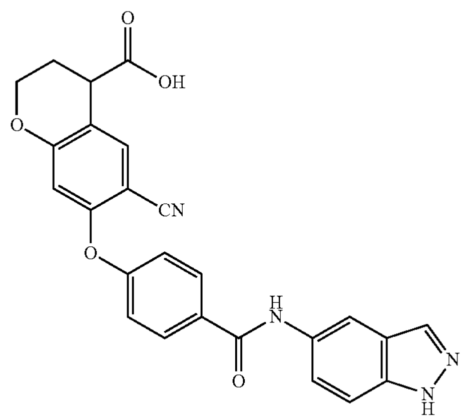 [SMILES: N#Cc1cc2c(cc1Oc1ccc(C(=O)Nc3ccc4[nH]ncc4c3)cc1)OCCC2C(=O)O] | 7-(4-(1H-indazol-5-ylcarbamoyl)phenoxy)-6-cyanochroman-4-carboxylic acid | m/z = 455.1 (esi, pos) |
| 193 | 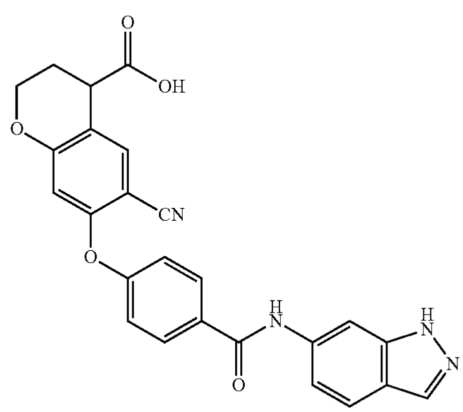 [SMILES: N#Cc1cc2c(cc1Oc1ccc(C(=O)Nc3ccc4cn[nH]c4c3)cc1)OCCC2C(=O)O] | 7-(4-(1H-indazol-6-ylcarbamoyl)phenoxy)-6-cyanochroman-4-carboxylic acid | m/z = 455.2 (esi, pos) |
| 194 | 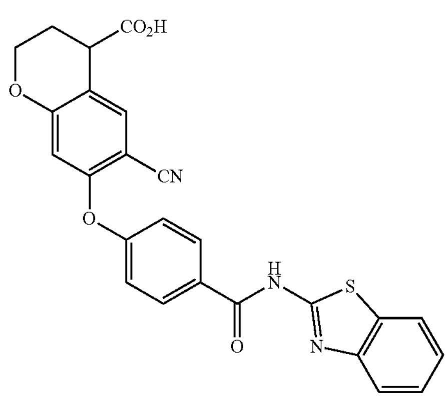 [SMILES: N#Cc1cc2c(cc1Oc1ccc(C(=O)Nc3nc4ccccc4s3)cc1)OCCC2C(=O)O] | 7-(4-(benzo[d]thiazol-2-ylcarbamoyl)phenoxy)-6-cyanochroman-4-carboxylic acid | m/z = 472.0 (apci, pos) |

| Ex. # | Structure | Name | Data |
|---|---|---|---|
| 195 | 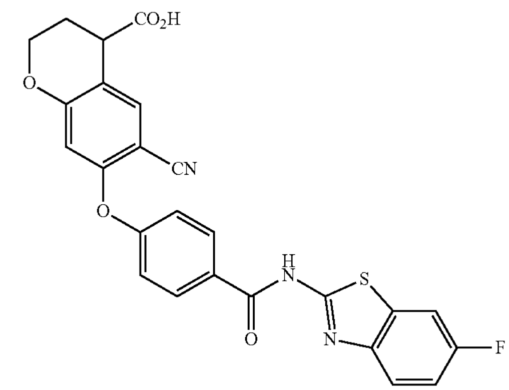 [SMILES: N#Cc1cc2c(cc1Oc1ccc(C(=O)Nc3nc4ccc(F)cc4s3)cc1)OCCC2C(=O)O] | 6-cyano-7-(4-(6-fluorobenzo[d]thiazol-2-ylcarbamoyl)phenoxy)chroman-4-carboxylic acid | m/z = 490.0 (apci, pos) |
| 196 | 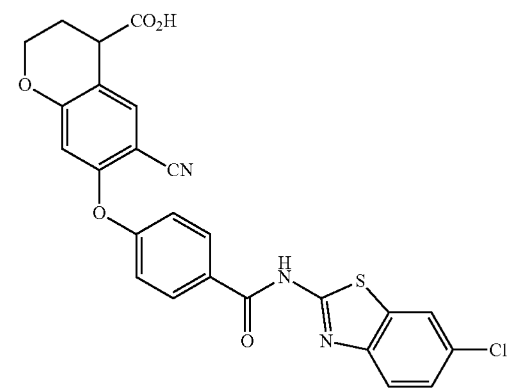 [SMILES: N#Cc1cc2c(cc1Oc1ccc(C(=O)Nc3nc4ccc(Cl)cc4s3)cc1)OCCC2C(=O)O] | 7-(4-6-chlorobenzo[d]thiazol-2-ylcarbamoyl)phenoxy)-6-cyanochroman-4-carboxylic acid | m/z = 506.0 (apci, pos) |
| 197 | 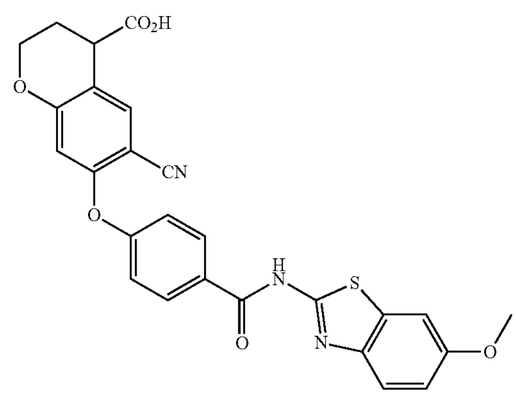 [SMILES: COc1ccc2nc(NC(=O)c3ccc(Oc4cc5c(cc4C#N)C(C(=O)O)CCO5)cc3)sc2c1] | 6-cyano-7-(4-(6-methoxybenzo[d]thiazol-2-ylcarbamoyl)phenoxy)chroman-4-carboxylic acid | m/z = 502.0 (apci, pos) |
| 198 | 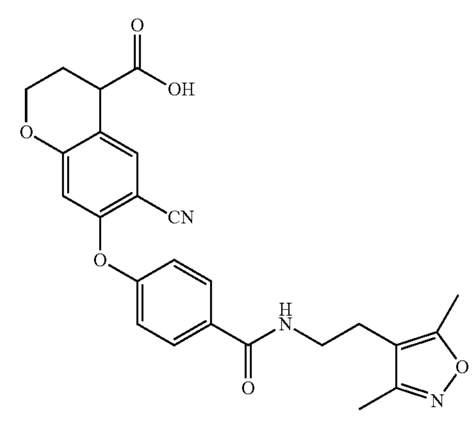 [SMILES: Cc1noc(C)c1CCNC(=O)c1ccc(Oc2cc3c(cc2C#N)C(C(=O)O)CCO3)cc1] | 6-cyano-7-(4-(2-(3,5-dimethylisoxazol-4-yl)ethylcarbamoyl)phenoxy)chroman-4-carboxylic acid | m/z = 462.0 (esi, pos) |

-continued

| Ex. # | Structure | Name | Data |
|---|---|---|---|
| 199 | 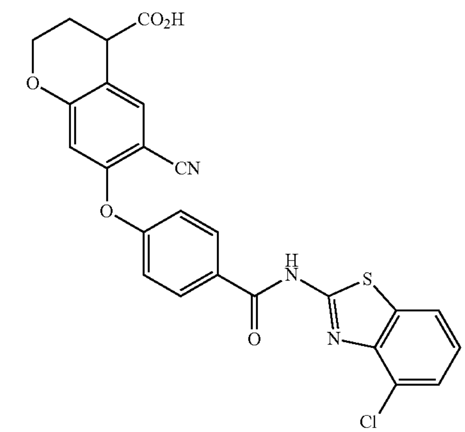 [SMILES: N#Cc1cc2c(cc1Oc1ccc(C(=O)Nc3nc4c(Cl)cccc4s3)cc1)OCCC2C(=O)O] | 7-(4-4-chlorobenzo[d]thiazol-2-ylcarbamoyl)phenoxy)-6-cyanochroman-4-carboxylic acid | m/z = 503.9 (M − 1) (apci) |
| 200 | 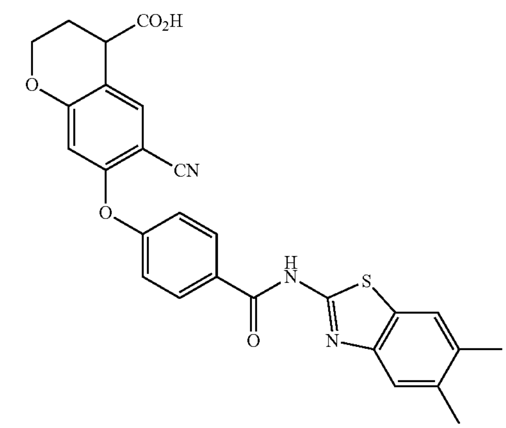 [SMILES: Cc1cc2nc(NC(=O)c3ccc(Oc4cc5c(cc4C#N)C(C(=O)O)CCO5)cc3)sc2cc1C] | 6-cyano-7-(4-(5,6-dimethylbenzo[d]thiazol-2-ylcarbamoyl)phenoxy)chroman-4-carboxylic acid | m/z = 498.0 (M − 1) (apci) |
| 201 | 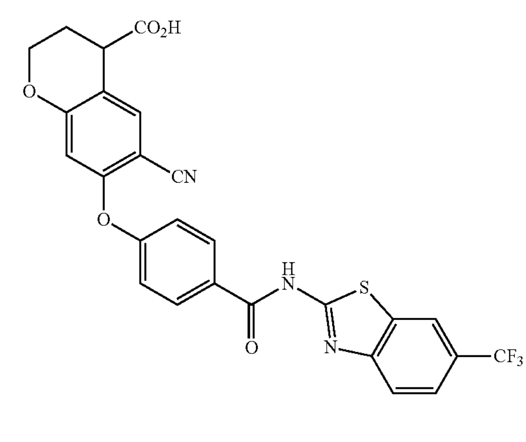 [SMILES: N#Cc1cc2c(cc1Oc1ccc(C(=O)Nc3nc4ccc(C(F)(F)F)cc4s3)cc1)OCCC2C(=O)O] | 6-cyano-7-(4-(6-(trifluoromethyl)benzo[d]thiazol-2-ylcarbamoyl)phenoxy)chroman-4-carboxylic acid | m/z = 539.9 (apci, pos) |

| Ex. # | Structure | Name | Data |
|---|---|---|---|
| 202 | 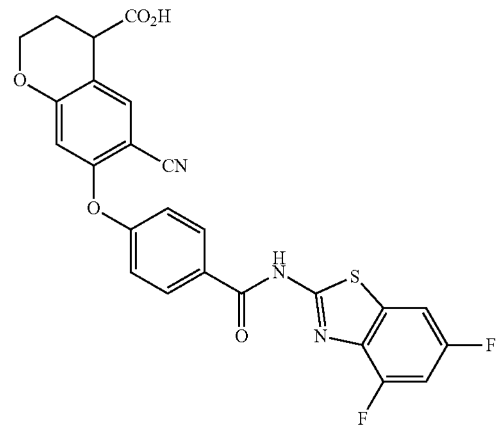 [SMILES: N#Cc1cc2c(cc1Oc1ccc(C(=O)Nc3nc4c(F)cc(F)cc4s3)cc1)OCCC2C(=O)O] | 6-cyano-7-(4-(4,6-difluorobenzo[d]thiazol-2-ylcarbamoyl)phenoxy)chroman-4-carboxylic acid | m/z = 507.9 (apci, pos) |
| 203 | 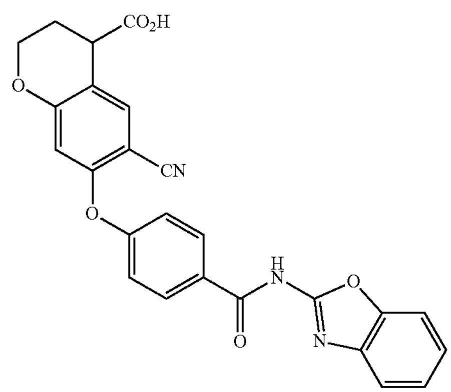 [SMILES: N#Cc1cc2c(cc1Oc1ccc(C(=O)Nc3nc4ccccc4o3)cc1)OCCC2C(=O)O] | 7-(4-(benzo[d]oxazol-2-ylcarbamoyl)phenoxy)-6-cyanochroman-4-carboxylic acid | m/z = 456.0 (esi, pos) |
| 204 | 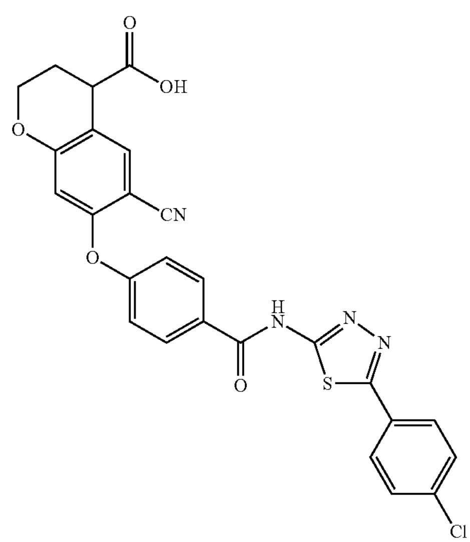 [SMILES: N#Cc1cc2c(cc1Oc1ccc(C(=O)Nc3nnc(-c4ccc(Cl)cc4)s3)cc1)OCCC2C(=O)O] | 7-(4-(5-(4-chlorophenyl)-1,3,4-thiadiazol-2-ylcarbamoyl)phenoxy)-6-cyanochroman-4-carboxylic acid | m/z = 533.1 (esi, pos) |

| Ex. # | Structure | Name | Data |
|---|---|---|---|
| 205 | 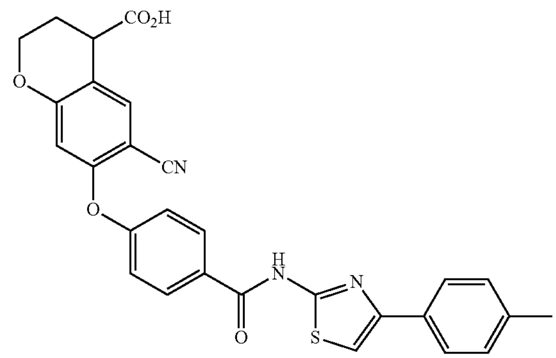 [SMILES: Cc1ccc(-c2csc(NC(=O)c3ccc(Oc4cc5c(cc4C#N)C(C(=O)O)CCO5)cc3)n2)cc1] | 6-cyano-7-(4-(4-p-tolylthiazol-2-ylcarbamoyl)phenoxy)chroman-4-carboxylic acid | m/z = 512.1 (apci, pos) |
| 206 | 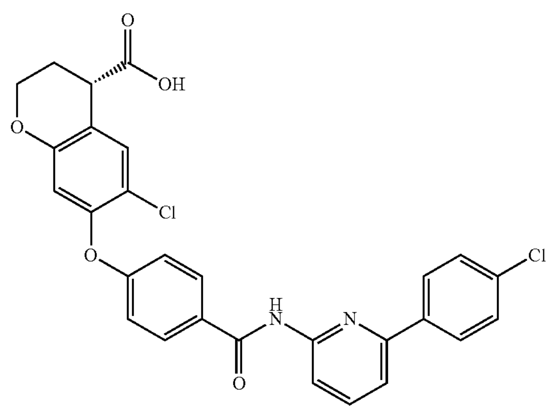 [SMILES: O=C(Nc1cccc(-c2ccc(Cl)cc2)n1)c1ccc(Oc2cc3c(cc2Cl)[C@@H](C(=O)O)CCO3)cc1] | (R)-6-chloro-7-(4-(6-(4-chlorophenyl)pyridin-2-ylcarbamoyl)phenoxy)chroman-4-carboxylic acid | m/z = 535.0 (apci, pos) |
| 207 | 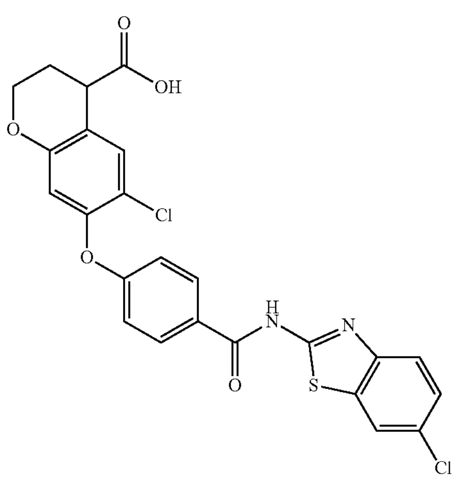 [SMILES: O=C(Nc1nc2ccc(Cl)cc2s1)c1ccc(Oc2cc3c(cc2Cl)C(C(=O)O)CCO3)cc1] | 6-chloro-7-(4-(6-chlorobenzo[d]thiazol-2-ylcarbamoyl)phenoxy)chroman-4-carboxylic acid | m/z = 514.8 (apci, posI) |

-continued

| Ex. # | Structure | Name | Data |
|---|---|---|---|
| 208 | 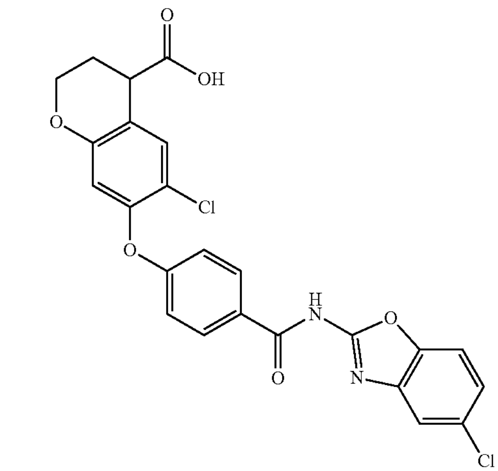 [SMILES: O=C(Nc1nc2cc(Cl)ccc2o1)c1ccc(Oc2cc3c(cc2Cl)C(C(=O)O)CCO3)cc1] | 6-chloro-7-(4-(5-chlorobenzo[d]oxazol-2-ylcarbamoyl)phenoxy)chroman-4-carboxylic acid | m/z = 498.8 (esi, pos) |
| 209 | 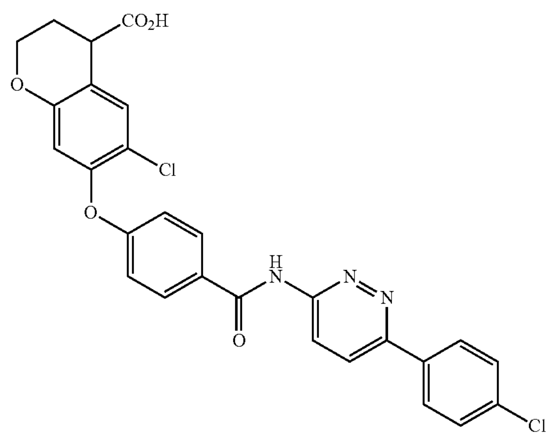 [SMILES: O=C(Nc1ccc(-c2ccc(Cl)cc2)nn1)c1ccc(Oc2cc3c(cc2Cl)C(C(=O)O)CCO3)cc1] | 6-chloro-7-(4-(6-(4-chlorophenyl)pyridazin-3-ylcarbamoyl)phenoxy)chroman-4-carboxylic acid | m/z = 536.0 (apci, pos); m/z = 535.8 (apci, neg) |
| 210 | 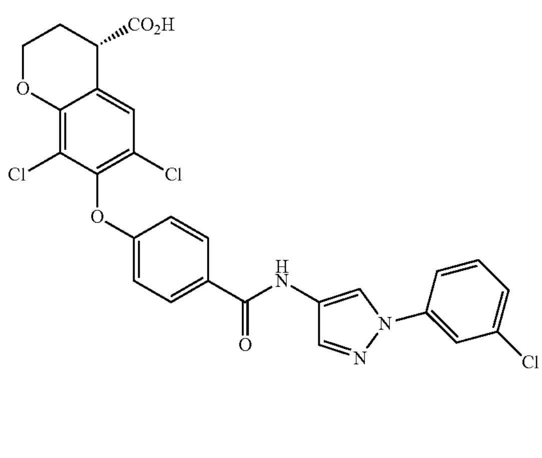 [SMILES: O=C(Nc1cnn(-c2cccc(Cl)c2)c1)c1ccc(Oc2c(Cl)cc3c(c2Cl)OCC[C@@H]3C(=O)O)cc1] | (S)-6,8-dichloro-7-(4-(1-(3-chlorophenyl)-1H-pyrazol-3-ylcarbamoyl)phenoxy)chroman-4-carboxylic acid | m/z = 556.7 (sodium salt, apci, negI) |

-continued

| Ex. # | Structure | Name | Data |
|---|---|---|---|
| 211 | 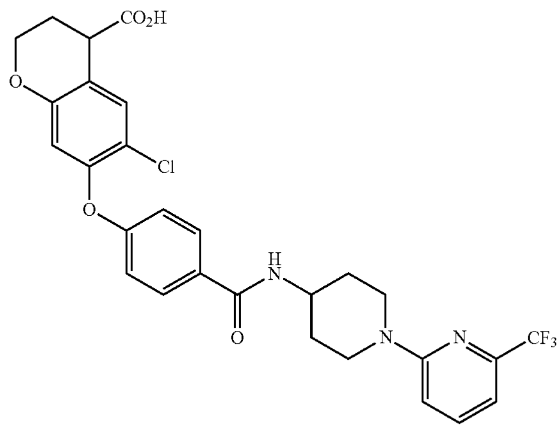 [SMILES: O=C(NC1CCN(c2cccc(C(F)(F)F)n2)CC1)c1ccc(Oc2cc3c(cc2Cl)C(C(=O)O)CCO3)cc1] | 6-chloro-7-(4-(1-(6-(trifluoromethyl)pyridin-2-yl)piperidin-4-yl)carbamoyl)phenoxy)chroman-4-carboxylic acid | m/z = 575.9 (sodium salt, apci, pos); m/z = 573.8 (sodium salt, apci, neg) |
| 212 | 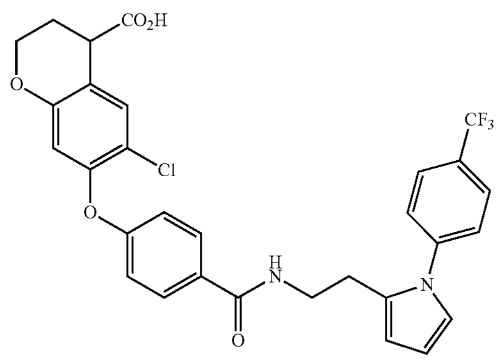 [SMILES: O=C(NCCc1cccn1-c1ccc(C(F)(F)F)cc1)c1ccc(Oc2cc3c(cc2Cl)C(C(=O)O)CCO3)cc1] | 6-chloro-7-(4-(2-(1-(4-(trifluoromethyl)phenyl)-1H-pyrrol-2-yl)ethylcarbamoyl)phenoxy)chroman-4-carboxylic acid | m/z = 584.9 (sodium salt, apci, pos); m/z = 582.8 (sodium salt, apci, neg) |
| 213 | 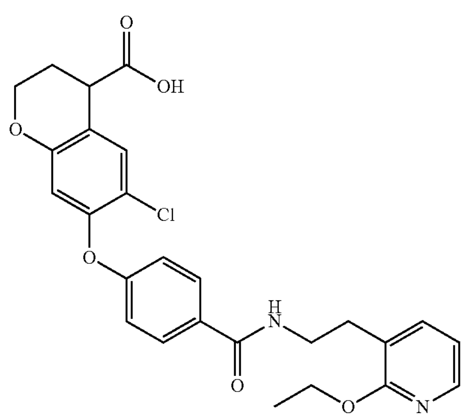 [SMILES: CCOc1ncccc1CCNC(=O)c1ccc(Oc2cc3c(cc2Cl)C(C(=O)O)CCO3)cc1] | 6-chloro-7-(4-(2-(2-ethoxypyridin-3-yl)ethylcarbamoyl)phenoxy)chroman-4-carboxylic acid | m/z = 497.1 (Sodium Salt, Pos, apci) |
| 214 | 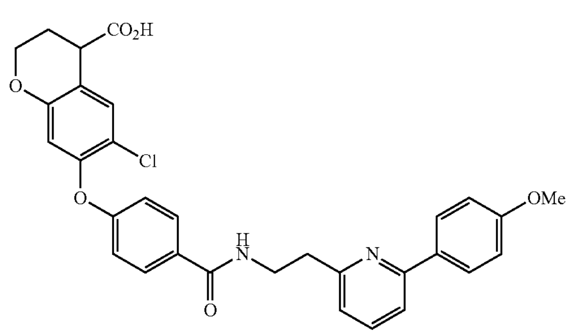 [SMILES: COc1ccc(-c2cccc(CCNC(=O)c3ccc(Oc4cc5c(cc4Cl)C(C(=O)O)CCO5)cc3)n2)cc1] | 6-chloro-7-(4-(2-(6-(4-methoxyphenyl)pyridin-2-yl)ethylcarbamoyl)phenoxy)chroman-4-carboxylic acid | m/z = 559.1 (sodium salt, apci, pos); m/z = 556.8 (sodium salt, apci, pos); |

-continued

| Ex. # | Structure | Name | Data |
|---|---|---|---|
| 215 | 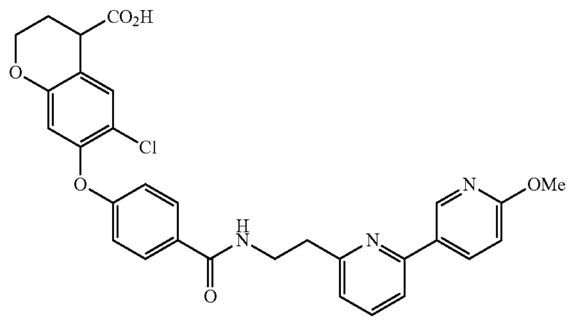 [SMILES: COc1ccc(-c2cccc(CCNC(=O)c3ccc(Oc4cc5c(cc4Cl)C(C(=O)O)CCO5)cc3)n2)cn1] | 6-chloro-7-(4-(2-(6'-methoxy-2,3'-bipyridin-6-yl)ethylcarbamoyl)phenoxy)chroman-4-carboxylic acid | m/z = 560.1 (sodium salt, apci, pos); m/z = 557.8 (sodium salt, apci, neg) |
| 216 | 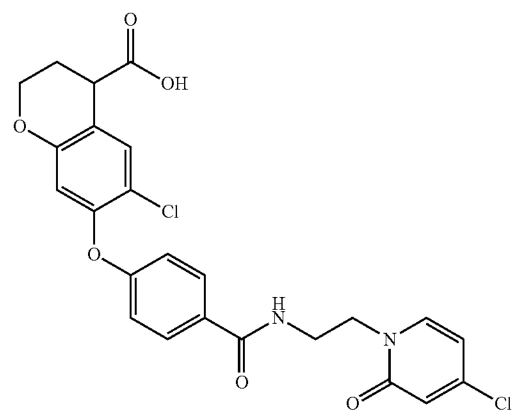 [SMILES: O=C(NCCn1ccc(Cl)cc1=O)c1ccc(Oc2cc3c(cc2Cl)C(C(=O)O)CCO3)cc1] | 6-chloro-7-(4-(2-(4-chloro-2-oxopyridin-1(2H)-yl)ethylcarbamoyl)phenoxy)chroman-4-carboxylic acid | m/z = 503.1 (Sodium Salt, Pos, APCI) |
| 217 | 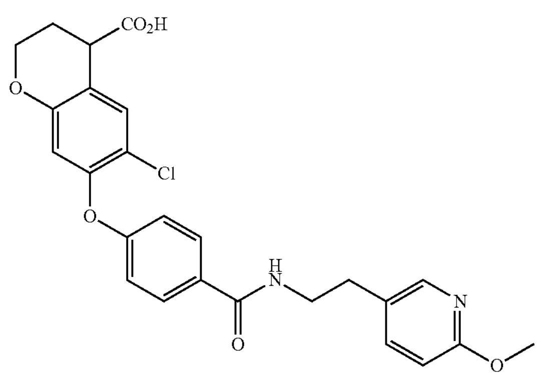 [SMILES: COc1ccc(CCNC(=O)c2ccc(Oc3cc4c(cc3Cl)C(C(=O)O)CCO4)cc2)cn1] | 6-chloro-7-(4-(2-(6-methoxypyridin-3-yl)ethylcarbamoyl)phenoxy)chroman-4-carboxylic acid | m/z = 483.2 (sodium salt, apci, pos); m/z = 480.7 (sodium salt, apci, neg) |
| 218 | 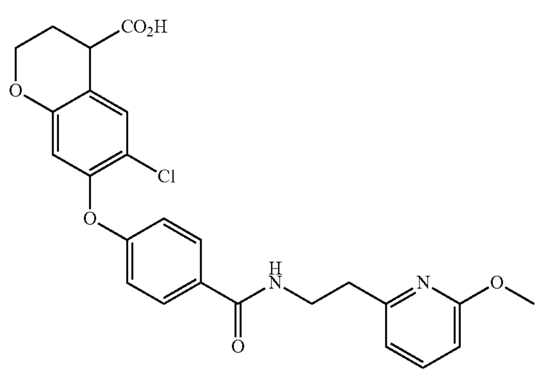 [SMILES: COc1cccc(CCNC(=O)c2ccc(Oc3cc4c(cc3Cl)C(C(=O)O)CCO4)cc2)n1] | 6-chloro-7-(4-(2-(6-methoxypyridin-2-yl)ethylcarbamoyl)phenoxy)chroman-4-carboxylic acid | m/z = 483.0 (sodium salt, apci, pos); m/z = 480.7 (sodium salt, apci, neg) |

-continued

| Ex. # | Structure | Name | Data |
|---|---|---|---|
| 219 | 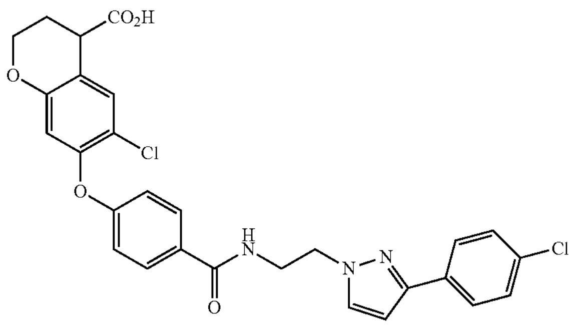 [SMILES: O=C(NCCn1ccc(-c2ccc(Cl)cc2)n1)c1ccc(Oc2cc3c(cc2Cl)C(C(=O)O)CCO3)cc1] | 6-chloro-7-(4-(2-(3-(4-chlorophenyl)-1H-pyrazol-1-yl)ethylcarbamoyl)phenoxy)chroman-4-carboxylic acid | m/z = 551.9 (sodium salt, apci, pos) |
| 220 | 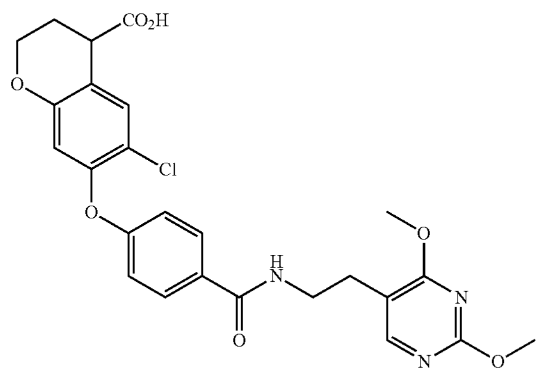 [SMILES: COc1ncc(CCNC(=O)c2ccc(Oc3cc4c(cc3Cl)C(C(=O)O)CCO4)cc2)c(OC)n1] | 6-chloro-7-(4-(2-(2,4-dimethoxypyrimidin-5-yl)ethylcarbamoyl)phenoxy)chroman-4-carboxylic acid | m/z = 514.1 (sodium salt, apci, pos); m/z = 511.7 (sodium salt, apci, neg) |
| 221 | 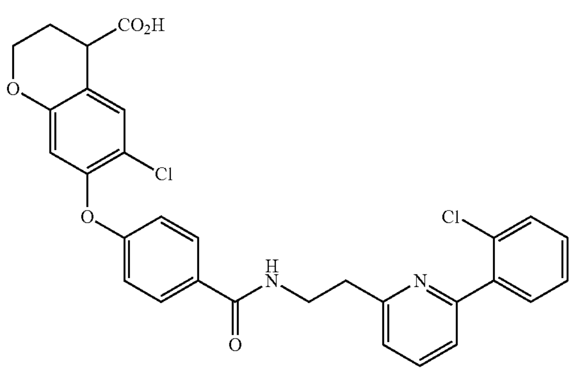 [SMILES: O=C(NCCc1cccc(-c2ccccc2Cl)n1)c1ccc(Oc2cc3c(cc2Cl)C(C(=O)O)CCO3)cc1] | 6-chloro-7-(4-(2-(6-(2-chlorophenyl)pyridin-2-yl)ethylcarbamoyl)phenoxy)chroman-4-carboxylic acid | m/z = 563.1 (apci, pos); m/z = 560.8 (apci, neg) |
| 222 | 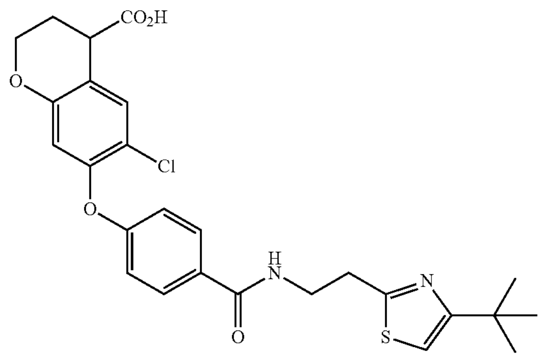 [SMILES: CC(C)(C)c1csc(CCNC(=O)c2ccc(Oc3cc4c(cc3Cl)C(C(=O)O)CCO4)cc2)n1] | 7-(4-(2-(4-tert-butylthiazol-2-yl)ethylcarbamoyl)phenoxy)-6-chlorochroman-4-carboxylic acid | m/z = 515.1 (sodium salt, apci, pos); m/z = 512.8 (sodium salt, apci, neg) |

-continued

| Ex. # | Structure | Name | Data |
|---|---|---|---|
| 223 | 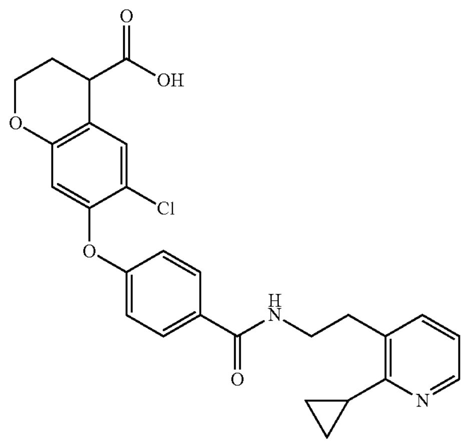 [SMILES: O=C(NCCc1cccnc1C1CC1)c1ccc(Oc2cc3c(cc2Cl)C(C(=O)O)CCO3)cc1] | 6-chloro-7-(4-(2-(2-cyclopropylpyridin-3-yl)ethylcarbamoyl)phenoxy)chroman-4-carboxylic acid | m/z = 493.1 (sodium salt, Pos, apci) |
| 224 | 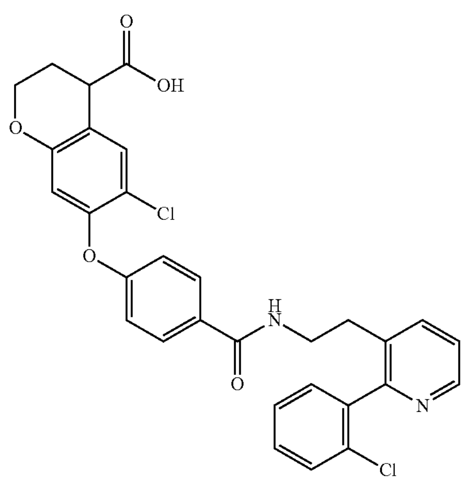 [SMILES: O=C(NCCc1cccnc1-c1ccccc1Cl)c1ccc(Oc2cc3c(cc2Cl)C(C(=O)O)CCO3)cc1] | 6-chloro-7-(4-(2-(2-(2-chlorophenyl)pyridin-3-yl)ethylcarbamoyl)phenoxy)chroman-4-carboxylic acid | m/z = 563.1 (sodium salt, Pos, apci) |
| 225 | 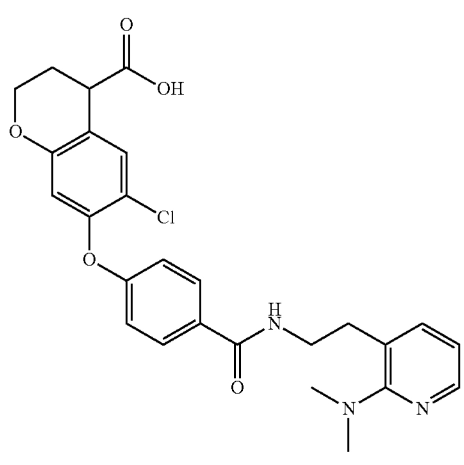 [SMILES: CN(C)c1ncccc1CCNC(=O)c1ccc(Oc2cc3c(cc2Cl)C(C(=O)O)CCO3)cc1] | 6-chloro-7-(4-(2-(2-(dimethylamino)pyridin-3-yl)ethylcarbamoyl)phenoxy)chroman-4-carboxylic acid | m/z = 496.2 (sodium salt, Pos, apci) |

| Ex. # | Structure | Name | Data |
|---|---|---|---|
| 226 | 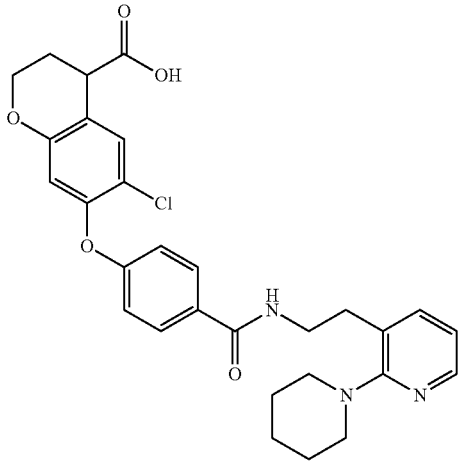 [SMILES: O=C(NCCc1cccnc1N1CCCCC1)c1ccc(Oc2cc3c(cc2Cl)C(C(=O)O)CCO3)cc1] | 6-chloro-7-(4-(2-(2-(piperidin-1-yl)pyridin-3-yl)ethylcarbamoyl)phenoxy)chroman-4-carboxylic acid | m/z = 536.2 (sodium salt, Pos, apci) |
| 227 | 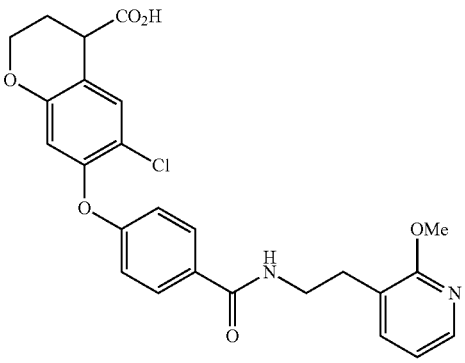 [SMILES: COc1ncccc1CCNC(=O)c1ccc(Oc2cc3c(cc2Cl)C(C(=O)O)CCO3)cc1] | 6-chloro-7-(4-(2-(2-methoxypyridin-3-yl)ethylcarbamoyl)phenoxy)chroman-4-carboxylic acid | m/z = 483.1 (sodium salt, apci, pos); m/z = 480.7 (sodium salt, apci, neg) |
| 228 | 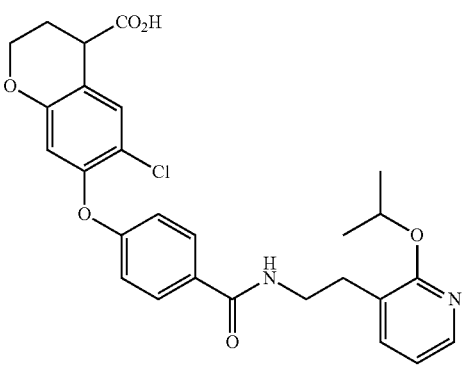 [SMILES: CC(C)Oc1ncccc1CCNC(=O)c1ccc(Oc2cc3c(cc2Cl)C(C(=O)O)CCO3)cc1] | 6-chloro-7-(4-(2-(2-isopropoxypyridin-3-yl)ethylcarbamoyl)phenoxy)chroman-4-carboxylic acid | m/z = 510.9 (sodium salt, apci, pos); m/z = 508.8 (sodium salt, apci, neg) |

What is claimed is:

1. A compound of general formula (I)

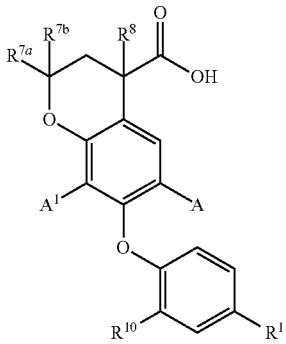

or a pharmaceutically acceptable salt thereof, wherein:
A is H, CN, Cl, F, cyclopropyl, (1-4 C)alkyl or OMe;
$A^1$ is H, Cl, Br, F, cyclopropyl, (1-4 C)alkyl or OMe;
$R^1$ is —W-$L^1$-hetAr$^1$;
W is —CONR$^{3a}$— or —NR$^{3b}$CO—;
$R^{3a}$ and $R^{3b}$ are each H or methyl;
$L^1$ is a —(CR$^a$R$^b$)$_n$— or

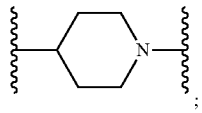 [SMILES: *C1CCN(*)CC1]

;

n is 0 or 2;
$R^a$ and $R^b$ are independently H, F, methyl, or cyclopropyl, or
$R^a$ and $R^b$ together with the carbon to which they are attached form a cyclopropyl ring;
hetAr$^1$ is heteroaryl ring having the structure:

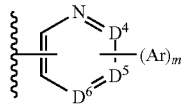

wherein m is 0 or 1 and said heteroaryl ring is optionally substituted with one or more R$^c$ substituents,
zero or one of D$^4$, D$^5$ and D$^6$ is N, the remainder being CH;
each R$^c$ is independently selected from halogen, CF$_3$, (1-6C)alkyl, —O(1-6C alkyl), cyclopropyl, —O—(CH$_2$CH$_2$)OMe, —S(1-6C alkyl), di(1-6C alkyl)amino, and a 5-6 membered azacycle;
Ar is phenyl optionally substituted with one or more R$^d$ substituents;
each R$^d$ is independently selected from (1-6C)alkyl, —O(1-6C)alkyl, halogen, —S(1-6C alkyl), and CF$_3$,
or two adjacent R$^d$ substituents together with the atoms to which they are attached form a 5-6 membered oxacyclic ring;
R$^{7a}$, R$^{7b}$ and R$^8$ are independently H or methyl; and
R$^{10}$ is H, Me or NH$_2$.

2. A compound according to claim 1, wherein:
A is H, CN, Cl, F, cyclopropyl, (1-4 C)alkyl or OMe;
$A^1$ is H, Cl, Br, F, cyclopropyl, (1-4 C)alkyl, or OMe;
$R^1$ is —W-$L^1$-hetAr$^1$;
W is —CONR$^{3a}$— or —NR$^{3b}$CO—;
$R^{3a}$ and $R^{3b}$ are each H or methyl;
$L^1$ is —(CR$^a$R$^b$)$_n$—;
n is 0 or 2;
$R^a$ and $R^b$ are independently H, F, methyl, or cyclopropyl, or
$R^a$ and $R^b$ together with the carbon to which they are attached form a cyclopropyl ring;
hetAr$^1$ is heteroaryl ring having the structure:

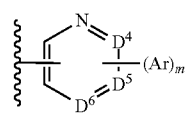

wherein m is 0 or 1 and said heteroaryl ring is optionally substituted with one or more R$^c$ substituents,
zero or one of D$^4$, D$^5$ and D$^6$ is N, the remainder being CH;
each R$^c$ is independently selected from halogen, CF$_3$, (1-6C)alkyl, —O(1-6C alkyl), cyclopropyl, —O—(CH$_2$CH$_2$)OMe, —S(1-6C alkyl) and di(1-6C alkyl)amino;
Ar is phenyl optionally substituted with one or more R$^d$ substituents;
each R$^d$ is independently selected from (1-6C)alkyl, —O(1-6C)alkyl, halogen, —S(1-6C alkyl), and CF$_3$,
or two adjacent R$^d$ substituents together with the atoms to which they are attached form a 5-6 membered oxacyclic ring;
R$^{7a}$, R$^{7b}$ and R$^8$ are independently H or methyl; and
R$^{10}$ is H, Me or NH$_2$.

3. A compound of claim 1, wherein —W-$L^1$- is —NHCO, —NHCOCH$_2$CH$_2$—, —CONH—, —CONHCH$_2$CH$_2$—, CONHCH$_2$cyclopropylidene-, or CONHcyclopropylidene-.

4. A compound according to claim 1, wherein —W-$L^1$- is —CONH— or CONHCH$_2$CH$_2$—.

5. A compound of claim 1, wherein m is 1.

6. A compound according to claim 1, wherein A is Cl.

7. A compound according to claim 1, wherein A is CN, Cl, or cyclopropyl and $A^1$ is H, cyclopropyl, Br or Cl.

8. A compound according to claim 1, wherein R$^{7a}$; and R$^{7b}$ are each hydrogen.

9. A compound according to claim 1, wherein R$^8$ is hydrogen.

10. A compound according to claim 1, wherein R$^{10}$ is hydrogen.

11. A pharmaceutical composition, which comprises a compound of Formula I as defined in claim 1, or a pharmaceutically acceptable salt thereof, and a pharmaceutically acceptable diluent or carrier.

12. A process for preparing a compound of claim 1 or a pharmaceutically acceptable salt thereof, which comprises:

(a) for a compound of Formula I in which A is CN and $A^1$ is hydrogen, reacting a corresponding compound having the formula (II):

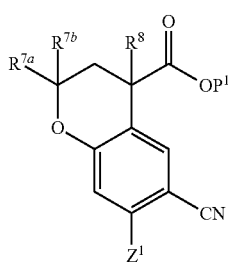

(II)

in which P¹ represents a hydrogen atom or a (1-6C)alkyl group and Z¹ represents a halogen or triflate, with a corresponding compound having the formula (III)

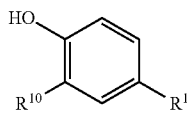

(III)

in the presence of a base; or (b) for a compound of Formula I in which A is H, Cl, (1-4C alkyl), OMe or cyclopropyl and A¹ is H, Cl, (1-4C alkyl), OMe or cyclopropyl, reacting a corresponding compound having the formula (IV)

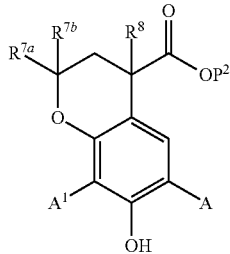

(IV)

in which P² is as defined for P¹, with a corresponding compound having the formula (V)

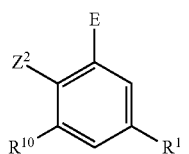

(V)

wherein E is an NO₂ group and Z² is a halogen, in the presence of an alkali metal carbonate, and if desired removing said NO₂ group; or (c) for a compound of Formula I in which A is H, Cl, (1-4C alkyl) or cyclopropyl and A¹ is (1-4C alkyl), Cl, Br or cyclopropyl, reacting a corresponding compound having the formula (VI)

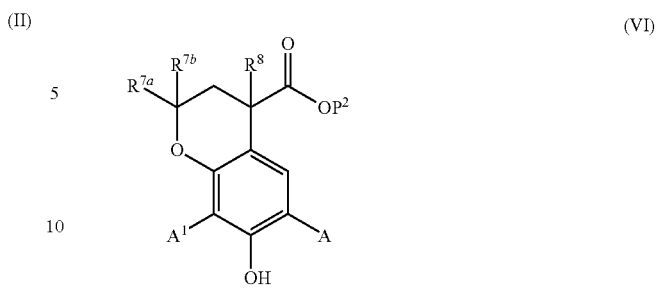

(VI)

in which P² is as defined for P¹, with a corresponding compound having the formula (VII)

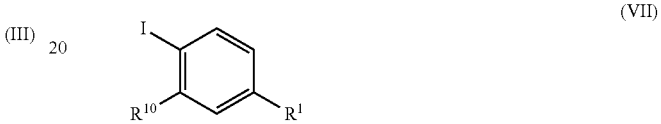

(VII)

in the presence of a copper salt or a palladium catalyst in the presence of a ligand selected from 2,2,6,6-tetramethyl-3,5-heptanedione, pyridine-type ligands, and phosphine-type ligands, and an alkali metal carbonate; or (d) for a compound of Formula I in which hetAr¹ is a heteroaryl ring having the structure

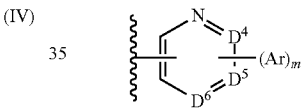

where m is 1, reacting a corresponding compound having the formula (VIIIa)

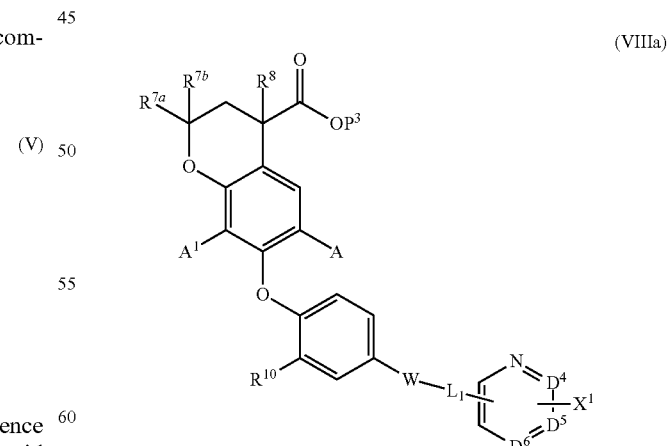

(VIIIa)

where P³ is as defined for P¹, and X¹ is halogen or triflate, with a compound having the formula ArB(OH)₂ or ArZnBr in the presence of a palladium catalyst and an alkali metal carbonate; or (e) reacting a corresponding compound of formula (IX)

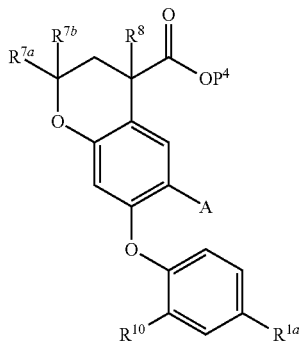

(IX)

in which $P^4$ is as defined for $P^1$, and $R^{1a}$ represents H—$X^a$H in which $X^a$ is HN or OC(=O), or an acid chloride thereof; with a compound of formula (X)

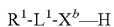 (X)

in which $X^b$ represents C(=O)O or NH, or a reactive derivative thereof;

(f) for a compound of Formula I where $L^1$ is a bond, reacting a corresponding compound having the formula (XI)

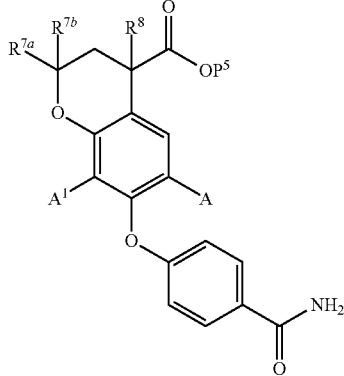

(XI)

in which $P^5$ is as defined for $P^1$, with a compound having the formula $X^2$—$R^1$, where $X^2$ is a triflate or halogen, in the presence of a palladium catalyst and a phosphine-type ligand;

(g) for a compound of Formula I where A is cyclopropyl, $A^1$ is cyclopropyl, and W is C(=O)NH, reacting a corresponding compound having the formula (XII)

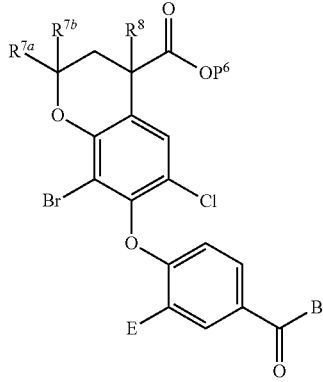

(XII)

wherein $P^6$ is as defined for $P^1$, E is an $NO_2$ group, and B is —O-tert-butyl, —$NH_2$ or —NH-$L^1$-$R^1$, with about 4 equivalents of cyclopropylboronic acid in the presence of an alkali metal phosphate, a metal catalyst and a ligand at temperatures between about 100° C. and 150° C., followed by removal of the $NO_2$ group, if desired, and reacting with a compound having the formula $H_2N$-$L^1$-$R^1$ when B is O-tBu or reacting with a compound having the formula $X^3$-$L^1$-$R^1$ when B is $NH_2$, where $X^3$ is a triflate or halogen; or (h) for a compound of Formula I where A is cyclopropyl, $A^1$ is hydrogen, and W is C(=O)NH, reacting a corresponding compound having the formula (XIII)

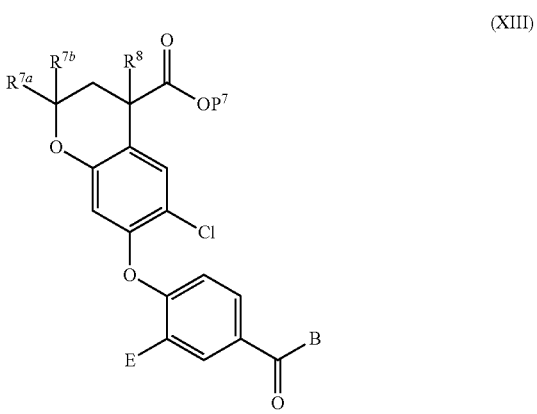

(XIII)

wherein $P^7$ is as defined for $P^1$, E is an $NO_2$ group, and B is O-tertbutyl, $NH_2$ or NH-$L^1$-$R^1$, with about 3 equivalents of cyclopropylboronic acid in the presence of a an alkali metal phosphate, a metal catalyst and a ligand at temperatures between about 90° C. and 150° C., followed by removal of the $NO_2$ group, if desired, and reacting with a compound having the formula $H_2N$-$L^1$-$R^1$ when B is O-tBu or reacting with a compound having the formula $X^3$-$L^1$-$R^1$ when B is $NH_2$, where $X^3$ is a triflate or halogen; and removing any protecting group or groups and, if desired, forming a salt.

13. A compound according to claim 1, selected from:
7-(4-((5-(Trifluoromethyl)pyridin-2-yl)carbamoyl)phenoxy)-6-cyanochroman-4-carboxylic acid;
7-(4-(5-Chloropyridin-2-ylcarbamoyl)phenoxy)-6-cyanochroman-4-carboxylic acid;
7-(4-((6-(Trifluoromethyl)pyridin-3-yl)carbamoyl)phenoxy)-6-cyanochroman-4-carboxylic acid;
6-Cyano-7-(4-(2-(6-(trifluoromethyl)pyridin-3-yl)ethylcarbamoyl)phenoxy)chroman-4-carboxylic acid;
6-Cyano-7-(4-(6-(3,4-dimethylphenyl)pyridin-2-ylcarbamoyl)phenoxy)chroman-4-carboxylic acid;
6-Cyano-7-(2-methyl-4-(6-(trifluoromethyl)pyridin-3-ylcarbamoyl)phenoxy)chroman-4-carboxylic acid;
6-chloro-7-(4-(6-phenylpyridin-2-ylcarbamoyl)phenoxy)chroman-4-carboxylic acid;
6-Chloro-7-(4-(6-(trifluoromethyl)pyridin-2-ylcarbamoyl)phenoxy)chroman-4-carboxylic acid;
6-Chloro-7-(4-(6-(trifluoromethyl)pyridin-3-ylcarbamoyl)phenoxy)chroman-4-carboxylic acid;
6-Chloro-7-(4-(4-(trifluoromethyl)pyridin-2-ylcarbamoyl)phenoxy)chroman-4-carboxylic acid;
6-Chloro-7-(4-(6-phenylpyrazin-2-ylcarbamoyl)phenoxy)chroman-4-carboxylic acid;
6-Chloro-7-(4-(6-(4-chlorophenyl)pyridin-2-ylcarbamoyl)phenoxy)chroman-4-carboxylic acid;
6-Chloro-7-(4-(6-(3-chlorophenyl)pyridin-2-ylcarbamoyl)phenoxy)chroman-4-carboxylic acid;

6-Cyano-7-(4-(2-(5-(trifluoromethyl)pyridin-2-yl)ethylcarbamoyl)phenoxy)chroman-4-carboxylic acid;
6-Cyano-7-(4-(6-(3,4-dimethylphenyl)pyridin-2-ylcarbamoyl)phenoxy)chroman-4-carboxylic acid;
6-Cyano-7-(4-(6-(2,3-dimethylphenyl)pyridin-2-ylcarbamoyl)-phenoxy)-chroman-4-carboxylic acid;
6-Cyano-7-(4-(6-(3-(trifluoromethyl)phenyl)pyridin-2-ylcarbamoyl)-phenoxy)chroman-4-carboxylic acid;
6-Cyano-7-(4-(6-(4-(trifluoromethyl)phenyl)pyridin-2-ylcarbamoyl)-phenoxy)chroman-4-carboxylic acid;
6-Chloro-7-(4-(6-(4-chlorophenyl)-5-fluoropyridin-2-ylcarbamoyl)phenoxy)chroman-4-carboxylic acid;
6-Cyano-7-(4-(6-(2,4-dichlorophenyl)pyridin-2-ylcarbamoyl)phenoxy)chroman-4-carboxylic acid;
7-(4-(6-(3-Chlorophenyl)pyridin-2-ylcarbamoyl)phenoxy)-6-cyanochroman-4-carboxylic acid;
7-(4-(6-(4-Chlorophenyl)pyridin-2-ylcarbamoyl)phenoxy)-6-cyanochroman-4-carboxylic acid;
6-Chloro-7-(4-(6-(3,4-dichlorophenyl)pyridin-2-ylcarbamoyl)phenoxy)chroman-4-carboxylic acid;
6-Chloro-7-(4-(6-(4-chloro-3-(trifluoromethyl)phenyl)pyridin-2-ylcarbamoyl)phenoxy)chroman-4-carboxylic acid;
6-Chloro-7-(4-(6-(2-chlorophenyl)pyridin-2-ylcarbamoyl)phenoxy)chroman-4-carboxylic acid;
6-Chloro-7-(4-(6-p-tolylpyridin-2-ylcarbamoyl)phenoxy)chroman-4-carboxylic acid;
6-Chloro-7-(4-(6-(4-methoxyphenyl)pyridin-2-ylcarbamoyl)phenoxy)chroman-4-carboxylic acid;
6-chloro-7-(4-(6-(2-chloro-4-(trifluoromethyl)phenyl)pyridazin-3-ylcarbamoyl)phenoxy)chroman-4-carboxylic acid;
6-chloro-7-(4-(6-(3-chloro-4-(trifluoromethyl)phenyl)pyridazin-3-ylcarbamoyl)phenoxy)chroman-4-carboxylic acid;
6-chloro-7-(4-(5-(4-(trifluoromethyl)phenyl)pyrazin-2-ylcarbamoyl)phenoxy)chroman-4-carboxylic acid;
6-chloro-7-(4-(6-p-tolylpyridazin-3-ylcarbamoyl)phenoxy)chroman-4-carboxylic acid;
6-chloro-7-(4-(6-(4-methoxyphenyl)pyridazin-3-ylcarbamoyl)phenoxy)chroman-4-carboxylic acid;
6-chloro-7-(4-(6-(4-(methylthio)phenyl)pyridazin-3-ylcarbamoyl)phenoxy)chroman-4-carboxylic acid;
6-chloro-7-(4-(6-(3,4-dichlorophenyl)pyridazin-3-ylcarbamoyl)phenoxy)chroman-4-carboxylic acid;
6-chloro-7-(4-(6-(4-fluorophenyl)pyridazin-3-ylcarbamoyl)phenoxy)chroman-4-carboxylic acid;
6-chloro-7-(4-(6-(4-chloro-3-fluorophenyl)pyridazin-3-ylcarbamoyl)phenoxy)chroman-4-carboxylic acid;
6-chloro-7-(4-(6-(2-fluoro-4-(trifluoromethyl)phenyl)pyridazin-3-ylcarbamoyl)phenoxy)chroman-4-carboxylic acid;
6-chloro-7-(4-(6-(2,4-difluorophenyl)pyridazin-3-ylcarbamoyl)phenoxy)chroman-4-carboxylic acid;
6-chloro-7-(4-(6-(4-chloro-2-fluorophenyl)pyridazin-3-ylcarbamoyl)phenoxy)chroman-4-carboxylic acid;
6-Chloro-7-(4-(6-(3-(trifluoromethyl)phenyl)pyridin-3-ylcarbamoyl)phenoxy)chroman-4-carboxylic acid;
6-Chloro-7-(4-(6-(4-(trifluoromethyl)phenyl)pyridin-3-ylcarbamoyl)phenoxy)chroman-4-carboxylic acid;
6-Chloro-7-(4-(6-ethoxypyridin-2-ylcarbamoyl)phenoxy)chroman-4-carboxylic acid;
6-chloro-7-(4-(6-(4-chlorophenyl)pyrazin-2-ylcarbamoyl)phenoxy)chroman-4-carboxylic acid;
6-chloro-7-(4-(2-(2-methoxy-6-(trifluoromethyl)pyridin-3-yl)ethylcarbamoyl)phenoxy)chroman-4-carboxylic acid;
6-Chloro-7-(4-(6-(3,4-difluorophenyl)pyridin-2-ylcarbamoyl)phenoxy)chroman-4-carboxylic acid;
6-Chloro-7-(4-(6-(2,4-difluorophenyl)pyridin-2-ylcarbamoyl)phenoxy)chroman-4-carboxylic acid;
6-Chloro-7-(4-(6-(4-(methylthio)phenyl)pyridin-2-ylcarbamoyl)phenoxy)chroman-4-carboxylic acid;
6-Chloro-7-(4-(6-(4-fluoro-3-methylphenyl)pyridin-2-ylcarbamoyl)phenoxy)chroman-4-carboxylic acid;
7-(4-(6-(4-tert-Butylphenyl)pyridin-2-ylcarbamoyl)phenoxy)-6-chlorochroman-4-carboxylic acid;
6-Chloro-7-(4-(6-(4-chloro-3-fluorophenyl)pyridin-2-ylcarbamoyl)phenoxy)chroman-4-carboxylic acid;
6-chloro-7-(4-(6-(4-chloro-2-fluorophenyl)pyridin-2-ylcarbamoyl)phenoxy)chroman-4-carboxylic acid;
6-Chloro-7-(4-(6-(3-fluoro-4-methylphenyl)pyridin-2-ylcarbamoyl)phenoxy)chroman-4-carboxylic acid;
6-chloro-7-(4-(6-(3,5-difluorophenyl)pyridin-2-ylcarbamoyl)phenoxy)chroman-4-carboxylic acid;
6-chloro-7-(4-(6-(2,3-difluorophenyl)pyridin-2-ylcarbamoyl)phenoxy)chroman-4-carboxylic acid;
7-(4-(6-(tert-Butylthio)pyridin-2-ylcarbamoyl)phenoxy)-6-chlorochroman-4-carboxylic acid;
6-Chloro-7-(4-(6-(3-chlorophenyl)pyrazin-2-ylcarbamoyl)phenoxy)chroman-4-carboxylic acid;
6-Chloro-7-(4-(6-(4-(trifluoromethyl)phenyl)pyrazin-2-ylcarbamoyl)phenoxy)chroman-4-carboxylic acid;
6-chloro-7-(4-(6-(3-(trifluoromethyl)phenyl)pyrazin-2-ylcarbamoyl)phenoxy)chroman-4-carboxylic acid;
6-Chloro-7-(4-(5-(4-chlorophenyl)pyrazin-2-ylcarbamoyl)phenoxy)chroman-4-carboxylic acid;
6-Chloro-7-(4-(5-(3-chlorophenyl)pyrazin-2-ylcarbamoyl)phenoxy)chroman-4-carboxylic acid;
6-Chloro-7-(4-(6-(3-chlorophenyl)pyridazin-3-ylcarbamoyl)phenoxy)chroman-4-carboxylic acid;
6-chloro-7-(4-(6-(4-(trifluoromethyl)phenyl)pyridazin-3-ylcarbamoyl)phenoxy)chroman-4-carboxylic acid;
6-chloro-7-(4-(6-(3-(trifluoromethyl)phenyl)pyridazin-3-ylcarbamoyl)phenoxy)chroman-4-carboxylic acid;
6-chloro-7-(4-(2-(4-chlorophenyl)pyrimidin-4-ylcarbamoyl)phenoxy)chroman-4-carboxylic acid;
6-chloro-7-(4-(6-(4-chlorophenyl)-2-methylpyrimidin-4-ylcarbamoyl)phenoxy) chroman-4-carboxylic acid;
6-chloro-7-(4-(6-methyl-2-(4-(trifluoromethyl)phenyl)pyrimidin-4-ylcarbamoyl)phenoxy)chroman-4-carboxylic acid;
6-chloro-7-(4-(6-(2,4-dichlorophenyl)pyridin-2-ylcarbamoyl)phenoxy)chroman-4-carboxylic acid;
6-chloro-7-(4-(6-(4-chloro-2-methoxyphenyl)pyridin-2-ylcarbamoyl)phenoxy)chroman-4-carboxylic acid;
6-Chloro-7-(4-(6-isobutylpyridin-2-ylcarbamoyl)phenoxy)chroman-4-carboxylic acid;
8-bromo-6-chloro-7-(4-(6-(4-chlorophenyl)pyridin-2-ylcarbamoyl)phenoxy)chroman-4-carboxylic acid;
7-(4-(6-(4-chlorophenyl)pyridin-2-ylcarbamoyl)phenoxy)-6,8-dicyclopropylchroman-4-carboxylic acid;
6-chloro-7-(4-(6-(4-chlorophenyl)pyridin-2-ylcarbamoyl)phenoxy)-8-cyclopropylchroman-4-carboxylic acid;
6-Chloro-7-(4-(6-(4-fluorophenyl)pyridin-2-ylcarbamoyl)phenoxy)chroman-4-carboxylic acid;
6-Chloro-7-(4-(6-(4-(trifluoromethyl)phenyl)pyridin-2-ylcarbamoyl)phenoxy)chroman-4-carboxylic acid;
6-Chloro-7-(4-(6-cyclopropylpyridin-2-ylcarbamoyl)phenoxy)chroman-4-carboxylic acid;
6-Chloro-7-(4-(6-(3-(trifluoromethyl)phenyl)pyridin-2-ylcarbamoyl)phenoxy)chroman-4-carboxylic acid;

7-(4-(6-tert-Butylpyridin-2-ylcarbamoyl)phenoxy)-6-chlorochroman-4-carboxylic acid;
6-Chloro-7-(4-(5-(4-chlorophenyl)pyridin-2-ylcarbamoyl)phenoxy)chroman-4-carboxylic acid;
6-Chloro-7-(4-(5-(3-chlorophenyl)pyridin-2-ylcarbamoyl)phenoxy)chroman-4-carboxylic acid;
6-Chloro-7-(4-(5-(2-chlorophenyl)pyridin-2-ylcarbamoyl)phenoxy)chroman-4-carboxylic acid;
6-Chloro-7-(4-(5-(4-(trifluoromethyl)phenyl)pyridin-2-ylcarbamoyl)phenoxy)chroman-4-carboxylic acid;
6-Chloro-7-(4-(5-(3-(trifluoromethyl)phenyl)pyridin-2-ylcarbamoyl)phenoxy)chroman-4-carboxylic acid;
6-Chloro-7-(4-(4-(4-chlorophenyl)pyridin-2-ylcarbamoyl)phenoxy)chroman-4-carboxylic acid;
6-Chloro-7-(4-(4-(3-chlorophenyl)pyridin-2-ylcarbamoyl)phenoxy)chroman-4-carboxylic acid;
6-Chloro-7-(4-(4-(2-chlorophenyl)pyridin-2-ylcarbamoyl)phenoxy)chroman-4-carboxylic acid;
6-Chloro-7-(4-(6-(4-chlorophenyl)pyridin-3-ylcarbamoyl)phenoxy)chroman-4-carboxylic acid;
6-Chloro-7-(4-(6-(3-chlorophenyl)pyridin-3-ylcarbamoyl)phenoxy)chroman-4-carboxylic acid;
6-Chloro-7-(4-(6-(2-chlorophenyl)pyridin-3-ylcarbamoyl)phenoxy)chroman-4-carboxylic acid;
6-Chloro-7-(4-(5-(4-chlorophenyl)pyridin-3-ylcarbamoyl)phenoxy)chroman-4-carboxylic acid;
6-Chloro-7-(4-(5-(3-chlorophenyl)pyridin-3-ylcarbamoyl)phenoxy)chroman-4-carboxylic acid;
6-Chloro-7-(4-(2-(4-chlorophenyl)pyridin-4-ylcarbamoyl)phenoxy)chroman-4-carboxylic acid;
6-Chloro-7-(4-(2-(3-chlorophenyl)pyridin-4-ylcarbamoyl)phenoxy)chroman-4-carboxylic acid;
6-Chloro-7-(4-(4-(4-(trifluoromethyl)phenyl)pyrimidin-2-ylcarbamoyl)phenoxy)chroman-4-carboxylic acid;
6-Chloro-7-(4-(4-(3-(trifluoromethyl)phenyl)pyrimidin-2-ylcarbamoyl)phenoxy)chroman-4-carboxylic acid;
6-Chloro-7-(4-(4-(4-chlorophenyl)pyrimidin-2-ylcarbamoyl)phenoxy)chroman-4-carboxylic acid;
6-Chloro-7-(4-(4-(3-chlorophenyl)pyrimidin-2-ylcarbamoyl)phenoxy)chroman-4-carboxylic acid;
6-Chloro-7-(4-(5-(3-chlorophenyl)pyrimidin-2-ylcarbamoyl)phenoxy)chroman-4-carboxylic acid;
6-Chloro-7-(4-(2-(3-chlorophenyl)pyrimidin-5-ylcarbamoyl)phenoxy)chroman-4-carboxylic acid;
6,8-Dichloro-7-(4-(6-(4-chlorophenyl)pyrazin-2-ylcarbamoyl)phenoxy)chroman-4-carboxylic acid;
6,8-Dichloro-7-(4-(2-(4-chlorophenyl)pyrimidin-4-ylcarbamoyl)phenoxy)chroman-4-carboxylic acid;
6-chloro-7-(4-(2-(3,5-dichloropyridin-2-yl)ethylcarbamoyl)phenoxy)chroman-4-carboxylic acid;
6-chloro-7-(4-(2-(2-(dimethylamino)-6-(trifluoromethyl)pyridin-3-yl)ethylcarbamoyl)phenoxy)chroman-4-carboxylic acid;
6-chloro-7-(4-(2-(2,6-dimethoxypyridin-3-yl)ethylcarbamoyl)phenoxy)chroman-4-carboxylic acid;
6-Chloro-7-(4-(6-(4-chlorophenyl)pyridin-2-ylcarbamoyl)phenoxy)chroman-4-carboxylic acid, Enantiomer 1;
6-Chloro-7-(4-(6-(4-chlorophenyl)pyridin-2-ylcarbamoyl)phenoxy)chroman-4-carboxylic acid, Enantiomer 2;
6,8-dichloro-7-(4-(6-(4-chlorophenyl)pyridin-2-ylcarbamoyl)phenoxy)-chroman-4-carboxylic acid;
6,8-dichloro-7-(4-(6-(3-chlorophenyl)pyridin-3-ylcarbamoyl)phenoxy)-chroman-4-carboxylic acid;
Enantiomer 2 of 6-Chloro-7-(4-(6-(4-chlorophenyl)pyridin-2-ylcarbamoyl)phenoxy)chroman-4-carboxylic acid;
6-Chloro-7-(4-(2-(6-cyclopropyl-2-methoxypyridin-3-yl)ethylcarbamoyl)phenoxy)chroman-4-carboxylic acid;
Enantiomer 2 of 6-Chloro-7-(4-(6-(4-(trifluoromethyl)phenyl)pyridazin-3-ylcarbamoyl)phenoxy)chroman-4-carboxylic acid;
6-Chloro-7-(4-(2-(2-cyclopropyl-6-(trifluoromethyl)pyridin-3-yl)ethylcarbamoyl)phenoxy)chroman-4-carboxylic acid;
6-chloro-7-(4-(2-(6-cyclopropyl-2-(dimethylamino)pyridin-3-yl)ethylcarbamoyl)phenoxy)chroman-4-carboxylic acid;
(R)-6-chloro-7-(4-(6-(4-chlorophenyl)pyridin-2-ylcarbamoyl)phenoxy)chroman-4-carboxylic acid;
7-(4-(6-(tert-butylthio)pyridin-2-ylcarbamoyl)phenoxy)-6-chlorochroman-4-carboxylic acid;
6-chloro-7-(4-(6-(4-chlorophenyl)pyridazin-3-ylcarbamoyl)phenoxy)chroman-4-carboxylic acid;
6-chloro-7-(4-(1-(6-(trifluoromethyl)pyridin-2-yl)piperidin-4-ylcarbamoyl)phenoxy)chroman-4-carboxylic acid;
6-chloro-7-(4-(2-(2-ethoxypyridin-3-yl)ethylcarbamoyl)phenoxy)chroman-4-carboxylic acid;
6-chloro-7-(4-(2-(6-(4-methoxyphenyl)pyridin-2-yl)ethylcarbamoyl)phenoxy)chroman-4-carboxylic acid;
6-chloro-7-(4-(2-(6-methoxypyridin-3-yl)ethylcarbamoyl)phenoxy)chroman-4-carboxylic acid;
6-chloro-7-(4-(2-(6-methoxypyridin-2-yl)ethylcarbamoyl)phenoxy)chroman-4-carboxylic acid;
6-chloro-7-(4-(2-(2,4-dimethoxypyrimidin-5-yl)ethylcarbamoyl)phenoxy)chroman-4-carboxylic acid;
6-chloro-7-(4-(2-(6-(2-chlorophenyl)pyridin-2-yl)ethylcarbamoyl)phenoxy)chroman-4-carboxylic acid;
6-chloro-7-(4-(2-(2-cyclopropylpyridin-3-yl)ethylcarbamoyl)phenoxy)chroman-4-carboxylic acid;
6-chloro-7-(4-(2-(2-(2-chlorophenyl)pyridin-3-yl)ethylcarbamoyl)phenoxy)chroman-4-carboxylic acid;
6-chloro-7-(4-(2-(2-(dimethylamino)pyridin-3-yl)ethylcarbamoyl)phenoxy)chroman-4-carboxylic acid;
6-chloro-7-(4-(2-(2-(piperidin-1-yl)pyridin-3-yl)ethylcarbamoyl)phenoxy)chroman-4-carboxylic acid;
6-chloro-7-(4-(2-(2-methoxypyridin-3-yl)ethylcarbamoyl)phenoxy)chroman-4-carboxylic acid;
6-chloro-7-(4-(2-(2-isopropoxypyridin-3-yl)ethylcarbamoyl)phenoxy)chroman-4-carboxylic acid;
and salts thereof.

14. The compound of claim 13, wherein the salt is a sodium salt.

* * * * *